United States Patent
Curry et al.

(10) Patent No.: US 8,435,970 B2
(45) Date of Patent: *May 7, 2013

(54) PHARMACEUTICAL COMBINATIONS OF 1-CYCLOPROPYL-3-[3-(5-MORPHOLIN-4-YLMETHYL-1H-BENZOIMIDAZOL-2-YL)-1H-PYRAZOL-4-YL]-UREA

(75) Inventors: Jayne Elizabeth Curry, Cambridge (GB); Neil James Gallagher, Basel (CH); John Francis Lyons, London (GB); Neil Thomas Thompson, Cambridge (GB)

(73) Assignee: Astex Therapeutics Limited, Cambridge (GB)

( * ) Notice: Subject to any disclaimer, the term of this patent is extended or adjusted under 35 U.S.C. 154(b) by 628 days.

This patent is subject to a terminal disclaimer.

(21) Appl. No.: 12/306,479

(22) PCT Filed: Jun. 29, 2007

(86) PCT No.: PCT/GB2007/002447
§ 371 (c)(1),
(2), (4) Date: Jun. 29, 2009

(87) PCT Pub. No.: WO2008/001115
PCT Pub. Date: Jan. 3, 2008

(65) Prior Publication Data
US 2010/0055094 A1    Mar. 4, 2010

Related U.S. Application Data

(60) Provisional application No. 60/806,214, filed on Jun. 29, 2006.

(51) Int. Cl.
*A61K 31/56*   (2006.01)
*A61K 31/535*  (2006.01)
*A61K 31/52*   (2006.01)
*A61K 31/44*   (2006.01)
*A61K 31/445*  (2006.01)

(52) U.S. Cl.
USPC ............... 514/171; 514/234.5; 514/263.2; 514/303; 514/322; 514/338

(58) Field of Classification Search .................. None
See application file for complete search history.

(56) References Cited

U.S. PATENT DOCUMENTS

| | | | |
|---|---|---|---|
| 5,952,368 | A  | 9/1999  | Kertesz et al. |
| 6,350,746 | B1 | 2/2002  | Buckman et al. |
| 6,358,978 | B1 | 3/2002  | Ritzeler et al. |
| 6,696,437 | B1 | 2/2004  | Lubisch et al. |
| 7,087,616 | B2 | 8/2006  | Fischer et al. |
| 7,977,477 | B2 | 7/2011  | Berdini et al. |
| 8,110,573 | B2 | 2/2012  | Berdini et al. |
| 2003/0207883 | A1 | 11/2003 | Renhowe et al. |
| 2004/0048868 | A1 | 3/2004  | Edwards et al. |
| 2004/0082798 | A1 | 4/2004  | Alonso-Alija et al. |
| 2004/0214814 | A1 | 10/2004 | Bebbington et al. |
| 2004/0242559 | A1 | 12/2004 | Ugolini et al. |
| 2005/0009894 | A1 | 1/2005  | Babin et al. |
| 2006/0293336 | A1 | 12/2006 | Sutton et al. |
| 2007/0021472 | A1 | 1/2007  | Zhu et al. |
| 2007/0105900 | A1 | 5/2007  | Berdini et al. |
| 2007/0135477 | A1 | 6/2007  | Berdini et al. |
| 2007/0208007 | A1 | 9/2007  | Saitou et al. |
| 2008/0132495 | A1 | 6/2008  | Berdini et al. |
| 2008/0312223 | A1 | 12/2008 | Berdini et al. |
| 2010/0004232 | A1 | 1/2010  | Berdini et al. |
| 2011/0105501 | A1 | 5/2011  | Gallagher et al. |
| 2011/0159111 | A1 | 6/2011  | Curry et al. |
| 2011/0224203 | A1 | 9/2011  | Berdini et al. |

FOREIGN PATENT DOCUMENTS

| | | |
|---|---|---|
| EP | 0169051 A2   | 1/1986 |
| EP | 0711768 A1   | 5/1996 |
| EP | 1264820 A1   | 12/2002 |
| EP | 1460067 A1   | 9/2004 |
| JP | 2007/045752 A | 2/2007 |
| WO | 94/14435 A1  | 7/1994 |

(Continued)

OTHER PUBLICATIONS

Clinical Trial NCT00238238 (dated Oct. 12, 2005).*
Blankley et al.: Antihypertensive Activity of 6-Arylpyrido[2,3-d] Pyrimidim-7-Amine Derivatives. 2. 7-Acyl Amide Analogues, *Journal of Medicinal Chemistry*, vol. 26, No. 3, Mar. 1, 1983, pp. 403-411.
Abd El-Wareth A O Sarhan et al.: Synthesis, Characterization and Reactions of 2-Deoxo-5-Deazaalloxazines, *Bioorganic & Medicinal Chemistry*, vol. 9, Jan. 1, 2001, pp. 2993-2998.
Mesguiche et al.: 4-Alkoxy-2,6-Diaminopyrimidine Derivatives: Inhibitors of Cyclin Dependent Kinases 1 and 2, *Bioorganic & Medicinal Chemistry Letters*, vol. 13, Jan. 1, 2003, pp. 217-222.
GB Search Report GB 0315657.7 filed Jul. 3, 2003.
GB Search Report GB 0324919.0 filed Oct. 24, 2003.

(Continued)

*Primary Examiner* — Craig Ricci
(74) *Attorney, Agent, or Firm* — Heslin Rothenberg Farley & Mesiti P.C.

(57) ABSTRACT

The invention provides combinations of an ancillary compound and a compound which is a salt of 1-cyclopropyl-3-[3-(5-morpholin-4-ylmethyl-1H-benzoimidazol-2-yl)-1H-pyrazol-4-yl]-urea selected from the lactate and citrate salts and mixtures thereof. Also provided are crystalline forms of the salts, methods for making the salts and their uses in treating cancers. The invention further provides combinations of an ancillary compound and a compound of the formula (I) as defined in PCT/GB2004/002824 (WO 2005/002552) or a compound of the formula (I')

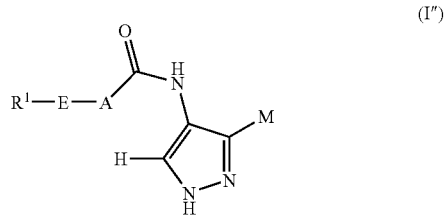

or a salt, solvate, tautomer or N-oxide thereof, wherein $R^1$, E, A and M are as defined in the claims.

15 Claims, 12 Drawing Sheets

FOREIGN PATENT DOCUMENTS

| | | |
|---|---|---|
| WO | 94/29300 A1 | 12/1994 |
| WO | 96/00218 A1 | 1/1996 |
| WO | 97/12615 A1 | 4/1997 |
| WO | 97/36585 A1 | 10/1997 |
| WO | 99/46244 A1 | 9/1999 |
| WO | 99/50247 A1 | 10/1999 |
| WO | 99/61426 A1 | 12/1999 |
| WO | 00/39108 A1 | 7/2000 |
| WO | 00/43384 A1 | 7/2000 |
| WO | 00/59902 A2 | 10/2000 |
| WO | 00/64888 A1 | 11/2000 |
| WO | 01/02385 A1 | 1/2001 |
| WO | 01/19788 A2 | 3/2001 |
| WO | 01/19798 A2 | 3/2001 |
| WO | 01/57022 A2 | 8/2001 |
| WO | 01/64642 A2 | 9/2001 |
| WO | 01/064642 A2 | 9/2001 |
| WO | 01/64643 A2 | 9/2001 |
| WO | 01/79198 A1 | 10/2001 |
| WO | 02/00647 A1 | 1/2002 |
| WO | 02/00651 A2 | 1/2002 |
| WO | 02/00655 A1 | 1/2002 |
| WO | 02/059111 A2 | 8/2002 |
| WO | WO 02/059106 * | 8/2002 |
| WO | 02/072549 A1 | 9/2002 |
| WO | 02/096426 A1 | 12/2002 |
| WO | 03/002566 A1 | 1/2003 |
| WO | 03/004488 A1 | 1/2003 |
| WO | 03/006465 A1 | 1/2003 |
| WO | 03/035065 A1 | 5/2003 |
| WO | 03/044014 A1 | 5/2003 |
| WO | 03/053941 A2 | 7/2003 |
| WO | 03/066629 A2 | 8/2003 |
| WO | 2004/041277 A1 | 5/2004 |
| WO | 2004/050636 A2 | 6/2004 |
| WO | 2004/052370 A2 | 6/2004 |
| WO | 2004/054515 A2 | 7/2004 |
| WO | 2004/056815 A1 | 7/2004 |
| WO | 2005/002552 A2 | 1/2005 |
| WO | 2005/002576 A2 | 1/2005 |
| WO | 2005/005414 A2 | 1/2005 |
| WO | WO 2005/002552 * | 1/2005 |
| WO | 2005/028624 A2 | 3/2005 |
| WO | 2005/047266 A1 | 5/2005 |
| WO | 2006/070195 A1 | 7/2006 |
| WO | 2006/071940 A2 | 7/2006 |
| WO | 2006/077425 A2 | 7/2006 |
| WO | WO 2006/070195 * | 7/2006 |
| WO | 2006/092430 A1 | 9/2006 |
| WO | 2006/094209 A2 | 9/2006 |
| WO | 2006/094235 A1 | 9/2006 |
| WO | 2006/124780 A2 | 11/2006 |
| WO | 2007/019416 A1 | 2/2007 |
| WO | 2007/063031 A2 | 6/2007 |
| WO | 2007/077435 A1 | 7/2007 |
| WO | 2008/001101 A2 | 1/2008 |
| WO | 2008/003857 A1 | 1/2008 |

OTHER PUBLICATIONS

International Search Report PCT/GB2004/002824 filed Jul. 5, 2004.
European Supplementary Search report EP Application No. 04 743 172.1.
GB search report GB 0428552.4 filed Dec. 30, 2004.
GB search report GB 0428554.0 filed Dec. 30, 2004.
International Search Report PCT/GB2005/005097 filed Dec. 30, 2005.
GB search report GB 0526607.7 filed Dec. 30, 2005.
International Search Report PCT/GB2006/004954 filed Dec. 29, 2006.
International Search Report PCT/GB2007/002447 filed Jun. 29, 2007.
International Search Report PCT/GB2007/002428 filed Jun. 29, 2007.
Souillac, Pierre, et al., Characterization of Delivery Systems, Differential Scanning Calorimetry, Encyclopedia of Controlled Drug Delivery, Wiley, 1999, pp. 212-227.
Vippagunta, Sudha R., et al., Crystalline solids, Advanced Drug Delivery Reviews, 48, 2001, pp. 3-26.
Morissette, Sherry L., et al., High-throughput crystallization: polymorphs, salts, co-crystals and solvates of pharmaceutical solids, Advanced Drug Delivery Reviews, 56, 2004, pp. 275-300.
Essassi et al.: Synthese et Hererocyclisation Des (Pyrazolyl-3-(5))-2 Benzimidazoles en Catalyse Par Transfert de Phase, *Bull. Soc. Chim. Belg.* vol. 96, pp. 63 - 67, 1987.

* cited by examiner

PHARMACEUTICAL COMBINATIONS OF 1-CYCLOPROPYL-3-[3-(5-MORPHOLIN-4-YLMETHYL-1H-BENZOIMIDAZOL-2-YL)-1H-PYRAZOL-4-YL]-UREA

CROSS REFERENCE TO RELATED APPLICATIONS

This application is a national phase filing under 35 U.S.C. §371 of PCT International Application PCT/GB2007/002447, filed Jun. 29, 2007, and published under PCT Article 21(2) in English as WO 2008/001115A2 on Jan. 3, 2008. PCT/GB2007/002447 claimed priority from U.S. provisional patent application No. 60/806,214 filed on Jun. 9, 2006. The entire contents of the prior applications are incorporated herein by reference.

TECHNICAL FIELD

This invention relates to combinations comprising (or consisting essentially of) one or more compounds of the formula (I') or (I) as defined herein (so including one or more specific salts of the compound 1-cyclopropyl-3-[3-(5-morpholin-4-ylmethyl-1H-benzoimidazol-2-yl)-1H-pyrazol-4-yl]-urea, or crystalline forms thereof), with one or more ancillary compounds, to processes for preparing the combinations, and to various therapeutic uses of the combinations. Also provided are pharmaceutical compositions containing the combinations.

BACKGROUND OF THE INVENTION

The compound 1-cyclopropyl-3-[3-(5-morpholin-4-yl methyl-1H-benzoimidazol-2-yl)-1H-pyrazol-4-yl]-urea free base and various salts thereof are disclosed in our earlier International patent application filed 30 Dec. 2005 claiming priority from U.S. Ser. No. 60/640,475 and GB0428552.4 as being inhibitors of Cyclin Dependent Kinases (CDK kinases), Aurora kinases and Glycogen Synthase Kinase-3 (GSK3).

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Cyclin Dependent Kinases

The process of eukaryotic cell division may be broadly divided into a series of sequential phases termed G1, S, G2 and M. Correct progression through the various phases of the cell cycle has been shown to be critically dependent upon the spatial and temporal regulation of a family of proteins known as cyclin dependent kinases (cdks) and a diverse set of their cognate protein partners termed cyclins. Cdks are cdc2 (also known as cdk1) homologous serine-threonine kinase proteins that are able to utilise ATP as a substrate in the phosphorylation of diverse polypeptides in a sequence dependent context. Cyclins are a family of proteins characterised by a homology region, containing approximately 100 amino acids, termed the "cyclin box" which is used in binding to, and defining selectivity for, specific cdk partner proteins.

Modulation of the expression levels, degradation rates, and activation levels of various cdks and cyclins throughout the cell cycle leads to the cyclical formation of a series of cdk/cyclin complexes, in which the cdks are enzymatically active. The formation of these complexes controls passage through discrete cell cycle checkpoints and thereby enables the process of cell division to continue. Failure to satisfy the prerequisite biochemical criteria at a given cell cycle checkpoint, i.e. failure to form a required cdk/cyclin complex, can lead to cell cycle arrest and/or cellular apoptosis. Aberrant cellular proliferation, as manifested in cancer, can often be attributed to loss of correct cell cycle control. Inhibition of cdk enzymatic activity therefore provides a means by which abnormally dividing cells can have their division arrested and/or be killed. The diversity of cdks, and cdk complexes, and their critical roles in mediating the cell cycle, provides a broad spectrum of potential therapeutic targets selected on the basis of a defined biochemical rationale.

Progression from the G1 phase to the S phase of the cell cycle is primarily regulated by cdk2, cdk3, cdk4 and cdk6 via association with members of the D and E type cyclins. The D-type cyclins appear instrumental in enabling passage beyond the G1 restriction point, where as the cdk2/cyclin E complex is key to the transition from the G1 to S phase. Subsequent progression through S phase and entry into G2 is thought to require the cdk2/cyclin A complex. Both mitosis, and the G2 to M phase transition which triggers it, are regulated by complexes of cdk1 and the A and B type cyclins.

During G1 phase Retinoblastoma protein (Rb), and related pocket proteins such as p130, are substrates for cdk(2, 4, & 6)/cyclin complexes. Progression through G1 is in part facilitated by hyperphosphorylation, and thus inactivation, of Rb and p130 by the cdk(4/6)/cyclin-D complexes. Hyperphosphorylation of Rb and p130 causes the release of transcription factors, such as E2F, and thus the expression of genes necessary for progression through G1 and for entry into S-phase, such as the gene for cyclin E. Expression of cyclin E facilitates formation of the cdk2/cyclin E complex which amplifies, or maintains, E2F levels via further phosphorylation of Rb. The cdk2/cyclin E complex also phosphorylates other proteins necessary for DNA replication, such as NPAT, which has been implicated in histone biosynthesis. G1 progression and the G1/S transition are also regulated via the mitogen stimulated Myc pathway, which feeds into the cdk2/cyclin E pathway. Cdk2 is also connected to the p53 mediated DNA damage response pathway via p53 regulation of p21 levels. p21 is a protein inhibitor of cdk2/cyclin E and is thus capable of blocking, or delaying, the G1/S transition. The cdk2/cyclin E complex may thus represent a point at which biochemical stimuli from the Rb, Myc and p53 pathways are to some degree integrated. Cdk2 and/or the cdk2/cyclin E complex therefore represent good targets for therapeutics designed at arresting, or recovering control of, the cell cycle in aberrantly dividing cells.

The exact role of cdk3 in the cell cycle is not clear. As yet no cognate cyclin partner has been identified, but a dominant negative form of cdk3 delayed cells in G1, thereby suggesting that cdk3 has a role in regulating the G1/S transition.

Although most cdks have been implicated in regulation of the cell cycle there is evidence that certain members of the cdk family are involved in other biochemical processes. This is exemplified by cdk5 which is necessary for correct neuronal development and which has also been implicated in the phosphorylation of several neuronal proteins such as Tau, NUDE-1, synapsin1, DARPP32 and the Munc18/Syntaxin1A complex. Neuronal cdk5 is conventionally activated by binding to the p35/p39 proteins. Cdk5 activity can, however, be deregulated by the binding of p25, a truncated version of p35. Conversion of p35 to p25, and subsequent deregulation of cdk5 activity, can be induced by ischemia, excitotoxicity, and β-amyloid peptide. Consequently p25 has been implicated in the pathogenesis of neurodegenerative diseases, such as Alzheimer's, and is therefore of interest as a target for therapeutics directed against these diseases.

Cdk7 is a nuclear protein that has cdc2 CAK activity and binds to cyclin H. Cdk7 has been identified as component of the TFIIH transcriptional complex which has RNA polymerase II C-terminal domain (CTD) activity. This has been associated with the regulation of HIV-1 transcription via a Tat-mediated biochemical pathway. Cdk8 binds cyclin C and has been implicated in the phosphorylation of the CTD of RNA polymerase II. Similarly the cdk9/cyclin-T1 complex (P-TEFb complex) has been implicated in elongation control of RNA polymerase II. PTEF-b is also required for activation of transcription of the HIV-1 genome by the viral transactivator Tat through its interaction with cyclin T1. Cdk7, cdk8, cdk9 and the P-TEFb complex are therefore potential targets for anti-viral therapeutics.

At a molecular level mediation of cdk/cyclin complex activity requires a series of stimulatory and inhibitory phosphorylation, or dephosphorylation, events. Cdk phosphorylation is performed by a group of cdk activating kinases (CAKs) and/or kinases such as wee1, Myt1 and Mik1. Dephosphorylation is performed by phosphatases such as cdc25(a & c), pp2a, or KAP.

Cdk/cyclin complex activity may be further regulated by two families of endogenous cellular proteinaceous inhibitors: the Kip/Cip family, or the INK family. The INK proteins specifically bind cdk4 and cdk6. $p16^{ink4}$ (also known as MTS1) is a potential tumour suppressor gene that is mutated, or deleted, in a large number of primary cancers. The Kip/Cip family contains proteins such as $p21^{Cip1,Waf1}$, $p27^{Kip1}$ and $p57^{kip2}$. As discussed previously p21 is induced by p53 and is able to inactivate the cdk2/cyclin(E/A) and cdk4/cyclin(D1/D2/D3) complexes. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of cdks, and their associated proteins, in co-ordinating and driving the cell cycle in proliferating cells have been outlined above. Some of the biochemical pathways in which cdks play a key role have also been described. The development of monotherapies for the treatment of proliferative disorders, such as cancers, using therapeutics targeted generically at cdks, or at specific cdks, is therefore potentially highly desirable. Cdk inhibitors could conceivably also be used to treat other conditions such as viral infections, autoimmune diseases and neuro-degenerative diseases, amongst others. Cdk targeted therapeutics may also provide clinical benefits in the treatment of the previously described diseases when used in combination therapy with either existing, or new, therapeutic agents. Cdk targeted anticancer therapies could potentially have advantages over many current antitumour agents as they would not directly interact with DNA and should therefore reduce the risk of secondary tumour development.

Diffuse Large B-Cell Lymphomas (DLBCL)

Cell cycle progression is regulated by the combined action of cyclins, cyclin-dependent kinases (CDKs), and CDK-inhibitors (CDKi), which are negative cell cycle regulators. p27KIP1 is a CDKi key in cell cycle regulation, whose degradation is required for G1/S transition. In spite of the absence of p27KIP1 expression in proliferating lymphocytes, some aggressive B-cell lymphomas have been reported to show an anomalous p27KIP1 staining. An abnormally high expression of p27KIP1 was found in lymphomas of this type. Analysis of the clinical relevance of these findings showed that a high level of p27KIP1 expression in this type of tumour is an adverse prognostic marker, in both univariate and multivariate analysis. These results show that there is abnormal p27KIP1 expression in Diffuse Large B-cell Lymphomas (DLBCL), with adverse clinical significance, suggesting that this anomalous p27KIP1 protein may be rendered non-functional through interaction with other cell cycle regulator proteins. (Br. J. Cancer. 1999 July;80(9):1427-34. p27KIP1 is abnormally expressed in Diffuse Large B-cell Lymphomas and is associated with an adverse clinical outcome. Saez A, Sanchez E, Sanchez-Beato M, Cruz M A, Chacon I, Munoz E, Camacho F I, Martinez-Montero J C, Mollejo M, Garcia J F, Piris M A. Department of Pathology, Virgen de la Salud Hospital, Toledo, Spain.)

Chronic Lymphocytic Leukemia

B-Cell chronic lymphocytic leukaemia (CLL) is the most common leukaemia in the Western hemisphere, with approximately 10,000 new cases diagnosed each year (Parker S L, Tong T, Bolden S, Wingo P A: Cancer statistics, 1997. Ca. Cancer. J. Clin. 47:5, (1997)). Relative to other forms of leukaemia, the overall prognosis of CLL is good, with even the most advanced stage patients having a median survival of 3 years.

The addition of fludarabine as initial therapy for symptomatic CLL patients has led to a higher rate of complete responses (27% v 3%) and duration of progression-free survival (33 v 17 months) as compared with previously used alkylator-based therapies. Although attaining a complete clinical response after therapy is the initial step toward improving survival in CLL, the majority of patients either do not attain complete remission or fail to respond to fludarabine. Furthermore, all patients with CLL treated with fludarabine eventually relapse, making its role as a single agent purely palliative (Rai K R, Peterson B, Elias L, Shepherd L, Hines J, Nelson D, Cheson B, Kolitz J, Schiffer C A: A randomized comparison of fludarabine and chlorambucil for patients with previously untreated chronic lymphocytic leukemia. A CALGB SWOG, CTG/NCI-C and ECOG Inter-Group Study. Blood 88:141a, 1996 (abstr 552, suppl 1). Therefore, identifying new agents with novel mechanisms of action that complement fludarabine's cytotoxicity and abrogate the resistance induced by intrinsic CLL drug-resistance factors will be necessary if further advances in the therapy of this disease are to be realized.

The most extensively studied, uniformly predictive factor for poor response to therapy and inferior survival in CLL patients is aberrant p53 function, as characterized by point mutations or chromosome 17p13 deletions. Indeed, virtually no responses to either alkylator or purine analog therapy have been documented in multiple single institution case series for those CLL patients with abnormal p53 function. Introduction of a therapeutic agent that has the ability to overcome the drug resistance associated with p53 mutation in CLL would potentially be a major advance for the treatment of the disease.

Flavopiridol and CYC 202, inhibitors of cyclin-dependent kinases induce in vitro apoptosis of malignant cells from B-cell chronic lymphocytic leukemia (B-CLL).

Flavopiridol exposure results in the stimulation of caspase 3 activity and in caspase-dependent cleavage of p27(kip1), a negative regulator of the cell cycle, which is overexpressed in B-CLL (Blood. 1998 Nov. 15;92(10):3804-16 Flavopiridol induces apoptosis in chronic lymphocytic leukemia cells via activation of caspase-3 without evidence of bcl-2 modulation or dependence on functional p53. Byrd J C, Shinn C, Waselenko J K, Fuchs E J, Lehman T A, Nguyen P L, Flinn I W, Diehl L F, Sausville E, Grever M R).

Aurora Kinases

Relatively recently, a new family of serine/threonine kinases known as the Aurora kinases has been discovered that are involved in the G2 and M phases of the cell cycle, and which are important regulators of mitosis.

The precise role of Aurora kinases has yet to be elucidated but that they play a part in mitotic checkpoint control, chromosome dynamics and cytokinesis (Adams et al., *Trends Cell Biol.*, 11: 49-54 (2001). Aurora kinases are located at the centrosomes of interphase cells, at the poles of the bipolar spindle and in the mid-body of the mitotic apparatus.

Three members of the Aurora kinase family have been found in mammals so far (E. A. Nigg, *Nat. Rev. Mol. Cell Biol.* 2: 21-32, (2001)). These are:

Aurora A (also referred to in the literature as Aurora 2);
Aurora B (also referred to in the literature as Aurora 1); and
Aurora C (also referred to in the literature as Aurora 3).

The Aurora kinases have highly homologous catalytic domains but differ considerably in their N-terminal portions (Katayama H, Brinkley W R, Sen S.; The Aurora kinases: role in cell transformation and tumorigenesis; Cancer Metastasis Rev. 2003 December;22(4):451-64).

The substrates of the Aurora kinases A and B have been identified as including a kinesin-like motor protein, spindle apparatus proteins, histone H3 protein, kinetochore protein and the tumour suppressor protein p53.

Aurora A kinases are believed to be involved in spindle formation and become localised on the centrosome during the early G2 phase where they phosphorylate spindle-associated proteins (Prigent et al., *Cell*, 114: 531-535 (2003). Hirota et al, *Cell*, 114:585-598, (2003) found that cells depleted of Aurora A protein kinase were unable to enter mitosis. Furthermore, it has been found (Adams, 2001) that mutation or disruption of the Aurora A gene in various species leads to mitotic abnormalities, including centrosome separation and maturation defects, spindle aberrations and chromosome segregation defects.

The Aurora kinases are generally expressed at a low level in the majority of normal tissues, the exceptions being tissues with a high proportion of dividing cells such as the thymus and testis. However, elevated levels of Aurora kinases have been found in many human cancers (Giet et al., *J. Cell. Sci.* 112: 3591-361, (1999) and Katayama (2003). Furthermore, Aurora A kinase maps to the chromosome 20q13 region that has frequently been found to be amplified in many human cancers.

Thus, for example, significant Aurora A over-expression has been detected in human breast, ovarian and pancreatic cancers (see Zhou et al., *Nat. Genet.* 20: 189-193, (1998), Tanaka et al., *Cancer Res.*, 59: 2041-2044, (1999) and Han et al., *cancer Res.*, 62: 2890-2896, (2002).

Moreover, Isola, *American Journal of Pathology* 147,905-911 (1995) has reported that amplification of the Aurora A locus (20q13) correlates with poor prognosis for patients with node-negative breast cancer.

Amplification and/or over-expression of Aurora-A is observed in human bladder cancers and amplification of Aurora-A is associated with aneuploidy and aggressive clinical behaviour, see Sen et al., *J. Natl. Cancer Inst,* 94: 1320-1329 (2002).

Elevated expression of Aurora-A has been detected in over 50% of colorectal cancers, (see Bischoff et al., *EMBO J.,* 17: 3052-3065, (1998) and Takahashi et al., *Jpn. J. Cancer Res.*, 91: 1007-1014 (2000)) ovarian cancers (see Gritsko et al. *Clin. Cancer Res.,* 9: 1420-1426 (2003), and gastric tumours Sakakura et al., *British Journal of Cancer,* 84: 824-831 (2001).

Tanaka et al. *Cancer Research,* 59: 2041-2044 (1999) found evidence of over-expression of Aurora A in 94% of invasive duct adenocarcinomas of the breast.

High levels of Aurora A kinase have also been found in renal, cervical, neuroblastoma, melanoma, lymphoma, pancreatic and prostate tumour cell lines Bischoff et al. (1998), EMBO J., 17: 3052-3065 (1998); Kimura et al. J. Biol. Chem., 274: 7334-7340 (1999); Zhou et al., Nature Genetics, 20: 189-193 (1998); Li et al., Clin Cancer Res. 9 (3): 991-7 (2003)].

Aurora-B is highly expressed in multiple human tumour cell lines, including leukemic cells [Katayama et al., Gene 244: 1-7)]. Levels of this enzyme increase as a function of Duke's stage in primary colorectal cancers [Katayama et al., J. Natl Cancer Inst., 91: 1160-1162 (1999)].

High levels of Aurora-3 (Aurora-C) have been detected in several tumour cell lines, even though this kinase tends to be restricted to germ cells in normal tissues (see Kimura et al. *Journal of Biological Chemistry,* 274: 7334-7340 (1999)). Over-expression of Aurora-3 in approximately 50% of colorectal cancers has also been reported in the article by Takahashi et al., *Jpn J. Cancer Res.* 91: 1007-1014 (2001)].

Other reports of the role of Aurora kinases in proliferative disorders may be found in Bischoff et al., *Trends in Cell Biology* 9: 454-459 (1999); Giet et al. *Journal of Cell Science,* 112: 3591-3601 (1999) and Dutertre, et al. *Oncogene,* 21: 6175-6183 (2002).

Royce et al report that the expression of the Aurora 2 gene (known as STK15 or BTAK) has been noted in approximately one-fourth of primary breast tumours. (Royce M E, Xia W, Sahin A A, Katayama H, Johnston D A, Hortobagyi G, Sen S, Hung M C; STK15/Aurora-A expression in primary breast tumours is correlated with nuclear grade but not with prognosis; *Cancer.* 2004 Jan. 1; 100(1): 12-9).

Endometrial carcinoma (EC) comprises at least two types of cancer: endometrioid carcinomas (EECs) are estrogen-related tumours, which are frequently euploid and have a good prognosis. Nonendometrioid carcinomas (NEECs; serous and clear cell forms) are not estrogen related, are frequently aneuploid, and are clinically aggressive. It has also been found that Aurora was amplified in 55.5% of NEECs but not in any EECs (P<or =0.001) (Moreno-Bueno G, Sanchez-Estevez C, Cassia R, Rodriguez-Perales S, Diaz-Uriarte R, Dominguez O, Hardisson D, Andujar M, Prat J, Matias-Guiu X, Cigudosa J C, Palacios *J. Cancer Res.* 2003 Sep. 15;63 (18):5697-702).

Reichardt et al (*Oncol Rep.* 2003 September-October; 10(5): 1275-9) have reported that quantitative DNA analysis by PCR to search for Aurora amplification in gliomas revealed that five out of 16tumours (31%) of differentWHO grade (1× grade II, 1× grade III, 3× grade IV) showed DNA amplification of the Aurora 2 gene. It was hypothesized that amplification of the Aurora 2 gene may be a non-random genetic alteration in human gliomas playing a role in the genetic pathways of tumourigenesis.

Results by Hamada et al (*Br. J. Haematol.* 2003 May;121 (3):439-47) also suggest that Aurora 2 is an effective candidate to indicate not only disease activity but also tumourigenesis of non-Hodgkin's lymphoma. Retardation of tumour cell growth resulting from the restriction of this gene's functions could be a therapeutic approach for non-Hodgkin's lymphoma.

In a study by Gritsko et al (*Clin Cancer Res.* 2003 April; 9(4): 1420-6)), the kinase activity and protein levels of Aurora A were examined in 92 patients with primary ovarian tumours. In vitro kinase analyses revealed elevated Aurora A kinase activity in 44 cases (48%). Increased Aurora A protein levels were detected in 52 (57%) specimens. High protein levels of Aurora A correlated well with elevated kinase activity.

Results obtained by Li et al (*Clin. Cancer Res.* 2003 March; 9(3):991-7) showed that the Aurora A gene is overexpressed in pancreatic tumours and carcinoma cell lines and suggest that overexpression of Aurora A may play a role in pancreatic carcinogenesis.

Similarly, it has been shown that Aurora A gene amplification and associated increased expression of the mitotic kinase it encodes are associated with aneuploidy and aggressive clinical behaviour in human bladder cancer. (*J. Natl. Cancer Inst.* 2002 Sep. 4; 94(17):1320-9).

Investigation by several groups (Dutertre S, Prigent C., Aurora-A overexpression leads to override of the microtubule-kinetochore attachment checkpoint; *Mol. Interv.* 2003 May; 3(3):127-30 and Anand S, Penrhyn-Lowe S, Venkitaraman A R., Aurora-A amplification overrides the mitotic spindle assembly checkpoint, inducing resistance to Taxol, *Cancer Cell.* 2003 January;3(1):51-62) suggests that overexpression of Aurora kinase activity is associated with resistance to some current cancer therapies. For example overexpression of Aurora A in mouse embryo fibroblasts can reduce the sensitivity of these cells to the cytotoxic effects of taxane derivatives. Therefore Aurora kinase inhibitors may find particular use in patients who have developed resistance to existing therapies.

On the basis of work carried out to date, it is apparent that inhibition of Aurora kinases, particularly Aurora kinase A and Aurora kinase B, will prove an effective means of arresting tumour development.

Harrington et al (*Nat Med.* 2004 March; 10(3):262-7) have demonstrated that an inhibitor of the Aurora kinases suppresses tumour growth and induces tumour regression in vivo. In the study, the Aurora kinase inhibitor blocked cancer cell proliferation, and also triggered cell death in a range of cancer cell lines including leukaemic, colorectal and breast cell lines. In addition, it has shown potential for the treatment of leukemia by inducing apoptosis in leukemia cells. VX-680 potently killed treatment-refractory primary Acute Myelogenous Leukemia (AML) cells from patients (Andrews, *Oncogene*, 2005, 24, 5005-5015).

Recent reports indicate that Aurora kinases A and B are overexpressed in human leukaemia cells and that a small molecule Aurora kinase inhibitor is active against the growth of primary acute myeloid cells in vitro (Harrington et al, 2004). Moreover it has recently been reported that the product of the PML gene that is disrupted in acute promyelocytic leukaemia by a t(15:17) translocation (PML3), interacts with Aurora A and suppresses its kinase activity. Further evidence is emerging that PML is a tumor suppressor and that its disruption is not limited to leukaemias but may also be common in lymphomas and some solid tumors (Xu et al, *Molecular Cell* 17: 721-732, 2005).

Cancers which may be particularly amenable to Aurora inhibitors include breast, bladder, colorectal, pancreatic, ovarian, non-Hodgkin's lymphoma, gliomas and nonendometrioid endometrial carcinomas. Leukemias particularly amenable to Aurora inhibitors include Acute Myelogenous Leukemia (AML), chronic myelogenous leukaemia (CML), B-cell lymphoma (Mantle cell), and Acute Lymphoblastic Leukemia (ALL). Further leukemias include acute promyelocytic leukaemia.

Overexpression of Aurora kinase A has been identified as an independent predictor of poor prognosis in patients with medulloblastoma, a highly malignant primitive neuroectodermal tumor of the cerebellum (Neben et al., *Cancer Research*, 64: 3103-3111 (2004).

Glycogen Synthase Kinase

Glycogen Synthase Kinase-3 (GSK3) is a serine-threonine kinase that occurs as two ubiquitously expressed isoforms in humans (GSK3α & beta GSK3β). GSK3 has been implicated as having roles in embryonic development, protein synthesis, cell proliferation, cell differentiation, microtubule dynamics, cell motility and cellular apoptosis. As such GSK3 has been implicated in the progression of disease states such as diabetes, cancer, Alzheimer's disease, stroke, epilepsy, motor neuron disease and/or head trauma. Phylogenetically GSK3 is most closely related to the cyclin dependent kinases (CDKs).

The consensus peptide substrate sequence recognised by GSK3 is (Ser/Thr)-X—X—X—(pSer/pThr), where X is any amino acid (at positions (n+1), (n+2), (n+3)) and pSer and pThr are phospho-serine and phospho-threonine respectively (n+4). GSK3 phosphorylates the first serine, or threonine, at position (n). Phospho-serine, or phospho-threonine, at the (n+4) position appear necessary for priming GSK3 to give maximal substrate turnover. Phosphorylation of GSK3α at Ser21, or GSK3β at Ser9, leads to inhibition of GSK3. Mutagenesis and peptide competition studies have led to the model that the phosphorylated N-terminus of GSK3 is able to compete with phospho-peptide substrate (S/TXXXpS/pT) via an autoinhibitory mechanism. There are also data suggesting that GSK3α and GSKβ may be subtly regulated by phosphorylation of tyrosines 279 and 216 respectively. Mutation of these residues to a Phe caused a reduction in in vivo kinase activity. The X-ray crystallographic structure of GSK3 βhas helped to shed light on all aspects of GSK3 activation and regulation.

GSK3 forms part of the mammalian insulin response pathway and is able to phosphorylate, and thereby inactivate, glycogen synthase. Upregulation of glycogen synthase activity, and thereby glycogen synthesis, through inhibition of GSK3, has thus been considered a potential means of combating type 11, or non-insulin-dependent diabetes mellitus (NIDDM): a condition in which body tissues become resistant to insulin stimulation. The cellular insulin response in liver, adipose, or muscle tissues, is triggered by insulin binding to an extracellular insulin receptor. This causes the phosphorylation, and subsequent recruitment to the plasma membrane, of the insulin receptor substrate (IRS) proteins. Further phosphorylation of the IRS proteins initiates recruitment of phosphoinositide-3 kinase (PI3K) to the plasma membrane where it is able to liberate the second messenger phosphatidylinosityl 3,4,5-trisphosphate (PIP3). This facilitates co-localisation of 3-phosphoinositide-dependent protein kinase 1 (PDK1) and protein kinase B (PKB or Akt) to the membrane, where PDK1 activates PKB. PKB is able to phosphorylate, and thereby inhibit, GSK3α and/or GSKβ through phosphorylation of Ser9, or ser21, respectively. The inhibition of GSK3 then triggers upregulation of glycogen synthase activity. Therapeutic agents able to inhibit GSK3 may thus be able to induce cellular responses akin to those seen on insulin stimulation. A further in vivo substrate of GSK3 is the eukaryotic protein synthesis initiation factor 2B (eIF2B). eIF2B is inactivated via phosphorylation and is thus able to suppress protein biosynthesis. Inhibition of GSK3, e.g. by inactivation of the "mammalian target of rapamycin" protein (mTOR), can thus upregulate protein biosynthesis. Finally there is some evidence for regulation of GSK3 activity via the mitogen activated protein kinase (MAPK) pathway through phosphorylation of GSK3 by kinases such as mitogen activated protein kinase activated protein kinase 1 (MAPKAP-K1 or RSK). These data suggest that GSK3 activity may be modulated by mitogenic, insulin and/or amino acid stimulii.

It has also been shown that GSK3β is a key component in the vertebrate Wnt signalling pathway. This biochemical pathway has been shown to be critical for normal embryonic development and regulates cell proliferation in normal tissues. GSK3 becomes inhibited in response to Wnt stimulii. This can lead to the de-phosphorylation of GSK3 substrates such as Axin, the adenomatous polyposis coli (APC) gene product and β-catenin. Aberrant regulation of the Wnt pathway has been associated with many cancers. Mutations in APC, and/or β-catenin, are common in colorectal cancer and other tumours. β-catenin has also been shown to be of importance in cell adhesion. Thus GSK3 may also modulate cellular adhesion processes to some degree. Apart from the biochemical pathways already described there are also data implicating GSK3 in the regulation of cell division via phosphorylation of cyclin-D1, in the phosphorylation of transcription factors such as c-Jun, CCAAT/enhancer binding protein α (C/EBPα), c-Myc and/or other substrates such as Nuclear Factor of Activated T-cells (NFATc), Heat Shock Factor-1 (HSF-1) and the c-AMP response element binding protein (CREB). GSK3 also appears to play a role, albeit tissue specific, in regulating cellular apoptosis. The role of GSK3 in modulating cellular apoptosis, via a pro-apoptotic mechanism, may be of particular relevance to medical conditions in which neuronal apoptosis can occur. Examples of these are head trauma, stroke, epilepsy, Alzheimer's and motor neuron diseases, progressive supranuclear palsy, corticobasal degeneration, and Pick's disease. In vitro it has been shown that GSK3 is able to hyper-phosphorylate the microtubule associated protein Tau. Hyperphosphorylation of Tau disrupts its normal binding to microtubules and may also lead to the formation of intra-cellular Tau filaments. It is believed that the progressive accumulation of these filaments leads to eventual neuronal dysfunction and degeneration. Inhibition of Tau phosphorylation, through inhibition of GSK3, may thus provide a means of limiting and/or preventing neurodegenerative effects.

C-Abl

A chromosomal translocation event which fuses a BCR encoded sequence to a truncated c-abl gene greatly increases c-abl's tyrosine kinase activity and is the transforming agent in 95% of all Chronic Myeloid Leukaemia (CML) patients. This translocation occurs between chromosomes 9 and 22 resulting in an altered chromosome 22, the Philadelphia (Ph+) chromosome, which can be distinguished by cytogenetic methods. The fusion of BCR and Abl gene sequences results in the oligomerization of the Bcr-Abl gene product, increased trans-autophosphorylation and activation. An autoinhibitory domain of the c-abl protein is also deleted as a result of the gene fusion. The sub-cellular localization of c-abl is also affected as a result of the gene fusion. The oncogenic effects of Bcr-Abl are complicated, but are believed to involve induction of G1 to S phase transition through activation of Ras, Erk and Jun pathways. Bcr-Abl also affects cell survival through the PI3K/Akt pathway. The oncogenic effects of Bcr-Abl have been demonstrated in animal models which indicate that the Bcr-Abl protein is able to establish CML symptoms in mice.

CML is a fatal disease, which progresses through three stages: chronic phase, accelerated phase, and blast crisis. CML is characterized in early stages by the proliferation of terminally differentiated neutrophils. As the disease progresses an excessive number of myeloid or lymphoid progenitor cells are produced. This chronic phase of the disease may last for years before advancing to an acute blast stage, characterized by multiple additional genetic mutations. CML primarily affects adults who have a mean survival of 5 years after the disease is manifested. CML has been successfully treated in early phases by an ATP competitive inhibitor of c-abl, imatinib (Gleevec). A 95% remission rate was demonstrated for this drug in a phase I clinical trial. Durable responses to imatinib have been observed for CML patients in the chronic phase, however remissions in blast phase only last 2-6 months. Unfortunately the development of acquired resistance to imatinib in CML patients is estimated to be as high as 15%/year.

Kinase domain mutations in BCR-ABL represent the most common mechanism of acquired resistance to imatinib, occurring in 50%-90% of cases. The most common cause of imatinib resistance is through the development of point mutations in the c-abl kinase domain, which directly or indirectly affect imatinib binding. More than 25 distinct Abl kinase domain mutations have been identified in imatinib treated CML patients and are associated with clinical resistance to imatinib (Hematology Shah 2005 (1): 183). These mutations have varying degrees of sensitivity to imatinib. Imatinib has been shown to bind to the ABL kinase domain in the inactive, or closed, conformation and to induce a variety of conformational changes to the protein upon binding. While some resistance-associated mutations occur at amino acid positions implicated in directly contacting imatinib, the majority are felt to prevent the kinase domain from adopting the specific conformation to which imatinib binds. Studies have shown that some mutations confer only a moderate degree of resistance, and as a result, dose escalation is predicted to recapture responses in some cases. Co-administration of second generation BCR-ABL inhibitors (e.g. BMS354825, AMN-107) have been shown to effectively inhibit many imatinib resistant cabl mutants. However there are no drugs in the clinic which have been shown to be efficacious against the most imatinib resistant c-abl mutation, T315I.

The Philadelphia chromosome is also found in a form of acute lymphoblastic leukemia (ALL). It seems highly probable that this form of ALL is due to the same chromosomal and molecular mechanisms as CML.

FMS-Like Tyrosine-Kinase 3 (FLT3)

FLT3 (short for fms-like tyrosine-kinase 3) is a class III receptor tyrosine kinase (RTK) structurally related to the receptors for platelet derived growth factor (PDGF), colony stimulating factor 1 (CSF1), and KIT ligand (KL). FLT3 contains an intracellular tyrosine kinase domain split in two by a specific hydrophilic insertion termed a kinase insert.

FLT3 and its specific ligand FLT3-ligand (FL) plays a role in regulation of haematopoietic progenitor cells and is expressed on haematopoietic cells including CD34-positive bone marrow cells, corresponding to multipotential, myeloid and B-lymphoid progenitor cells, and on monocytic cells.

Activating mutations of FLT3 are one of the most frequent mutations observed in acute myeloid leukaemia. The most frequent mutations are referred to as length mutations (LM) or internal tandem duplications (ITD) and consist of a duplicated sequence or insert belonging to exon 11 and sometimes involving intron 11 and exon 12.

Internal tandem duplications and/or insertions and, rarely, deletions in the FLT3-gene are implicated in 20-25% of all acute myeloid leukemias (AML) and 5-10% myelodysplastic syndromes (MDS) and some cases with acute lymphoblastic leukemia (ALL).

The mutation of the FLT3 protein causes constitutive activation of the tyrosine kinase activity due to disruption of a negative regulatory domain. This activation results in stimulation of several growth factor dependent pathways including the raf-MEK-ERK pathway and contributes to the growth and survival of the leukaemic cells. Thus inhibition of the kinase activity of FLT3 would be an effective treatment for diseases such as those described above which are dependent upon the FLT3 activity.

3-Phosphoinositide-Dependent Protein Kinase-1 (PDK1)

The 3-phosphoinositide-dependent protein kinase-1 (PDK1) plays a key role in regulating the activity of a number of kinases belonging to the AGC subfamily of protein kinases (Alessi, D. et al., Biochem. Soc. Trans, 29, p1-14, 2001). These include protein kinase B (PKB/AKT), p70 ribosomal S6 kinase (S6K) (Avruch, J. et al., Prog. Mol. Subcell. Biol., 2001, p115-154, 2001) and p90 ribosomal S6 kinase (Frodin, M. et al., EMBO J., 19, p 2924-2934, 2000). Kinase activity of serum and glucocordicoid regulated kinase (SGK) can also be phosphorylated and activated by PDK-1. Other potential substrates include protein kinase C, cAMP-dependent protein kinase (PKA), PRK1 and Protein kinase G.

PDK1 mediated signalling is activated in response to insulin and growth factors and as a consequence of attachment of the cell to the extracellular matrix (integrin signalling). Once activated these enzymes mediate many diverse cellular events by phosphorylating key regulatory proteins that play important roles controlling processes such as cell survival, growth, proliferation and glucose regulation (Lawlor, M. A. et al., J. Cell Sci., 114, p 2903-2910, 2001), (Lawlor, M. A. et al., EMBO J., 21, p 3728-3738, 2002). PDK-1 inhibitors therefore may provide novel therapeutic treatment for diseases such as diabetes and cancer.

PDK1 is a 556 amino acid protein, with an N-terminal catalytic domain and a C-terminal pleckstrin homology (PH) domain, which activates its substrates by phosphorylating these kinases at their activation loop (Belham, C. et al., Curr. Biol., 9, pR93-96, 1999). Many human cancers including prostate and NSCL have elevated PDK1 signalling pathway function resulting from a number of distinct genetic events such as PTEN mutations or over-expression of certain key regulatory proteins [(Graff, J. R., Expert Opin. Ther. Targets, 6, p 103-13, 2002), (Brognard, J., et al., Cancer Res., 61 p 3986-97, 2001)]. Inhibition of PDK1 as a potential mechanism to treat cancer was demonstrated by transfection of a PTEN negative human cancer cell line (IJ87MG) with antisense oligonucleotides directed against PDK1. The resulting decrease in PDK1 protein levels led to a reduction in cellular proliferation and survival (Flynn, P., et al., Curr. Biol., 10, p 1439-42, 2000). Therefore inhibition of PDK-1 could offer an attractive target for cancer therapy.

PDK-1-mediated phosphorylation of PKB/AKT, which is largely present in an inactive form in unstimulated cells, converts the enzyme to a catalytically active form. This occurs through the phosphorylation of the activation loop domain of AKT at threonine-309 in AKT2 and theonine-308 in AKT1. Although AKT displays low, basal levels of activation in normal, unstimulated cells, AKT often becomes constitutively activated in tumor cells. This occurs through the up-regulation of a variety of different signalling molecules or the presence of oncogenenic mutations commonly found in cancer cells that can promote the activation of AKT, such as PI-3 kinase, growth factor receptors (e.g., EGFR family members), Ras, Src, and BCR-ABL activation. Loss of the tumor suppressor PTEN is another means of greatly increasing AKT activity in cancer cells (Besson, A. et al., Eur. J. Biochem. (1999), Vol. 263, No. 3, pp. 605-611). PTEN mutation or down regulation of PTEN protein is found in a large number of tumors and cancer cell lines. PTEN is a phosphatase that removes the D-3 phosphate from the products of PI-3 kinase such as phosphatidylinositol 3,4,5-trisphosphate and phosphatidylinosito 13,4-bisphosphate (Myers, M. P. et al., Proc. Natl. Acad. Sci. USA (1998), Vol. 95, No. 23, pp. 13513-13518; Stambolic, V. et al., Cell (1998), Vol. 95 p 29-39). Loss of PTEN, therefore has the effect of increasing products of PI-3 kinase and promoting constitutive activation of AKT. Cancers with highly upregulated levels of AKT may be especially sensitive to the effects of PDK-1/AKT pathway inhibitors.

Therefore PDK1 is a critical mediator of the PI3K signalling pathway, which regulates a multitude of cellular function including growth, proliferation and survival. Consequently, inhibition of this pathway affects many defining requirements for cancer progression, so that a PDK1 inhibitor has an effect on the growth of a very wide range of human cancers.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels. (Folkman, *EXS,* 79, 1-81 (1997); Folkman, *Nature Medicine,* 1, 27-31 (1995); Folkman and Shing, *J. Biol. Chem.,* 267, 10931(1992)).

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, *Ann. Rhum. Dis.,* 51, 919 (1992)). In diabetes (and in many different eye diseases), new vessels invade the macula or retina or other ocular structures, and may cause blindness (Brooks, et al., *Cell,* 79, 1157 (1994)). The process of atherosclerosis has been linked to angiogenesis (Kahlon, et al., *Can. J. Cardiol.*, 8, 60 (1992)). Tumor growth and metastasis have been found to be angiogenesis-dependent (Folkman, *Cancer Biol*, 3, 65 (1992); Denekamp, *Br. J. Rad.*, 66, 181 (1993); Fidler and Ellis, *Cell*, 79, 185 (1994)).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly, et al., *Cell*, 79, 315 (1994); Ingber, et al., *Nature*, 348, 555 (1990)), ocular diseases (Friedlander, et al., *Science*, 270, 1500 (1995)), arthritis (Peacock, et al., *J. Exp. Med.*, 175, 1135 (1992); Peacock et al., *Cell. Immun.*, 160, 178 (1995)) and hemangioma (Taraboletti, et al., *J. Natl. Cancer Inst.*, 87, 293 (1995)).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al., *The Oncologist*, 5 (90001), 1-2 (2000)). VEGFR(s) are protein tyrosine kinases (PTKs). PTKs catalyze the phosphorylation of specific tyrosine residues in proteins involved in cell function thus regulating of cell growth, survival and differentiation. (Wilks, A. F., *Progress in Growth Factor Research*, 2, 97-111 (1990); Courtneidge, S. A., *Dev. Supp. I*, 57-64 (1993); Cooper, J. A., *Semin. Cell Biol.*, 5(6), 377-387 (1994); Paulson, R. F., *Semin. Immunol.*, 7(4), 267-277 (1995); Chan, A. C., *Curr. Opin. Immunol.*, 8(3), 394-401 (1996)).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T., et al., *J. Cell Biol.*, 129, 895-898 (1995)).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G., *The Oncologist*, 5(90001), 3-10 (2000)).

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

Janus kinases (JAKs)

The Janus kinases (JAKs) consist of four known mammalian family members, JAK1, JAK2, JAK3 and TYK2 and are intra cellular tyrosine kinases. The JAK-STAT pathway is activated through specific membrane bound receptors. Upon cytokine and growth factor binding, JAKs are recruited to the intracellular domains of the receptors and phosphorylate cytoplasmic proteins including the Signal Transducers and Activators of Transcription (STATs). Specific cytokine receptors recruit and activate distinct pairs of JAK and STAT proteins. The STATs dimerize on phosphorylation and directly activate transcription after nuclear translocation.

JAK2 is the primary tyrosine kinase activated by erythropoietin (EPO) and is essential for definitive erythropoiesis (Parganas et al., Cell 1998; 93(3): 385-95).

Constitutive activation of the JAK-STAT pathway through mechanisms such as point mutations resulting in deregulation of JAK2 activity have been shown to result in ligand independent survival and hypersensitivity and have been observed in some leukaemic cell types (Levine et al., 2005; Jelinek., 2005; Staerk et al 2005).

An activating mutation in the tyrosine kinase JAK2 has been observed in polycythemia vera, essential thrombocythemia and myeloid metaplasia with myelofibrosis (Levine et al., Cancer Cell 2005; 7, 387-97). JAK2 mutation 1849G>T is rare in acute leukaemias but can be found in CMML, Philadelphia chromosome-negative CML, and megakaryocytic leukaemia (Jelinek, Blood 2005; 106: 3370-3). Chronic Myelomonocytic Leukemias (CMML) include two types: an adult type referred to as CMML and a form of childhood leukemia called Juvenile Myelomonocytic Leukemia (JMML) or Juvenile Chronic Myelogenous Leukemia (JCML). CMML leukemias have features that are characteristic of myelogenous leukemia. In the past, CMML was sometimes classified and referred to as a type of myelodysplastic syndrome (MDS). CMML is more rapidly progressive than "typical" chronic myelogenous leukemia and less rapidly progressive than a type of acute leukemia known as acute myelomonocytic leukemia. Juvenile myelomonocytic leukemia differs in several ways from the adult CMML.

A high proportion (>50%) of patients with myeloproliferative disorders (MPD; (polycythemia vera, essential thrombocythemia, idiopathic myelofibrosis) carry a dominant gainof-function V617F mutation in the JH2 kinase-like domain of JAK2. The majority of Polycythemia Vera (PV) patients harbor a unique somatic mutation (V617F) in the pseudokinase domain of JAK2, which leads to constitutive signaling (Staerk et al, J. Biol. Chem, 10.1074/jbc.C500358200). This mutation leads to deregulation of the kinase activity, and thus to constitutive tyrosine phosphorylation activity. The incidence of the V617F mutation in different studies ranges from 65-97% in polycythemia vera, from 41-57% in patients with essential thrombocythemia, and from 23-95% in patients with idiopathic myelofibrosis. In MPD the mutation is heterozygous in most patients and homozygous only in a minor subset. Mitotic recombination probably causes both 9p LOH and the transition from heterozygosity to homozygosity. The same mutation was also found in roughly 20% of Ph-negative atypical CML, in more than 10% of CMML, in about 15% of patients with megakaryocytic AML (AML M7), and ⅕ patients with juvenile myelomonocytic leukemia (JMML). The V617F mutation seems to occur exclusively in hematopietic malignancies of the myeloid lineage.

JAK2 has been described in a novel somatic point mutation (a G-C to T-A transversion, at nucleotide 1849 of exon 12, resulting in the substitution of valine to phenylalanine at codon 617; JAK2V617F) in classic, BCR/ABL-negative MPD including polycythemia vera (PV), essential thrombocythemia (ET), and myelofibrosis with myeloid metaplasia (MMM) (Blood, 15 Nov. 2005, Vol. 106, No. 10, pp. 3335-3336). Following the initial wave of studies that reported a relatively high incidence of JAK2V617F in PV (65%-97%), ET (23%-57%), and MMM (35%-57%), subsequent studies disclosed the occurrence of the same mutation in a spectrum of atypical MPDs as well as in myelodysplastic syndrome (MDS), albeit at a much lower mutational frequency (3%-33%). In one of these latter studies, JAK2V617F and other oncogenic kinase mutations including BCR/ABL and FIP1L1-PDGFRA were shown to be mutually exclusive events.

Checkpoint Kinase 1 (Chk 1) and Checkpoint Kinase 2 (Chk2)

Checkpoint kinase 1 (Chk 1) and Checkpoint kinase 2 (Chk2) are unrelated serine/threonine kinases involved in the DNA damage checkpoint at the G2M boundary (M. J. O'Connell et al, EMBO J., 1997, 16, 545-554). Chk1 is an essential DNA damage and replication checkpoint kinase. It is phosphorylated by ataxia-telangiectasia mutated and Rad3-related kinase (ATR) in response to formation of single-stranded DNA and other DNA lesions (and replication stress) which is induced during DNA damage processing. This phosphorylation correlates with its ability to arrest cells in G2 (Walworth and Bernards 1996). Chk1 phosphorylates Cdc25 phosphatase inhibiting the removal of two inactivating phosphates on cyclin dependent kinases (CDKs) (Zeng et al, Nature, 1998, 395, 507-510) leading to cell cycle arrest. DNA damaging agents available in the clinic, which cause p53-dependent cell cycle arrest and apoptosis, may have reduced efficacy against p53 mutant tumour cells. If Chk1 activity is also inhibited in p53-negative cancers, all ability to arrest and repair DNA in response to DNA damage is removed, resulting in mitotic catastrophe and enhancing the effect of the DNA damaging agents (Koniaras et al., Oncogene 2001; 20(51): 7453-63.).

Thus combining the inhibition of CHK1/2 with DNA targeting agents such as topoisomerase inhibitors, alkylating agents, antimetabolites, DNA binders, cisplatin, cyclophosphamide, doxorubicin, irinotecan, fludarabine mitomycin C and radiotherapy, may be beneficial by overcoming some of the mechanisms used by cancer cell to evade current chemotherapy.

Chk2 similarly plays a critical role in the DNA damage checkpoint via double-strand breaks and ataxia-telangiectasia mutated kinase (ATM). Chk2 inhibition therefore could also protect normal sensitive tissues from some chemotherapeutic agents. Targeting Chk1 and Chk2 may significantly increase the therapeutic window of DNA damaging agents available in the clinic.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of these extracellular signaling molecules, which act as autocrine as well as paracrine factors. Autocrine FGF signaling may be particularly important in the progression of steroid hormone-dependent cancers and to a hormone independent state (Powers, et al., Endocr. Relat. Cancer, 7, 165-197 (2000)).

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Ozawa, et al., Teratog. Carcinog. Mutagen., 21, 27-44 (2001)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors numbered 1 to 4 (FGFR1 to FGFR4). Upon ligand binding, the receptors dimerize and auto- or trans-phosphorylate specific cytoplasmic tyrosine residues to transmit an intracellular signal that ultimately regulates nuclear transcription factor effectors.

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signaling in intramembranous bone formation. For example, in Apert (AP) syndrome, characterized by premature cranial suture ossification, most cases are associated with point mutations engendering gain-of-function in fibroblast growth factor receptor 2 (Lemonnier, et al., J. Bone Miner. Res., 16, 832-845 (2001)).

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene (Meyers, et al., Am. J. Hum. Genet., 58, 491-498 (1996); Plomp, et al., Am. J. Med. Genet., 75, 245-251 (1998)), and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signaling and suggests that the severe phenotypes of these disease syndromes result from ectopic ligand-dependent activation of fibroblast growth factor receptor 2 (Yu, et al., Proc. Natl. Acad. Sci. U.S.A., 97, 14536-14541 (2000)).

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas (Powers, C. J., et al., Endocr. Rel. Cancer, 7, 165 (2000), Qiu, W., et. al., World Journal Gastroenterol, 11 (34) 2005). Accordingly, FGFR3 inhibitors would be useful in the treatment of multiple myeloma, bladder and cervical carcinomas.

As such, the compounds are useful in providing a means of preventing the growth or inducing apoptosis of neoplasias and in tumours, particularly by inhibiting angiogenesis. The compounds are useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Over expression of FGFR4 has been linked to poor prognosis in both prostate and thyroid carcinomas (Ezzat, S., et al. The Journal of Clinical Investigation, 109, 1 (2002), Wang et al. Clinical Cancer Research, 10 (2004)). In addition a germline polymorphism (Gly388Arg) is associated with increased incidence of lung, breast, colon and prostate cancers (Wang et al. Clinical Cancer Research, 10 (2004)).

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. Clin Cancer Res. 2006 12(22): 6652-6662.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis (Inoue, et al, 1997 & 2002; Barrios, et al. 1997)). TGFβ1 and PDGF have been reported to be involved in the fibrogenic process (reviewed by Atamas & White, 2003) and further published work suggests the elevation of FGF's and consequent increase in fibroblast proliferation, may be in response to elevated TGFβ1 (Khalil, et al., 2005). The potential therapeutic relevance of this pathway in fibrotic conditions is suggested by the reported clinical effect of Pirfenidone (Arata, et al., 2005) in idiopathic pulmonary fibrosis (IPF).

Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

RET

The Ret proto-oncogene encodes a receptor tyrosine kinase that is expressed during development in a variety of tissues, including the peripheral and central nervous systems and the kidney. The abnormalities present in ret null mice suggest that Ret is critical for the migration and innervation of enteric neurons to the hindgut, and for proliferation and branching of the ureteric bud epithelium during kidney development (Nature 367, 380-383, 1994).

Mutations in the RET receptor tyrosine kinase provides a classic example of phenotypic heterogeneity in a variety of diseases. Gain-of-function mutations of RET are associated with human cancer and in particular cause inherited and non-inherited thyroid cancer. Gene rearrangements juxtaposing the tyrosine kinase domain of RET to heterologous gene partners have been found in sporadic papillary carcinomas of the thyroid (PTC). These rearrangements generate chimeric RET/PTC oncogenes. In germline cancers, point mutations of RET are responsible for multiple endocrine neoplasia type 2 (MEN 2A and 2B) and familial medullary thyroid carcinoma (FMTC). Both MEN 2 mutations and PTC gene rearrangements potentiate the intrinsic tyrosine kinase activity of RET and, ultimately, activate targets downstream of RET.

Thus somatic gene rearrangements of RET have been found in papillary thyroid carcinoma (PTC) and germline point mutations in multiple endocrine neoplasia (MEN) types 2A and 2B and familial medullary thyroid carcinoma (FMTC). Conversely, loss-of-function mutations are responsible for the development of Hirschsprung's disease, a congenital malformation of the enteric nervous system. (Naoya Asai et al, Pathology International, Volume 56 Page 164, April 2006)

Eph

The largest subfamily of receptor tyrosine kinases (RTKs), the Eph family, and their ligands (ephrins), play important roles in physiologic and pathologic vascular processes. Both the Ephs (receptors) and ephrins (ligands) are divided into two groups, A and B subfamilies (Eph Nomenclature Committee, 1997). The binding of ephrin ligands to Eph receptors is dependent on cell-cell interactions. The interactions of ephrins and Ephs have recently been shown to function via bi-directional signalling. The ephrins binding to Eph receptors initiate phosphorylation at specific tyrosine residues in the cytoplasmic domain of the Eph receptors. In response to Eph receptor binding, the ephrin ligand also undergoes tyrosine phosphorylation, so-called 'reverse' signalling (Holland, S. J., et al., Nature, 383, 722-725 (1996); Bruckner et al, Science 275: 1640-1643 (1997)).

Eph RTKs and their ephrin ligands play important roles in embryonic vascular development. Disruption of specific Eph receptors and ligands (including ephrin-B2) leads to defective vessel remodelling, organisation, and sprouting resulting in embryonic death (Wang, H. U., et al., Cell, 93: 741-753 (1998); Adams, R. H., et al., Genes Dev, 13, 295-306 (1999); Gale and Yancopoulos, Genes Dev, 13, 1055-1066 (1999); Helbling, P. M., et al., Development, 127, 269-278 (2000)). Coordinated expression of the Eph/ephrin system determines the phenotype of embryonic vascular structures: ephrin-B2 is present on arterial endothelial cells (ECs), whereas EphB4 is present on venous ECs (Gale and Yancopoulos, Genes Dev, 13,1055-1066 (1999); Shin, D., et al., Dev Biol, 230, 139-150 (2001)). Recently, specific Ephs and ephrins have been implicated in tumour growth and angiogenesis.

The Ephs and ephrins have been found to be overexpressed in many human tumours. In particular, the role of EphB2 has been identified in small cell lung carcinoma (Tang, X. X., et al., Clin Cancer Res, 5, 455-460 (1999)), human neuroblastomas (Tang, X. X., et al., Clin Cancer Res, 5, 1491-1496 (1999)) and colorectal cancers (Liu, W., et al., Brit. J. Canc., 90, 1620-1626 (2004)), and higher expression levels of Ephs and ephrins, including EphB2, have been found to correlate with more aggressive and metastatic tumours (Nakamoto, M. and Bergemann, A. D., Microsc. Res Tech, 59, 58-67 (2002)).

Consequently, inhibition of EphB2 will serve to disrupt angiogenesis, in particular in certain tumours where overexpression occurs.

As discussed previously, there are also publications that teach that inhibitors of angiogenesis, working by diverse mechanisms, are beneficial in diseases such as cancer and metastasis (O'Reilly, et al., Cell, 79, 315 (1994); Ingber, et al., Nature, 348, 555 (1990)), ocular diseases (Friedlander, et al., Science, 270, 1500 (1995)), arthritis (Peacock, et al., J. Exp. Med., 175, 1135 (1992); Peacock et al., Cell. Immun., 160, 178 (1995)) and hemangioma (Taraboletti, et al., J. Natl. Cancer Inst., 87, 293 (1995)).

SRC

The Src family kinases (SFK) comprises nine members of which three (Src, Fyn Yes) are ubiquitously expressed. Src itself is implicated in the pathogenesis of human malignancies. Activated mutants of c-Src can transform human cells in culture and Src protein expression and/or activity is increased in epithelial cancers. In colon cancer there is frequent elevation of Src activity compared to adjacent normal mucosa. Furthermore the Src activation is often elevated in metastases compared to the primary tumour implying a possible role for the protein in invasion and metastasis. Moreover Src expression is strongly correlated with disease progression. Similarly Src expression and activation are also elevated in breast, pancreatic, oesophageal, ovarian, lung, head and neck and gastric cancers compared to normal tissues.

EGFR and PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. One driver for growth is the epidermal growth factor (EGF), and the receptor for EGF (EGFR) has been implicated in the development and progression of a number of human solid tumours including those of the lung, breast, prostate, colon, ovary, head and neck. EGFR is a member of a family of four receptors, namely EGFR (HER1 or ErbB1), ErbB2 (HER2/neu), ErbB3 (HER3), and ErbB4 (HER4). These receptors are large proteins that reside in the cell membrane, each having a specific external ligand binding domain, a transmembrane domain and an internal domain which has tyrosine kinase enzyme activity. When EGF attaches to EGFR, it activates the tyrosine kinase, triggering reactions that cause the cells to grow and multiply. EGFR is found at abnormally high levels on the surface of many types of cancer cells, which may divide excessively in the presence of EGF. Inhibition of EGFR activity has therefore been a target for chemotherapeutic research in the treatment of cancer. Such inhibition can be effected by direct interference with the target EGFR on the cell surface, for example by the use of antibodies, or by inhibiting the subsequent tyrosine kinase activity.

Examples of agents which target EGFR tyrosine kinase activity include the tyrosine kinase inhibitors gefitinib and erlotinib. Gefitinib which has the chemical name 4-(3-chloro-4-fluoroanilino)-7-methoxy-6-(3-morpholinopropoxy) quinazoline, is used for the treatment of non-small-cell lung cancer, and is also under development for other solid tumours that over-express EGF receptors such as breast and colorectal cancer. Erlotinib, which has the chemical name N-(3-ethynyl-phenyl)-6,7-bis(2-methoxyethoxy)-4-quinazoline, has also been used for the treatment of non-small-cell lung cancer, and is being developed for the treatment of various other solid tumours such as pancreatic cancer.

Another growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment of chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. In addition, sorafenib (BAY 43-9006) which has the chemical name 4-(4-(3-(4-chloro-3 (trifluoromethyl)phenyl)ureido)phenoxy)-N2-methylpyridine-2-carboxamide, targets both the Raf signalling pathway to inhibit cell proliferation and the VEGFR/PDGFR signalling cascades to inhibit tumour angiogenesis. Sorafenib is being investigated for the treatment of a number of cancers including liver and kidney cancer.

There are conditions which are dependent on activation of PDGFR such as hypereosinophilic syndrome. PDGFR activation is also associated with other malignancies, which include chronic myelomonocytic leukemia (CMML). In another disorder, dermatofibrosarcoma protuberans, an infiltrative skin tumor, a reciprocal translocation involving the gene encoding the PDGF-B ligand results in constitutive secretion of the chimeric ligand and receptor activation. Imatinib has which is a known inhibitor of PDGFR has activity against all three of these diseases.

Compounds of Formula (I')

A wide variety of compounds of the formula (I') find application in the combinations of the invention, as described in detail below.

The compounds of formula (I') for use in the combinations of the invention therefore include the compound classes (a) and (b) as described herein, so including the compounds of WO 2005/002552 and WO 2006/070195 corresponding to those of formula (I') described therein and sub-groups, embodiments and examples thereof (as also therein defined). The content of PCT/GB2004/002824 (WO 2005/002552) describing the various subgroups, embodiments and examples of compounds of formula (I') are hereby incorporated herein by reference, as are the compounds of the formula (I') described in WO 2006/070195 (the contents of which are also incorporated herein by reference).

Ancillary Compounds

A wide variety of ancillary compounds find application in the combinations of the invention, as described in detail below. The ancillary compounds may be anti-cancer agents.

Particularly preferred ancillary compounds for use in the combinations of the invention are checkpoint targeting agents (as herein defined).

WO 02/34721 from Du Pont discloses a class of indeno[1,2-c]pyrazol-4-ones as inhibitors of cyclin dependent kinases.

WO 01/81348 from Bristol Myers Squibb describes the use of 5-thio-, sulphinyl- and sulphonylpyrazolo[3,4-b]-pyridines as cyclin dependent kinase inhibitors.

WO 00/62778 also from Bristol Myers Squibb discloses a class of protein tyrosine kinase inhibitors.

WO 01/72745A1 from Cyclacel describes 2-substituted 4-heteroaryl-pyrimidines and their preparation, pharmaceutical compositions containing them and their use as inhibitors of cyclin-dependant kinases (cdks) and hence their use in the treatment of proliferative disorders such as cancer, leukaemia, psoriasis and the like.

WO 99/21845 from Agouron describes 4-aminothiazole derivatives for inhibiting cyclin-dependent kinases (cdks), such as CDK1, CDK2, CDK4, and CDK6. The invention is also directed to the therapeutic or prophylactic use of pharmaceutical compositions containing such compounds and to methods of treating malignancies and other disorders by administering effective amounts of such compounds.

WO 01/53274 from Agouron discloses as CDK kinase inhibitors a class of compounds which can comprise an amide-substituted benzene ring linked to an N-containing heterocyclic group.

WO 01/98290 (Pharmacia & Upjohn) discloses a class of 3-aminocarbonyl-2-carboxamido thiophene derivatives as protein kinase inhibitors. The compounds are stated to have multiple protein kinase activity.

WO 01/53268 and WO 01/02369 from Agouron disclose compounds that mediate or inhibit cell proliferation through the inhibition of protein kinases such as cyclin dependent kinase or tyrosine kinase. The Agouron compounds have an aryl or heteroaryl ring attached directly or though a CH═CH or CH═N group to the 3-position of an indazole ring.

WO 00/39108 and WO 02/00651 (both to Du Pont Pharmaceuticals) describe broad classes of heterocyclic compounds that are inhibitors of trypsin-like serine protease enzymes, especially factor Xa and thrombin. The compounds are stated to be useful as anticoagulants or for the prevention of thromboembolic disorders.

US 2002/0091116 (Zhu et al.), WO 01/1978 and WO 01/64642 each disclose diverse groups of heterocyclic compounds that have activity against Factor Xa.

WO 03/035065 (Aventis) discloses a broad class of benzimidazole derivatives as protein kinase inhibitors but does not disclose activity against CDK kinases or GSK kinases.

WO 97/36585 and U.S. Pat. No. 5,874,452 (both to Merck) disclose biheteroaryl compounds that are inhibitors of farnesyl transferase.

WO 03/066629 (Vertex) discloses benzimidazolylpyrazole amines as GSK-3 inhibitors.

WO 97/12615 (Warner Lambert) discloses benzimidazoles as 15-lipoxygenase inhibitors.

WO 2004/54515 (SmithKline Beecham Corporation) discloses a class of benzimidazoles as thrombopoietin mimetics.

WO 2004/41277 (Merck) discloses a class of amino-benzimidazoles as androgen receptor modulators.

WO 2005/028624 (Plexxikon) discloses molecular scaffolds for compounds having activity against protein kinases.

WO 2005/002552 (Astex Technology Limited) discloses various compounds of formula (I') having activity as inhibitors of cyclin dependent kinases, glycogen synthase kinase-3 and Aurora kinases for use in the treatment of disease states and conditions such as cancer that are mediated by the kinases.

WO 2006/070195 (Astex Therapeutics Limited) discloses various compounds of formula (I'') having activity as inhibitors of cyclin dependent kinases, glycogen synthase kinase-3 and Aurora kinases.

SUMMARY OF THE INVENTION

In a first aspect, the invention provides a combination comprising (or consisting essentially of) an ancillary compound and a compound of formula (I') which is a salt of 1-cyclopropyl-3-[3-(5-morpholin-4-ylmethyl-1H-benzoimidazol-2-yl)-1H-pyrazol-4-yl]-urea selected from the lactate and citrate salts and mixtures thereof.

In another aspect, the invention provides a combination comprising (or consisting essentially of) an ancillary compound and a compound which is:

(I) a compound of the formula (I'):

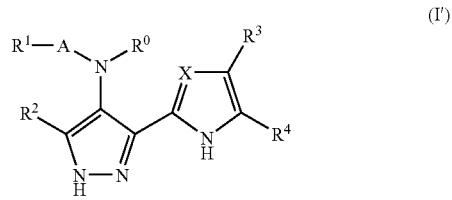

(I')

corresponding to formula (I) in PCT/GB2004/002824 (WO 2005/002552), and sub-groups, embodiments and examples thereof as defined in WO 2005/002552; and wherein $R^1$, $R^2$, $R^3$, $R^4$, A and X are as defined in PCT/GB2004/002824 (WO 2005/002552); or (II) a compound of the formula (I'')

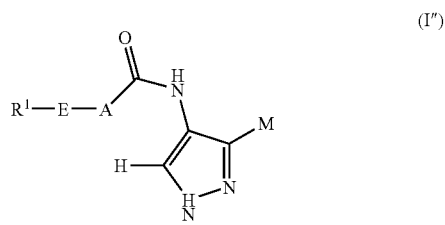

(I'')

or a salt, solvate, tautomer or N-oxide thereof, wherein M is selected from a group D1 and a group D2:

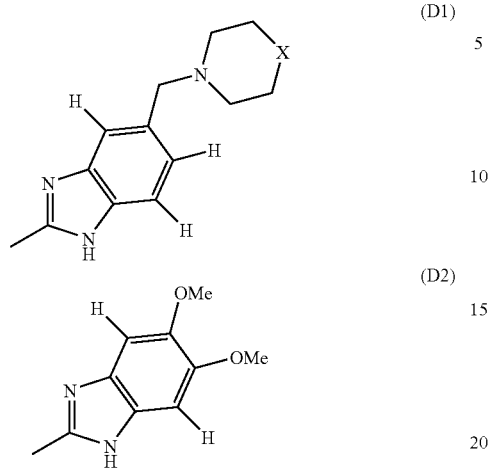

(D1)

(D2)

and wherein:
(A) when M is a group D1:
X is selected from O, NH and NCH$_3$;
A is selected from a bond and a group NR$^2$ where R$^2$ is hydrogen or methyl;
E is selected from a bond, CH$_2$, CH(CN) and C(CH$_3$)$_2$;
R$^1$ is selected from:
  (i) a cycloalkyl group of 3 to 5 ring members optionally substituted by hydroxy, fluorine, amino, methylamino, methyl or ethyl;
  (ii) a saturated heterocyclic group of 4 to 6 ring members containing 1 or 2 heteroatom ring members selected from O, N, S and SO$_2$, the heterocyclic group being optionally substituted by C$_{1-4}$ alkyl, amino or hydroxy; but excluding unsubstituted 4-morpholinyl, unsubstituted tetrahydropyran-4-yl, unsubstituted 2-pyrrolidinyl, and unsubstituted and 1-substituted piperidine-4-yl;
  (iii) a 2,5-substituted phenyl group of the formula:

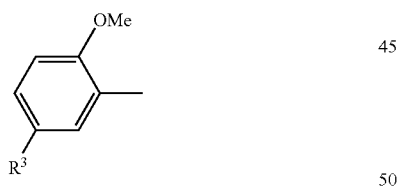

wherein (a) when X is NH or N—CH$_3$, R$^3$ is selected from chlorine and cyano;
and (b) when X is O, R$^3$ is CN;
  (iv) a group CR$^6$R$^7$R$^8$ wherein R$^6$ and R$^7$ are each selected from hydrogen and methyl, and R$^8$ is selected from hydrogen, methyl, C$_{1-4}$ alkylsulphonylmethyl, hydroxymethyl and cyano;
  (v) a pyridazin-4-yl group optionally substituted by one or two substituents selected from methyl, ethyl, methoxy and ethoxy;
  (vi) a substituted imidazothiazole group wherein the substituents are selected from methyl, ethyl, amino, fluorine, chlorine, amino and methylamino; and
  (vii) an optionally substituted 1,3-dihydro-isoindol-2-yl or optionally substituted 2,3-dihydro-indol-1-yl group wherein the optional substituents in each case are selected from halogen, cyano, amino, C$_{1-4}$ mono- and dialkylamino, CONH$_2$ or CONH—C$_{1-4}$ alkyl C$_{1-4}$ alkyl and C$_{1-4}$ alkoxy wherein the C$_{1-4}$ alkyl and C$_{1-4}$ alkoxy groups are optionally substituted by hydroxy, methoxy, or amino;
  (viii) 3-pyridyl optionally substituted by one or two substituents selected from hydroxy, halogen, cyano, amino, C$_{1-4}$ mono- and dialkylamino, CONH$_2$ or CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino, but excluding the compounds 2-oxo-1,2-dihydro-pyridine-3-carboxylic acid [3-(5-morpholin-4-ylmethyl-1H-benzoimidazol-2-yl)-1H-pyrazol-4-yl]-amide and 2,6-dimethoxy-N-[3-(5-morpholin-4-ylmethyl-1H-benzoimidazol-2-yl)-1H-pyrazol-4-yl]-nicotinamide;
  (ix) thiomorpholine or an S-oxide or S,S-dioxide thereof optionally substituted by one or two substituents selected from halogen, cyano, amino, C$_{1-4}$ mono- and dialkylamino, CONH$_2$ or CONH—C$_{1-4}$ alkyl C$_{1-4}$ alkyl and C$_{1-4}$ alkoxy wherein the C$_{1-4}$ alkyl and C$_{1-4}$ alkoxy groups are optionally substituted by hydroxy, methoxy, or amino; and
when E-A is NR$^2$, R$^1$ is additionally selected from:
  (x) 2-fluorophenyl, 3-fluorophenyl, 4-fluorophenyl, 2,4-difluorophenyl, 3,4-difluorophenyl, 2,5-difluorophenyl, 3,5-difluorophenyl, 2,4,6-trifluorophenyl, 2-methoxyphenyl, 5-chloro-2-methoxyphenyl, cyclohexyl, unsubstituted 4-tetrahydropyranyl and tert-butyl;
  (xi) a group NR$^{10}$R$^{11}$ where R$^{10}$ and R$^{11}$ are each C$_{1-4}$ alkyl or R$^{10}$ and R$^{11}$ are linked so that NR$^{10}$R$^{11}$ forms a saturated heterocyclic group of 4 to 6 ring members optionally containing a second heteroatom ring member selected from O, N, S and SO$_2$, the heterocyclic group being optionally substituted by C$_{1-4}$ alkyl, amino or hydroxy;
  (xii) pyridone optionally substituted by one or two substituents selected from hydroxy, halogen, cyano, amino, C$_{1-4}$ mono- and dialkylamino, CONH$_2$, CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino; when E-A is C(CH$_3$)$_2$NR$^2$ or CH$_2$—NR$^2$, R$^1$ is additionally selected from:
  (xiii) unsubstituted 2-furyl and 2,6-difluorophenyl; and
when E-A is C(CH$_3$)$_2$NR$^2$, R$^1$ is additionally selected from:
  (xiv) unsubstituted phenyl; and
when E is CH$_2$, R$^1$ is additionally selected from:
  (xv) unsubstituted tetrahydropyran-4-yl; and
(B) when M is a group D2:
A is selected from a bond and a group NR$^2$ where R$^2$ is hydrogen or methyl;
E is selected from a bond, CH$_2$, CH(CN) and C(CH$_3$)$_2$;
R$^1$ is selected from:
  (xvi) a 2-substituted 3-furyl group of the formula:

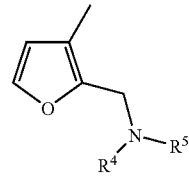

wherein R⁴ and R⁵ are the same or different and are selected from hydrogen and $C_{1-4}$ alkyl, or R⁴ and R⁵ are linked so that $NR^4R^5$ forms a 5- or 6-membered saturated heterocyclic group optionally containing a second heteroatom or group selected from O, NH, NMe, S or $SO_2$, the 5- or 6membered saturated ring being optionally substituted by hydroxy, fluorine, amino, methylamino, methyl or ethyl;

(xvii) a 5-substituted 2-furyl group of the formula:

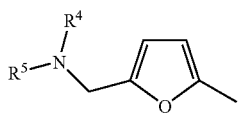

wherein R⁴ and R⁵ are the same or different and are selected from hydrogen and $C_{1-4}$ alkyl, or R⁴ and R⁵ are linked so that $NR^4R^5$ forms a 5- or 6-membered saturated heterocyclic group optionally containing a second heteroatom or group selected from O, NH, NMe, S or $SO_2$, the 5- or 6-membered saturated heterocyclic group being optionally substituted by hydroxy, fluorine, amino, methylamino, methyl or ethyl; with the proviso that the compound is not 5-piperidin-1-ylmethyl-furan-2-carboxylic acid [3-(5,6-dimethoxy-1H-benzoimidazol-2-yl)-1H-pyrazol-4-yl]-amide;

(xviii) a group of the formula:

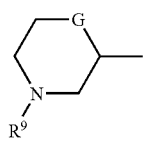

wherein R⁹ is hydrogen, methyl, ethyl or isopropyl; G is CH, O, S, SO, $SO_2$ or NH and the group is optionally substituted by one, two or three substituents selected from $C_{1-4}$ hydrocarbyl, hydroxy, $C_{1-4}$ hydrocarbyloxy, fluorine, amino, mono- and di-$C_{1-4}$ alkylamino and wherein the $C_{1-4}$ hydrocarbyl and $C_{1-4}$ hydrocarbyloxy groups are each optionally substituted by hydroxy, fluorine, amino, mono- or di-$C_{1-4}$ alkylamino; and (xix) a 3,5-disubstituted phenyl group of the formula:

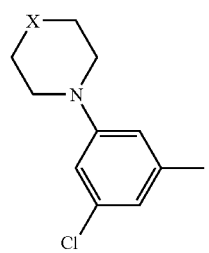

wherein X is selected from O, NH and $NCH_3$; and
(C) when M is a group D1:
and X is O; A is a group $NR^2$ where $R^2$ is hydrogen; E is a bond; and $R^1$ is 2,6-difluorophenyl; then the compound of the formula (I) is an acid addition salt selected from salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, hydrochloric, isethionic, isobutyric, lactic (e.g. (+)-L-lactic and (±)-DL-lactic), lactobionic, laurylsulphonic, maleic, malic, (−)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

In another aspect, the invention provides a combination comprising (or consisting essentially of) an ancillary compound and a lyophilized formulation (e.g. in the form of a pharmaceutical composition) comprising 1-cyclopropyl-3-[3-(5-morpholin-4-yl methyl-1H-benzoimidazol-2-yl)-1H-pyrazol-4-yl]-urea in protonated form together with one or more counter ions selected from L-lactate and citrate and mixtures thereof; and optionally (i) one or more further counter ions such as a chloride ions and/or (ii) one or more I.V. excipients such as tonicity adjusting agents (e.g. hexose sugars such as glucose, preferably D-glucose).

In another aspect, the invention provides the use of a combination of the invention for the manufacture of a medicament for the prophylaxis or treatment of a disease state or condition mediated by a cyclin dependent kinase or glycogen synthase kinase-3.

In another aspect, the invention provides a method for the prophylaxis or treatment of a disease state or condition mediated by a cyclin dependent kinase or glycogen synthase kinase-3, which method comprises administering to a subject in need thereof a combination of the invention.

In another aspect, the invention provides a method for alleviating or reducing the incidence of a disease state or condition mediated by a cyclin dependent kinase or glycogen synthase kinase-3, which method comprises administering to a subject in need thereof a combination of the invention.

In another aspect, the invention provides a method for treating a disease or condition comprising or arising from abnormal cell growth in a mammal, which method comprises administering to the mammal a combination of the invention in an amount effective in inhibiting abnormal cell growth.

In another aspect, the invention provides a method for alleviating or reducing the incidence of a disease or condition comprising or arising from abnormal cell growth in a mammal, which method comprises administering to the mammal a combination of the invention in an amount effective in inhibiting abnormal cell growth.

In another aspect, the invention provides a method for treating a disease or condition comprising or arising from abnormal cell growth in a mammal, the method comprising administering to the mammal a combination of the invention in an amount effective to inhibit a cdk kinase (such as cdk1 or cdk2) or glycogen synthase kinase-3 activity.

In another aspect, the invention provides a method for alleviating or reducing the incidence of a disease or condition comprising or arising from abnormal cell growth in a mammal, the method comprising administering to the mammal a combination of the invention in an amount effective to inhibit a cdk kinase (such as cdk1 or cdk2) or glycogen synthase kinase-3 activity.

In another aspect, the invention provides a method of inhibiting a cyclin dependent kinase or glycogen synthase kinase-3, which method comprises contacting the kinase with a kinase-inhibiting combination of the invention.

In another aspect, the invention provides a method of modulating a cellular process (for example cell division) by inhibiting the activity of a cyclin dependent kinase or glycogen synthase kinase-3 using a combination of the invention.

In another aspect, the invention provides the use of a combination of the invention for the manufacture of a medicament for prophylaxis or treatment of a disease or condition characterised by up-regulation of an Aurora kinase (e.g. Aurora A kinase and/or Aurora B kinase).

In another aspect, the invention provides a method for the prophylaxis or treatment of a disease or condition characterised by up-regulation of an Aurora kinase (e.g. Aurora A kinase and/or Aurora B kinase), the method comprising administering a combination of the invention.

In another aspect, the invention provides a method for alleviating or reducing the incidence of a disease or condition characterised by up-regulation of an Aurora kinase (e.g. Aurora A kinase and/or Aurora B kinase), the method comprising administering a combination of the invention.

In another aspect, the invention provides a method for the prophylaxis or treatment of (or alleviating or reducing the incidence of) cancer in a patient suffering from or suspected of suffering from cancer; which method comprises (i) subjecting a patient to a diagnostic test to determine whether the patient possesses the Ile31 variant of the Aurora A gene; and (ii) where the patient does possess the said variant, thereafter administering to the patient a combination of the invention having Aurora kinase inhibiting activity.

In another aspect, the invention provides a method for the prophylaxis or treatment of (or alleviating or reducing the incidence of) a disease state or condition characterised by up-regulation of an Aurora kinase (e.g. Aurora A kinase and/or Aurora B kinase); which method comprises (i) subjecting a patient to a diagnostic test to detect a marker characteristic of up-regulation of the Aurora kinase and (ii) where the diagnostic test is indicative of up-regulation of Aurora kinase, thereafter administering to the patient combination of the invention.

In another aspect, the invention provides a method for the prophylaxis or treatment of (or alleviating or reducing the incidence of) a disease state or condition characterised by (a) over-activation of CDK kinase; and/or (b) sensitisation of a pathway to normal CDK activity; and/or (c) up-regulation of cyclin E; which method comprises (i) subjecting a patient to a diagnostic test to detect a marker characteristic of (a) and/or (b) and/or (c); and (ii) where the diagnostic test is indicative of (a) and/or (b) and/or (c), thereafter administering to the patient a combination of the invention having CDK kinase inhibiting activity.

In another aspect, the invention provides a method of treatment, medical use or compound for use wherein a combination of the invention is administered (e.g. in a therapeutically effective amount) to a sub-population of patients identified through any one or more of the diagnostics tests described herein as having a disease or condition which should be susceptible to treatment with the said compound.

In another aspect, the invention provides various pharmaceutical compositions comprising a combination of the invention and a pharmaceutically acceptable carrier.

In another aspect, the invention provides the use of a compound of formula (I') as defined herein for the manufacture of a medicament for the prophylaxis or treatment of a disease state or condition mediated by a cyclin dependent kinase or glycogen synthase kinase-3 in a subject undergoing treatment with an ancillary compound.

In another aspect, the invention provides a method for the prophylaxis or treatment of a disease state or condition mediated by a cyclin dependent kinase or glycogen synthase kinase-3, which method comprises administering to a subject in need thereof a compound of formula (I') as defined herein, wherein the subject is undergoing treatment with an ancillary compound.

In another aspect, the invention provides a method for alleviating or reducing the incidence of a disease state or condition mediated by a cyclin dependent kinase or glycogen synthase kinase-3, which method comprises administering to a subject in need thereof a compound of formula (I') as defined herein, wherein the subject is undergoing treatment with an ancillary compound.

In another aspect, the invention provides a method for treating a disease or condition comprising or arising from abnormal cell growth in a mammal, which method comprises administering to the mammal a compound of formula (I') as defined herein in an amount effective in inhibiting abnormal cell growth, wherein the mammal is undergoing treatment with an ancillary compound.

In another aspect, the invention provides a method for alleviating or reducing the incidence of a disease or condition comprising or arising from abnormal cell growth in a mammal, which method comprises administering to the mammal a compound of formula (I') as defined herein in an amount effective in inhibiting abnormal cell growth, wherein the mammal is undergoing treatment with an ancillary compound.

In another aspect, the invention provides a method for treating a disease or condition comprising or arising from abnormal cell growth in a mammal, the method comprising administering to the mammal a compound of formula (I') as defined herein in an amount effective to inhibit a cdk kinase (such as cdk1 or cdk2) or glycogen synthase kinase-3 activity, wherein the mammal is undergoing treatment with an ancillary compound.

In another aspect, the invention provides a method for alleviating or reducing the incidence of a disease or condition comprising or arising from abnormal cell growth in a mammal, the method comprising administering to the mammal a compound of formula (I') as defined herein in an amount effective to inhibit a cdk kinase (such as cdk1 or cdk2) or glycogen synthase kinase-3 activity, wherein the mammal is undergoing treatment with an ancillary compound.

In another aspect, the invention provides a method of inhibiting a cyclin dependent kinase or glycogen synthase kinase-3 in a subject undergoing treatment with an ancillary compound, which method comprises contacting the kinase with a kinase-inhibiting compound of formula (I') as defined herein.

In another aspect, the invention provides a method of modulating a cellular process (for example cell division) in a subject undergoing treatment with an ancillary compound, which method comprises inhibiting the activity of a cyclin dependent kinase or glycogen synthase kinase-3 using a compound of formula (I') as defined herein.

In another aspect, the invention provides the use of a compound of formula (I') as defined herein for the manufacture of a medicament for prophylaxis or treatment of a disease or condition characterised by up-regulation of an Aurora kinase (e.g. Aurora A kinase and/or Aurora B kinase) in a subject undergoing treatment with an ancillary compound.

In another aspect, the invention provides the use of a compound of formula (I') as defined herein for the manufacture of a medicament for the prophylaxis or treatment of a cancer in a subject undergoing treatment with an ancillary compound, the cancer being one which is characterised by up-regulation of an Aurora kinase (e.g. Aurora A kinase and/or Aurora B kinase).

In another aspect, the invention provides the use of a compound of formula (I') as defined herein for the manufacture of a medicament for the prophylaxis or treatment of cancer in a patient selected from a sub-population possessing the Ile31 variant of the Aurora A gene and undergoing treatment with an ancillary compound.

In another aspect, the invention provides the use of a compound of formula (I') as defined herein for the manufacture of a medicament for the prophylaxis or treatment of cancer in a patient who has been diagnosed as forming part of a sub-population possessing the Ile31 variant of the Aurora A gene and is undergoing treatment with an ancillary compound.

In another aspect, the invention provides a method for the prophylaxis or treatment of a disease or condition characterised by up-regulation of an Aurora kinase (e.g. Aurora A kinase and/or Aurora B kinase), the method comprising administering a compound of formula (I') as defined herein to a subject undergoing treatment with an ancillary compound.

In another aspect, the invention provides a method for alleviating or reducing the incidence of a disease or condition characterised by up-regulation of an Aurora kinase (e.g. Aurora A kinase and/or Aurora B kinase), the method comprising administering a compound of formula (I') as defined herein to a subject undergoing treatment with an ancillary compound.

In another aspect, the invention provides a method for the prophylaxis or treatment of (or alleviating or reducing the incidence of) cancer in a patient suffering from or suspected of suffering from cancer; which method comprises (i) subjecting a patient to a diagnostic test to determine whether the patient possesses the Ile31 variant of the Aurora A gene; and (ii) where the patient does possess the said variant, thereafter administering to the patient a compound of formula (I') as defined herein having Aurora kinase inhibiting activity, wherein the patient is undergoing treatment with an ancillary compound.

In another aspect, the invention provides a method for the prophylaxis or treatment of (or alleviating or reducing the incidence of) a disease state or condition characterised by up-regulation of an Aurora kinase (e.g. Aurora A kinase and/or Aurora B kinase); which method comprises (i) subjecting a patient to a diagnostic test to detect a marker characteristic of up-regulation of the Aurora kinase and (ii) where the diagnostic test is indicative of up-regulation of Aurora kinase, thereafter administering to the patient compound of formula (I') as defined herein having Aurora kinase inhibiting activity, wherein the patient is undergoing treatment with an ancillary compound.

In another aspect, the invention provides a method for the prophylaxis or treatment of (or alleviating or reducing the incidence of) a disease state or condition characterised by (a) over-activation of CDK kinase; and/or (b) sensitisation of a pathway to normal CDK activity; and/or (c) up-regulation of cyclin E; which method comprises (i) subjecting a patient to a diagnostic test to detect a marker characteristic of (a) and/or (b) and/or (c); and (ii) where the diagnostic test is indicative of (a) and/or (b) and/or (c), thereafter administering to the patient a compound of formula (I') as defined herein having CDK kinase inhibiting activity, wherein the patient is undergoing treatment with an ancillary compound.

In another aspect, the invention provides a method of treatment, medical use or compound for use wherein a compound of formula (I') as defined herein is administered (e.g. in a therapeutically effective amount) to a sub-population of patients identified through any one or more of the diagnostics tests described herein as having a disease or condition which should be susceptible to treatment with the said compound and which are undergoing treatment with an ancillary compound.

In another aspect, the invention provides the use of a compound of formula (I') for the manufacture of a medicament for the prophylaxis or treatment of a disease state as described herein in a subject undergoing treatment with an ancillary compound.

In another aspect, the invention provides a compound of formula (I') for use in medicine in a subject undergoing treatment with an ancillary compound, for example in the prophylaxis or treatment of a disease state as described herein.

In another aspect, the invention provides a method for the prophylaxis or treatment of (or alleviating or reducing the incidence of) a disease state or condition as described herein, the method comprising administering to the mammal a therapeutically effective amount of a compound of formula (I') as defined herein, wherein the mammal is undergoing treatment with an ancillary compound.

In another aspect, the invention provides an ancillary compound (e.g. an ancillary compound selected from any of the ancillary compounds disclosed herein) for use in combination therapy with a compound of formula (I') as defined herein.

In another aspect, the invention provides a compound of formula (I') as defined herein for use in combination therapy with an ancillary compound (e.g. an ancillary compound selected from any of the ancillary compounds disclosed herein).

In another aspect, the invention provides the use of an ancillary compound (e.g. an ancillary compound selected from any of the ancillary compounds disclosed herein) for the manufacture of a medicament for use in the treatment or prophylaxis of a patient undergoing treatment with a compound of formula (I') as defined herein.

In another aspect, the invention provides the use of a compound of formula (I') as defined herein for the manufacture of a medicament for use in the treatment or prophylaxis of a patient undergoing treatment with an ancillary compound (e.g. an ancillary compound selected from any of the ancillary compounds disclosed herein).

In another aspect, the invention provides a method for the treatment of a cancer in a warm-blooded animal such as a human, which comprises administering to said animal an effective amount of an ancillary compound (e.g. an ancillary compound selected from any of the ancillary compounds disclosed herein) sequentially e.g. before or after, or simultaneously with an effective amount of a compound of formula (I') as defined herein.

In another aspect, the invention provides a method of combination cancer therapy in a mammal comprising administering a therapeutically effective amount of an ancillary compound (e.g. an ancillary compound selected from any of the ancillary compounds disclosed herein) and a therapeutically effective amount of a compound of formula (I') as defined herein.

In another aspect, the invention provides a compound of formula (I') as defined herein for use in combination therapy with an ancillary compound (e.g. an ancillary compound selected from any of the ancillary compounds disclosed herein) to alleviate or reduce the incidence of a disease or condition comprising or arising from abnormal cell growth in a mammal.

In another aspect, the invention provides a compound of formula (I') as defined herein for use in combination therapy with an ancillary compound (e.g. an ancillary compound selected from any of the ancillary compounds disclosed herein) to inhibit tumour growth in a mammal.

In another aspect, the invention provides a compound of formula (I') as defined herein for use in combination therapy with an ancillary compound (e.g. an ancillary compound selected from any of the ancillary compounds disclosed herein) to prevent, treat or manage cancer in a patient in need thereof.

In another aspect, the invention provides a compound of formula (I') as defined herein for use in enhancing or potentiating the response rate in a patient suffering from a cancer where the patient is being treated with an ancillary compound (e.g. an ancillary compound selected from any of the ancillary compounds disclosed herein).

In another aspect, the invention provides a method of enhancing or potentiating the response rate in a patient suffering from a cancer where the patient is being treated with an ancillary compound (e.g. an ancillary compound selected from any of the ancillary compounds disclosed herein), which method comprises administering to the patient, in combination with the ancillary compound, a compound of formula (I') as defined herein.

The combination of the invention may comprise two or more ancillary compounds. In such embodiments, each of the two ore more ancillary compounds may be independently selected from any of the ancillary compounds described herein.

In another aspect, the invention provides a process for the production of a combination of the invention, which process comprises combining a compound of formula (I') with an ancillary compound.

In another aspect, the invention provides a process for preparing a combination of the invention comprising a compound of the formula (XXVII) or (XXVIII) or a salt thereof:

(XXVII)

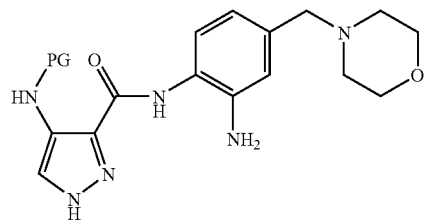

or (XXVIII)

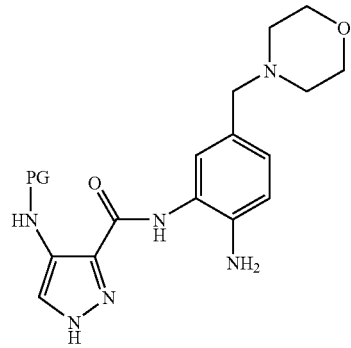

which process comprises the reaction of a compound of the formula (XXIX):

XXIX

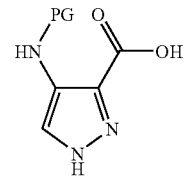

where PG is an amine-protecting group with a compound of the formula (XXXI):

(XXXI)

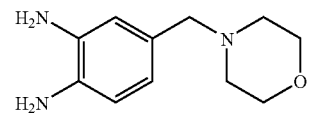

in an organic solvent in the presence of a coupling agent such as EDC and HOBt

In another aspect, the invention provides a process for preparing a combination of the invention comprising 3-(5-morpholin-4-ylmethyl-1H-benzoimidazol-2-yl )-1H-pyrazol-4-ylamine or a salt thereof, which process comprises:
(i) treating a compound of the formula (XXVIIa) or (XXVIIIa):

(XXVIIa)

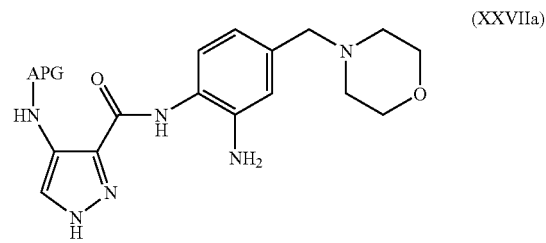

(XXVIIIa)

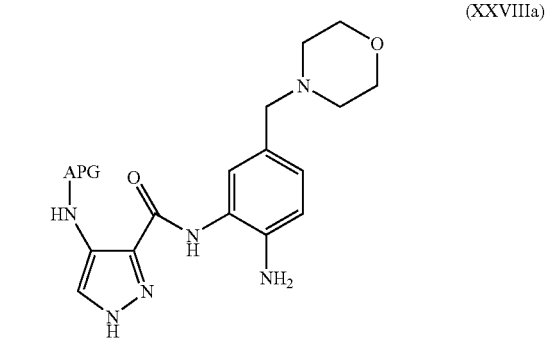

with an acid in a solvent, optionally with heating; and
(ii) neutralizing the reaction.

In another aspect, the invention provides a process for preparing a combination of the invention comprising 1-cyclopropyl-3-[3-(5-morpholin-4-yl methyl-1H-benzoimidazol-2-yl)-1H-pyrazol-4-yl]-urea or a salt thereof, which process comprises:
(i) treating a compound of the formula (XXVIIa) as defined in claim 158 with an acid in a solvent, optionally with heating;
(ii) neutralizing the reaction;
(iii) reacting the product of step (ii) with carbonylating reagent; and (iv) reacting the product of step (iii) with cyclopropylamine.

In another aspect, the invention provides a process for preparing a combination of the invention comprising 1-cyclopropyl-3-[3-(5-morpholin-4-yl methyl-1H-benzoimidazol-2-yl)-1H-pyrazol-4-yl]-urea; which process comprises reacting a compound of the formula (XXXIII) or (XXXIIIa):

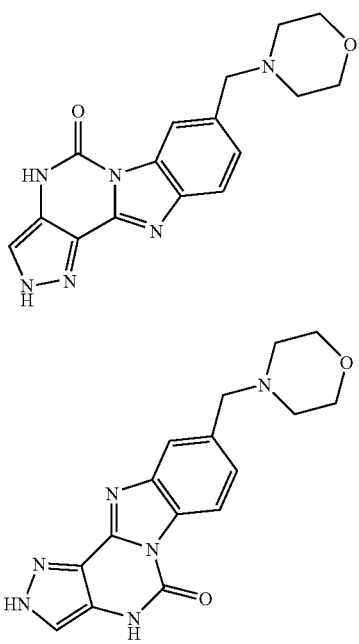

(XXXIII)

(XXXIIIa)

with cyclopropylamine, and thereafter optionally forming an acid addition salt.

The compound of formula (I') may be the L-lactate salt of 1-cyclopropyl-3-[3-(5-morpholin-4-ylmethyl-1H-benzoimidazol-2-yl)-1H-pyrazol-4-yl]-urea wherein the salt is crystalline and may be characterised by any one or more (in any combination) or all of the following parameters, namely that the salt:

(a) has a crystal structure as set out in FIGS. 4 and 5; and/or (b) has a crystal structure as defined by the coordinates in Table 4 in Example 71 of WO 2006/070195 at pages 205 to 209 (the content of which is incorporated herein by reference); and/or (c) has crystal lattice parameters at 97(2) K a=9.94(10), b=15.03(10), c=16.18(10) Å, α=β=γ=90°; and/or (d) has crystal lattice parameters at room temperature a=10.08(10), b=15.22(10), c=16.22(10) Å, α=β=γ=90°; and/or (e) has a crystal structure that belongs belong to an orthorhombic space group P2$_1$2$_1$2$_1$ (#19); and/or (f) has an X-ray powder diffraction pattern characterised by the presence of major peaks at the diffraction angles (2θ) of 17.50, 18.30, 19.30, 19.60, and 21.85 degrees, and more particularly additionally at 12.40, 15.20, 15.60, 17.50, 18.30, 18.50, 19.30, 19.60, 21.85, and 27.30 degrees, and/or interplanar spacings (d) of 5.06, 4.85, 4.60, 4.53, and 4.07, and more particularly additionally at 7.13, 5.83, 5.68, 5.06, 4.85, 4.79, 4.60, 4.53, 4.07, and 3.26 angstrom; and/or (g) exhibits peaks at the same diffraction angles as those of the X-ray powder diffraction pattern shown in FIG. 6 or Table 5 of Example 72 of WO 2006/070195 at pages 209 to 211 (the content of which is incorporated herein by reference) and optionally wherein the peaks have the same relative intensity as the peaks in FIG. 6; or Table 5 (as incorporated herein) and/or (h) has an X-ray powder diffraction pattern substantially as shown in FIG. 6; and/or (i) is anhydrous and exhibits onset at 190° C. and/or an endothermic peak at 194-197° C. when subjected to DSC; and/or (j) exhibits an infra-red spectrum, when analysed using the KBr disc method, that contains characteristic peaks at 3229, 2972 and 1660 cm$^{-1}$.

In another aspect, the invention provides a combination of the invention for the prevention or treatment (e.g. prophylaxis or alleviation) of:

A. a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc); or B. a cancer in which the cancer cells thereof contain a drug resistant kinase mutation which is:
(a) a threonine gatekeeper mutation; or
(b) a drug-resistant gatekeeper mutation; or
(c) an imatinib resistant mutation; or
(d) a nilotinib resistant mutation; or
(e) a dasatinib resistant mutation; or
(f) a T670I mutation in KIT; or
(g) a T674I mutation in PDGFR; or
(h) T790M mutation in EGFR; or
(i) a T315I mutation in abl; or C. a cancer which expresses a mutated molecular target which is a mutated form of BCRabl, c-kit, PDGF, EGF receptor or ErbB2; or D. a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2.

In further aspects, the invention provides a combination of the invention:

for the prophylaxis or treatment of a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc).

for the prophylaxis or treatment of a disease state or condition mediated by a kinase which is BCR-abl, VEGFR, Flt3, JAK, C-abl, PDK1, Chk1, Chk2, FGFR (e.g. FGFR3), Ret, Eph (e.g. EphB2 or EphB4), or cSrc.

for the treatment or prophylaxis of a disease state or condition which is a malignancy driven by BCR-abl.

for the treatment or prophylaxis of a disease state or condition which is a malignancy driven by BCR-abl and wherein the malignancy is selected from Philadelphia chromosome positive malignancies, for example Philadelphia chromosome-positive leukamias such as Philadelphia chromosome positive CML and Philadelphia chromosome positive ALL; and myeloproliferative syndrome.

for the treatment or prophylaxis of a disease state or condition mediated by VEGFR.

for the treatment or prophylaxis of a disease state or condition mediated by VEGFR; wherein the disease state or condition is an ocular disease or condition such as the disease and conditions selected from age-related macular degeneration (e.g. wet form of age-related macular degeneration); ischemic proliferative retinopathies (e.g. retinopathy of prematurity (ROP) and diabetic retinopathy); and hemangioma.

for the treatment or prophylaxis of a disease state or condition mediated by a kinase which is Flt3, JAK, C-abl, PDK1, Chk1 or Chk2.

for the treatment or prophylaxis of a disease state or condition mediated by a kinase which is Flt3, JAK, C-abl, PDK1, Chk1 or Chk2; and wherein the disease state or condition is any one or more diseases or conditions (in any combination) selected from polycythemia vera, essential thrombocythemia, idiopathic myelofibrosis, juvenile myelomonocytic leukemia (JMML), Chronic Myelomonocytic Leukemias (CMML), megakaryocytic leukaemia, megakaryocytic AML (AML M7), Philadelphia chromosome-negative CML and imatinib resistant CML.

for the treatment or prophylaxis of a disease state or condition mediated by a kinase which is Flt3, JAK, C-abl, PDK1, Chk1 or Chk2; wherein the the disease state or condition is selected from myeloproliferative disorders (MPD) such as polycythemia vera, essential thrombocythemia and idiopathic myelofibrosis including myelofibrosis with myeloid metaplasia (MMM).

for the treatment or prophylaxis of a disease state or condition mediated by a kinase which is FGFR (e.g. FGFR3), Ret, Eph (e.g. EphB2 or EphB4), or cSrc.

for the treatment or prophylaxis of a disease state or condition mediated by a kinase which is FGFR (e.g. FGFR3), Ret, Eph (e.g. EphB2 or EphB4), or cSrc; and wherein the disease state or condition is (in any combination) selected from papillary thyroid carcinoma, multiple endocrine neoplasia (MEN) types 2A and 2B, familial medullary thyroid carcinoma (FMTC), Hirschsprung's disease, Apert (AP) syndrome, Crouzon syndrome, Jackson-Weiss syndrome, Beare-Stevenson cutis gyrata syndrome, Pfeiffer Syndrome (PS), multiple myelomas, head and neck cancers and epithelial cancers.

for the treatment or prophylaxis of a disease state or condition mediated by a kinase which is FGFR (e.g. FGFR3), Ret, Eph (e.g. EphB2 or EphB4), or cSrc; and wherein the disease state or condition is selected from abnormalities in human skeletal development such as Apert (AP) syndrome, Crouzon syndrome, Jackson-Weiss syndrome, Beare-Stevenson cutis gyrata syndrome and Pfeiffer Syndrome (PS).

for the treatment or prophylaxis of a disease state or condition mediated by a kinase which is FGFR (e.g. FGFR3), Ret, Eph (e.g. EphB2 or EphB4), or cSrc; and wherein the disease state or condition is selected from thyroid cancers such as papillary thyroid carcinoma, familial medullary thyroid carcinoma (FMTC), multiple endocrine neoplasia (MEN) types 2A and 2B.

for the treatment or prophylaxis of a cancer in which the cancer cells thereof contain a drug resistant kinase mutation which is:
  (a) a threonine gatekeeper mutation; or
  (b) a drug-resistant gatekeeper mutation; or
  (c) an imatinib resistant mutation; or
  (d) a nilotinib resistant mutation; or
  (e) a dasatinib resistant mutation; or
  (f) a T670I mutation in KIT; or
  (g) a T674I mutation in PDGFR; or
  (h) T790M mutation in EGFR; or
  (i) a T315I mutation in abl for the treatment or prophylaxis of a cancer in which the cancer cells thereof contain a drug resistant kinase mutation which is:
  (a) a threonine gatekeeper mutation; or
  (b) a drug-resistant gatekeeper mutation; or
  (c) a T315I imatinib resistant mutation; or
  (d) a T670I mutation in KIT; or
  (e) a T674I mutation in PDGFR; or
  (f) T790M mutation in EGFR.

for the manufacture of a medicament for the treatment or prophylaxis of a cancer in which the cancer cells thereof contain a drug resistant kinase mutation which is:
  (a) a threonine gatekeeper mutation; or
  (b) a drug-resistant gatekeeper mutation; or
  (c) a T315I imatinib resistant mutation; or
  (d) a T670I mutation in KIT; or
  (e) a T674I mutation in PDGFR.

for the manufacture of a medicament for the treatment or prophylaxis of a cancer in which the cancer cells thereof contain a drug resistant kinase mutation which is:
  (a) a threonine gatekeeper mutation; or
  (b) a drug-resistant gatekeeper mutation; or
  (c) an imatinib resistant mutation; or
  (d) a nilotinib resistant mutation; or
  (e) a dasatinib resistant mutation; or
  (f) a T670I mutation in KIT; or
  (g) a T674I mutation in PDGFR; or
  (h) T790M mutation in EGFR; or
  (i) a T315I mutation in abl;
wherein the medicament is for the treatment or prophylaxis of any one of more (in any combination) of gastrointestinal stromal tumors (GISTs), chronic myelomonocytic leukaemia (CMML), the hypereosinophilic syndrome, and dermatofibrosarcoma protuberans.

for the treatment or prophylaxis of a cancer in which the cancer cells thereof contain a drug resistant kinase mutation which is:
  (c) an imatinib resistant mutation; or
  (d) a nilotinib resistant mutation; or
  (e) a dasatinib resistant mutation; or
wherein the medicament is for the treatment or prophylaxis of nilotinib-, dasatinib- or imatinib-resistant CML.

for the treatment or prophylaxis of a cancer which expresses a mutated molecular target which is a mutated form of BCRabl, c-kit, PDGF, EGF receptor or ErbB2.

for the treatment or prophylaxis of a disease mediated by a kinase containing a mutation in a region of the protein that binds to or interacts with other cancer agents but does not bind to or interact with the combinations of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2.

for the prophylaxis or treatment of any one or more (in any combination) of diseases and conditions selected from ocular diseases or conditions (such as age-related macular degeneration [e.g. wet form of age-related macular degeneration]; ischemic proliferative retinopathies [e.g. retinopathy of prematurity (ROP) and diabetic retinopathy]; and hemangioma); myeloproliferative disorders (MPD) (such as polycythemia vera, essential thrombocythemia and idiopathic myelofibrosis including myelofibrosis with myeloid metaplasia (MMM)); juvenile myelomonocytic leukemia (JMML); Chronic Myelomonocytic Leukemias (CMML); megakaryocytic leukaemia (including megakaryocytic AML (AML M7)); Philadelphia chromosome-negative CML; imatinib resistant CML; nilotinib-resistant CML; dasatinib-resistant CML; gastrointestinal stromal tumours (GISTs); glioblastomas such as glioblastoma multiformi, chronic myelomonocytic leukemia (CMML); the hypereosinophilic syndrome; dermatofibrosarcoma protuberans; Philadelphia chromosome positive malignancies (for example Philadelphia chromosome-positive leukamias such as Philadelphia chromosome positive CML and Philadelphia chromosome positive ALL); myeloproliferative syndrome; multiple myelomas, epithelial cancers, head and neck cancers, abnormalities in human skeletal development (such as Apert (AP) syndrome, Crouzon syndrome, Jackson-Weiss syndrome, Beare-Stevenson cutis gyrata syndrome and Pfeiffer Syndrome (PS)), thyroid cancers (such as papillary thyroid carcinoma, familial medullary thyroid carcinoma (FMTC), multiple endocrine neoplasia (MEN) types 2A and 2B); and Hirschsprung's disease.

for the treatment or prophylaxis of any one or more (in any combination) of diseases and conditions selected from ocular diseases or conditions (such as age-related macular degeneration [e.g. wet form of age-related macular degeneration]; ischemic proliferative retinopathies [e.g. retinopathy of prematurity (ROP) and diabetic retinopathy]; and hemangioma); myeloproliferative disorders (MPD) (such as polycythemia vera, essential thrombocythemia and idiopathic myelofibrosis including myelofibrosis with myeloid metaplasia (MMM)); juvenile myelomonocytic leukemia (JMML); Chronic Myelomonocytic Leukemias (CMML); megakaryocytic leukaemia (including megakaryocytic AML (AML M7)); Philadelphia chromosome-negative CML; imatinib resistant CML; gastrointestinal stromal tumors (GISTs); glioblastomas such as glioblastoma multiformi, chronic myelomonocytic leukemia (CMML); the hypereosinophilic syndrome; dermatofibrosarcoma protuberans; Philadelphia chromosome positive malignancies (for example Philadelphia chromosome-positive leukamias such as Philadelphia chromosome positive CML and Philadelphia chromosome positive ALL); myeloproliferative syndrome; multiple myelomas, epithelial cancers, head and neck cancers, abnormalities in human skeletal development (such as Apert (AP) syndrome, Crouzon syndrome, Jackson-Weiss syndrome, Beare-Stevenson cutis gyrata syndrome and Pfeiffer Syndrome (PS)), thyroid cancers (such as papillary thyroid carcinoma, familial medullary thyroid carcinoma (FMTC), multiple endocrine neoplasia (MEN) types 2A and 2B); and Hirschsprung's disease.

for the treatment or prophylaxis of any one or more ocular diseases or conditions such as the diseases and conditions (in any combination) selected from age-related macular degeneration (e.g. wet form of age-related macular degeneration); ischemic proliferative retinopathies (e.g. retinopathy of prematurity (ROP) and diabetic retinopathy); and hemangioma.

for the treatment or prophylaxis of any one or more diseases or conditions (in any combination) selected from any one or more diseases or conditions (in any combination) selected from myeloproliferative disorders (MPD) such as polycythemia vera, essential thrombocythemia and idiopathic myelofibrosis including myelofibrosis with myeloid metaplasia (MMM); juvenile myelomonocytic leukemia (JMML); Chronic Myelomonocytic Leukemias (CMML); megakaryocytic leukaemia including megakaryocytic AML (AML M7); Philadelphia chromosome-negative CML; and imatinib resistant CML.

for the treatment or prophylaxis of malignancies driven by BCR-abl, particularly Philadelphia chromosome positive malignancies, for example Philadelphia chromosome-positive leukamias such as Philadelphia chromosome positive CML and Philadelphia chromosome positive ALL.

for the treatment or prophylaxis of myeloproliferative syndrome.

for the treatment or prophylaxis of any one or more diseases or conditions (in any combination) selected from multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B and Hirschsprung's disease.

for the treatment or prophylaxis of a disease state or condition selected from gastrointestinal stromal tumors (GISTs); glioblastomas such as glioblastoma multiformi, chronic myelomonocytic leukemia (CMML); the hypereosinophilic syndrome; dermatofibrosarcoma protuberans.

for the treatment or prophylaxis of a disease state or condition selected from imatinib resistant CML; nilotinib-resistant CML; and dasatinib-resistant CML.

for the treatment or prophylaxis of imatinib resistant CML.

for the treatment or prophylaxis of myelofibrosis with myeloid metaplasia (MMM).

In addition, the invention also provides a combination of the invention for the treatment of:

ocular diseases such as age-related macular degeneration in particular wet form of age-related macular degeneration and hemangioma and Philadelphia chromosome positive ALL;

polycythemia vera; essential thrombocythemia; idiopathic myelofibrosis; juvenile myelomonocytic leukemia (JMML); Chronic Myelomonocytic Leukemias (CMML); megakaryocytic leukaemia including megakaryocytic AML (AML M7); Philadelphia chromosome-negative CML, imatinib resistant CML, gastrointestinal stromal tumors (GISTs), the hypereosinophilic syndrome or dermatofibrosarcoma protuberans by administering to a patient in need of such treatment a combination of the formula (I) as defined herein and in PCT/GB2004/002824 (WO 2005/002552) or a combination of the formula (I');

ocular diseases such as age-related macular degeneration in particular wet form of age-related macular degeneration and hemangioma, and Philadelphia chromosome positive ALL, by administering to a patient in need of such treatment a combination of the formula (I) as defined herein and in PCT/GB2004/002824 (WO 2005/002552) or a combination of the formula (I');

ocular diseases such as age-related macular degeneration in particular wet form of age-related macular degeneration, Ischemic proliferative retinopathies such as retinopathy of prematurity (ROP) and diabetic retinopathy and hemangioma;

ocular diseases such as age-related macular degeneration in particular wet form of age-related macular degeneration, Ischemic proliferative retinopathies such as retinopathy of prematurity (ROP) and diabetic retinopathy and hemangioma by administering to a patient in need of such treatment a combination of the formula (I) as defined herein and in PCT/GB2004/002824 (WO 2005/002552) or a combination of the formula (I');

the treatment of Philadelphia chromosome positive ALL.

the treatment of multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B and Hirschsprung's disease;

the treatment of multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B or Hirschsprung's disease;

the treatment of multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B or Hirschsprung's disease.

The invention also provides the further combinations, uses, methods, compounds and processes as set out in the claims below.

General Preferences and Definitions

In this specification, unless the context indicates otherwise, references to formula (I') are to be understood to include references to formulae (I), (I") and all other sub-groups, preferences and examples thereof as defined herein (e.g. compounds of formulae (II") to (VIII")). Furthermore, and as explained below, any references to formula (I") herein shall also be taken to refer to formulae (II") to (VIII") and any other sub-group of compounds within formula (I") unless the context requires otherwise.

As used herein, the term "modulation", as applied to the activity of cyclin dependent kinase (CDK), Aurora kinases and glycogen synthase kinase (GSK, e.g. GSK-3) and/or any other kinase as described herein, is intended to define a change in the level of biological activity of the kinase(s). Thus, modulation encompasses physiological changes which effect an increase or decrease in the relevant kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of the kinase activity e.g. Aurora kinase, cyclin dependent kinase (CDK) and/or glycogen synthase kinase-3 (GSK-3) activity and/or activity of any other kinase described herein, or at the level of enzyme (e.g. cyclin dependent kinase (CDK) and/or glycogen synthase kinase-3 (GSK-3)) activity and/or any other kinase described herein (for example by allosteric mechanisms, competitive inhibition, active-site inactivation, perturbation of feedback inhibitory pathways etc.). Thus, modulation may imply elevated/suppressed expression or over- or under-expression of the kinase (e.g. cyclin dependent kinase (CDK) and/or glycogen synthase kinase-3 (GSK-3) or any other kinase described herein), including gene amplification (i.e. multiple gene copies) and/or increased or decreased expression by a transcriptional effect, as well as hyper- (or hypo-)activity and (de)activation of the protein kinase(s) (e.g. cyclin dependent kinase (CDK) and/or glycogen synthase kinase-3 (GSK-3) and/or any other protein kinase described herein) (including (de)activation) by mutation(s). The terms "modulated", "modulating" and "modulate" are to be interpreted accordingly.

The term "upregulation of Aurora kinase" as used herein is defined as including elevated expression or over-expression of Aurora kinase, including gene amplification (i.e. multiple gene copies) and increased expression by a transcriptional effect, and hyperactivity and activation of Aurora kinase, including activation by mutations.

As used herein, the term "mediated", as used e.g. in conjunction with a kinase as described herein (e.g. cyclin dependent kinases (CDK) and/or glycogen synthase kinase-3 (GSK-3) as described herein) (and applied for example to various physiological processes, diseases, states, conditions, therapies, treatments or interventions) is intended to operate limitatively so that the various processes, diseases, states, conditions, treatments and interventions to which the term is applied are those in which the kinase (e.g. cyclin dependent kinase (CDK) and/or glycogen synthase kinase-3 (GSK-3)) plays a biological role. In cases where the term is applied to a disease, state or condition, the biological role played by the kinase (e.g. cyclin dependent kinase (CDK) and/or glycogen synthase kinase-3 (GSK-3)) may be direct or indirect and may be necessary and/or sufficient for the manifestation of the symptoms of the disease, state or condition (or its aetiology or progression). Thus, kinase activity (e.g. cyclin dependent kinase (CDK) and/or glycogen synthase kinase-3 (GSK-3) activity) (and in particular aberrant levels of cyclin dependent kinase (CDK) and/or glycogen synthase kinase-3 (GSK-3)activity, e.g. cyclin dependent kinases (CDK) and/or glycogen synthase kinase-3 (GSK-3) over-expression) need not necessarily be the proximal cause of the disease, state or condition: rather, it is contemplated that the kinase mediated diseases, states or conditions (e.g. CDK- and/or GSK- (e.g. GSK-3-) mediated diseases, states or conditions) include those having multifactorial aetiologies and complex progressions in which the kinase (e.g. CDK and/or GSK-3) is only partially involved. In cases where the term is applied to treatment, prophylaxis or intervention (e.g. in the "CDK-mediated treatments" and "GSK-3-mediated prophylaxis" of the invention), the role played by the kinase (e.g. CDK and/or GSK-3) may be direct or indirect and may be necessary and/or sufficient for the operation of the treatment, prophylaxis or outcome of the intervention. Thus, a disease state or condition mediated by the kinase (e.g. cyclin dependent kinases (CDK) and/or glycogen synthase kinase-3 (GSK-3) and/or Aurora kinase and/or any other kinase as described herein) includes a disease state or condition which has arisen as a consequence of the development of resistance to any particular cancer drug or treatment (including in particular resistance to one or more of the ancillary compounds described herein).

The term "intervention" is a term of art used herein to define any agency which effects a physiological change at any level. Thus, the intervention may comprise the induction or repression of any physiological process, event, biochemical pathway or cellular/biochemical event. The interventions of the invention typically effect (or contribute to) the therapy, treatment or prophylaxis of a disease or condition.

The combinations of the invention may produce a therapeutically efficacious effect relative to the therapeutic effect of the individual compounds when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect.

A "synergistic" effect in the present context refers to a therapeutic effect produced by the combination which is larger than the sum of the therapeutic effects of the components of the combination when presented individually.

An "additive" effect in the present context refers to a therapeutic effect produced by the combination which is larger than the therapeutic effect of any of the components of the combination when presented individually.

The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

As used herein, the term "combination", as applied to two or more compounds and/or agents (also referred to herein as the components), is intended tomay define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:
  compositions (e.g. unitary formulations) comprising the two or more compounds/agents in admixture (for example within the same unit dose);
  compositions comprising material in which the two or more compounds/agents are chemically/physicochemically linked (for example by crosslinking, molecular agglomeration or binding to a common vehicle moiety);
  compositions comprising material in which the two or more compounds/agents are chemically/physicochemically co-packaged (for example, disposed on or within lipid vesicles, particles (e.g. micro- or nanoparticles) or emulsion droplets);
  pharmaceutical kits, pharmaceutical packs or patient packs in which the two or more compounds/agents are co-packaged or co-presented (e.g. as part of an array of unit doses);

Examples of non-physically associated combined compounds/agents include:
  material (e.g. a non-unitary formulation) comprising at least one of the two or more compounds/agents together with instructions for the extemporaneous association of the at least one compound to form a physical association of the two or more compounds/agents;
  material (e.g. a non-unitary formulation) comprising at least one of the two or more compounds/agents together with instructions for combination therapy with the two or more compounds/agents;
  material comprising at least one of the two or more compounds/agents together with instructions for administration to a patient population in which the other(s) of the two or more compounds/agents have been (or are being) administered;
  material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The combinations of the invention may produce a therapeutically efficacious effect relative to the therapeutic effect of the individual compounds/agents when administered separately.

The term "ancillary compound" as used herein may define a compound which yields an efficacious combination (as herein defined) when combined with a compound of the formula (I') as defined herein. The ancillary compound may therefore act as an adjunct to the compound of the formula (I')

as defined herein, or may otherwise contribute to the efficacy of the combination (for example, by producing a synergistic or additive effect or improving the response rate, as herein defined).

The term "checkpoint targeting agent" is used herein to define a functional class of agents which act to initiate activation of a cell cycle checkpoint or agents that interfere with or modulate the normal action of the cell cycle checkpoint in replicating tumour cells. The term therefore covers various agents (including, for example, platinum compounds, nucleoside analogues, CDK inhibitors, taxanes, epothilones, vinca alkaloids, polo-like kinase inhibitors, CHK kinase inhibitors, inhibitors of the BUB kinase family and kinesin inhibitors) that target the cell cycle checkpoint. Particularly preferred checkpoint targeting agents are those that disrupt the mitotic checkpoint such as taxanes and vinca alkaloids. The targeting of the checkpoint may be mediated by any mechanism, including for example via stabilisation of spindle microtubules (so preventing spindle contraction, as mediated e.g. by various taxanes) or by prevention of spindle formation (as mediated e.g. by various vinca alkaloids) or by agents which cause damage to cellular components (e.g. DNA as caused by the platinum compounds or nucleoside analogues) thus causing activation of the checkpoint during cell proliferation. Thus, the checkpoint targeting agents typically cause chromosome mis-alignment or premature cytokinesis leading to death of the tumour cell. Checkpoint targeting agents may be identified by various techniques known to those skilled in the art for assessing cell cycle dynamics (e.g. for detecting multinucleation events), including for example flow cytometry, DNA staining, Western blot analysis for cell cycle markers (e.g. cylins) and direct visualization by various microscopic techniques (e.g. focal microscopy).

Compounds of Formula (I')

A wide variety of compounds of the formula (I') find application in the combinations of the invention, as described in detail below. Thus, the compounds of formula (I') for use in the combinations of the invention include the following compound classes (a) and (b):

(a) Compounds of WO 2005/002552

The compounds of WO 2005/002552 correspond to those of formula (I) described in PCT/GB2004/002824 (WO 2005/002552), and sub-groups, embodiments and examples thereof as defined in WO 2005/002552; and wherein $R^1$, $R^2$, $R^3$, $R^4$, A and X are as defined in PCT/GB2004/002824 (WO 2005/002552). The content of PCT/GB2004/002824 (WO 2005/002552) describing the various subgroups, embodiments and examples of compounds of formula (I) are hereby incorporated herein by reference.

The formula (I) of PCT/GB2004/002824 (WO 2005/002552) is herein referred to as formula (I') and references to formula (I') herein are to be interpreted accordingly.

Thus, the compound of formula (I') for use in the combinations of the invention has the formula:

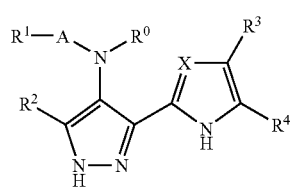

(I')

corresponding to formula (I) in PCT/GB2004/002824 (WO 2005/002552), and sub-groups, embodiments and examples thereof as defined in WO 2005/002552; and wherein $R^1$, $R^2$, $R^3$, $R^4$, A and X are as defined in PCT/GB2004/002824 (WO 2005/002552).

Preferred compounds of formula (I') for use in the combinations of the invention are compounds of formula (I"):

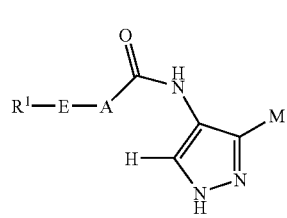

(I")

or a salt, solvate, tautomer or N-oxide thereof,
wherein M is selected from a group D1 and a group D2:

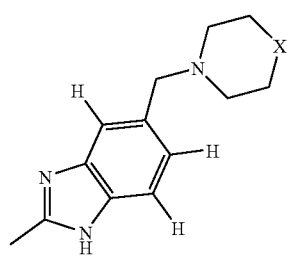

(D1)

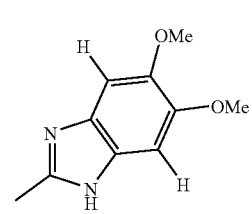

(D2)

and wherein:
(A) when M is a group D1:
X is selected from O, NH and NCH$_3$;
A is selected from a bond and a group NR$^2$ where R$^2$ is hydrogen or methyl;
E is selected from a bond, CH$_2$, CH(CN) and C(CH$_3$)$_2$;
R$^1$ is selected from:
(i) a cycloalkyl group of 3 to 5 ring members optionally substituted by hydroxy, fluorine, amino, methylamino, methyl or ethyl;
(ii) a saturated heterocyclic group of 4 to 6 ring members containing 1 or 2 heteroatom ring members selected from O, N, S and SO$_2$, the heterocyclic group being optionally substituted by C$_{1-4}$ alkyl, amino or hydroxy; but excluding unsubstituted 4-morpholinyl, unsubstituted tetrahydropyran-4-yl, unsubstituted 2-pyrrolidinyl, and unsubstituted and 1-substituted piperidine-4-yl;
(iii) a 2,5-substituted phenyl group of the formula:

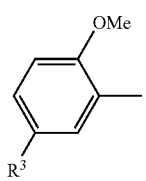

wherein (a) when X is NH or N—CH$_3$, R$^3$ is selected from chlorine and cyano; and (b) when X is O, R$^3$ is CN;

(iv) a group CR$^6$R$^7$R$^8$ wherein R$^6$ and R$^7$ are each selected from hydrogen and methyl, and R$^8$ is selected from hydrogen, methyl, C$_{1-4}$ alkylsulphonylmethyl, hydroxymethyl and cyano;

(v) a pyridazin-4-yl group optionally substituted by one or two substituents selected from methyl, ethyl, methoxy and ethoxy;

(vi) a substituted imidazothiazole group wherein the substituents are selected from methyl, ethyl, amino, fluorine, chlorine, amino and methylamino; and (vii) an optionally substituted 1,3-dihydro-isoindol-2-yl or optionally substituted 2,3-dihydro-indol-1-yl group wherein the optional substituents in each case are selected from halogen, cyano, amino, C$_{1-4}$ mono- and dialkylamino, CONH$_2$ or CONH—C$_{1-4}$ alkyl C$_{1-4}$ alkyl and C$_{1-4}$ alkoxy wherein the C$_{1-4}$ alkyl and C$_{1-4}$ alkoxy groups are optionally substituted by hydroxy, methoxy, or amino;

(viii) 3-pyridyl optionally substituted by one or two substituents selected from hydroxy, halogen, cyano, amino, C$_{1-4}$ mono- and dialkylamino, CONH$_2$ or CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino, but excluding the compounds 2-oxo-1,2-dihydro-pyridine-3-carboxylic acid [3-(5-morpholin-4-ylmethyl-1H-benzoimidazol-2-yl)-1H-pyrazol-4-yl]-amide and 2,6-dimethoxy-N-[3-(5-morpholin-4-ylmethyl-1H-benzoimidazol-2-yl)-1H-pyrazol-4-yl]-nicotinamide;

(ix) thiomorpholine or an S-oxide or S,S-dioxide thereof optionally substituted by one or two substituents selected from halogen, cyano, amino, C$_{1-4}$ mono- and dialkylamino, CONH$_2$ or CONH—C$_{1-4}$ alkyl C$_{1-4}$ alkyl and C$_{1-4}$ alkoxy wherein the C$_{1-4}$ alkyl and C$_{1-4}$ alkoxy groups are optionally substituted by hydroxy, methoxy, or amino; and when E-A is NR$^2$, R$^1$ is additionally selected from:

(x) 2-fluorophenyl, 3-fluorophenyl, 4-fluorophenyl, 2,4-difluorophenyl, 3,4-difluorophenyl, 2,5-difluorophenyl, 3,5-difluorophenyl, 2,4,6-trifluorophenyl, 2-methoxyphenyl, 5-chloro-2-methoxyphenyl, cyclohexyl, unsubstituted 4-tetrahydropyranyl and tert-butyl;

(xi) a group NR$^{10}$R$^{11}$ where R$^{10}$ and R$^{11}$ are each C$_{1-4}$ alkyl or R$^{10}$ and R$^{11}$ are linked so that NR$^{10}$R$^{11}$ forms a saturated heterocyclic group of 4 to 6 ring members optionally containing a second heteroatom ring member selected from O, N, S and SO$_2$, the heterocyclic group being optionally substituted by C$_{1-4}$ alkyl, amino or hydroxy;

(xii) pyridone optionally substituted by one or two substituents selected from hydroxy, halogen, cyano, amino, C$_{1-4}$ mono- and dialkylamino, CONH$_2$, CONH—C$_{1-4}$ alkyl, C$_{1-4}$ alkyl and C$_{1-4}$ alkoxy wherein the C$_{1-4}$ alkyl and C$_{1-4}$ alkoxy groups are optionally substituted by hydroxy, methoxy, or amino;

when E-A is C(CH$_3$)$_2$NR$^2$ or CH$_2$—NR$^2$, R$^1$ is additionally selected from:

(xiii) unsubstituted 2-furyl and 2,6-difluorophenyl; and when E-A is C(CH$_3$)$_2$NR$^2$, R$^1$ is additionally selected from:

(xiv) unsubstituted phenyl; and when E is CH$_2$, R$^1$ is additionally selected from:

(xv) unsubstituted tetrahydropyran-4-yl; and (B) when M is a group D2:

A is selected from a bond and a group NR$^2$ where R$^2$ is hydrogen or methyl;

E is selected from a bond, CH$_2$, CH(CN) and C(CH$_3$)$_2$;

R$^1$ is selected from:

(xvi) a 2-substituted 3-furyl group of the formula:

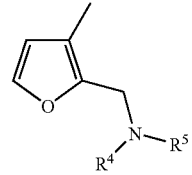

wherein R$^4$ and R$^5$ are the same or different and are selected from hydrogen and C$_{1-4}$ alkyl, or R$^4$ and R$^5$ are linked so that NR$^4$R$^5$ forms a 5- or 6-membered saturated heterocyclic group optionally containing a second heteroatom or group selected from O, NH, NMe, S or SO$_2$, the 5- or 6-membered saturated ring being optionally substituted by hydroxy, fluorine, amino, methylamino, methyl or ethyl;

(xvii) a 5-substituted 2-furyl group of the formula:

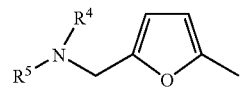

wherein R$^4$ and R$^5$ are the same or different and are selected from hydrogen and C$_{1-4}$ alkyl, or R$^4$ and R$^5$ are linked so that NR$^4$R$^5$ forms a 5- or 6-membered saturated heterocyclic group optionally containing a second heteroatom or group selected from O, NH, NMe, S or SO$_2$, the 5- or 6-membered saturated heterocyclic group being optionally substituted by hydroxy, fluorine, amino, methylamino, methyl or ethyl; with the proviso that the compound is not 5-piperidin-1-ylmethyl-furan-2-carboxylic acid [3-(5,6-dimethoxy-1H-benzoimidazol-2-yl)-1H-pyrazol-4-yl]-amide;

(xviii) a group of the formula:

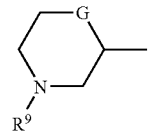

wherein R$^9$ is hydrogen, methyl, ethyl or isopropyl; G is CH, O, S, SO, SO$_2$ or NH and the group is optionally substituted by one, two or three substituents selected from C$_{1-4}$ hydrocarbyl, hydroxy, C$_{1-4}$ hydrocarbyloxy, fluorine, amino, mono- and di-C$_{1-4}$ alkylamino and wherein the C$_{1-4}$ hydrocarbyl and C$_{1-4}$ hydrocarbyloxy groups are each optionally substituted by hydroxy, fluorine, amino, mono- or di-C$_{1-4}$ alkylamino; and (xix) a 3,5-disubstituted phenyl group of the formula:

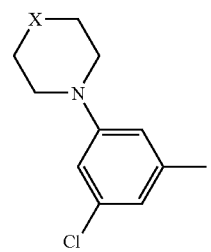

wherein X is selected from O, NH and NCH$_3$; and (C) when M is a group D1:
and X is O; A is a group NR² where R² is hydrogen; E is a bond; and R¹ is 2,6-difluorophenyl; then the compound of the formula (I) is an acid addition salt selected from salts formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, hydrochloric, isethionic, isobutyric, lactic (e.g. (+)-L-lactic and (±)-DL-lactic), lactobionic, laurylsulphonic, maleic, malic, (−)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

(b) Compounds of Formula (I): 1-cyclopropyl-3-[3-(5-morpholin-4-ylmethyl-1H-benzoimidazol-2-yl)-1H-pyrazol-4-yl]-urea and its Analogues The compound of formula (I') for use in the combinations of the invention may be the free base of 1-cyclopropyl-3-[3-(5-morpholin-4-ylmethyl-1H-benzoimidazol-2-yl)-1H-pyrazol-4-yl]-urea having the formula (I):

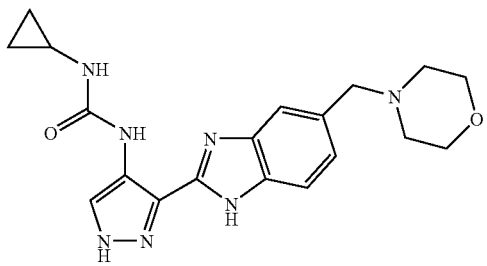

(I)

The compound of the formula (I) may be referred to in this application by its chemical name, 1-cyclopropyl-3-[3-(5-morpholin-4-ylmethyl-1H-benzoimidazol-2-yl)-1H-pyrazol-4-yl]-urea, or, for convenience, as "the compound I" or "the compound of formula (I)". Each of these synonyms refers to the compound shown in formula (I) above and having the chemical name 1-cyclopropyl-3-[3-(5-morpholin-4-ylmethyl-1H-benzoimidazol-2-yl)-1H-pyrazol-4-yl]-urea.

The lactate and citrate salts of the compound 1-cyclopropyl-3-[3-(5-morpholin-4-ylmethyl-1H-benzoimidazol-2-yl)-1H-pyrazol-4-yl]-urea and crystalline forms thereof are preferred compounds of formula (I) for use in the combinations of the invention.

References to the compound 1-cyclopropyl-3-[3-(5-morpholin-4-ylmethyl-1H-benzoimidazol-2-yl)-1H-pyrazol-4-yl]-urea free base and its lactate or citrate salts or mixtures thereof include within their scope all solvates, tautomers and isotopes thereof and, where the context admits, N-oxides, other ionic forms and prodrugs. Therefore reference to the alternative tautomer of formula (I), 1-cyclopropyl-3-[3-(6-morpholin-4-ylmethyl-1H-benzoimidazol-2-yl)-1H-pyrazol-4-yl]-urea is to be understood to refer to compound (I).

Compounds of formula (I) are generically and specifically described in WO 2006/070195, the contents of which are incorporated herein by reference.

Particular and Preferred Compounds of the Formula (I')

The compounds of Formula (I') correspond to those of formula (I) described in PCT/GB2004/002824 (WO 2005/002552), and sub-groups, embodiments and examples thereof as defined in WO 2005/002552; and wherein R¹, R², R³, R⁴, A and X are as defined in PCT/GB2004/002824 (WO 2005/002552). The content of PCT/GB2004/002824 (WO 2005/002552) describing the various subgroups, embodiments and examples of compounds of formula (I) are hereby incorporated herein by reference.

The formula (I) of PCT/GB2004/002824 (WO 2005/002552) is herein referred to as formula (I') and references to formula (I') herein are to be interpreted accordingly.

Thus, the compound of formula (I') for use in the combinations of the invention has the formula:

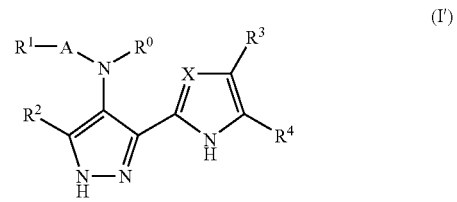

(I')

corresponding to formula (I) in PCT/GB2004/002824 (WO 2005/002552), and sub-groups, embodiments and examples thereof as defined in WO 2005/002552; and wherein R¹, R², R³, R⁴, A and X are as defined in PCT/GB2004/002824 (WO 2005/002552). Particular compounds of the formula (I') are those defined in, for example, the compounds of formulae (II) to (IXa) and any sub-groups thereof in PCT/GB2004/002824 (WO 2005/002552), the compounds listed in PCT/GB2004/002824 (WO 2005/002552) and the compounds exemplified in the Examples section of PCT/GB2004/002824 (WO 2005/002552).

Compound of Formula (I')

The compound of formula (I') for use in the combinations of the invention has the formula:

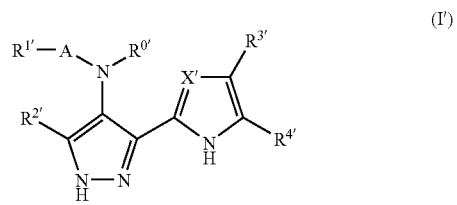

(I')

or a salt, solvate, tautomer or N-oxide thereof;
wherein
X' is CR⁵' or N;
A' is a bond or —(CH₂)$_m$—(B')$_n$—;
B' is C═O, NR⁹(C═O) or O(C═O) wherein R$^g$ is hydrogen or C$_{1-4}$ hydrocarbyl optionally substituted by hydroxy or C$_{1-4}$ alkoxy;
m is 0, 1 or 2;
n is 0 or 1;
R⁰' is hydrogen or, together with NR$^g$ when present, forms a group —(CH₂)$_p$— wherein p is 2 to 4;
R¹' is hydrogen, a carbocyclic or heterocyclic group having from 3 to 12 ring members, or an optionally substituted C$_{1-8}$ hydrocarbyl group;

$R^{2'}$ is hydrogen, halogen, methoxy, or a $C_{1-4}$ hydrocarbyl group optionally substituted by halogen, hydroxyl or methoxy;

$R^{3'}$ and $R^{4'}$ together with the carbon atoms to which they are attached form an optionally substituted fused carbocyclic or heterocyclic ring having from 5 to 7 ring members of which up to 3 can be heteroatoms selected from N, O and S; and $R^{5'}$ is hydrogen, a group $R^{2'}$ or a group $R^{10'}$ wherein $R^{10'}$ is selected from halogen, hydroxy, trifluoromethyl, cyano, nitro, carboxy, amino, mono- or di-$C_{1-4}$ hydrocarbylamino, carbocyclic and heterocyclic groups having from 3 to 12 ring members; a group $R^a$—$R^b$ wherein $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^b$ is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, carbocyclic and heterocyclic groups having from 3 to 12 ring members and wherein one or more carbon atoms of the $C_{1-8}$ hydrocarbyl group may optionally be replaced by O, S, SO, $SO_2$, $NR^c$, $X^1C(X^2)$, $C(X^2)X^1$ or $X^1C(X^2)$ $X^1$;

$R^c$ is selected from hydrogen and $C_{1-4}$ hydrocarbyl; and $X^1$ is O, S or $NR^c$ and $X^2$ is =O, =S or =$NR^c$;

and salts, N-oxides, tautomers and solvates thereof: or

Particular compounds of the formula (I') for use in the present invention are the compounds of formula (III) from WO 2005/002552:

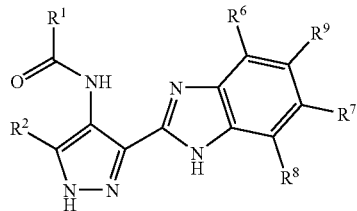

(III)

wherein $R^1$, $R^2$ and $R^6$ to $R^9$ are as defined in WO2005/002552.

A further group of compounds for use in the invention can be represented by the formula (Va) of WO2005/002552:

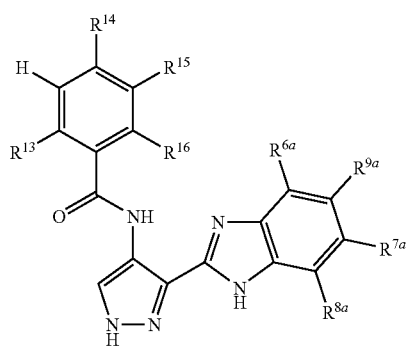

(Va)

wherein $R^{6a}$, to $R^{9a}$, $R^{13}$, $R^{14}$ and $R^{16}$, and subgroups thereof, are defined in WO2005/002552.

Another group of compounds for use in the invention are the compounds of formula (VII) and (VIIa) of WO2005/002552:

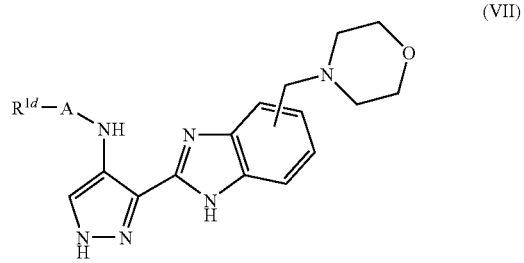

(VII)

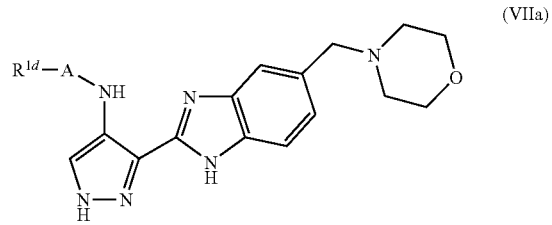

(VIIa)

wherein $R^{1d}$ is a group $R^1$, $R^{1a}$, $R^{1b}$ or $R^{1c}$ as defined in WO2005/002552.

The example of Formula (I') as outlined below can be prepared as described in WO 2005/002552 at pages 109-257.

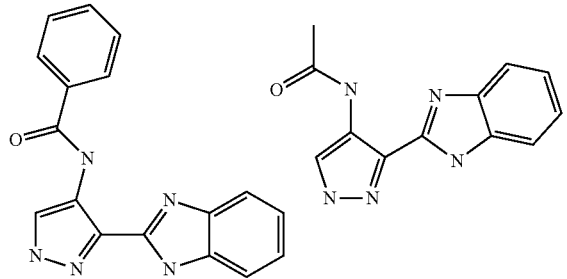

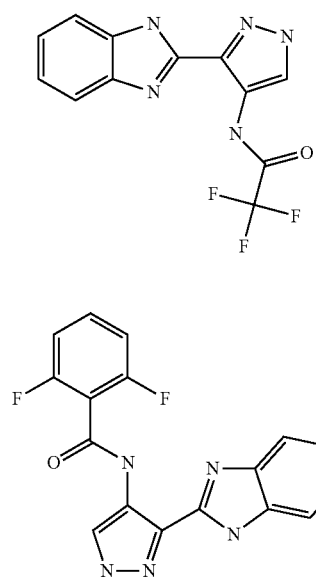

51
-continued
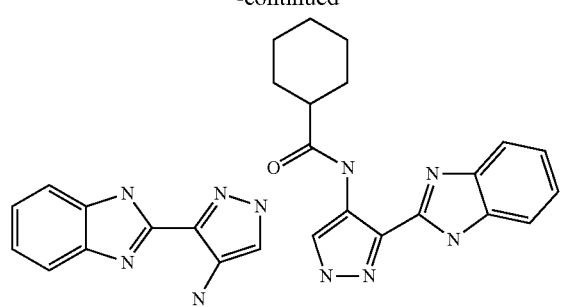
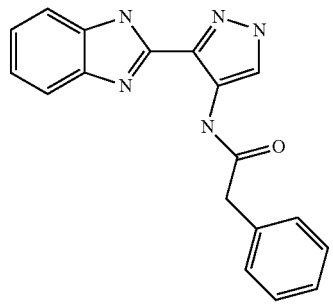
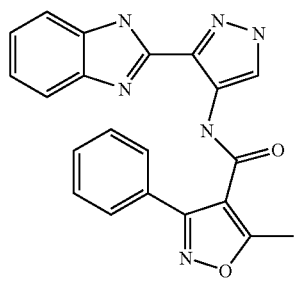
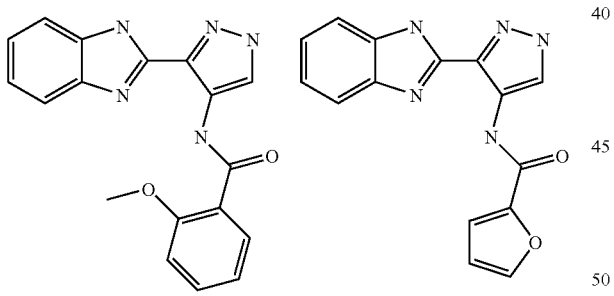
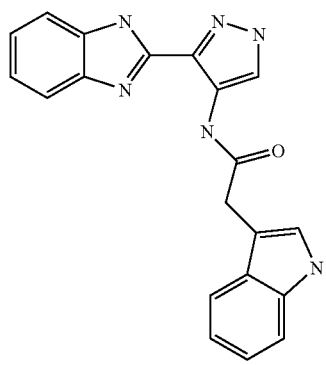
52
-continued
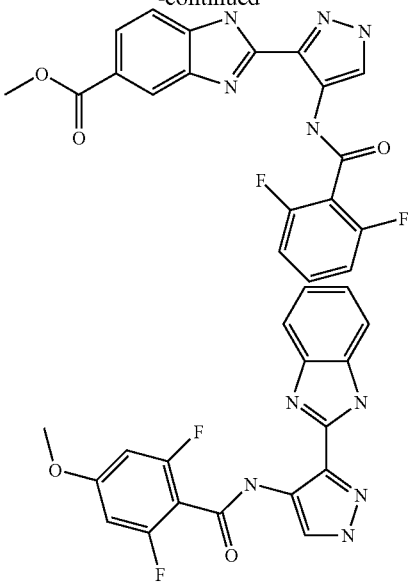
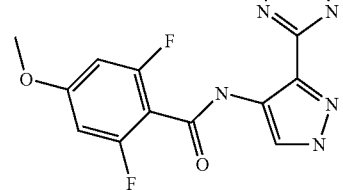
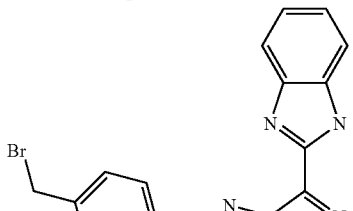
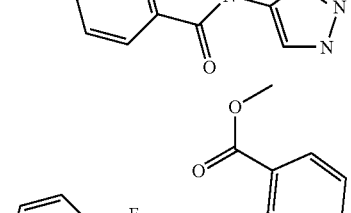
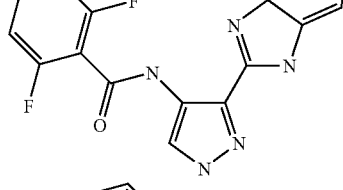
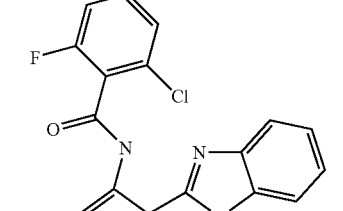
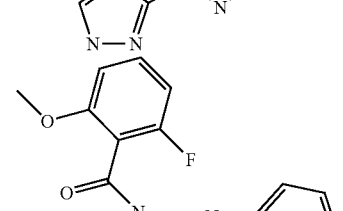
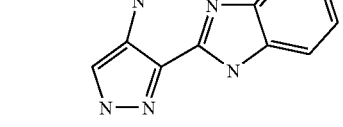

53
-continued
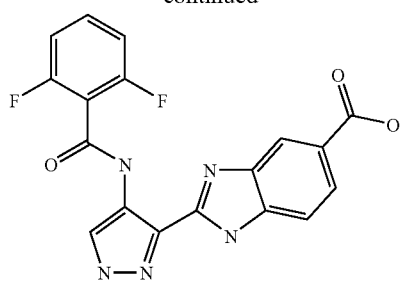
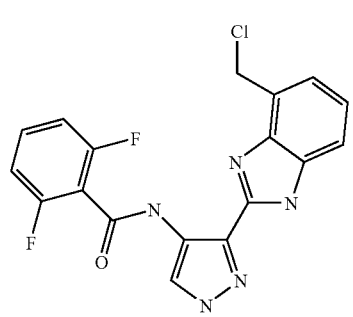
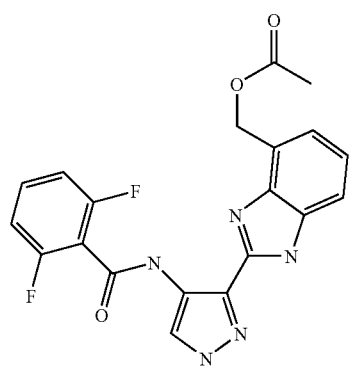
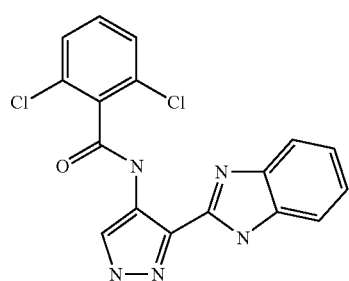
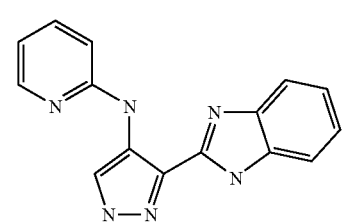
54
-continued
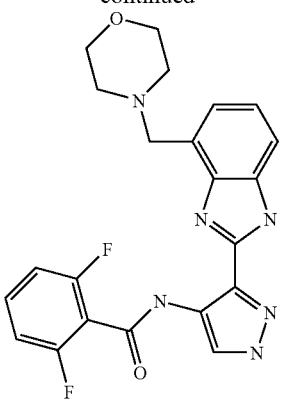
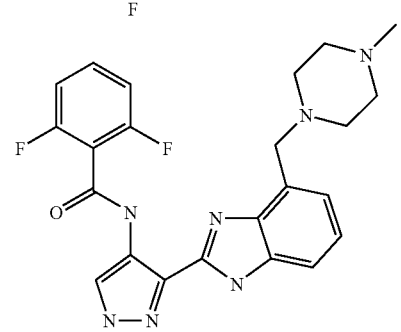
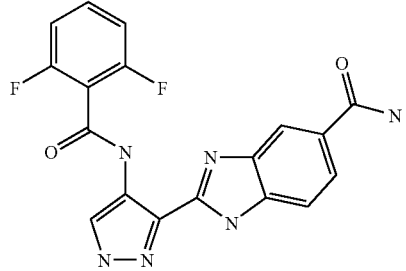
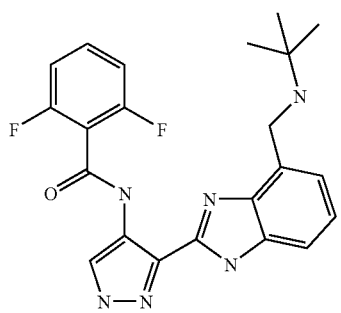
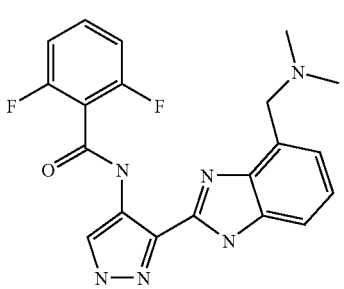

55
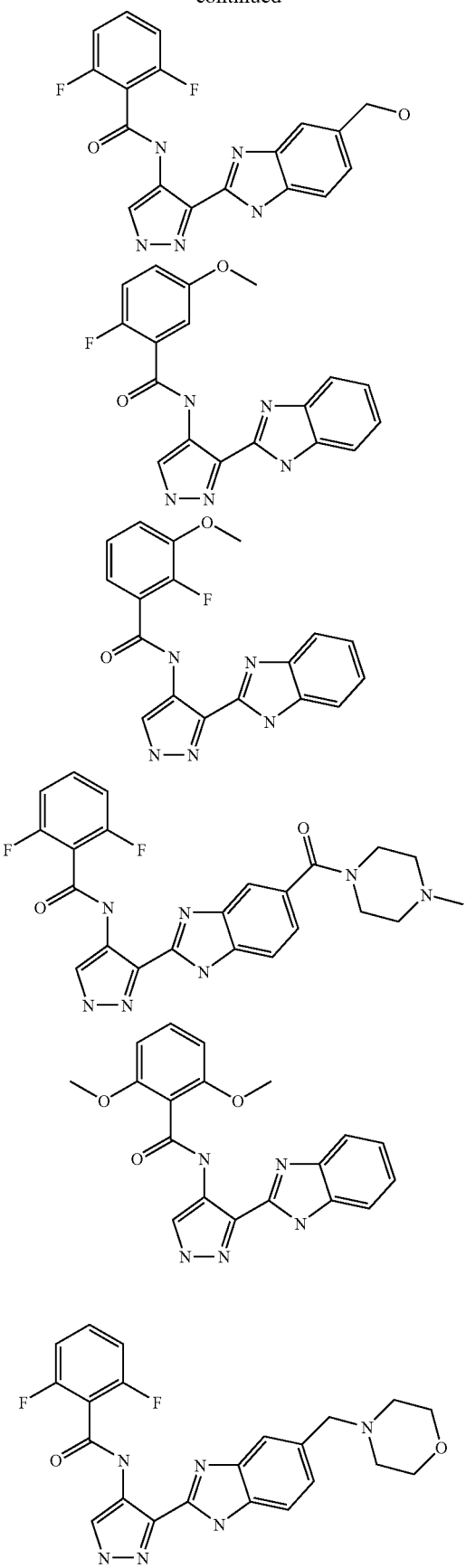
56
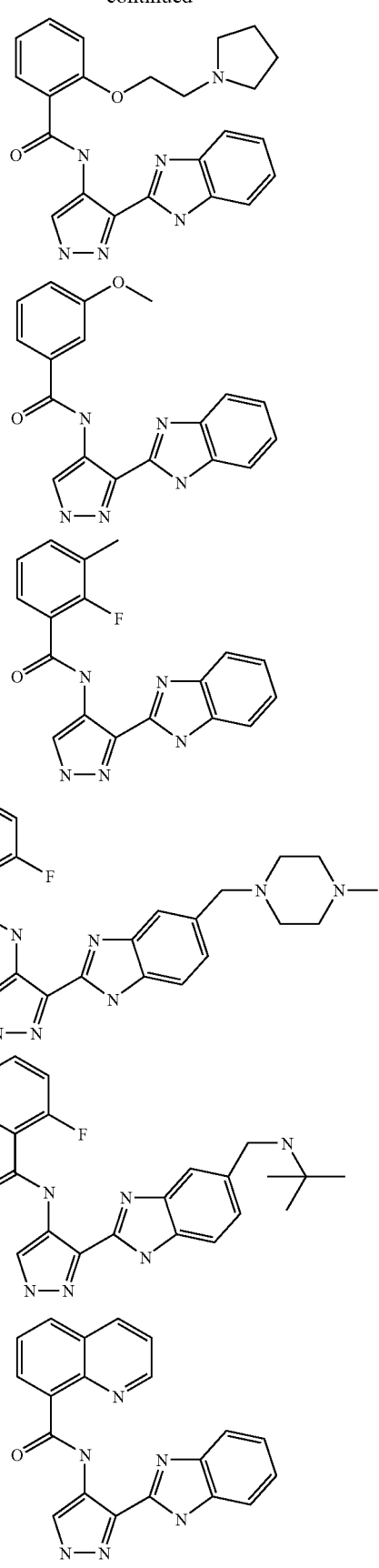

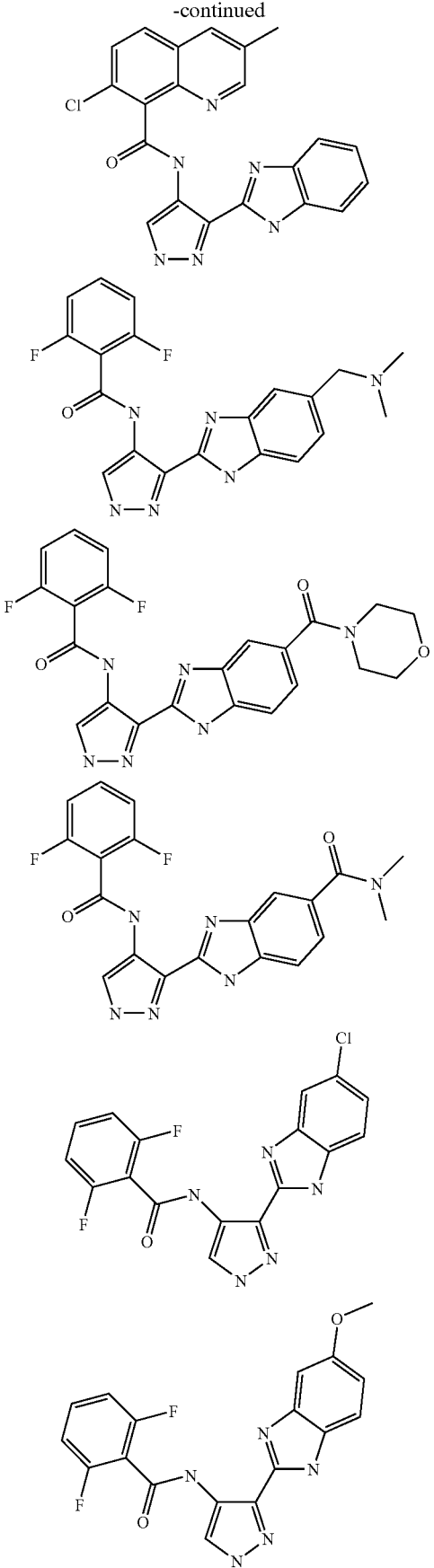
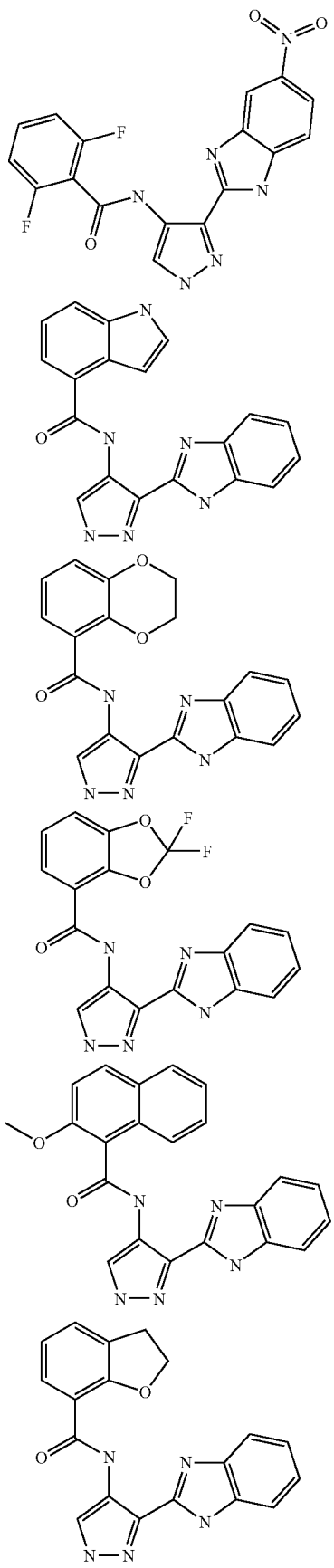

59
-continued
60
-continued
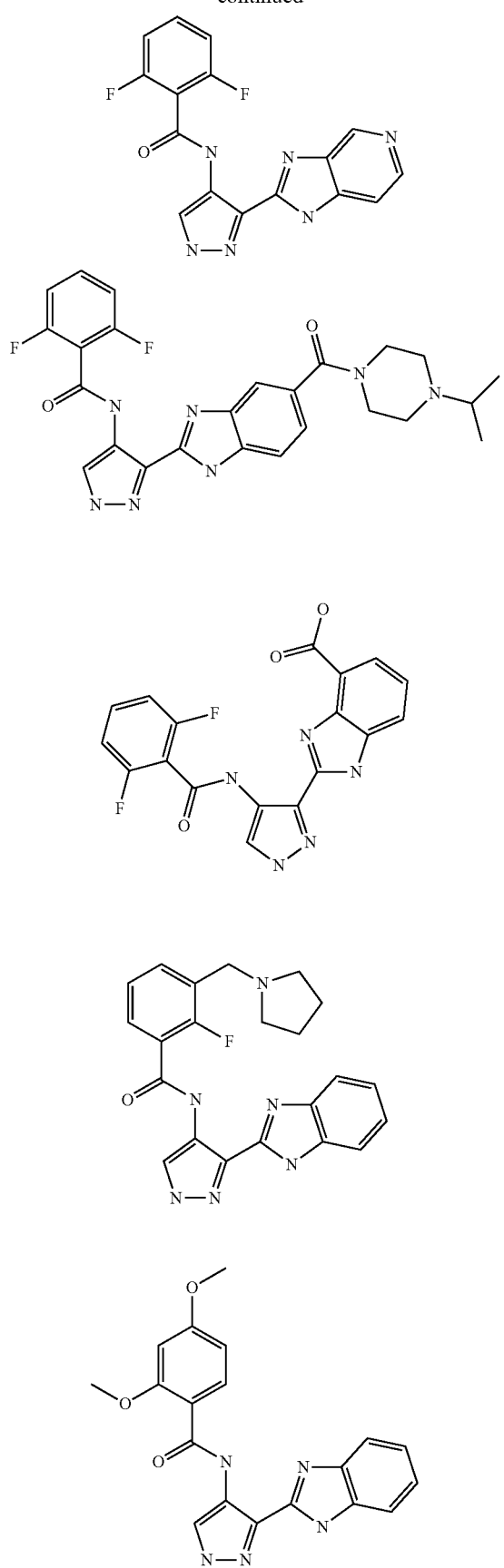
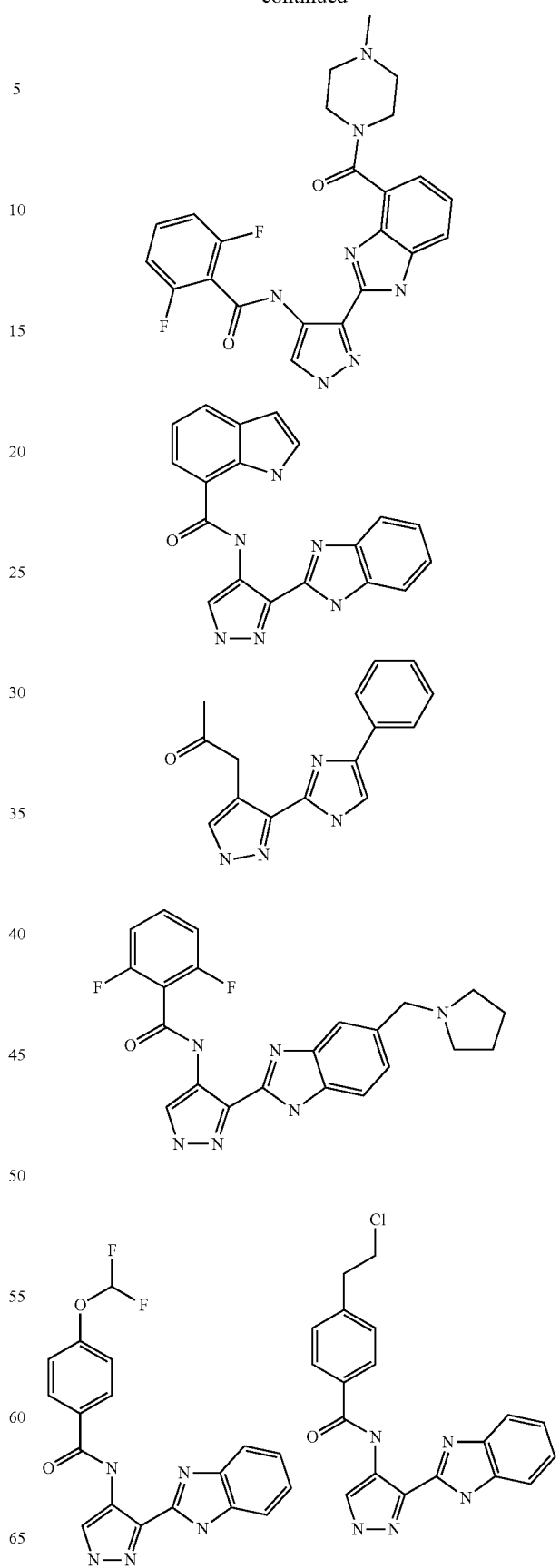

61
-continued
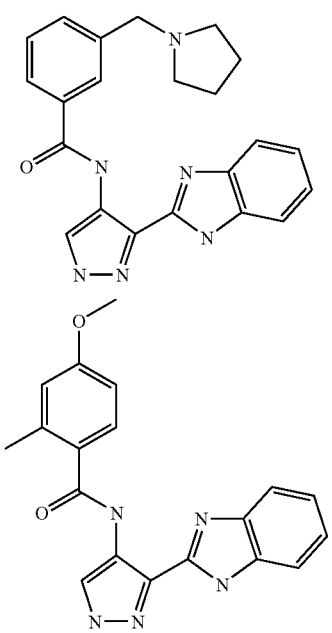
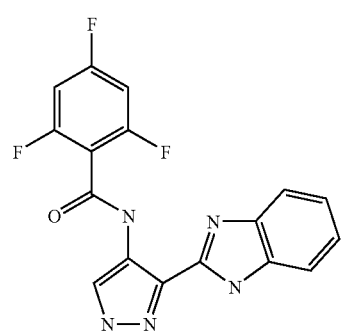
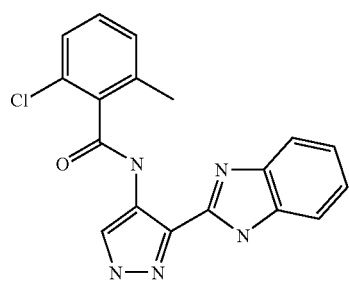
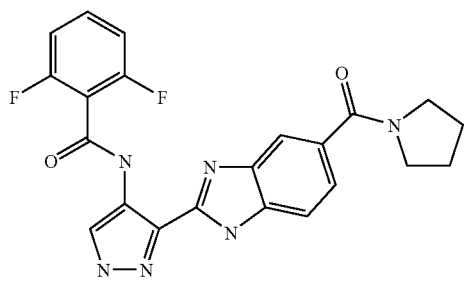
62
-continued
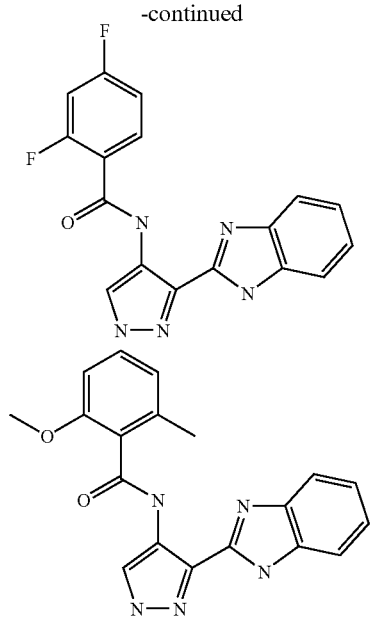
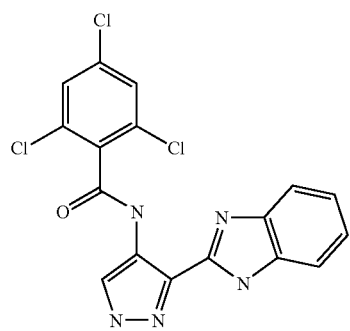
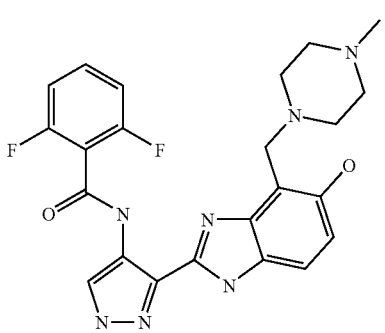
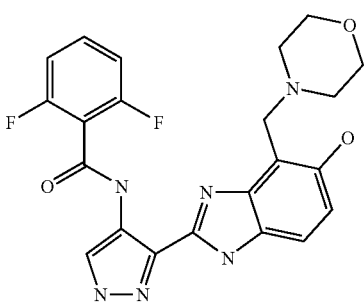

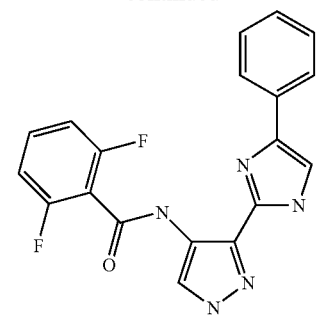
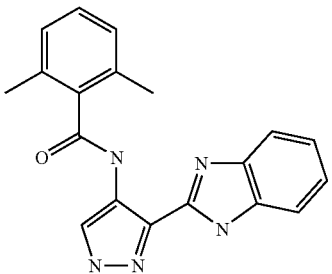
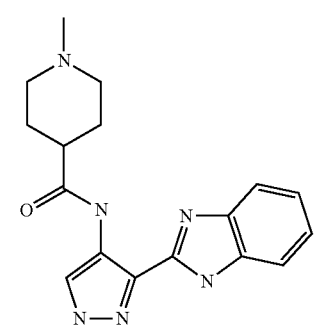
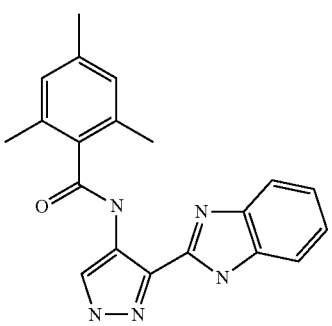
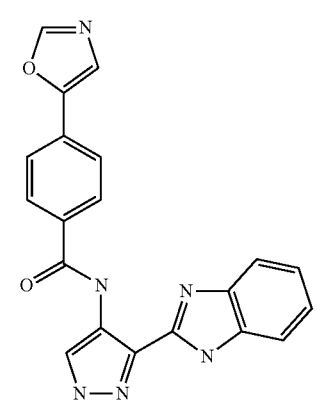
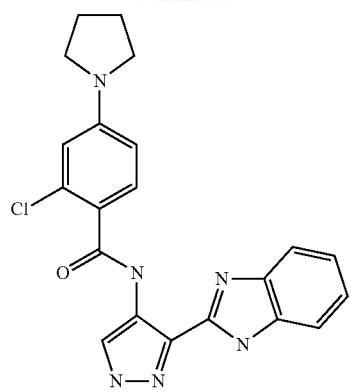
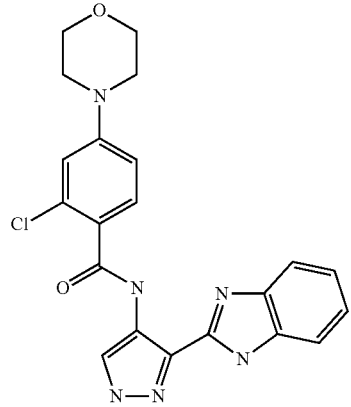
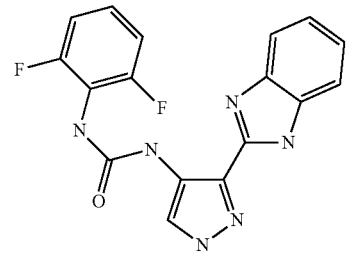
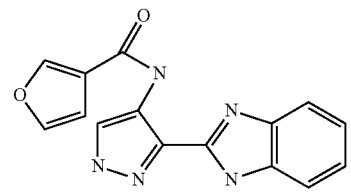
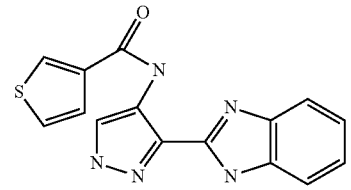
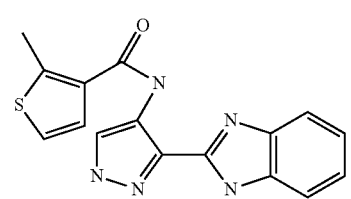

65
-continued
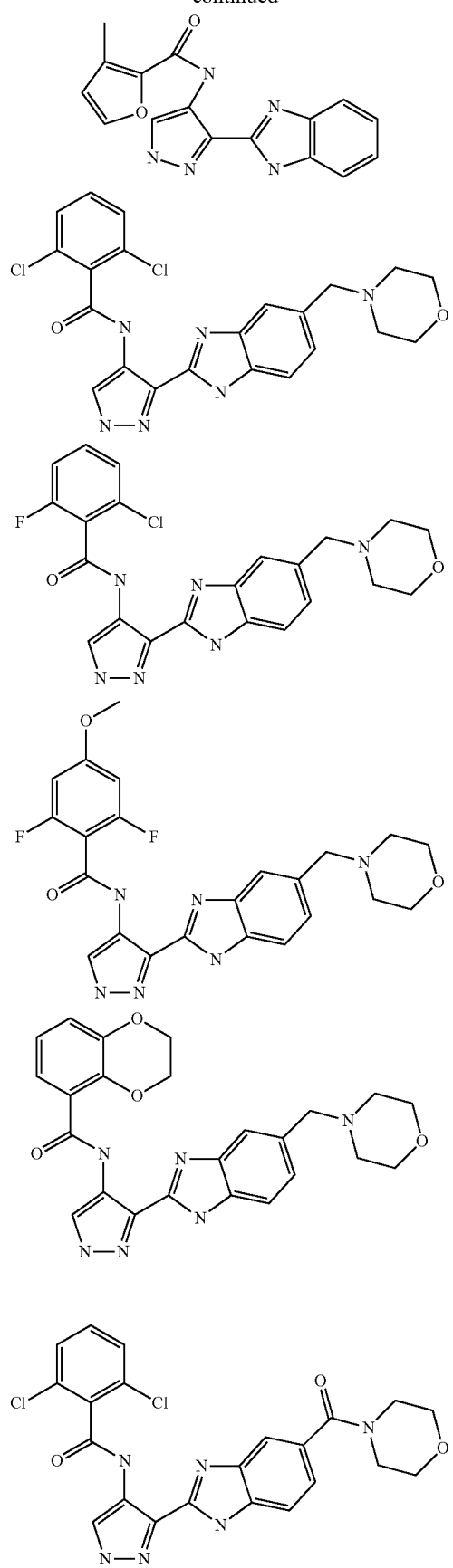
66
-continued
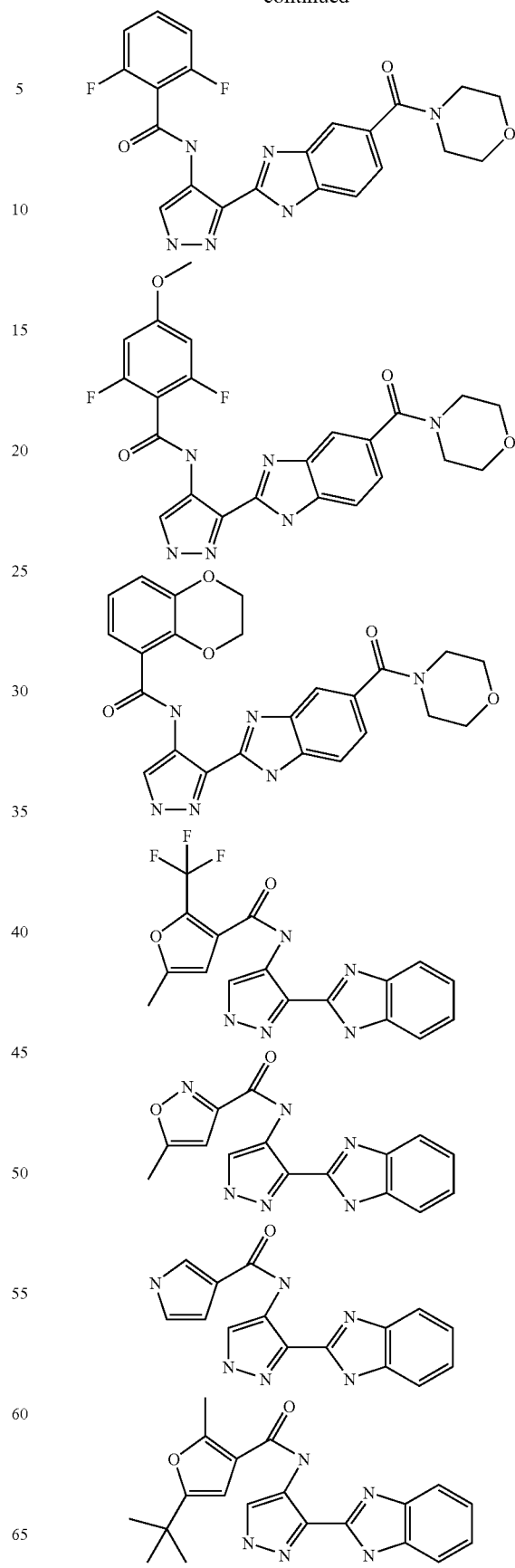

67
-continued
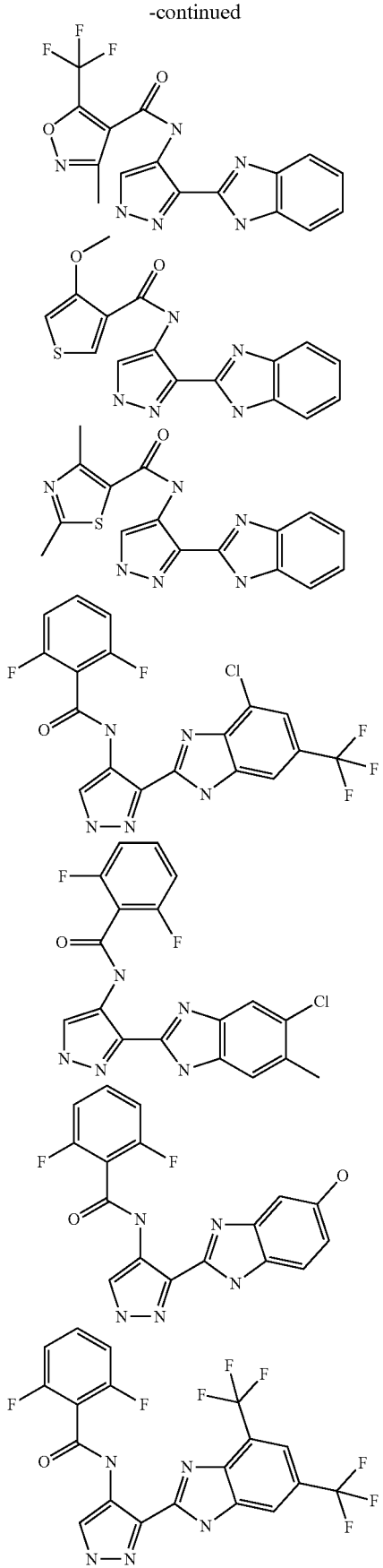
68
-continued
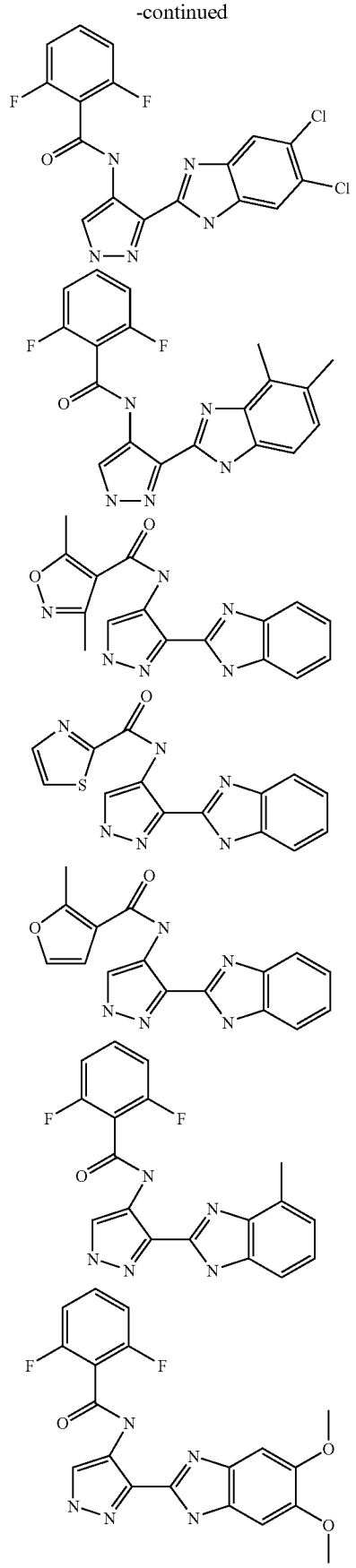

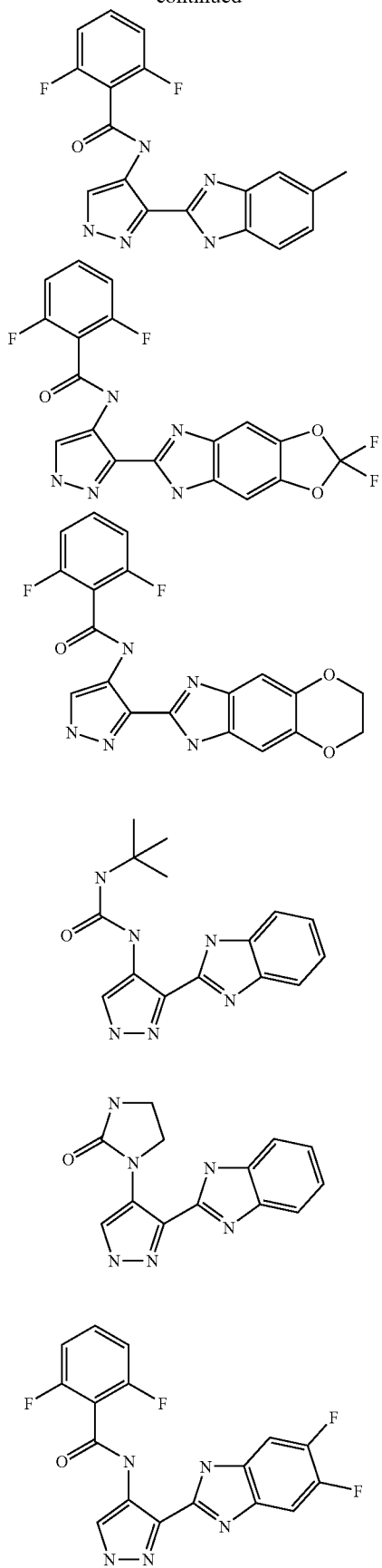
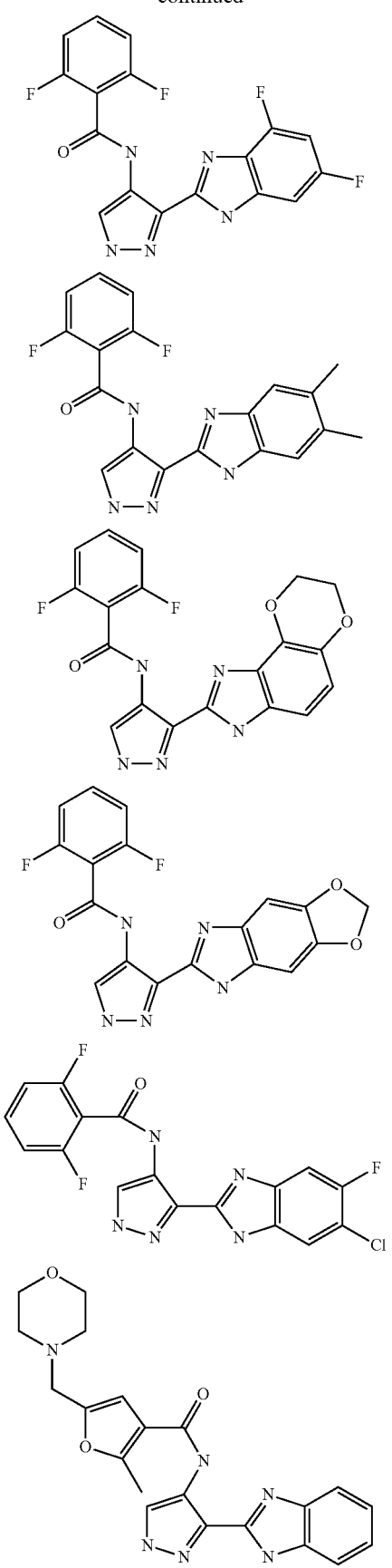

71
-continued
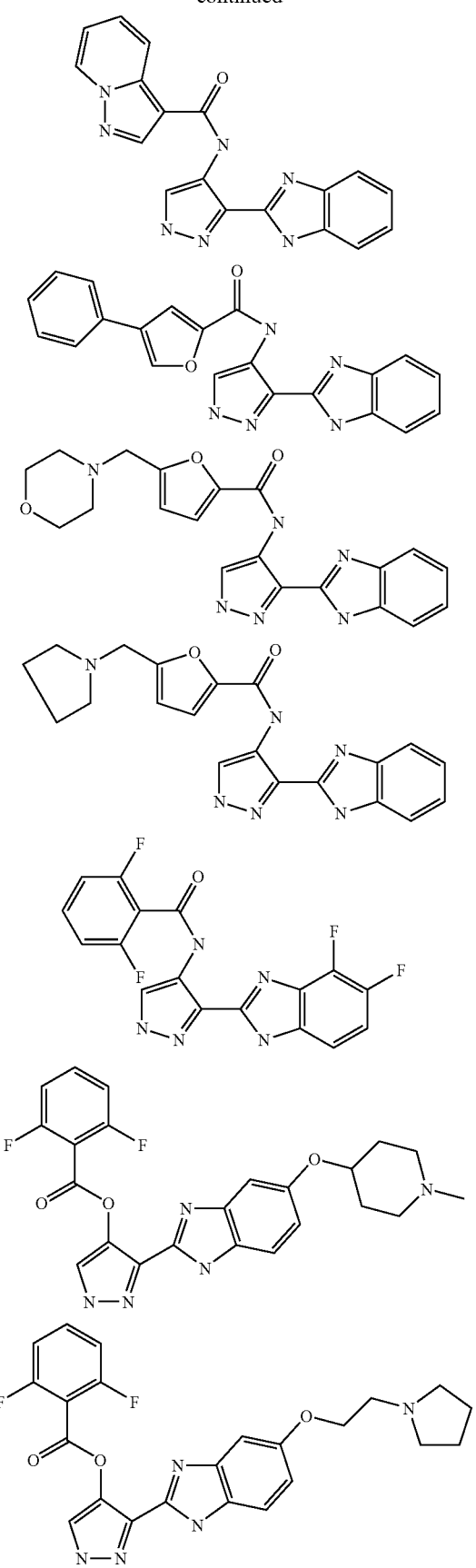
72
-continued
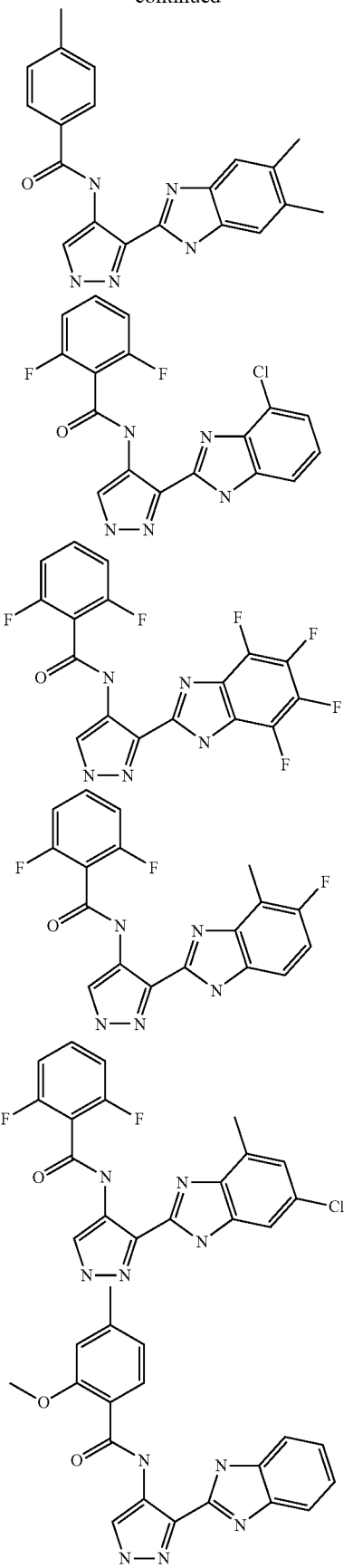

73
-continued
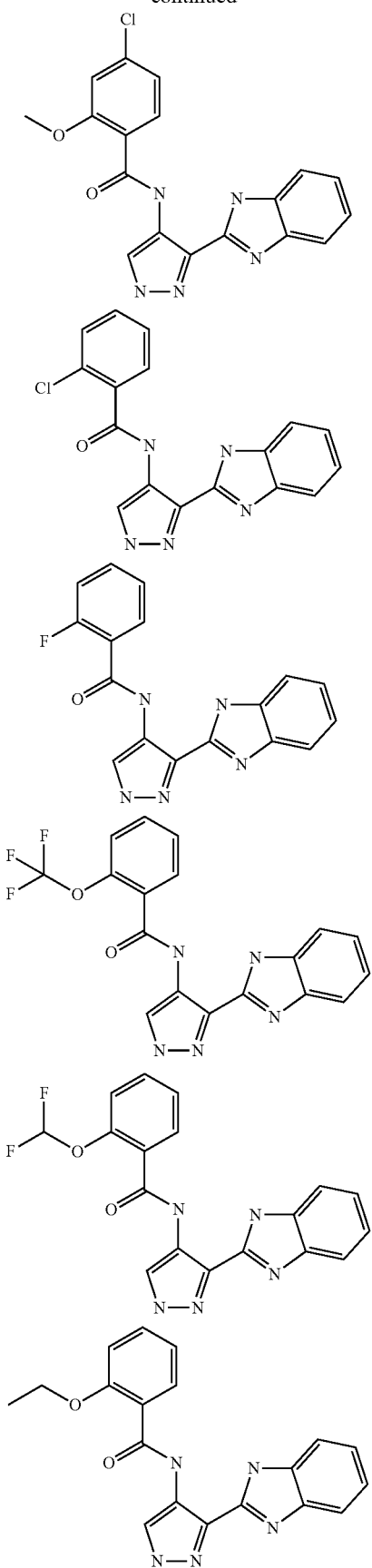
74
-continued
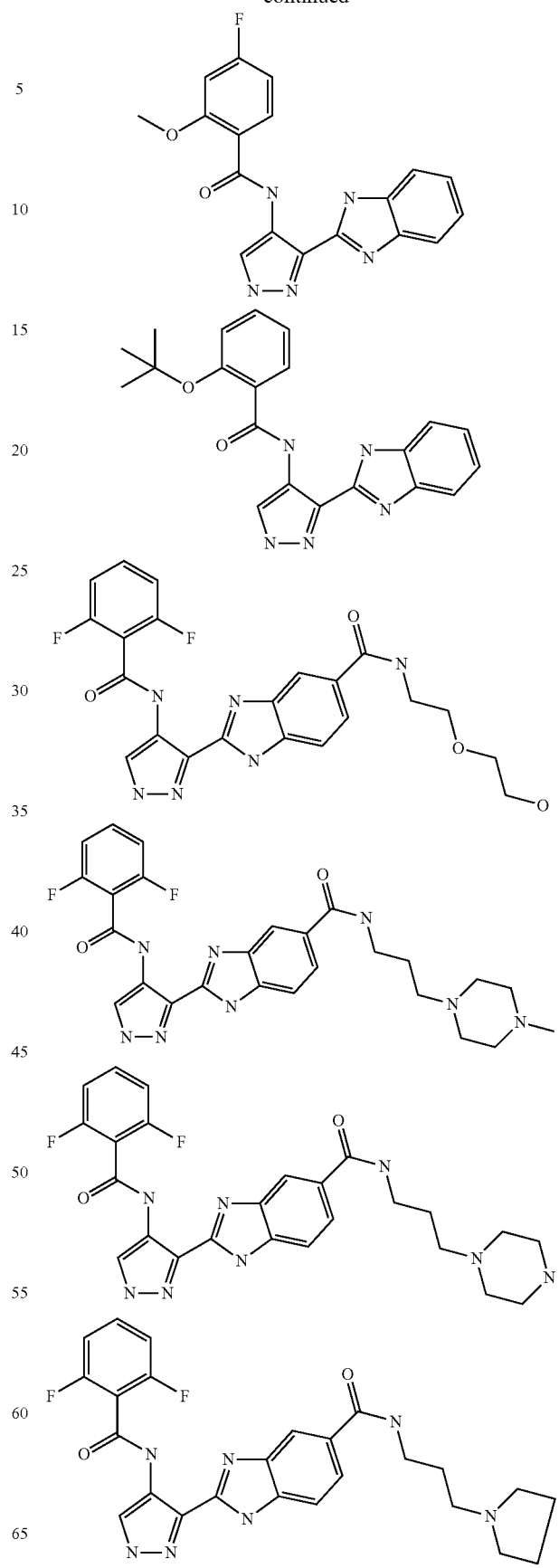

75
-continued
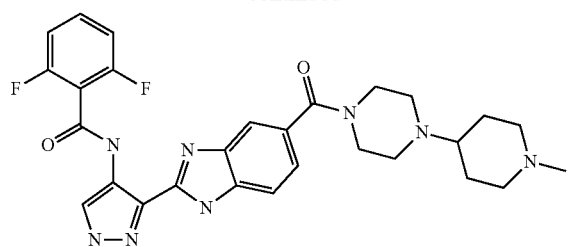
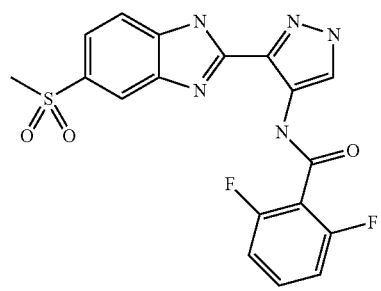
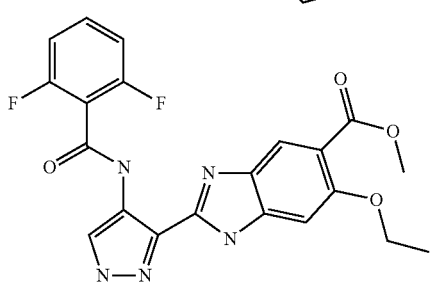
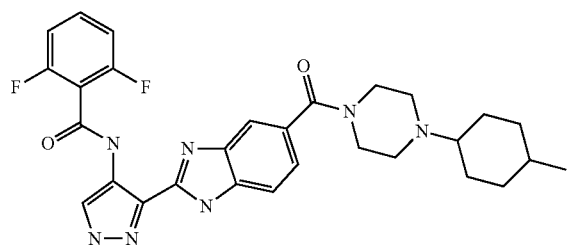
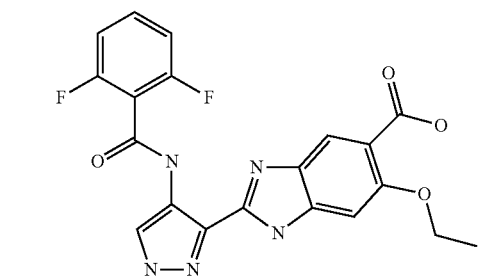
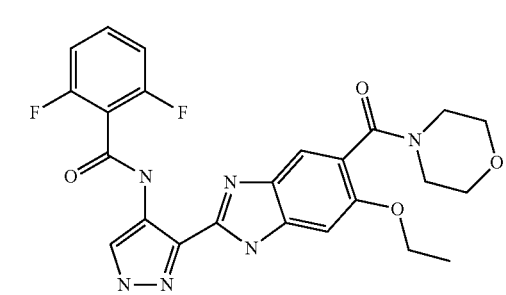
76
-continued
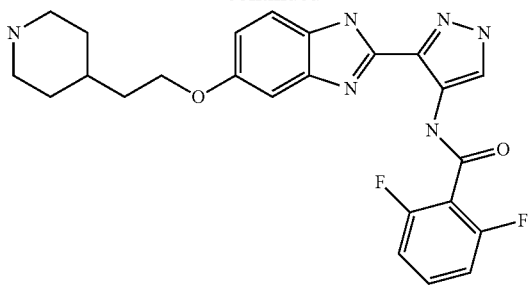
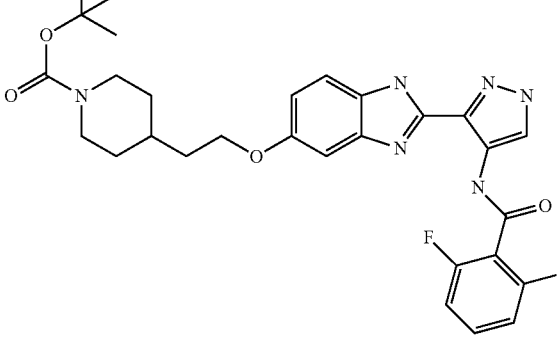
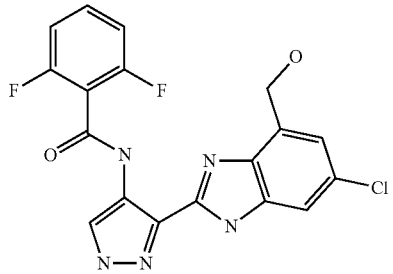
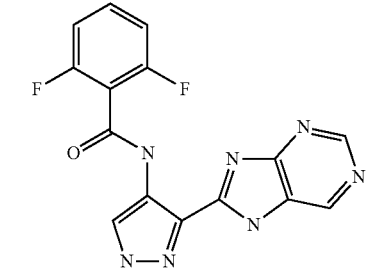
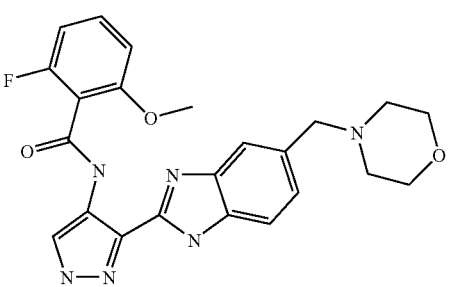

77
-continued
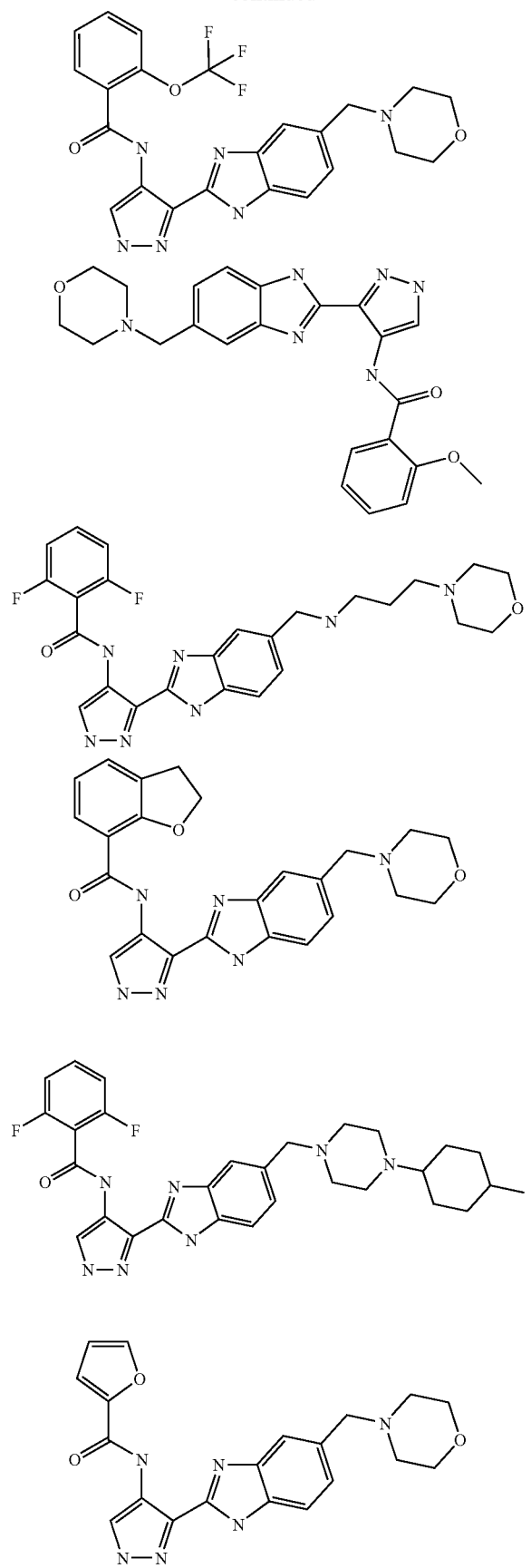
78
-continued
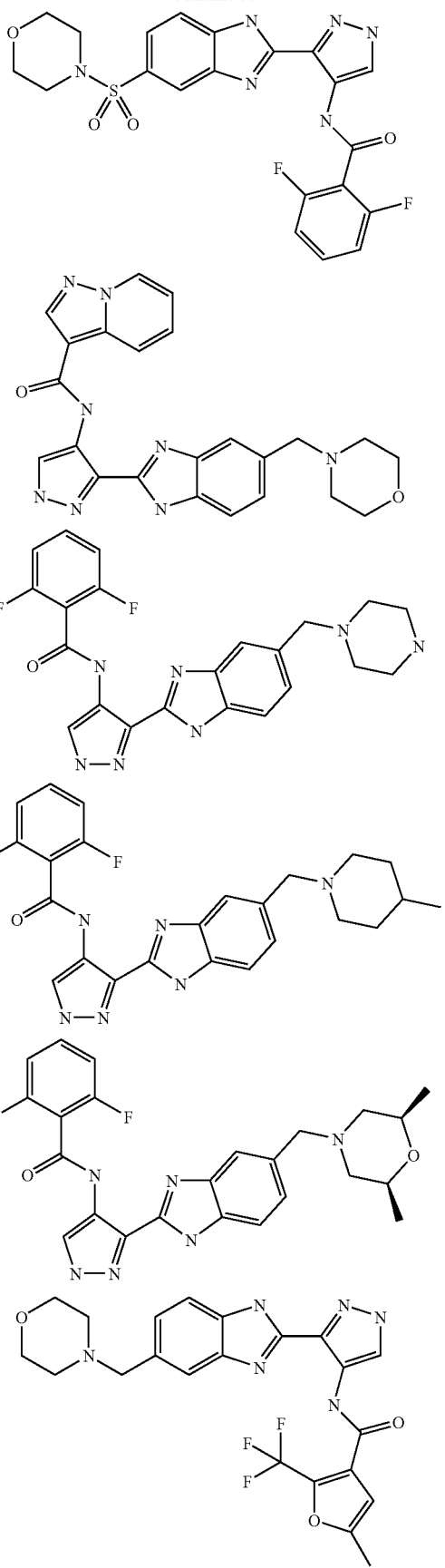

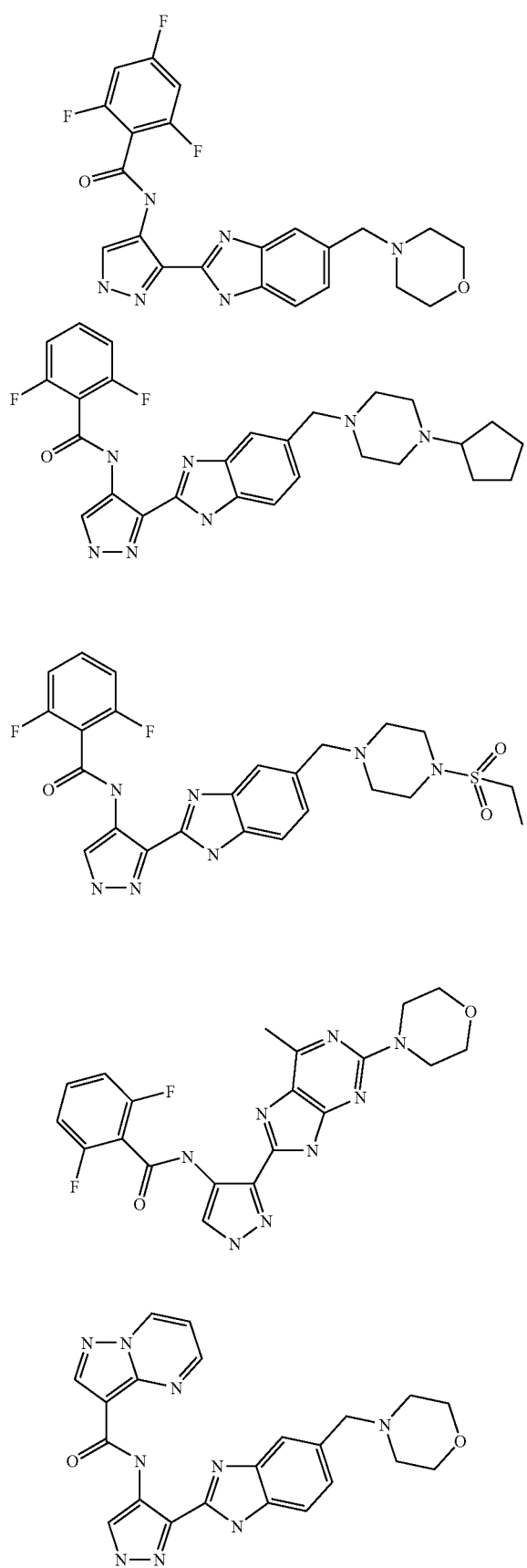
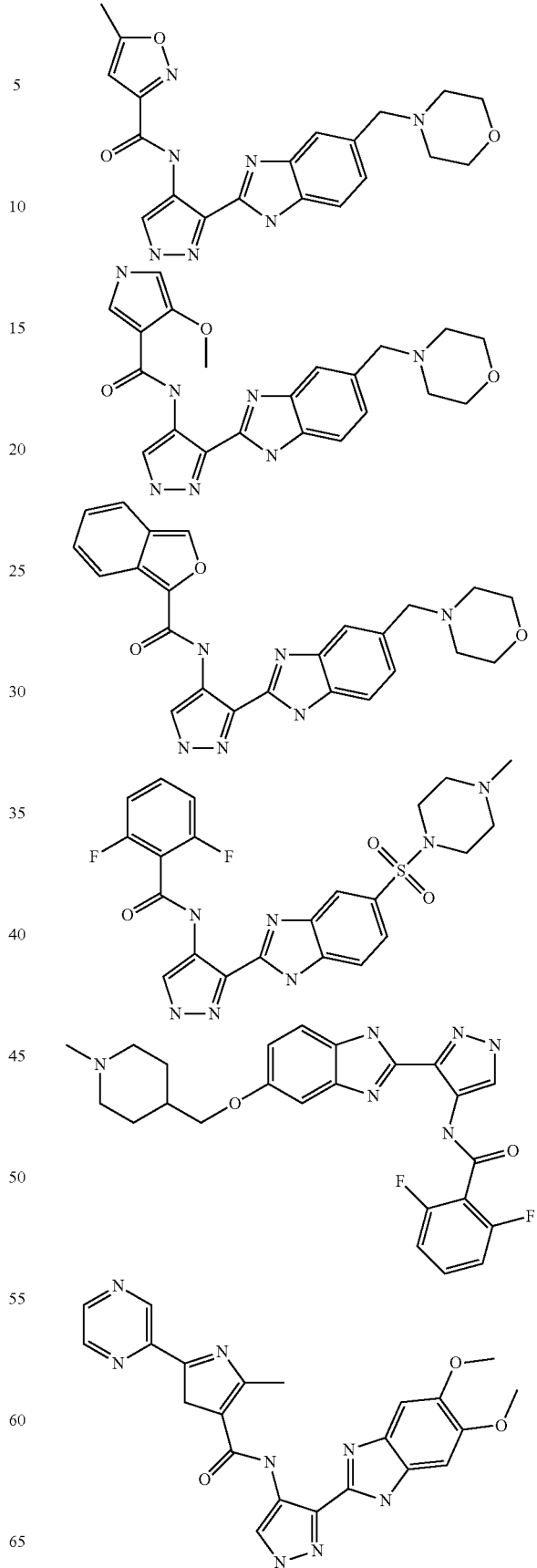

81
-continued
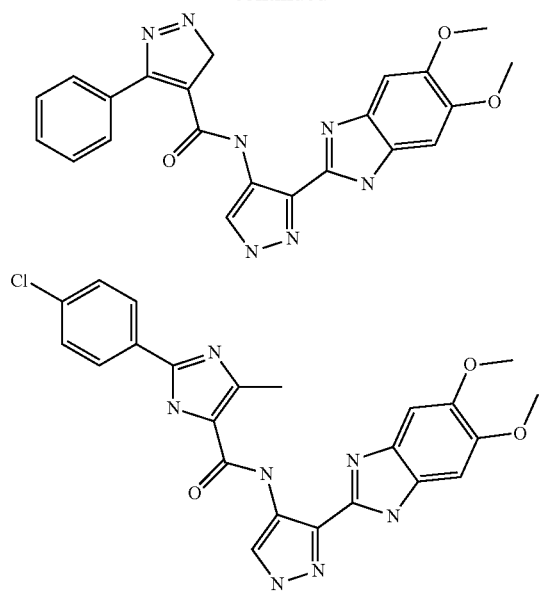
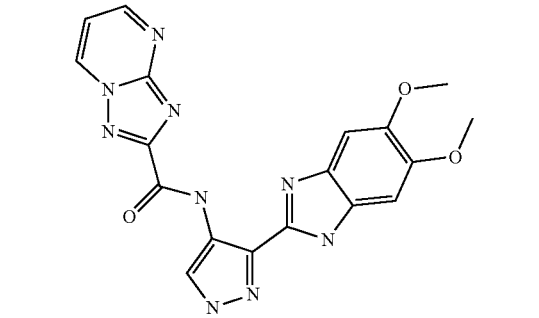
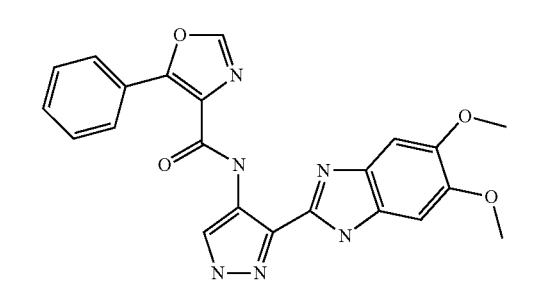
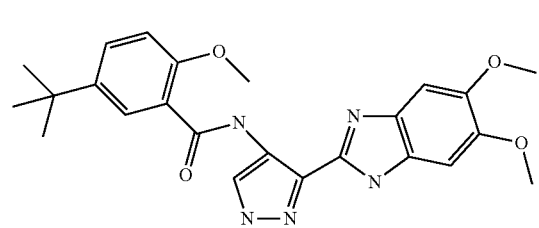
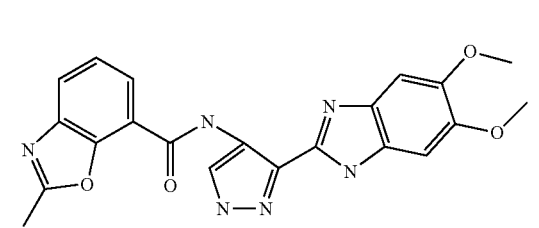
82
-continued
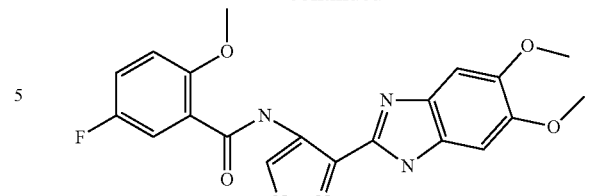
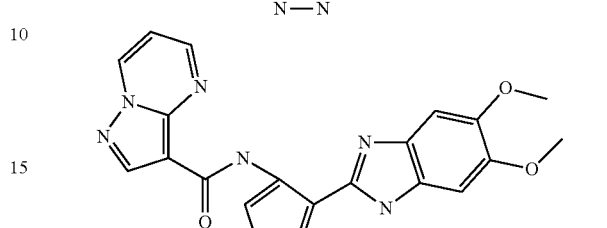
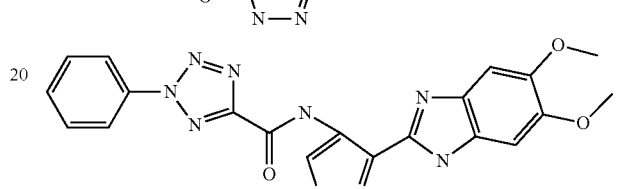
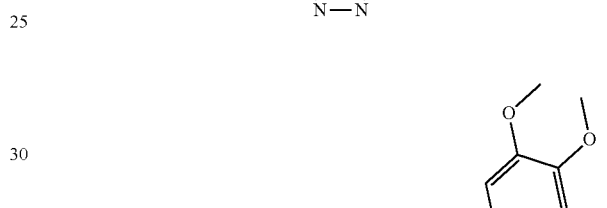
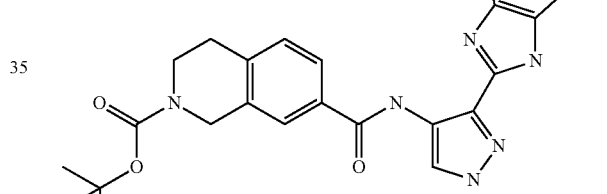
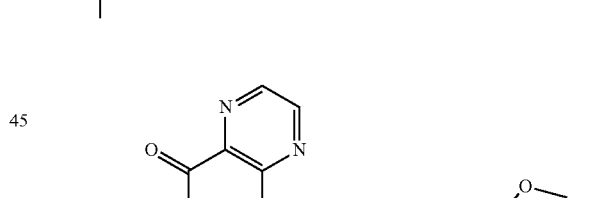
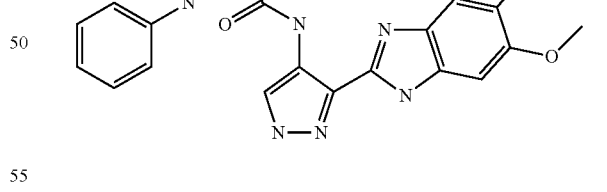
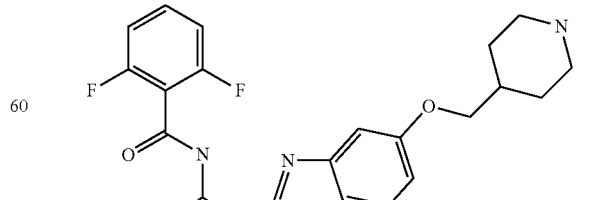

83
-continued
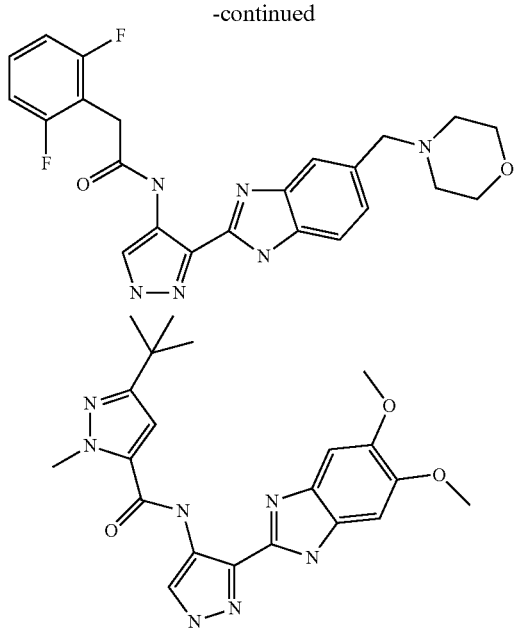
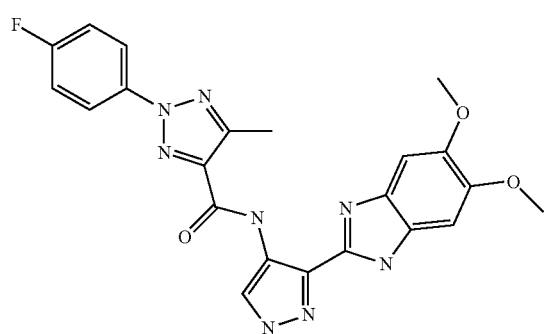
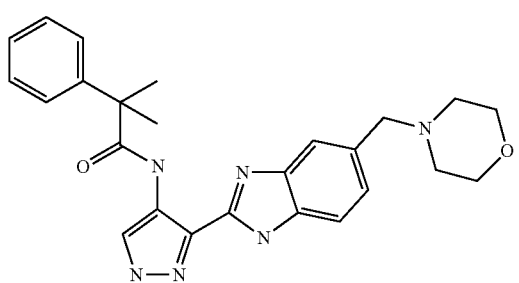
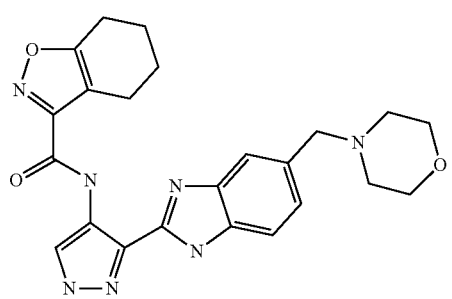
84
-continued
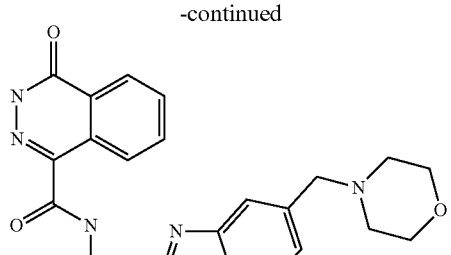
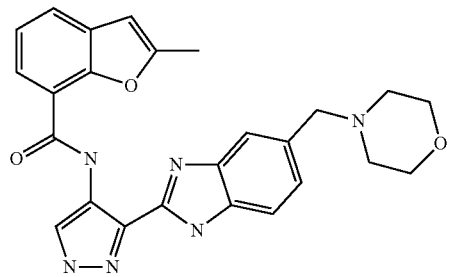
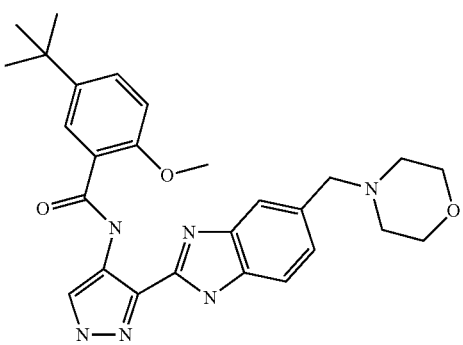
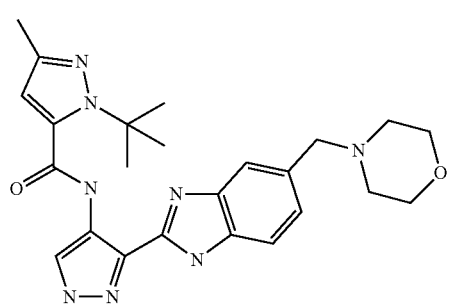
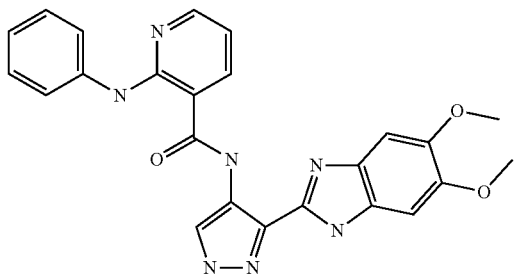

85
-continued
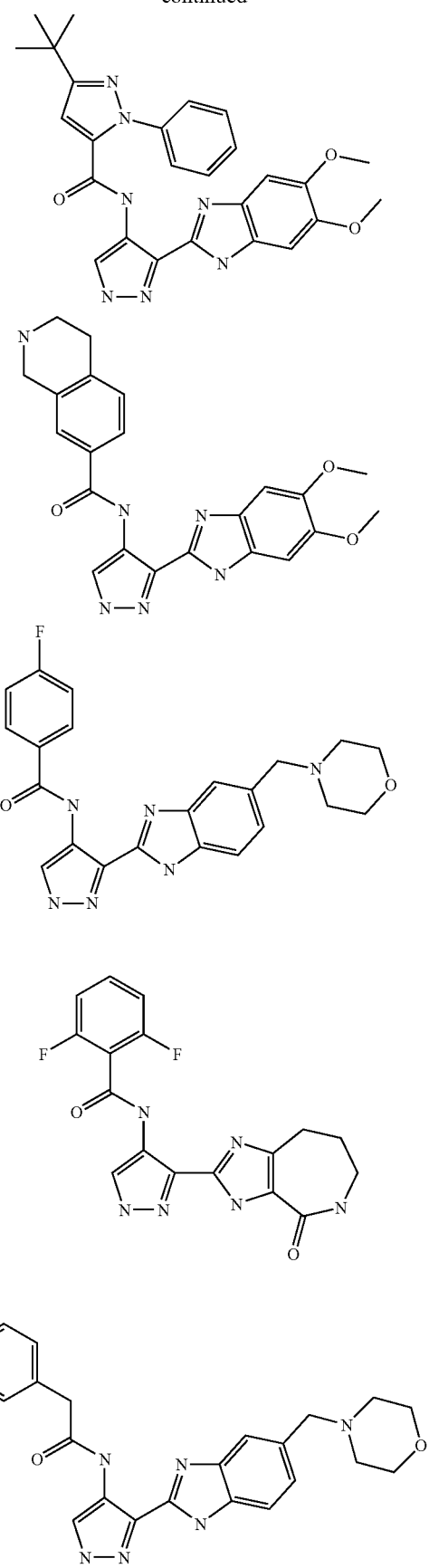
86
-continued
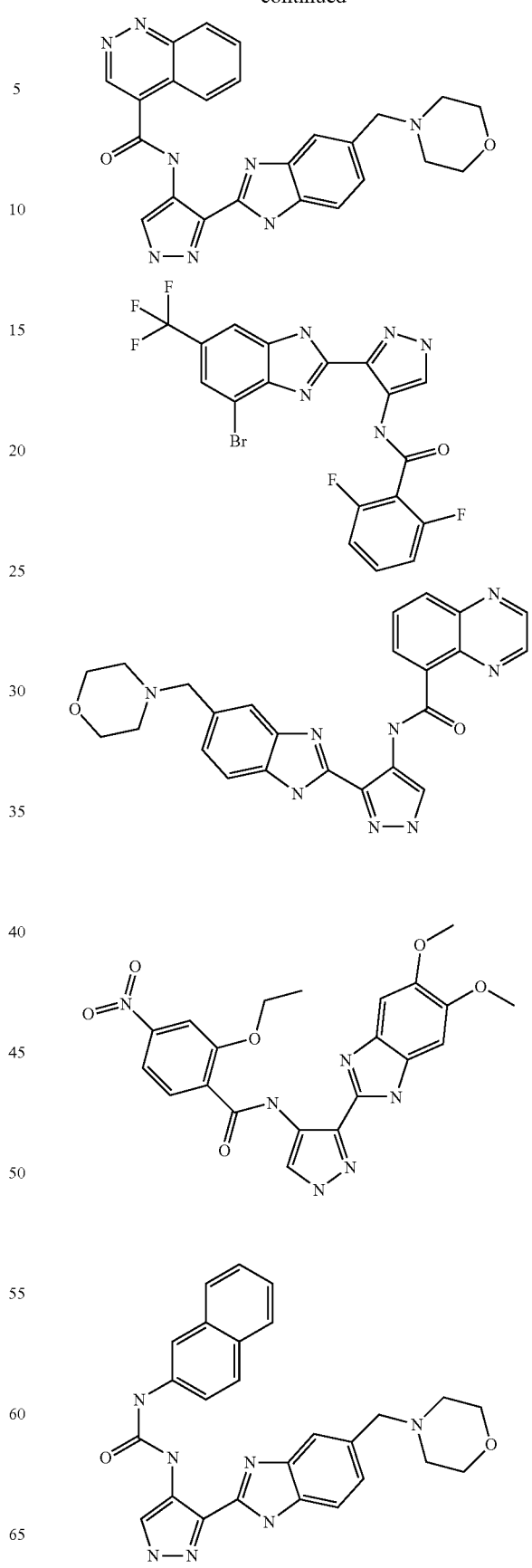

87
-continued
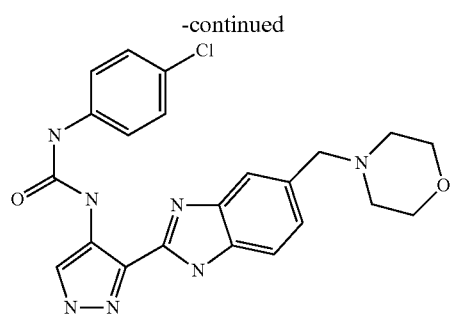
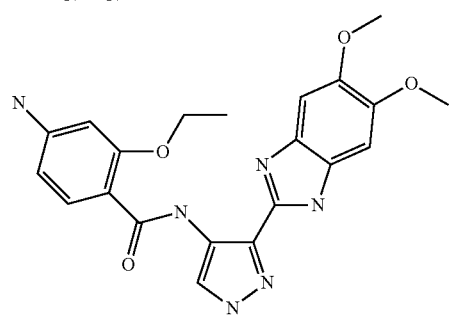
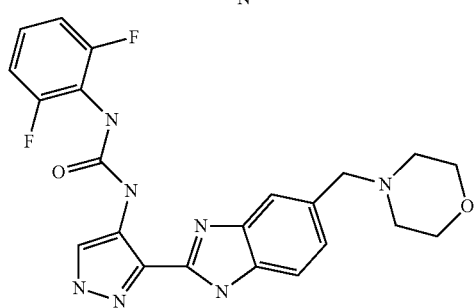
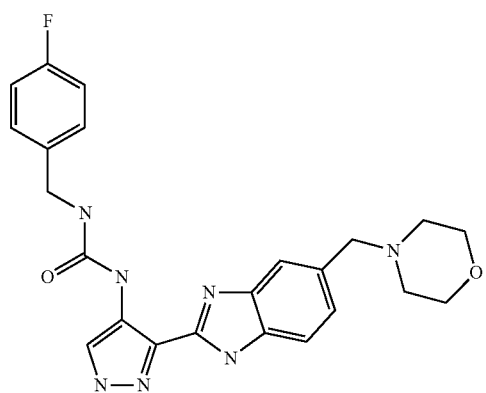
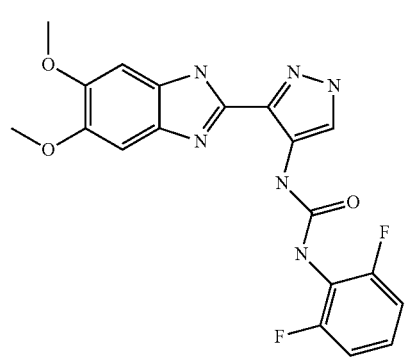
88
-continued
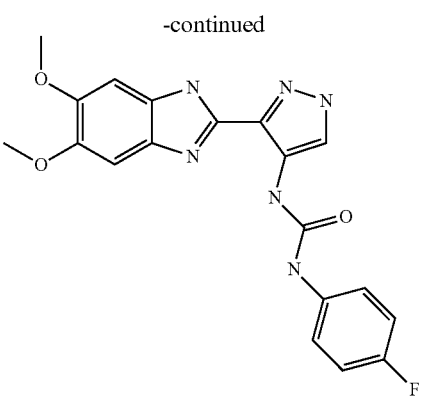
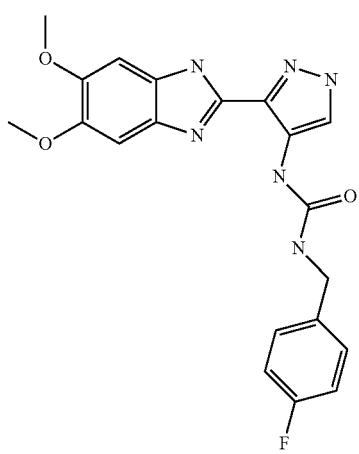
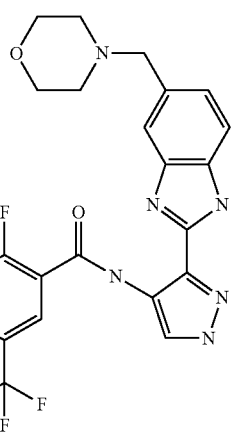
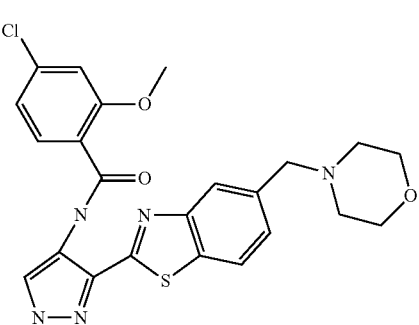

89
-continued
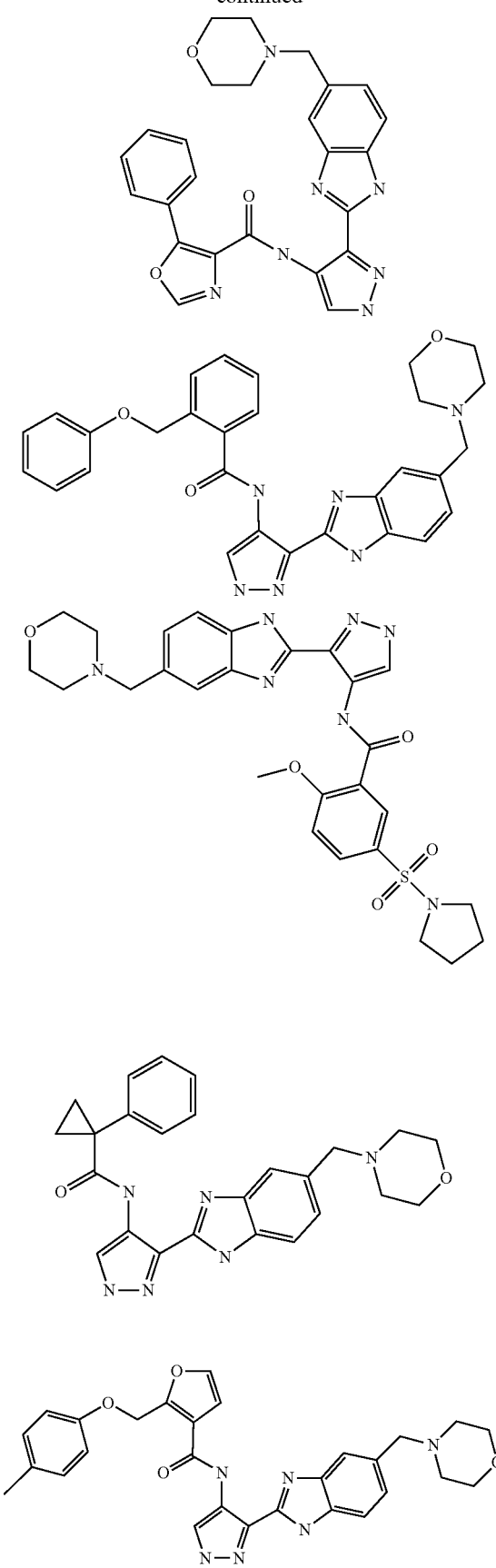
90
-continued
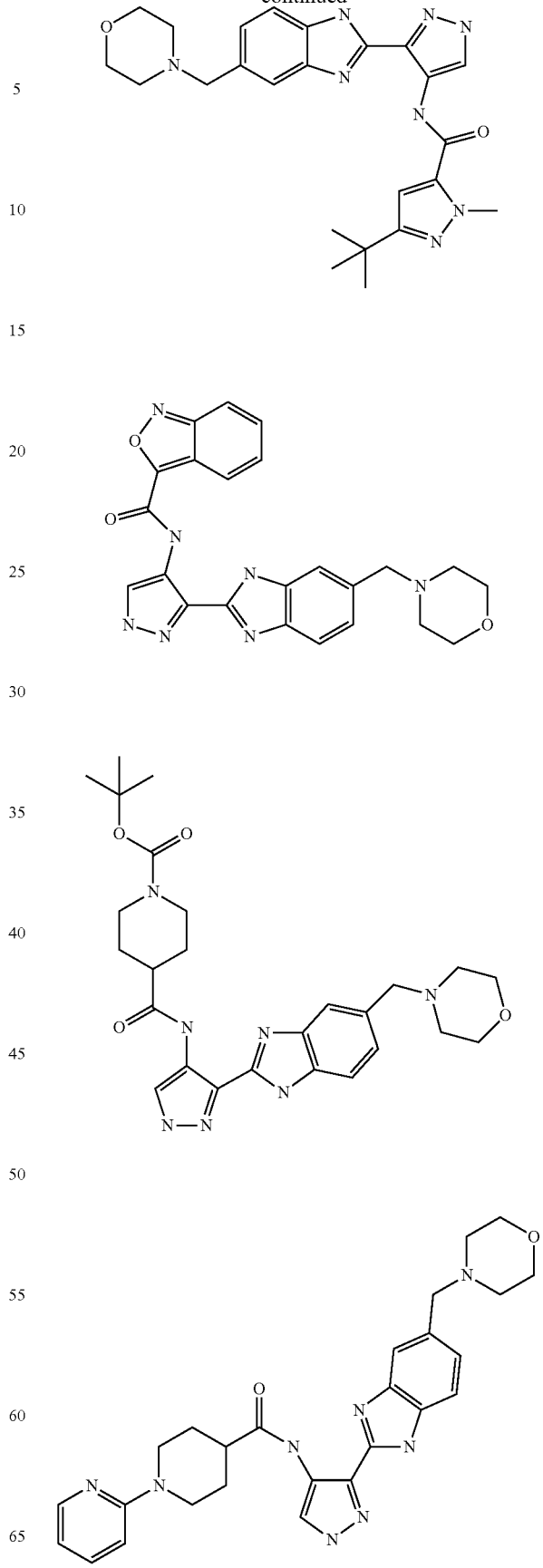

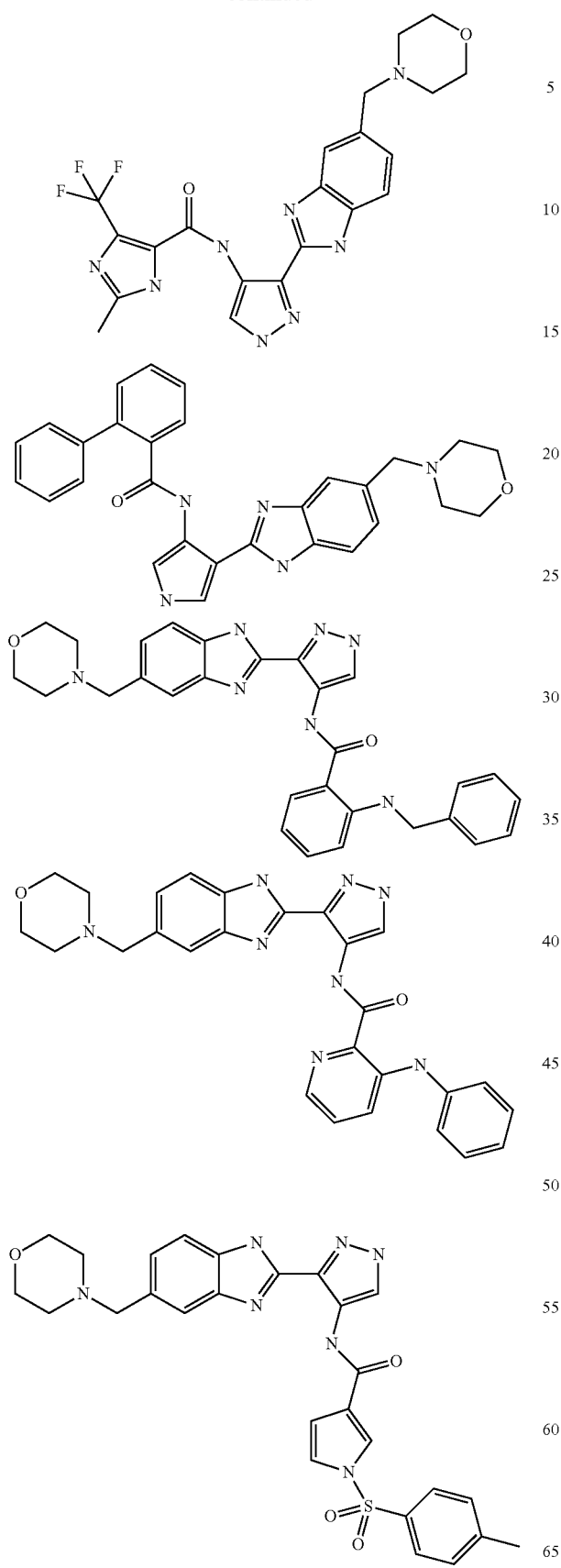
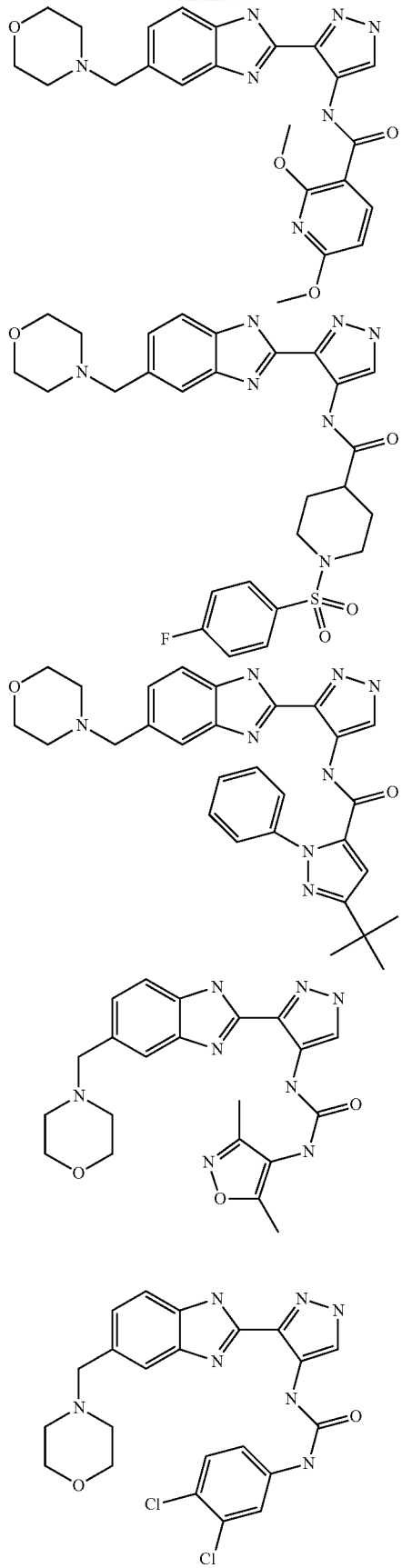

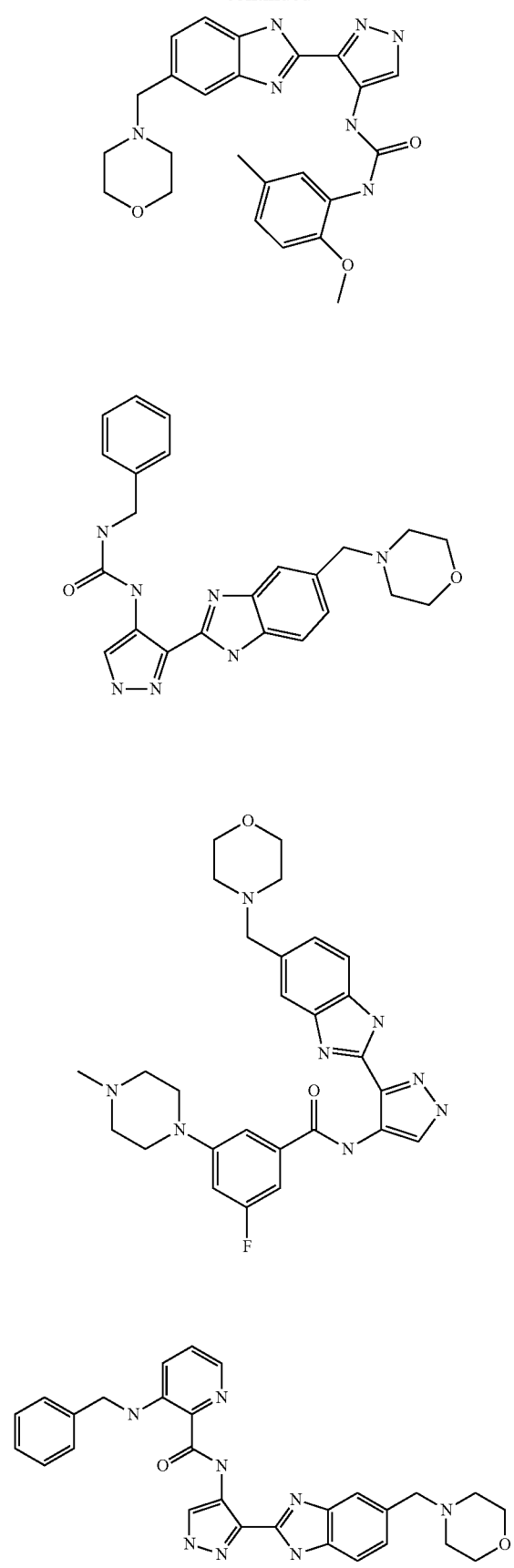

95
-continued
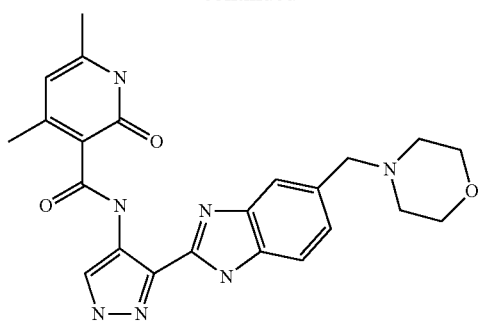 [SMILES: Cc1cc(C)c(C(=O)Nc2c[nH]nc2-c2nc3cc(CN4CCOCC4)ccc3[nH]2)c(=O)[nH]1]
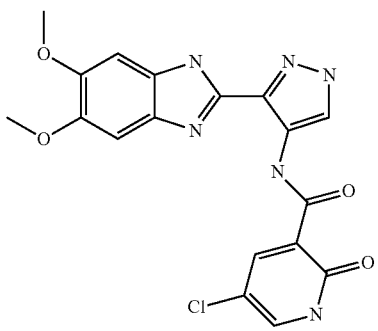
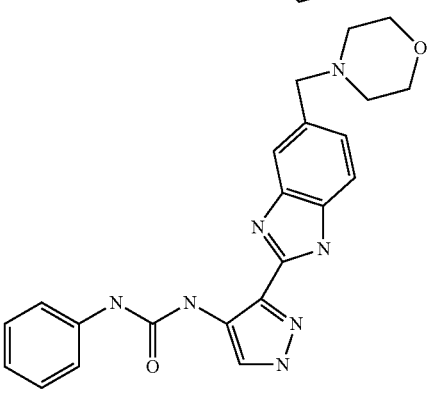
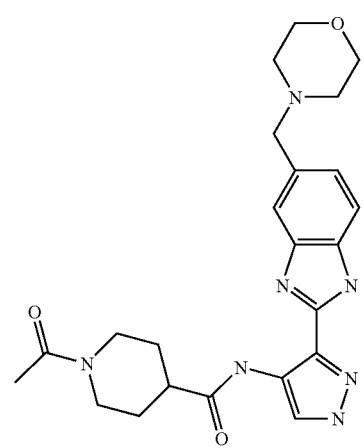
96
-continued
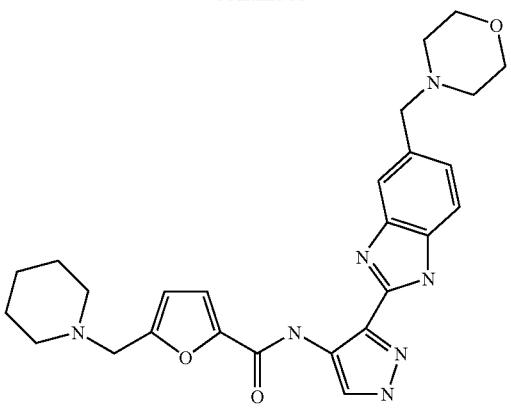
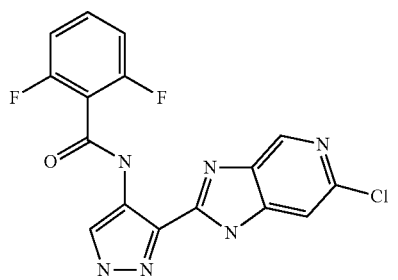

97
-continued
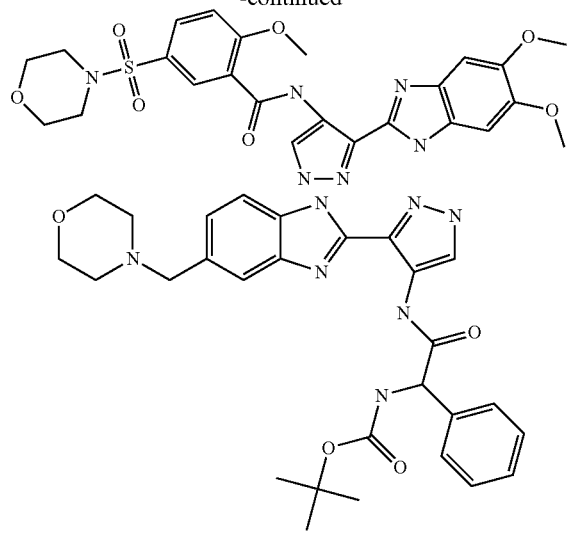
98
-continued
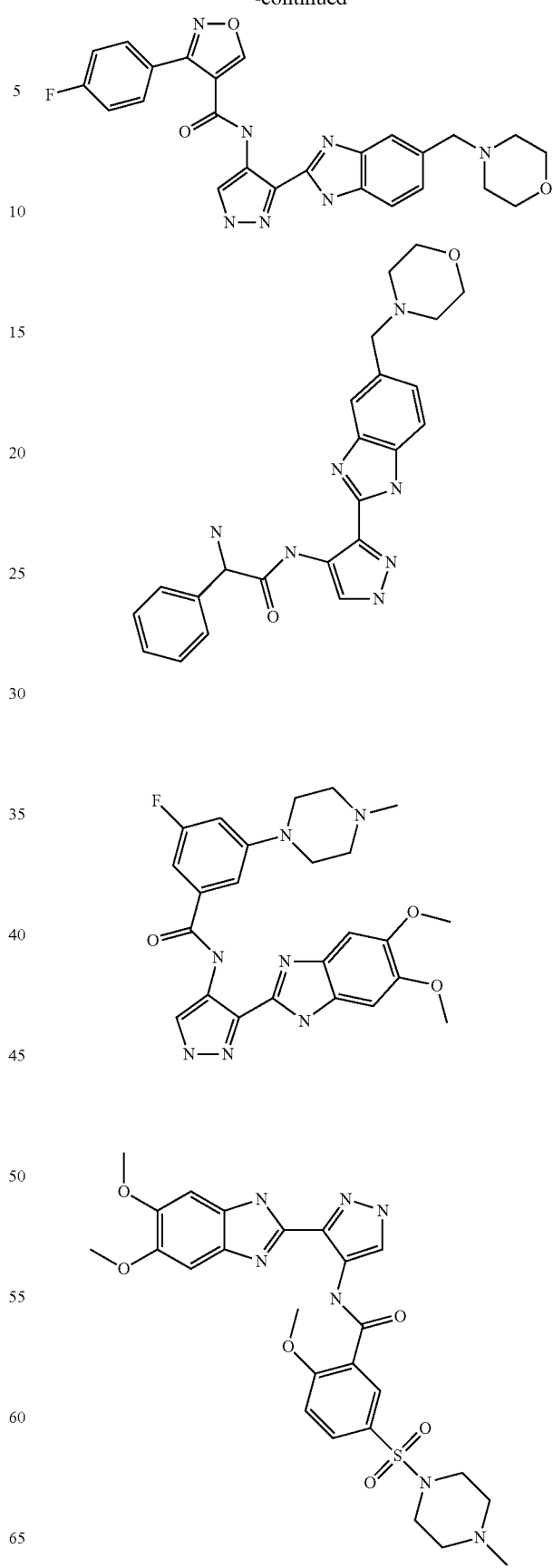

99
-continued
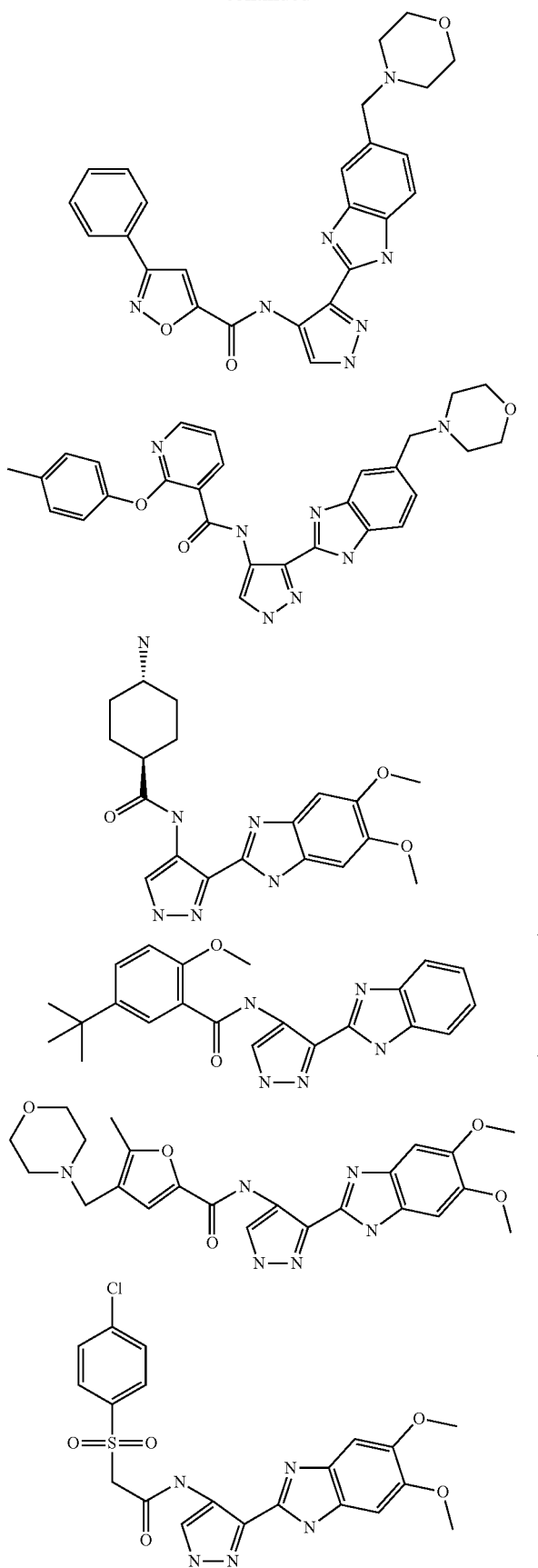
100
-continued
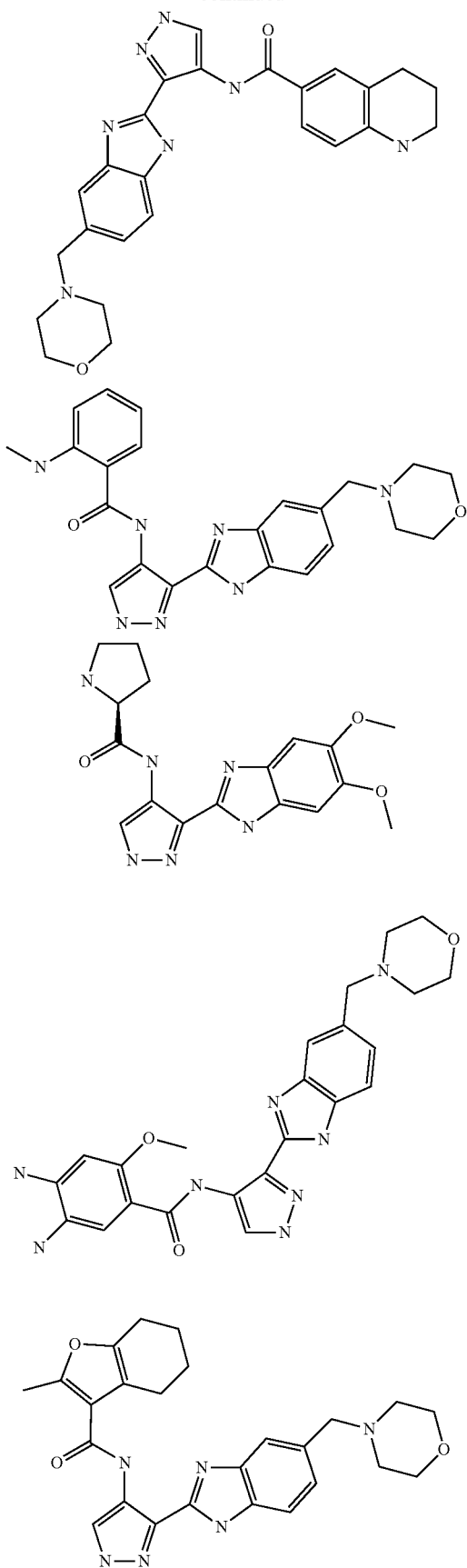

-continued

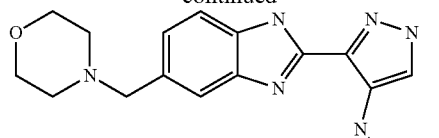
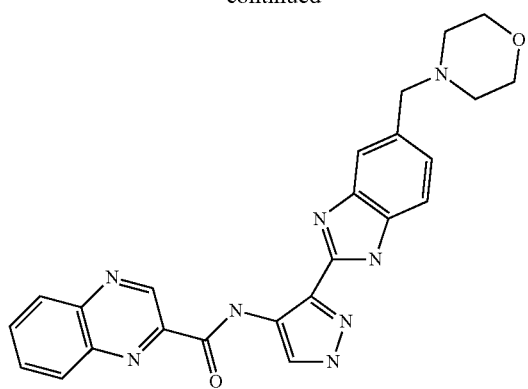
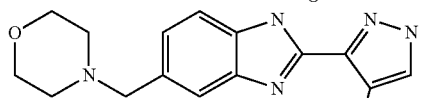
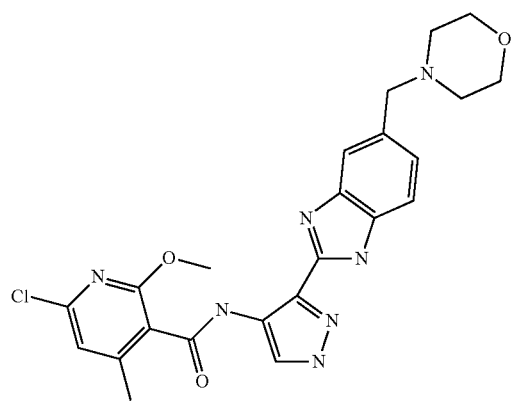
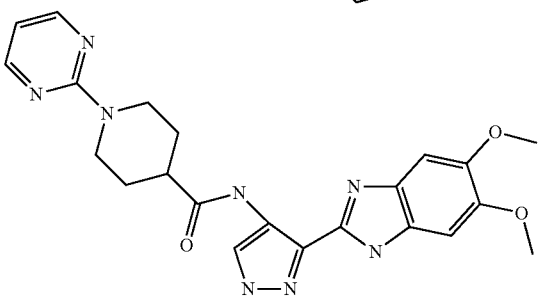
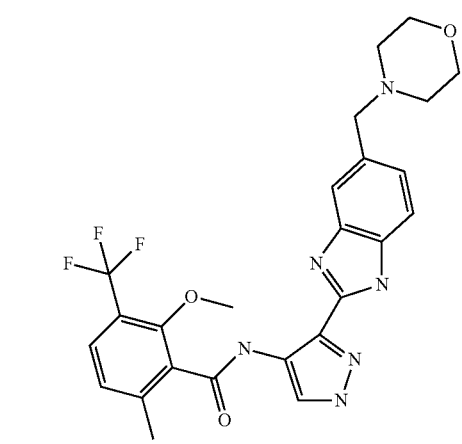
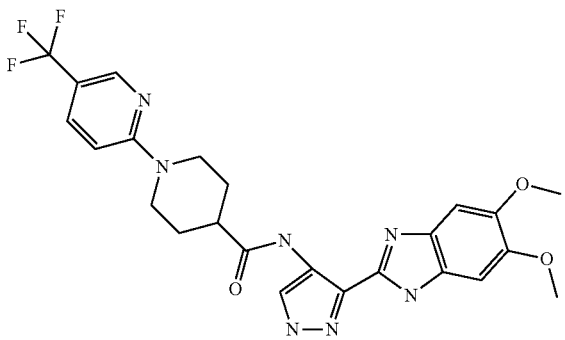
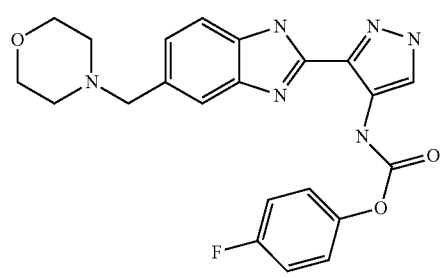
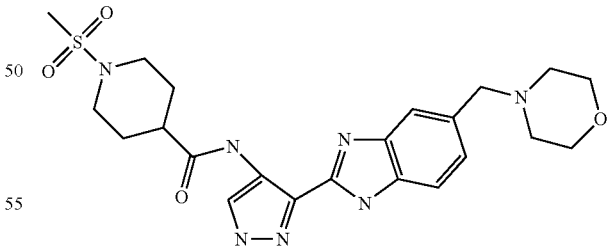

A preferred compound of the formula (I') is 1-(2,6-difluorophenyl)-N-[3-(5-morpholin-4-ylmethyl-1H-benzimidazol-2-yl)-1H-pyrazol-4-yl]-urea and its salts, N-oxides, tautomers and solvates, and in particular its salts.

General Preferences and Definitions for Compounds of the Formula (I")

The following general preferences and definitions shall apply to each of the moieties D1, D2, A, E, X, $X^a$ and $R^1$ to $R^9$ in formula (I″) and their various sub-groups, sub-definitions, examples and embodiments unless the context indicates otherwise.

Any references to formula (I″) herein shall also be taken to refer to formulae (II″) to (VIII″) and any other sub-group of compounds within formula (I″) unless the context requires otherwise.

The term "saturated" as used herein refers to rings where there are no multiple bonds between ring atoms.

The term "hydrocarbyl" as used herein, whether on its own or as part of a composite term such as "hydrocarbyloxy" is a generic term encompassing aliphatic and alicyclic groups having an all-carbon backbone. Examples of hydrocarbyl groups include alkyl, cycloalkyl, cycloalkenyl, alkenyl, alkynyl, cycloalkylalkyl, cycloalkenylalkyl. Particular hydrocarbyl groups are saturated groups such as alkyl and cycloalkyl groups.

Examples of hydrocarbyloxy groups include alkoxy, cycloalkoxy, cycloalkenoxy, alkenyloxy, alkynyloxy, cycloalkylalkyloxy, cycloalkenylalkyoxy. Particular hydrocarbyloxy groups are saturated groups such as alkoxy.

The prefix "$C_{1-n}$" (where n is an integer) as used herein refers to the number of carbon atoms in a given group. Thus, a $C_{1-4}$ hydrocarbyl group contains from 1 to 4 carbon atoms, whilst a $C_{1-3}$ hydrocarbyloxy group contains from 1 to 3 carbon atoms, and so on.

Examples of $C_{1-4}$ hydrocarbyl groups include $C_{1-3}$ hydrocarbyl groups or $C_{1-2}$ hydrocarbyl groups, specific examples being any individual value or combination of values selected from $C_1$, $C_2$, $C_3$ and $C_4$ hydrocarbyl groups.

The term "alkyl" covers both straight chain and branched chain alkyl groups. Examples of alkyl groups are methyl, ethyl, propyl, isopropyl, n-butyl, isobutyl, and tert-butyl.

Examples of cycloalkyl groups are those derived from cyclopropane, cyclobutane and cyclopentane.

Examples of alkenyl groups are ethenyl (vinyl), 1-propenyl, 2-propenyl (allyl), isopropenyl, butenyl and buta-1,4-dienyl.

Examples of cycloalkenyl groups are cyclopropenyl and cyclobutenyl.

Examples of alkynyl groups are ethynyl and 2-propynyl (propargyl) groups.

Examples of cycloalkylalkyl and cycloalkenylalkyl include cyclopropylmethyl.

Examples of alkoxy groups are methoxy, ethoxy, n-propyloxy, i-propyloxy, n-butoxy, isobutoxy and tert-butoxy.

When an alkyl group forms part of a mono-alkylamino or dialkylamino group, the alkyl group may be any of the examples of alkyl groups set out above. Particular alkylamino and dialkylamino groups are methylamino, dimethylamino, ethylamino, diethylamino, n-propylamino, isopropylamino, butylamino, isobutylamino and i-butylamino. Particular alkyl- and dialkylamino groups are methylamino and dimethylamino.

The term "saturated heterocyclic group" as used herein refers to a heterocyclic group containing no multiple bonds between adjacent ring members. The saturated heterocyclic groups may contain 1 or 2 heteroatom ring members selected from O, S and N.

Depending on the context, the heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

The saturated heterocyclic groups are typically monocyclic and usually contain 4, 5 or 6 ring members unless otherwise stated.

A particular example of saturated heterocyclic groups containing 4 ring members is the azetidine group.

Examples of saturated heterocyclic groups containing 5 ring members include pyrrolidine (e.g. 1-pyrrolidinyl, 2-pyrrolidinyl and 3-pyrrolidinyl), pyrrolidone, tetrahydrofuran, and tetrahydrothiophene.

Examples of saturated heterocyclic groups containing 6 ring members include morpholine, thiomorpholine, thiomorpholine S-oxide, thiomorpholine S,S-dioxide, piperidine (e.g. 1-piperidinyl, 2-piperidinyl, 3-piperidinyl and 4-piperidinyl), piperidone, dioxane, tetrahydropyran (e.g. 4-tetrahydropyranyl), piperazone, piperazine, and N-alkyl piperazines such as N-methyl piperazine.

Specific Embodiments of and Preferences for D1, D2, A, E, $R^1$ to $R^9$ and X in Sub-Groups (A) and (B) of Formula (I″)

In one general embodiment, M is a group D1.

In another general embodiment, M is a group D2.

X is selected from O, NH and $NCH_3$. In one particular embodiment X is O.

A is selected from a bond and a group $NR^2$ where $R^2$ is hydrogen or methyl.

In one embodiment, A is a bond.

In another embodiment, A is a group $NR^2$ where $R^2$ is hydrogen or methyl.

E is selected from a bond, $CH_2$, CH(CN) and $C(CH_3)_2$.

In one sub-group of compounds E is a bond.

In another sub-group of compounds E is $CH_2$.

In a further sub-group of compounds E is CH(CN).

In another sub-group of compounds E is $C(CH_3)_2$.

When M is a group D1, $R^1$ can be selected from groups (i), (ii), (iii), (iv), (v), (vi), (vii), (viii), (ix), (x), (xi), (xii), (xiii), (xiv) and (xv).

Each individual group in the list of groups (i) to (xv) represents a separate embodiment for use in the combinations of the invention.

In embodiment (i) $R^1$ is a cycloalkyl group of 3 to 5 ring members optionally substituted by hydroxy, fluorine, amino, methylamino, methyl or ethyl.

Particular cycloalkyl groups are optionally substituted cyclopropyl and cyclobutyl groups, more typically optionally substituted cyclopropyl groups. In a preferred embodiment, $R^1$ is an unsubstituted cyclopropyl group.

In embodiment (ii), $R^1$ is a saturated heterocyclic group of 4 to 6 ring members containing 1 or 2 heteroatom ring members selected from O, N, S and $SO_2$, the heterocyclic group being optionally substituted by $C_{1-4}$ alkyl, amino or hydroxy; but excluding unsubstituted 4-morpholinyl, unsubstituted tetrahydropyran-4-yl, unsubstituted 2-pyrrolidinyl, and unsubstituted and 1-substituted piperidine-4-yl.

Examples of saturated heterocyclic groups are as set out in the General Preferences and Definitions section above.

Particular examples of saturated heterocyclic groups include:
  five membered rings containing a single heteroatom ring member selected from O, N and S (other than unsubstituted 2-pyrrolidinyl);
  six membered rings containing two heteroatom ring members selected from O, N and S (other than unsubstituted 4-morpholinyl).

The saturated heterocyclic groups may be substituted or unsubstituted. In one embodiment, they are unsubstituted. In another embodiment, they are substituted by one or two $C_{1-4}$ alkyl groups, for example one or two methyl groups.

One particular saturated heterocyclic group is an optionally substituted tetrahydrofuran group (e.g. tetrahydrofuran-2yl and tetrahydrofuran-3-yl), more preferably an unsubstituted tetrahydrofuran group.

In embodiment (iii) $R^1$ is a 2,5-substituted phenyl group of the formula:

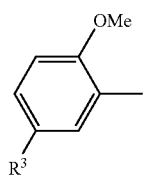

wherein (a) when X is NH or N—$CH_3$, $R^3$ is selected from chlorine and cyano; and (b) when X is O, $R^3$ is CN.

In one sub-group of compounds within embodiment (iii), X is N—$CH_3$ and $R^3$ is selected from chlorine and cyano.

In another sub-group of compounds within embodiment (iii), X is O and $R^3$ is CN.

In embodiment (iv) $R^1$ is a group $CR^6R^7R^8$ wherein $R^6$ and $R^7$ are each selected from hydrogen and methyl, and $R^8$ is selected from hydrogen, methyl, $C_{1-4}$ alkylsulphonylmethyl, hydroxymethyl and cyano.

Within embodiment (iv), particular examples of $R^1$ are methyl, cyanomethyl, $HOCH_2C(CH_3)_2$— and 2-methylsulphonylethyl.

Within embodiment (iv), further particular examples of $R^1$ are methyl and isopropyl.

In embodiment (v) $R^1$ is a pyridazin-4-yl group optionally substituted by one or two substituents selected from methyl, ethyl, methoxy and ethoxy. The pyridazinyl group may be a pyridazin-3-yl or pyridazin-4-yl group but typically is a pyridazin-4-yl. Particular substituents are methoxy groups and, for example, the pyridazinyl group may bear two methoxy substituents.

In embodiment (vi) $R^1$ is a substituted imidazothiazole group wherein the substituents are selected from methyl, ethyl, amino, fluorine, chlorine, amino and methylamino. A particular substituent is methyl.

In embodiment (vii) $R^1$ is an optionally substituted 1,3-dihydro-isoindol-2-yl or optionally substituted 2,3-dihydro-indol-1-yl group wherein the optional substituents in each case are selected from halogen, cyano, amino, $C_{1-4}$ mono- and dialkylamino, $CONH_2$ or CONH—$C_{1-4}$ alkyl $C_{1-4}$ alkyl and $C_{1-4}$ alkoxy wherein the $C_{1-4}$ alkyl and $C_{1-4}$ alkoxy groups are optionally substituted by hydroxy, methoxy, or amino.

Particular substituents are selected from methyl, ethyl, fluorine, chlorine (preferably only on the aryl ring of the dihydroindole or dihydroisoindole), $CONH_2$, amino, methylamino, dimethylamino and methoxy.

In one sub-group of compounds in embodiment (vii), the dihydroisoindole or dihydroindole are each unsubstituted.

In embodiment (viii) $R^1$ is 3-pyridyl optionally substituted by one or two substituents selected from hydroxy, halogen, cyano, amino, $C_{1-4}$ mono- and dialkylamino, $CONH_2$ or CONH—$C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino; but excluding the compounds 2-oxo-1,2-dihydro-pyridine-3-carboxylic acid [3-(5-morpholin-4-ylmethyl-1H-benzoimidazol-2-yl)-1H-pyrazol-4-yl]-amide and 2,6-dimethoxy-N-[3-(5-morpholin-4-ylmethyl-1H-benzoimidazol-2-yl)-1H-pyrazol-4-yl]-nicotinamide.

In one embodiment $R^1$ is 3-pyridyl optionally substituted by one or two substituents selected from hydroxy, halogen, cyano, amino, $C_{1-4}$ mono- and dialkylamino, $CONH_2$ or CONH—$C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino but where $R^1$ is 3-pyridyl, X is O, A is a bond and E is a bond the pyridyl has one or two substituents selected from halogen, cyano, amino, $C_{1-4}$ mono- and dialkylamino, $CONH_2$ or CONH—$C_{1-4}$ alkyl, $C_{1-4}$ alkyl and $C_{2-4}$ alkoxy wherein the $C_{1-4}$ alkyl and $C_{1-4}$ alkoxy groups are optionally substituted by hydroxy, methoxy, or amino.

Particular substituents are selected from methyl, ethyl, fluorine, chlorine, $CONH_2$, amino, methylamino, dimethylamino and methoxy. Further particular substituents are selected from methyl, ethyl, fluorine, chlorine, $CONH_2$, amino, methylamino, and dimethylamino.

In one sub-group of compounds, the 3-pyridyl group is unsubstituted.

In embodiment (ix) $R^1$ is thiomorpholine or an S-oxide or S,S-dioxide thereof optionally substituted by one or two substituents selected from halogen, cyano, amino, $C_{1-4}$ mono- and dialkylamino, $CONH_2$ or CONH—$C_{1-4}$ alkyl $C_{1-4}$ alkyl and $C_{1-4}$ alkoxy wherein the $C_{1-4}$ alkyl and $C_{1-4}$ alkoxy groups are optionally substituted by hydroxy, methoxy, or amino.

In one sub-group of compounds, the thiomorpholine or S-oxide or S,S-dioxide thereof is unsubstituted.

In embodiment (x), E-A is $NR^2$ and $R^1$ is selected from: 2-fluorophenyl, 3-fluorophenyl, 4-fluorophenyl, 2,4-difluorophenyl, 3,4-difluorophenyl, 2,5-difluorophenyl, 3,5-difluorophenyl, 2,4,6-trifluorophenyl, 2-methoxyphenyl, 5-chloro-2-methoxyphenyl, cyclohexyl, unsubstituted 4-tetrahydropyranyl and tert-butyl.

In embodiment (xi) E-A is $NR^2$ and $R^1$ is a group $NR^{10}R^{11}$ where $R^{10}$ and $R^{11}$ are each $C_{1-4}$ alkyl or $R^{10}$ and $R^{11}$ are linked so that $NR^{10}R^{11}$ forms a saturated heterocyclic group of 4 to 6 ring members optionally containing a second heteroatom ring member selected from O, N, S and $SO_2$, the heterocyclic group being optionally substituted by $C_{1-4}$ alkyl, amino or hydroxy.

Within this embodiment, one sub-group of compounds is the group of compounds wherein $R^{10}$ and $R^{11}$ are each $C_{1-4}$ alkyl, particularly methyl.

Another sub-group of compounds is the group of compounds wherein $R^{10}$ and $R^{11}$ are linked so that $NR^{10}R^{11}$ forms a saturated heterocyclic group of 4 to 6 ring members optionally containing a second heteroatom ring member selected from O, N, S and $SO_2$, the heterocyclic group being optionally substituted by $C_{1-4}$ alkyl, amino or hydroxy. The saturated heterocyclic group can be any of the nitrogen containing saturated heterocyclic groups listed above in the General Preferences and Definitions section but particular saturated heterocyclic groups include pyrrolidinyl, morpholinyl, piperazinyl and N—$C_{1-4}$ alkyl-piperazinyl groups. Such groups are typically unsubstituted or substituted by one or two methyl groups and, in one particular embodiment, are unsubstituted.

In embodiment (xii), E-A is $NR^2$ and $R^1$ is a pyridone group optionally substituted by one or two substituents selected from hydroxy, halogen, cyano, amino, $C_{1-4}$ mono- and dialkylamino, $CONH_2$, CONH—$C_{1-4}$ alkyl, $C_{1-4}$ alkyl and $C_{1-4}$ alkoxy wherein the $C_{1-4}$ alkyl and $C_{1-4}$ alkoxy groups are optionally substituted by hydroxy, methoxy, or amino.

The pyridone group may be N-substituted, for example with an alkyl group such as methyl, and may otherwise be unsubstituted.

In embodiment (xiii), E-A is C(CH$_3$)$_2$NR$^2$ or CH$_2$—NR$^2$ and R$^1$ is selected from unsubstituted 2-furyl and 2,6-difluorophenyl.

In embodiment (xiv), E-A is C(CH$_3$)$_2$NR$^2$ and R$^1$ is unsubstituted phenyl.

In embodiment (xv), E is CH$_2$ and R$^1$ is unsubstituted tetrahydropyran-4-yl.

When M is a group D2, R$^1$ can be selected from groups (xvi), (xvii), (xviii) and (xix).

Each individual group in the list of groups (xvi) to (xix) represents a separate embodiment for use in the combinations of the invention.

In embodiment (xvi) R$^1$ is a 2-substituted 3-furyl group of the formula:

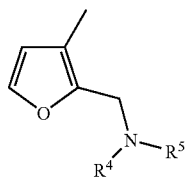

wherein R$^4$ and R$^5$ are the same or different and are selected from hydrogen and C$_{1-4}$ alkyl, or R$^4$ and R$^5$ are linked so that NR$^4$R$^5$ forms a 5- or 6-membered saturated heterocyclic group optionally containing a second heteroatom or group selected from O, NH, NMe, S or SO$_2$, the 5- or 6-membered saturated ring being optionally substituted by hydroxy, fluorine, amino, methylamino, methyl or ethyl.

In one embodiment R$^1$ is a 2-substituted 3-furyl group of the formula:

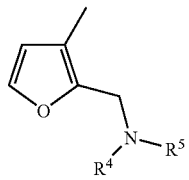

wherein R$^4$ and R$^5$ are the same or different and are selected from hydrogen and C$_{1-4}$ alkyl, or R$^4$ and R$^5$ are linked so that NR$^4$R$^5$ forms a 5- or 6-membered saturated heterocyclic group optionally containing a second heteroatom or group selected from O, NH, NMe, S or SO$_2$, the 5- or 6-membered saturated ring being optionally substituted by hydroxy, fluorine, amino, methylamino, methyl or ethyl but where A is bond and E is a bond, R$^4$ and R$^5$ are not linked so that NR$^4$R$^5$ forms a unsubstituted piperidine Particular saturated heterocyclic groups are as set out above in the General Preferences and Definitions section but particular saturated heterocyclic groups include pyrrolidinyl, morpholinyl, piperazinyl and N—C$_{1-4}$ alkyl-piperazinyl groups. Such groups are typically unsubstituted or substituted by one or two methyl groups and, in one particular embodiment, are unsubstituted.

Particular examples of compounds wherein R$^4$ and R$^5$ are selected from hydrogen and C$_{1-4}$ alkyl are methylamino and dimethylamino groups, more typically a dimethylamino group.

In embodiment (xvii), R$^1$ is a 5-substituted 2-furyl group of the formula:

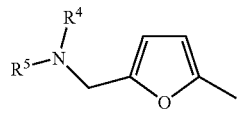

wherein R$^4$ and R$^5$ are the same or different and are selected from hydrogen and C$_{1-4}$ alkyl, or R$^4$ and R$^5$ are linked so that NR$^4$R$^5$ forms a 5- or 6-membered saturated heterocyclic group optionally containing a second heteroatom or group selected from O, NH, NMe, S or SO$_2$, the 5- or 6-membered saturated heterocyclic group being optionally substituted by hydroxy, fluorine, amino, methylamino, methyl or ethyl; with the proviso that the compound is not 5-piperidin-1-ylmethyl-furan-2-carboxylic acid [3-(5,6-dimethoxy-1H-benzoimidazol-2-yl)-1H-pyrazol-4-yl]-amide.

Particular saturated heterocyclic groups are as set out above in the General Preferences and Definitions section but particular saturated heterocyclic groups include pyrrolidinyl, morpholinyl, piperazinyl and N—C$_{1-4}$ alkyl-piperazinyl groups. Such groups are typically unsubstituted or substituted by one or two methyl groups and, in one particular embodiment, are unsubstituted.

In embodiment (xviii), R$^1$ is a group of the formula:

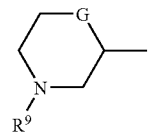

wherein R$^9$ is hydrogen, methyl, ethyl or isopropyl; G is CH, O, S, SO, SO$_2$ or NH and the group is optionally substituted by one, two or three substituents selected from C$_{1-4}$ hydrocarbyl, hydroxy, C$_{1-4}$ hydrocarbyloxy, fluorine, amino, mono- and di-C$_{1-4}$ alkylamino and wherein the C$_{1-4}$ hydrocarbyl and C$_{1-4}$ hydrocarbyloxy groups are each optionally substituted by hydroxy, fluorine, amino, mono- or di-C$_{1-4}$ alkylamino.

In one sub-group of compounds within embodiment (xix), G is selected from O and CH.

In embodiment (xviii), the group R$^1$ is typically unsubstituted or substituted by one or two methyl groups, and more typically is unsubstituted.

In embodiment (xix) R$^1$ is a 3,5-disubstituted phenyl group of the formula:

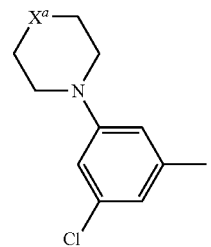

wherein X$^a$ is as X is selected from O, NH and NCH$_3$.
Preferably X$^a$ is N—CH$_3$.

Particular examples of the moiety R¹-A- are shown in Table X, the asterisk indicating the point of attachment to the carbonyl group C=O in the group R¹-E-A-C(=O)—NH—.
TABLE X
| Examples of the Moiety R¹-E-A- | |
|---|---|
| 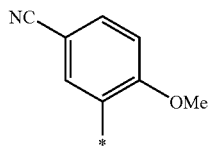 | A1 |
| 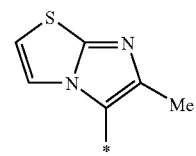 | A2 |
|  | A3 |
| 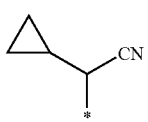 | A4 |
| 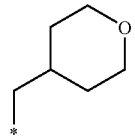 | A5 |
|  | A6 |
|  | A7 |
| 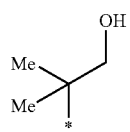 | A8 |
| 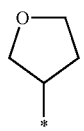 | A9 |
|  | A10 |
| 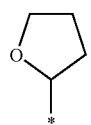 | A11 |
TABLE X-continued
| Examples of the Moiety R¹-E-A- | |
|---|---|
| 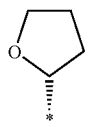 | A12 |
|  | A13 |
|  | A14 |
| 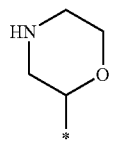 | A15 |
| 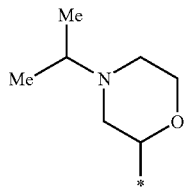 | A16 |
| 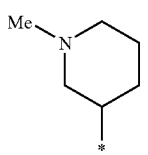 | A17 |
| 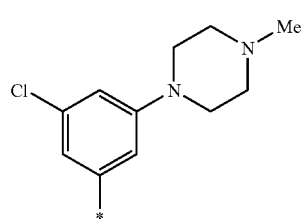 [SMILES: *c1cc(Cl)cc(N2CCN(C)CC2)c1] | A18 |
| 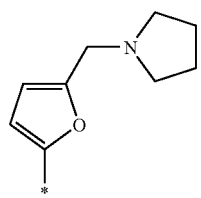 | A19 |
| 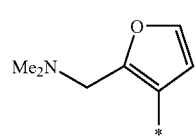 | A20 |

TABLE X-continued

Examples of the Moiety R¹-E-A-

| Structure | Label |
|---|---|
| morpholine-N-CH2-(3-furyl)-* | A21 |
| 4-Cl, 2-OMe phenyl-* | A22 |
| 2,6-difluorobenzyl-NH-* | A23 |
| cyclopropyl-NH-* | A24 |
| (2R,6S)-2,6-dimethylmorpholine-N-* | A25 |
| (tetrahydropyran-4-yl)methyl-NH-* | A26 |
| tetrahydropyran-4-yl-NH-* | A27 |
| isoindoline-N-* | A28 |
| indoline-N-* | A29 |
| pyrrolidin-1-yl-NH-* | A30 |
| Me2N-NH-* | A31 |
| morpholine-N-NH-* | A32 |
| Me-SO2-CH2CH2-NH-* | A33 |
| cyclopropyl-CH2-NH-* | A34 |
| pyridin-3-yl-NH-* | A35 |
| thiomorpholine-N-* | A36 |
| 4-F-phenyl-N(Me)-* | A37 |

TABLE X-continued
Examples of the Moiety R¹-E-A-
| | |
|---|---|
| 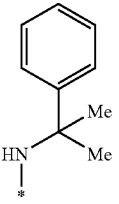 | A38 |
| 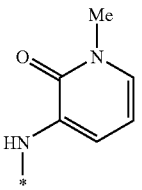 | A39 |
| 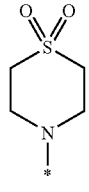 | A40 |
| 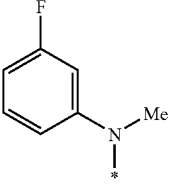 | A41 |
|  | A42 |
| 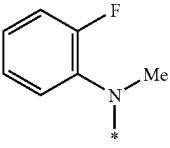 | A43 |
| 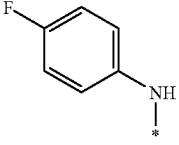 | A44 |
| 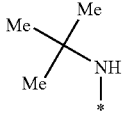 | A45 |
| 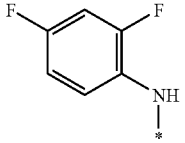 [SMILES: *Nc1ccc(F)cc1F] | A46 |
| 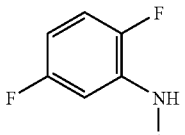 | A47 |
| 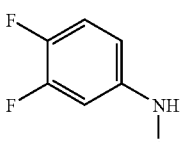 | A48 |
| 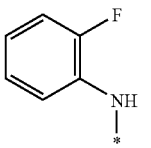 | A49 |
| 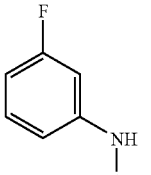 | A50 |
| 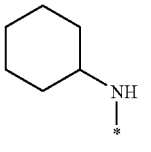 [SMILES: *NC1CCCCC1] | A51 |
| 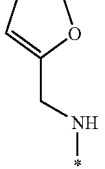 | A52 |
| 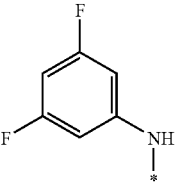 [SMILES: *Nc1cc(F)cc(F)c1] | A53 |
|  | A54 |

TABLE X-continued

Examples of the Moiety R¹-E-A-

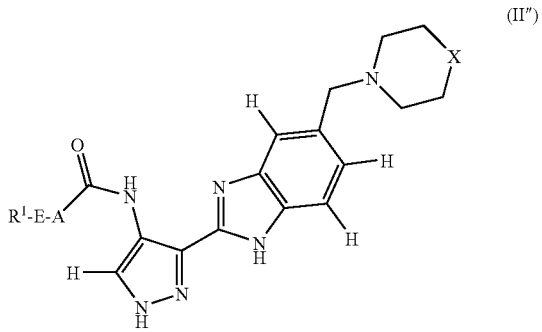

| | |
|---|---|
| (OMe, NH) | A55 |
| (Cl, OMe, NH) | A56 |
| (HN-iPr) | A57 |
| (HN-cyclobutyl) | A58 |
| (N(CH₃)-) | A59 |

In Table X, preferred groups R¹-E-A- include A1, A4, A10, A11, A13, A20, A22, A23, A24, A29, A30, A31, A32, A38, A42, A43, A44, A46, A47, A49, A54 and A56.

In another embodiment the group R¹-E-A is A57, A58 or A59.

A preferred sub-set of groups R¹-E-A- includes A1, A4, A20, A24, A30, A44, A46 and A54. Within this sub-set, one particular group R¹-A- is the group A24.

One sub-group of compounds for use in the combinations of the invention is represented by the formula (II″):

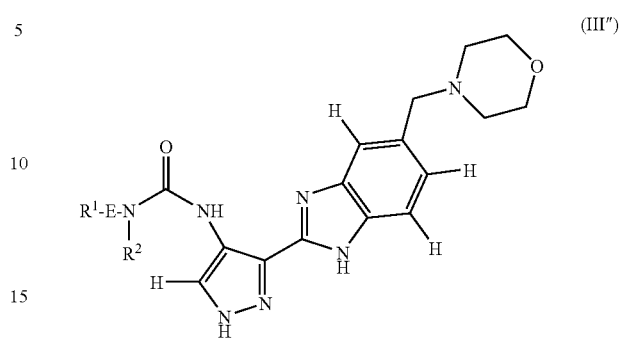

(II″)

wherein R¹, E, A and X are as defined herein.

Within formula (II″), one subset of compounds is the sub-set wherein X is O.

One sub-group of compounds of the formula (II″) can be represented by the formula (III″):

(III″)

Within formula (III), one sub-set of compounds is the sub-set wherein E is a bond.

Another sub-set of compounds within formula (III″) is the sub-set wherein E is CH₂ or C(CH₃)₂.

In one particularly preferred embodiment within formula (III″), E is a bond, R² is H and R¹ is a cycloalkyl group (i) as defined herein. In one embodiment the cycloalkyl group can be cyclopropyl or cyclobutyl. More preferably R¹ is a cyclopropyl group.

For the avoidance of doubt, it is to be understood that each general and specific preference, embodiment and example of the groups R¹ may be combined with each general and specific preference, embodiment and example of the groups R² and/or R³ and/or R⁴ and/or R⁵ and/or R⁶ and/or R⁷ and/or R⁸ and/or R⁹ and/or R¹⁰ and/or R¹¹ and/or D1 and/or D2 and/or A and/or E and/or X and/or Xᵃ and any sub-groups thereof as defined herein and that all such combinations are embraced by this application.

The various functional groups and substituents making up the compounds of the formula (I') are typically chosen such that the molecular weight of the compound of the formula (I') does not exceed 1000. More usually, the molecular weight of the compound will be less than 750, for example less than 700, or less than 650, or less than 600, or less than 550. More preferably, the molecular weight is less than 525 and, for example, is 500 or less.

Compounds of Sub-Group (C) of Formula (I″)

In one sub-group of compounds of the formula (I″) (i.e. sub-group (C) of formula (I″)), M is a group D1; X is O; A is a group NR² where R² is hydrogen; E is a bond; R¹ is 2,6-difluorophenyl; and the compound is an acid addition salt formed from a selected group of acids.

Accordingly, in one embodiment, the combinations comprise an acid addition salt of 1-(2,6-difluorophenyl)-N-[3-(5-morpholin-4-ylmethyl-1H-benzimidazol-2-yl)-1H-pyrazol-4-yl]-urea which is a salt formed with an acid selected from the group consisting of acetic, adipic, alginic, ascorbic (e.g. L-ascorbic), aspartic (e.g. L-aspartic), benzenesulphonic, benzoic, camphoric (e.g. (+) camphoric), capric, caprylic, carbonic, citric, cyclamic, dodecanoate, dodecylsulphuric, ethane-1,2-disulphonic, ethanesulphonic, fumaric, galactaric, gentisic, glucoheptonic, D-gluconic, glucuronic (e.g. D-glucuronic), glutamic (e.g. L-glutamic), α-oxoglutaric, glycolic, hippuric, hydrochloric, isethionic, isobutyric, lactic (e.g. (+)-L-lactic and (±)-DL-lactic), lactobionic, laurylsulphonic, maleic, malic, (−)-L-malic, malonic, methanesulphonic, mucic, naphthalenesulphonic (e.g. naphthalene-2-sulphonic), naphthalene-1,5-disulphonic, nicotinic, oleic, orotic, oxalic, palmitic, pamoic, phosphoric, propionic, sebacic, stearic, succinic, sulphuric, tartaric (e.g. (+)-L-tartaric), thiocyanic, toluenesulphonic (e.g. p-toluenesulphonic), valeric and xinafoic acids.

In one embodiment, the acid addition salt is formed from an acid selected from the group consisting of adipic, alginic, ascorbic (e.g. L-ascorbic), aspartic (e.g. L-aspartic), benzoic, camphoric (e.g. (+) camphoric), capric, caprylic, carbonic, cyclamic, dodecanoate, dodecylsulphuric, ethane-1,2-disulphonic, galactaric, gentisic, glucoheptonic, D-gluconic, glutamic (e.g. L-glutamic), α-oxoglutaric, glycolic, hippuric, isobutyric, laurylsulphonic, mucic, naphthalene-1,5-disulphonic, nicotinic, oleic, orotic, oxalic, palmitic, pamoic, sebacic, stearic, tartaric (e.g. (+)-L-tartaric), thiocyanic and xinafoic acids.

In another embodiment, the acid addition salt is formed from an acid selected from the group consisting of acetic, adipic, ascorbic, aspartic, citric, DL-lactic, fumaric, gluconic, glucuronic, hippuric, hydrochloric, glutamic, DL-malic, p-toluenesulphonic, methanesulphonic (mesylate), ethanesulphonic (esylate), sebacic, stearic, succinic and tartaric acids.

In a further embodiment, the acid addition salt is formed from an acid selected from the group consisting of adipic, ascorbic, aspartic, gluconic, hippuric, glutamic, sebacic, stearic and tartaric acids.

In another particular embodiment, the compound is an acid addition salt formed with hydrochloric acid.

Preferred salts are salts having a solubility in a given liquid carrier (e.g. water) of greater than 25 mg/ml of the liquid carrier (e.g. water), more typically greater than 50 mg/ml and preferably greater than 100 mg/ml. Such salts are particularly advantageous for administration in a liquid form, for example by injection or infusion.

Salts for use in the combinations of the invention that have a solubility of greater than 25 mg/ml include the D-glucuronate, mesylate, esylate and DL-lactate salts, the latter three of which have solubilities in excess of 100 mg/ml.

Accordingly, in one particular embodiment, the combinations comprise a mesylate salt of 1-(2,6-difluorophenyl)-N-[3-(5-morpholin-4-ylmethyl-1H-benzimidazol-2-yl)-1H-pyrazol-4-yl]-urea.

In another particular embodiment, the combinations comprise an esylate (ethanesulphonate) salt of 1-(2,6-difluorophenyl)-N-[3-(5-morpholin-4-ylmethyl-1H-benzimida-zol-2-yl)-1H-pyrazol-4-yl]-urea.

In a further particular embodiment, the combinations comprise a DL lactate salt of 1-(2,6-difluorophenyl)-N-[3-(5-morpholin-4-ylmethyl-1H-benzimidazol-2-yl)-1H-pyrazol-4-yl]-urea. In one embodiment, the lactate salt is the L-lactate.

The free base or parent compound from which the compounds (i.e. acid addition salts) of sub-group (C) of Formula (I') are derived have the formula (IA):

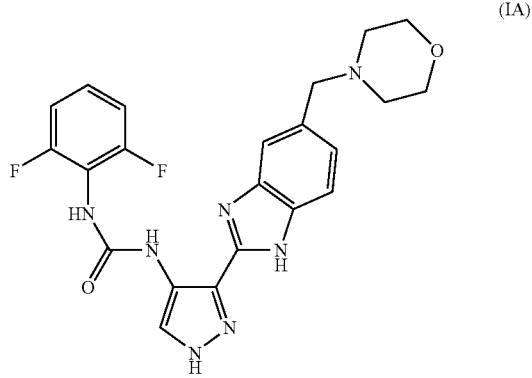 [SMILES: O=C(Nc1c[nH]nc1-c1nc2cc(CN3CCOCC3)ccc2[nH]1)Nc1c(F)cccc1F]

(IA)

Particular compounds for use in the combinations of the invention are as illustrated in the examples below.

One preferred compound for use in the combinations of the invention is 1-cyclopropyl-3-[3-(5-morpholin-4-ylmethyl-1H-benzoimidazol-2-yl)-1H-pyrazol-4-yl]-urea and salts (e.g. the lactate or citrate salts or mixtures thereof), solvates and tautomers thereof.

In one embodiment, the salt of 1-cyclopropyl-3-[3-(5-morpholin-4-ylmethyl-1H-benzoimidazol-2-yl)-1H-pyrazol-4-yl]-urea may be the acetate, mesylate, ethanesulphonate, DL-lactate, adipate, D-glucuronate, D-gluconate or hydrochloride salt.

Lactate and Citrate Salts, Mixtures and Crystal Thereof of Formula (I)

The invention provides inter alia combinations comprising an ancillary compound and one or more lactate and/or citrate salts of the compound 1-cyclopropyl-3-[3-(5-morpholin-4-ylmethyl-1H-benzoimidazol-2-yl)-1H-pyrazol-4-yl]-urea (or crystalline forms thereof).

The invention also provides novel processes for preparing combinations comprising the compound, the lactate salts and crystalline forms thereof.

The invention further provides therapeutic uses of the combinations.

Accordingly, in a first aspect, the invention provides a combination comprising an ancillary compound and a salt of 1-cyclopropyl-3-[3-(5-morpholin-4-ylmethyl-1H-benzoimidazol-2-yl)-1H-pyrazol-4-yl]-urea selected from the lactate, citrate and mixtures thereof.

The free base of 1-cyclopropyl-3-[3-(5-morpholin-4-ylmethyl-1H-benzoimidazol-2-yl)-1H-pyrazol-4-yl]-urea from which the salts are derived has the formula (I):

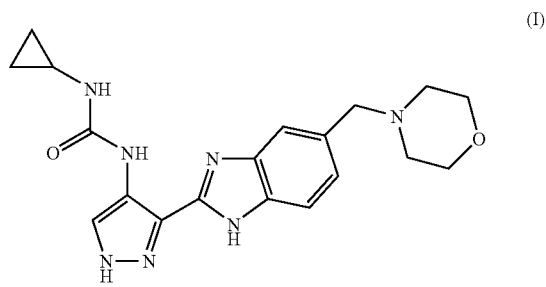 [SMILES: O=C(Nc1c[nH]nc1-c1nc2cc(CN3CCOCC3)ccc2[nH]1)NC1CC1]

(I)

The compound of the formula (I) may be referred to in this application by its chemical name, 1-cyclopropyl-3-[3-(5-morpholin-4-ylmethyl-1H-benzoimidazol-2-yl)-1H-pyrazol-4-yl]-urea, or, for convenience, as "the compound I", "the compound of formula (I)". Each of these synonyms refers to the compound shown in formula (I) above and having the chemical name 1-cyclopropyl-3-[3-(5-morpholin-4-ylmethyl-1H-benzoimidazol-2-yl)-1H-pyrazol-4-yl]-urea.

References to the compound 1-cyclopropyl-3-[3-(5-morpholin-4-ylmethyl-1H-benzoimidazol-2-yl)-1H-pyrazol-4-yl]-urea free base and its lactate or citrate salts or mixtures thereof include within their scope all solvates, tautomers and isotopes thereof and, where the context admits, N-oxides, other ionic forms and prodrugs. Therefore reference to the alternative tautomer of formula (I), 1-cyclopropyl-3-[3-(6-morpholin-4-ylmethyl-1H-benzoimidazol-2-yl)-1H-pyrazol-4-yl]-urea is to be understood to refer to compound (I).

The invention also provides the further combinations, uses, methods and processes as set out in the claims below.

For convenience the salts formed from L-lactic acid, and citric acid may be referred to herein as the L-lactate salts and citrate salts respectively.

In one particular embodiment the salt is the L-lactate or D-lactate, preferably L-lactate.

In another embodiment, the salt is a salt formed with citric acid.

More particularly the salts are a mixture of the L-lactate salts and citrate salts.

In the solid state, the lactate (particularly the L-lactate) or citrate salts for use in the combinations of the invention can be crystalline or amorphous or a mixture thereof.

In one embodiment, the lactate (particularly the L-lactate) or citrate salts are amorphous.

In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

In another embodiment, the lactate (particularly the L-lactate) or citrate salts are substantially crystalline i.e. they may be from 50% to 100% crystalline, and more particularly they may be at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

In a further embodiment, the lactate or citrate salts are selected from the group consisting of lactate (particularly the L-lactate) or citrate salts that are from 50% to 100% crystalline, for example at least 50% crystalline, at least 60% crystalline, at least 70% crystalline, at least 80% crystalline, at least 90% crystalline, at least 95% crystalline, at least 98% crystalline, at least 99% crystalline, at least 99.5% crystalline, and at least 99.9% crystalline, for example 100% crystalline.

More preferably the lactate (particularly the L-lactate) or citrate salts may be those (or may be selected from the group consisting of those) that are 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

One example of a substantially crystalline salt is a crystalline salt formed with L-lactic acid.

Another example of a substantially crystalline salt is a crystalline salt formed with citric acid.

The salts for use in the combinations of the invention, in the solid state, can be solvated (e.g. hydrated) or non-solvated (e.g. anhydrous).

In one embodiment, the salts are non-solvated (e.g. anhydrous).

A further example of a non-solvated salt is the crystalline salt formed with lactic acid (particularly L-lactic acid) as defined herein.

In one embodiment the crystalline form of the salt of Formula (I') is selected from L-lactate salt and citrate salt, in particular the L-lactate salt.

The term "anhydrous" as used herein does not exclude the possibility of the presence of some water on or in the salt (e.g. a crystal of the salt). For example, there may be some water present on the surface of the salt (e.g. salt crystal), or minor amounts within the body of the salt (e.g. crystal). Typically, an anhydrous form contains fewer than 0.4 molecules of water per molecule of compound, and more preferably contains fewer than 0.1 molecules of water per molecule of compound, for example 0 molecules of water.

In another embodiment, the lactate (particularly the L-lactate) or citrate salts are solvated. Where the salts are hydrated, they can contain, for example, up to three molecules of water of crystallisation, more usually up to two molecules of water, e.g. one molecule of water or two molecules of water. Non-stoichiometric hydrates may also be formed in which the number of molecules of water present is less than one or is otherwise a non-integer. For example, where there is less than one molecule of water present, there may be for example 0.4, or 0.5, or 0.6, or 0.7, or 0.8, or 0.9 molecules of water present per molecule of compound.

Other solvates include alcoholates such as ethanolates and isopropanolates.

In one embodiment, the lactic acid salt (particularly the L-lactate) is solvated for example with water and/or ethanol.

The lactate (particularly the L-lactate) or citrate salts for use in the combinations of the present invention can be synthesized from the parent compound 1-cyclopropyl-3-[3-(5-morpholin-4-ylmethyl-1H-benzoimidazol-2-yl)-1H-pyrazol-4-yl]-urea by conventional chemical methods such as methods described in Pharmaceutical Salts: *Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the parent compound 1-cyclopropyl-3-[3-(5-morpholin-4-ylmethyl-1H-benzoimidazol-2-yl)-1H-pyrazol-4-yl]-urea with the appropriate acid in water or in an organic solvent, or in a mixture of the two; generally, non-aqueous media such as ether, ethyl acetate, ethanol, isopropanol, or acetonitrile are used.

The combinations may be prepared by a method which comprises preparing a lactate (particularly the L-lactate) or citrate salt of 1-cyclopropyl-3-[3-(5-morpholin-4-ylmethyl-1H-benzoimidazol-2-yl)-1H-pyrazol-4-yl]-urea, which method comprises forming a solution of 1-cyclopropyl-3-[3-(5-morpholin-4-ylmethyl-1H-benzoimidazol-2-yl)-1H-pyrazol-4-yl]-urea free base in a solvent (typically an organic solvent) or mixture of solvents, and treating the solution with an acid to form a precipitate of the salt.

The acid may be added as a solution in a solvent which is miscible with the solvent in which the free base is dissolved. The solvent in which the free base is initially dissolved may be one in which the salt thereof is insoluble. Alternatively, the solvent in which the free base is initially dissolved may be one in which the salt is at least partially soluble, a different solvent in which the salt is less soluble subsequently being added such that the salt precipitates out of solution.

In an alternative method of forming a salt, 1-cyclopropyl-3-[3-(5-morpholin-4-ylmethyl-1H-benzoimidazol-2-yl)-1H-pyrazol-4-yl]-urea is dissolved in a solvent comprising a volatile acid and optionally a co-solvent, thereby to form a solution of the salt with the volatile acid, and the resulting solution is then concentrated or evaporated to isolate the salt.

The combinations may be prepared by a method which comprises forming a lactate (particularly the L-lactate) or citrate salt of 1-cyclopropyl-3-[3-(5-morpholin-4-ylmethyl-1H-benzoimidazol-2-yl)-1H-pyrazol-4-yl]-urea as defined herein, which method comprises treating a compound of the formula (I):

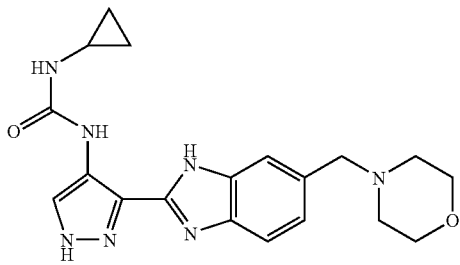

(I)

with an organic or inorganic acid as defined herein in an organic solvent, and optionally isolating the salt thus formed.

The lactate (particularly the L-lactate) or citrate salt is typically precipitated from the organic solvent as it is formed and hence can be isolated by separation of the solid from the solution, e.g. by filtration.

One salt form can be converted to the free base and optionally to another salt form by methods well known to the skilled person. For example, the free base can be formed by passing the salt solution through a column containing an amine stationary phase (e.g. a Strata-$NH_2$ column). Alternatively, a solution of the salt in water can be treated with sodium bicarbonate to decompose the salt and precipitate out the free base. The free base may then be combined with another acid by one of the methods described above or elsewhere herein.

The lactate (particularly the L-lactate) or citrate salts have a number of advantages over the corresponding free base. For example, the salts will enjoy one or more of the following advantages over the free base in that they:
  will be more soluble in particular they will have improved solubility in aqueous solution and hence will be better for i.v. administration (e.g. by infusion)
  will allow control of solution pH and therefore better for i.v. administration;
  will have better stability for example thermal stability (e.g. improved shelf life);
  will have advantages for production;
  will have better physicochemical properties;
  may have improved anti-cancer activity; and
  may have an improved therapeutic index.

The crystalline lactate salt (particularly the L-lactate) for use in the combinations of the invention is particularly advantageous as it is:
  non-hygroscopic
  anhydrous and does not form hydrates
  single polymorphic form
  crystalline
  stable to storage
  has sharp melting point and no form changes in DSC experiment.
  has good solubility in water, and gives better solubility in buffer systems.

The term 'stable' or 'stability' as used herein includes chemical stability and solid state (physical) stability. The term 'chemical stability' means that the compound can be stored in an isolated form, or in the form of a formulation in which it is provided in admixture with for example, pharmaceutically acceptable carriers, diluents or adjuvants as described herein, under normal storage conditions, with little or no chemical degradation or decomposition. 'Solid-state stability' means the compound can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g. hydration, dehydration, solvatisation, desolvatisation, crystallisation, recrystallisation or solid-state phase transition).

Preferred salts for use in the preparation of liquid (e.g. aqueous) pharmaceutical compositions are the salts of the compounds of formulae (I) and (I') described herein (i.e. the lactate or citrate or mixtures thereof as defined herein) having a solubility in a given liquid carrier (e.g. water or buffered systems) of greater than 1 mg/ml, typically greater than 5 mg/ml of the liquid carrier (e.g. water), more typically greater than 15 mg/ml, more typically greater than 20 mg/ml and preferably greater than 25 mg/ml.

In another aspect, there is provided a pharmaceutical composition comprising combinations based on an aqueous solution containing the lactate salt (particularly the L-lactate) or citrate salt or mixtures thereof of 1-cyclopropyl-3-[3-(5-morpholin-4-ylmethyl-1H-benzoimidazol-2-yl)-1H-pyrazol-4-yl]-urea (such as) in a concentration of greater than 1 mg/ml, typically greater than 5 mg/ml of the liquid carrier (e.g. water or buffered systems), more typically greater than 15 mg/ml, more typically greater than 20 mg/ml and preferably greater than 25 mg/ml.

In a preferred embodiment, the pharmaceutical composition comprises a combination based on an aqueous solution containing the L-lactate salt of 1-cyclopropyl-3-[3-(5-morpholin-4-ylmethyl-1H-benzoimidazol-2-yl)-1H-pyrazol-4-yl]-urea in a concentration of greater than 1 mg/ml, typically greater than 5 mg/ml of the liquid carrier (e.g. water), more typically greater than 15 mg/ml, typically greater than 20 mg/ml and preferably greater than 25 mg/ml.

In another aspect, the invention provides a combination based on an aqueous solution of the lactate salt (particularly the L-lactate) or citrate salt or mixtures thereof of 1-cyclopropyl-3-[3-(5-morpholin-4-ylmethyl-1H-benzoimidazol-2-yl)-1H-pyrazol-4-yl]-urea, wherein the aqueous solution has a pH of 2 to 6, for example 2 to 5, and more particularly 4 to 6 such as 4 to 5.

In the aqueous solutions defined above, the salt may be any of the salts described herein but, in one preferred embodiment is the L-lactate salt. In one preferred embodiment, the salt is a mixture of L-lactate and citrate salts.

The invention also provides combinations based on an aqueous solution of 1-cyclopropyl-3-[3-(5-morpholin-4-ylmethyl-1H-benzoimidazol-2-yl)-1H-pyrazol-4-yl]-urea in protonated form together with one or more counter ions and optionally one or more further counter ions. In one embodiment one of the counter ions is selected from lactate and citrate. In another embodiment one of the counter ions is from the formulation buffer as described herein such as citrate. In a further embodiment there may be one or more further counter ions such as a chloride ion (e.g. from saline).

The invention therefore provides combinations based on an aqueous solution of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate, and optionally one or more further counter ions such as a chloride ion.

In the situation where there is more than one counter ions the aqueous solution of 1-cyclopropyl-3-[3-(5-morpholin-4-ylmethyl-1H-benzoimidazol-2-yl)-1H-pyrazol-4-yl]-urea in protonated form will potentially contain a mixture of counter ions for example a mixture of L-lactate and citrate counter ions and optionally one or more further counter ions such as a chloride ion.

The invention therefore provides combinations based on an aqueous solution of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate and optionally one or more further counter ions such as a chloride ion, and a mixture thereof.

The invention also provides combinations based on an aqueous solution of 1-cyclopropyl-3-[3-(5-morpholin-4-ylmethyl-1H-benzoimidazol-2-yl)-1H-pyrazol-4-yl]-urea in protonated form together with one or more counter ions and optionally one or more IV excipients for dilution to achieve isotonic formulation. In one embodiment one of the counter ions is selected from L-lactate and citrate. In another embodiment one of the counter ions is from the formulation buffer as described herein such as citrate. In a further embodiment there may be one or more IV excipients as detailed in the United States Pharmacopoeia and the National Formulary such as a hexose sugar e.g. dextrose (D-glucose). The invention therefore provides combinations based on an aqueous solution of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate, and optionally one or more IV excipients such as dextrose. In the situation where there is more than one counter ions the aqueous solution of 1-cyclopropyl-3-[3-(5-morpholin-4-ylmethyl-1H-benzoimidazol-2-yl)-1H-pyrazol-4-yl]-urea in protonated form will potentially contain a mixture of counter ions for example a mixture of lactate and citrate counter ions and optionally one or more further IV excipients such as a dextrose. The invention therefore provides combinations based on an aqueous solution of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate and optionally one or more further IV excipients such as a dextrose, and a mixture thereof.

The aqueous solutions can be formed inter alia by dissolving a lactate salt in a solution of citrate ions (e.g a citrate buffer) or by dissolving a citrate salt in a solution of lactate ions. The lactate and citrate ions may be present in the solution in a lactate:citrate ratio of from 10:1 or less, for example 10:1 to 1:10, more preferably less then 8:1, or less than 7:1, or less than 6:1, or less than 5:1 or less than 4:1 or less than 3:1 or less than 2:1 or less than 1:1, more particularly from 1:1 to 1:10. In one embodiment, the lactate and citrate ions are present in the solution in a lactate:citrate ratio of from 1:1 to 1:10, for example 1:1 to 1:8, or 1:1 to 1:7 or 1:1 to 1:6 or 1:1 to 1:5, e.g. approximately 1:4.4.

The aqueous solutions of the salts may be buffered or unbuffered but in one embodiment are buffered.

In another aspect, there is provided a combination based on pharmaceutical composition comprising a lyophilised formulation containing the lactate salt or citrate salt or mixtures thereof of 1-cyclopropyl-3-[3-(5-morpholin-4-ylmethyl-1H-benzoimidazol-2-yl)-1H-pyrazol-4-yl]-urea, wherein the formulation has a pH of 2 to 6, for example 2 to 5, and more particularly 4 to 6 such as 4 to 5.

In one preferred embodiment the lyophilised formulation defined above, the salt is the L-lactate.

The invention also provides a combination based on a lyophilised formulation of 1-cyclopropyl-3-[3-(5-morpholin-4-ylmethyl-1H-benzoimidazol-2-yl)-1H-pyrazol-4-yl]-urea in protonated form together with one or more counter ions. In one embodiment one of the counter ions is L-lactate. In another embodiment one of the counter ions is from the formulation buffer as described herein such as citrate.

The invention therefore provides a combinations based on a lyophilised formulation of 1-cyclopropyl-3-[3-(5-morpholin-4-ylmethyl-1H-benzoimidazol-2-yl)-1H-pyrazol-4-yl]-urea in protonated form together with one or more counter ions selected from L-lactate and citrate. In the situation where there is more than one counter ions the aqueous solution of 1-cyclopropyl-3-[3-(5-morpholin-4-ylmethyl-1H-benzoimidazol-2-yl)-1H-pyrazol-4-yl]-urea in protonated form will potentially contain a mixture of counter ions for example a mixture of L-lactate and citrate counter ions.

The invention therefore provides a combination based on lyophilised formulation of 1-cyclopropyl-3-[3-(5-morpholin-4-ylmethyl-1H-benzoimidazol-2-yl)-1H-pyrazol-4-yl]-urea in protonated form together with one or more counter ions selected from lactate, citrate and a mixture thereof.

In one preferred embodiment the lyophilised formulation defined above, the salt is a L-lactate and the buffer salt is citrate.

In one embodiment, the lactate and citrate ions are present in the lyophilised formulation in a lactate:citrate ratio of from 10:1 or less, for example 10:1 to 1: 10, more preferably less then 8:1, or less than 7:1, or less than 6:1, or less than 5:1 or less than 4:1 or less than 3:1 or less than 2:1 or less than 1:1, more particularly from 1:1 to 1: 10, for example 1:1 to 1:8, or 1:1 to 1:7 or 1:1 to 1:6 or 1:1 to 1:5, e.g. approximately 1:4.4.

The lyophilised formulation of the salts may be buffered or unbuffered but in one embodiment are buffered.

In the context of the salt formed with lactic acid, a preferred buffer is a buffer formed from citric acid and corrected with NaOH or HCl to the correct pH, for example at a solution pH of approximately 4.5. At this pH and in the citrate buffer, the free base has a solubility of about 80 mg/ml respectively.

The lyophilised formulation is then reconstituted into a sterile aqueous solution containing an IV excipient such as saline or dextrose, preferably dextrose.

The salts for use in the combinations of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms therefore also find utility according to the invention.

The compound 1-cyclopropyl-3-[3-(5-morpholin-4-ylmethyl-1H-benzoimidazol-2-yl)-1H-pyrazol-4-yl]-urea may also form N-oxides. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compound 1-cyclopropyl-3-[3-(5-morpholin-4-yl methyl-1H-benzoimidazol-2-yl)-1H-pyrazol-4-yl]-urea, from which the lactate or citrate salts for use in the invention are derived, may exist in a number of different tautomeric forms and references in this application to the compound include all such forms.

More particularly, in the lactate or citrate salts of 1-cyclopropyl-3-[3-(5-morpholin-4-ylmethyl-1H-benzoimidazol-2-yl)-1H-pyrazol-4-yl]-urea for use in the combinations of the invention, the benzoimidazole group may take either of the following two tautomeric forms A and B. For simplicity, the general formula (I) illustrates forms A but the formula is to be taken as embracing all four tautomeric forms.

A

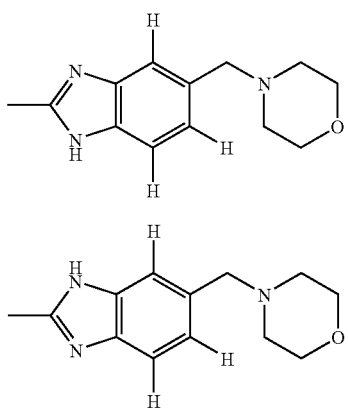

B

Moreover, in the context of the the lactate or citrate salts of 1-cyclopropyl-3-[3-(6-morpholin-4-ylmethyl-1H-benzoimidazol-2-yl)-1H-pyrazol-4-yl]-urea, references to the alternative tautomer, are clearly references to the lactate or citrate salts of the same compound as 1-cyclopropyl-3-[3-(5-morpholin-4-ylmethyl-1H-benzoimidazol-2-yl)-1H-pyrazol-4-yl]-urea.

The pyrazole ring may also exhibit tautomerism and can exist in the two tautomeric forms C and D below.

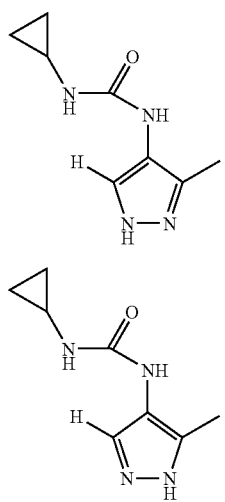

C

D

In addition cis and trans conformations of the urea are possible.

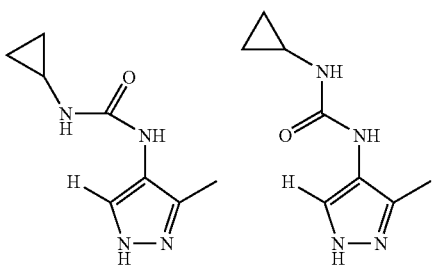

References to the lactate or citrate salts (e.g. the L-lactate salt) of 1-cyclopropyl-3-[3-(5-morpholin-4-ylmethyl-1H-benzoimidazol-2-yl)-1H-pyrazol-4-yl]-urea and the salts for use in the combinations of the invention also include variants with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one case, the compounds contain no radioactive isotopes. Such compounds are preferred for therapeutic use. In another case, however, the compound may contain one or more radioisotopes. Compounds containing such radioisotopes may be useful in a diagnostic context.

Also encompassed by references to 1-cyclopropyl-3-[3-(5-morpholin-4-ylmethyl-1H-benzoimidazol-2-yl)-1H-pyrazol-4-yl]-urea and the salts are any polymorphic forms, solvates (e.g. hydrates), complexes (e.g. inclusion complexes or clathrates with compounds such as cyclodextrins, or complexes with metals) thereof.

Crystal Structures of 1-Cyclopropyl-3-[3-(5-morpholin-4-ylmethyl-1H-benzoimidazol-2-yl)-1H-pyrazol-4-yl]-urea As described above, the lactate or citrate salts of 1-cyclopropyl-3-[3-(5-morpholin-4-ylmethyl-1H-benzoimidazol-2-yl)-1H-pyrazol-4-yl]-urea can be amorphous or substantially crystalline. In one particular embodiment, the lactate or citrate salts are substantially crystalline, the term "substantially crystalline" having the meaning defined above. In particular the lactate salt of 1-cyclopropyl-3-[3-(5-morpholin-4-ylmethyl-1H-benzoimidazol-2-yl)-1H-pyrazol-4-yl]-urea is substantially crystalline.

Where the lactate salt (particularly the L-lactate) of 1-cyclopropyl-3-[3-(5-morpholin-4-ylmethyl-1H-benzoimidazol-2-yl)-1H-pyrazol-4-yl]-urea is substantially crystalline, one single crystalline form may predominate, although other crystalline forms may be present in minor and preferably negligible amounts.

The crystalline forms of 1-cyclopropyl-3-[3-(5-morpholin-4-ylmethyl-1H-benzoimidazol-2-yl)-1H-pyrazol-4-yl]-urea contain less than or equal to about 5% by weight other crystalline forms of 1-cyclopropyl-3-[3-(5-morpholin-4-ylmethyl-1H-benzoimidazol-2-yl)-1H-pyrazol-4-yl]-urea, in particular containing less than or equal to about 1% by weight of other crystalline forms.

In a preferred embodiment, the invention provides combinations based on a substantially crystalline salt (e.g. a lactate salt (particularly the L-lactate) as defined herein) of 1-cyclopropyl-3-[3-(5-morpholin-4-ylmethyl-1H-benzoimidazol-2-yl)-1H-pyrazol-4-yl]-urea containing a single crystalline form of the salt and no more than 5% by weight of any other crystalline forms of the salt.

Preferably, the single crystalline form is accompanied by less than 4%, or less than 3%, or less than 2% of other crystalline forms, and in particular contains less than or equal to about 1 % by weight of other crystalline forms. More preferably, the single crystalline form is accompanied by less than 0.9%, or less than 0.8%, or less than 0.7%, or less than 0.6%, or less than 0.5%, or less than 0.4%, or less than 0.3%, or less than 0.2%, or less than 0.1 %, or less than 0.05%, or less than 0.01 %, by weight of other crystalline forms, for example 0% by weight of other crystalline forms.

The crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD.

Determination of the crystal structure of a compound can be performed by X-ray crystallography which can be carried out according to the conventional methods such as those described herein and in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal.

The crystal structure of the lactate salt and the dihydrate free base of 1-cyclopropyl-3-[3-(5-morpholin-4-ylmethyl-1H-benzoimidazol-2-yl)-1H-pyrazol-4-yl]-urea has been determined by X-ray crystallography as described in WO 2006/070195.

Tables 2 and 4 of WO 2006/070195 give coordinate data for crystals of 1-cyclopropyl-3-[3-(5-morpholin-4-ylmethyl-1H-benzoimidazol-2-yl)-1H-pyrazol-4-yl]-urea in Crystallographic Information File (CIF) Format (see Hall, Allen and Brown, *Acta Cryst.* (1991). A47, 655-685; http://www.iucr.ac.uk/iucr-top/cif/home.html). Alternative file formats such as a PDB file format (e.g. format consistent with that of the EBI Macromolecular Structure Database (Hinxton, UK)) may be used or preferred by others of skill in the art. However it will be apparent that the use of a different file format to present or manipulate the coordinates of the Tables of WO 2006/070195 (the content of which is incorporated herein by reference) is contemplated. The numbers in brackets in these Tables represent the deviation (s.u., standard uncertainty). The crystal structure of the lactate salt is illustrated in FIGS. 4 and 5 of WO 2006/070195.

In one embodiment the invention provides combinations based on a lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and has a crystal structure as defined by the coordinates in Table 4 in Example 71 of WO 2006/070195 at page 205 (the content of which is incorporated herein by reference).

In another embodiment the invention provides combinations based on a lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and has a crystal structure as set out in FIGS. 4 and 5 of WO 2006/070195.

In another embodiment the invention provides combinations based on a lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and has a crystal structure that belongs belong to an orthorhombic space group $P2_12_12_1$ (#19) and has crystal lattice parameters at 97(2) K a=9.94(10), b=15.03(10), c=16.18(10) Å, $\alpha=\beta=\gamma=90°$.

In another embodiment the invention provides combinations based on a lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and has crystal lattice parameters at room temperature a=10.08 (10), b=15.22(10), c=16.22(10) Å, $\alpha=\beta=\gamma=90°$.

Accordingly, in another embodiment, the invention provides combinations based on a lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and:

(a) has a crystal structure as set out in FIGS. 4 and 5; and/or
(b) has a crystal structure as defined by the coordinates in Table 4 in Example 71 of WO 2006/070195 at page 205-209 (the content of which is incorporated herein by reference); and/or
(c) has crystal lattice parameters at 97(2) K a=9.94(10), b=15.03(10), c=16.18(10) Å, $\alpha=\beta=\gamma=90°$; and/or
(d) has crystal lattice parameters at room temperature a=10.08(10), b=15.22(10), c=16.22(10) Å, $\alpha=\beta=\gamma=90°$; and/or
(e) has a crystal structure that belongs belong to an orthorhombic space group $P2_12_12_1$ (#19).

The substantially crystalline salts preferably are substantially free of residual organic solvent used, e.g. to recrystallise or otherwise purify the salt, or other solvent such as water.

In one embodiment the crystals of the lactate salt (particularly the L-lactate) of the compounds of Formula (I) in particular lactate salt of 1-cyclopropyl-3-[3-(5-morpholin-4-ylmethyl-1H-benzoimidazol-2-yl)-1H-pyrazol-4-yl]-urea are crystals which contain less than 10% by weight of residual solvent (e.g. water or an organic solvent), for example less than 5% residual solvent.

In one embodiment, the crystalline salts (e.g. the lactate salts -particularly the L-lactate) are anhydrous, the term "anhydrous" having the meaning defined above.

In another embodiment the crystalline lactate salt of 1-cyclopropyl-3-[3-(5-morpholin-4-ylmethyl-1H-benzoimidazol-2-yl)-1H-pyrazol-4-yl]-urea contains residual organic solvent e.g. ethanol in the range of about 0 to 5% by weight for example about 2% ethanol.

Alternatively, the crystalline structure of a compound can be analysed by the solid state technique of X-ray Powder Diffraction (XRPD). XRPD can be carried out according to the conventional methods such as those described in WO 2006/070195 and in Introduction to X-ray Powder Diffraction, Ron Jenkins and Robert L. Snyder (John Wiley & Sons, New York, 1996). The presence of defined peaks (as opposed to random background noise) in an XRPD diffractogram indicates that the compound has a degree of crystallinity.

A compound's X-ray powder pattern is characterised by the diffraction angle ($2\theta$) and interplanar spacing (d) parameters of an X-ray diffraction spectrum. These are related by Bragg's equation, $n\lambda=2d \sin \theta$, (where n=1; $\lambda$=wavelength of the cathode used; d=interplanar spacing; and $\theta$=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually mean ones which coincide in the range of $2\theta\pm0.2°$. The peaks mean main peaks and include peaks not larger than medium at diffraction angles other than those stated above.

Both the lactate salt and free base forms of 1-cyclopropyl-3-[3-(5-morpholin-4-ylmethyl-1H-benzoimidazol-2-yl)-1H-pyrazol-4-yl]-urea have been characterised by XRPD. In each case, the powder X-ray diffraction patterns are expressed in terms of the diffraction angle ($2\theta$), inter planar spacing (d) and/or relative intensities. Tables 3, 5 and 6 of WO 2006/070195 (the content of which is incorporated herein by reference) show the interplanar spacing (d) values of the X-ray diffraction spectrum that correspond to the diffraction angle values of the free base, lactate salt and dihydrate free base forms of 1-cyclopropyl-3-[3-(5-morpholin-4-ylmethyl-1H-benzoimidazol-2-yl)-1H-pyrazol-4-yl]-urea.

Therefore 1-cyclopropyl-3-[3-(5-morpholin-4-ylmethyl-1H-benzoimidazol-2-yl)-1H-pyrazol-4-yl]-urea has X-ray powder diffraction patterns essentially as shown in FIG. 3, 6, 7 or 8 and/or Tables 3, 5 or 6 of WO 2006/070195 (the content of which is incorporated herein by reference).

The invention therefore provides combinations based on crystals of salts (e.g. lactate—particularly the L-lactate) of 1-cyclopropyl-3-[3-(5-morpholin-4-ylmethyl-1H-benzoimidazol-2-yl)-1H-pyrazol-4-yl]-urea having an X-ray powder diffraction patterns which are substantially as in FIG. 3, 6, 7 or 8 of WO 2006/070195. Preferably the compound for use in the combinations of the invention is a compound which exhibits peaks at the same diffraction angles as those of the X-ray powder diffraction pattern shown in FIG. 3, 6, 7 or 8 of WO 2006/070195 and/or Table 3 in Example 70 of WO 2006/070195 at pages 204 to 205 (the content of which is incorporated herein by reference) and/or Table 5 in Example 72 of WO 2006/070195 at pages 209 to 210 (the content of which is incorporated herein by reference) and/or Table 6 in Example 72 of WO 2006/070195 at page 211 (the content of which is incorporated herein by reference) and optionally has same the relative intensity.

The invention further provides combinations based on crystals of 1-cyclopropyl-3-[3-(5-morpholin-4-ylmethyl-1H-benzoimidazol-2-yl)-1H-pyrazol-4-yl]-urea lactic acid salt (particularly the L-lactate) which has an X-ray powder diffraction pattern essentially as shown in FIG. 6 of WO 2006/070195. Accordingly, in another embodiment, the invention provides combinations based on a substantially crystalline lactate salt (particularly the L-lactate) of 1-cyclopropyl-3-[3-(5-morpholin-4-ylmethyl-1H-benzoimidazol-2-yl)-1H-pyrazol-4-yl]-urea which exhibits peaks at the same diffraction angles as those of the X-ray powder diffraction pattern shown in FIG. 6. Preferably the peaks have the same relative intensity as the peaks in FIG. 6. Therefore the invention provides combinations based on a substantially crystalline lactic acid salt (particularly the L-lactate) of 1-cyclopropyl-3-[3-(5-morpholin-4-ylmethyl-1H-benzoimidazol-2-yl)-1H-pyrazol-4-yl]-urea having an X-ray powder diffraction pattern substantially as shown in FIG. 6.

The X-ray powder diffraction pattern of the lactate salt may be characterised by the presence of peaks at the diffraction angles (2θ) and interplanar spacings (d), and preferably the intensities shown in Table 5 in Example 72 of WO 2006/070195 (the content of which is incorporated herein by reference).

Therefore the invention provides combinations based on crystals of cyclopropyl-3-[3-(6-morpholin-4-ylmethyl-1H-benzoimidazol-2-yl)-1H-pyrazol-4-yl]-urea lactate (particularly the L-lactate), which shows an X-ray powder diffraction pattern having characteristic peaks at a diffraction angle (2θ±1.0 degree such as ±0.2 degree, in particular ±0.1 degree) of Table 5 in Example 72 of WO 2006/070195 (the content of which is incorporated herein by reference).

The invention also provides combinations based on crystals of cyclopropyl-3-[3-(6-morpholin-4-ylmethyl-1H-benzoimidazol-2-yl)-1H-pyrazol-4-yl]-urea lactate salt (particularly the L-lactate) having an X-ray powder diffraction pattern showing major peaks of diffraction angles 2θ of 17.50, 18.30, 19.30, 19.60, and 21.85±1.0 degree such as ±0.2 degree, in particular ±0.1 degree.

Therefore in one embodiment the invention provides combinations based on a crystalline form of cyclopropyl-3-[3-(6-morpholin-4-ylmethyl-1H-benzoimidazol-2-yl)-1H-pyrazol-4-yl]-urea lactate salt (particularly the L-lactate) characterized by peaks in the X-ray diffraction pattern at 12.40, 15.20, 15.60, 17.50, 18.30, 18.50, 19.30, 19.60, 21.85, and 27.30±1.0 degrees two-theta.

The crystal of cyclopropyl-3-[3-(6-morpholin-4-ylmethyl-1H-benzoimidazol-2-yl)-1H-pyrazol-4-yl]-urea lactate salt (particularly the L-lactate) is also characterised in that the characterisitic X-ray powder diffraction pattern is represented by the spacings between lattice planes, d (Å) of Table 5 (as incorporated herein).

In a further embodiment the invention provides combinations based on crystals of cyclopropyl-3-[3-(6-morpholin-4-ylmethyl-1H-benzoimidazol-2-yl)-1H-pyrazol-4-yl]-urea lactate salt (particularly the L-lactate), which possess an X-ray powder diffraction pattern whose characteristic peaks appear as the lattice spacing (d) of the powder X-ray diffraction at 5.06, 4.85, 4.60, 4.53, and 4.07, more particularly lattice spacing (d) of the powder X-ray diffraction at 7.13, 5.83, 5.68, 5.06, 4.85, 4.79, 4.60, 4.53, 4.07, and 3.26 angstrom.

Therefore, in another embodiment, the invention provides combinations based on a substantially crystalline L-lactate salt (particularly the L-lactate) of 1-cyclopropyl-3-[3-(5-morpholin-4-ylmethyl-1H-benzoimidazol-2-yl)-1H-pyrazol-4-yl]-urea having an X-ray powder diffraction pattern characterised by the presence of major peaks at the diffraction angles (2θ) of 17.50, 18.30, 19.30, 19.60, and 21.85 degrees, more particularly 12.40, 15.20, 15.60, 17.50, 18.30, 18.50, 19.30, 19.60, 21.85, and 27.30 degrees, and interplanar spacings (d) of 5.06, 4.85, 4.60, 4.53, and 4.07, more particularly 7.13, 5.83, 5.68, 5.06, 4.85, 4.79, 4.60, 4.53, 4.07, and 3.26 angstrom.

In a further embodiment, the invention provides combinations based on a substantially crystalline L-lactate salt of 1-cyclopropyl-3-[3-(5-morpholin-4-ylmethyl-1H-benzoimidazol-2-yl)-1H-pyrazol-4-yl]-urea having an X-ray powder diffraction pattern characterised by the presence of peaks at the diffraction angles (2θ) and interplanar spacings (d), and preferably the intensities shown in Table 5 in Example 72 of WO 2006/070195 (the content of which is incorporated herein by reference).

The crystalline salts for use in the combinations of the invention can also be characterised by differential scanning calorimetry (DSC).

The lactate salt has been analysed by DSC and exhibits onset at 190° C. and a peak at 194-197° C.

Accordingly, in another aspect, the invention provides combinations based on a lactate salt (particularly the L-lactate) of which is anhydrous and exhibits onset at 190° C. and/or an endothermic peak at 194-197° C. when subjected to DSC.

Therefore a further aspect of the invention is a combination based on the lactate salt (particularly the L-lactate) of 1-cyclopropyl-3-[3-(5-morpholin-4-ylmethyl-1H-benzoimidazol-2-yl)-1H-pyrazol-4-yl]-urea which exhibits peaks at the same diffraction angles as those of the X-ray powder diffraction pattern shown in FIG. 6, 7 or 8 and further exhibits onset at 190° C. and/or an endothermic peak accompanying decomposition in the vicinity of peak at 194-197° C. according to thermal analysis (DSC).

The behaviour of the salts for use in the combinations of the invention in conditions of high humidity can be analysed by standard gravimetric vapour sorption (GVS) methods, for example as described in Example 68 of WO 2006/070195.

The lactate salt can exist in a stable anhydrous crystalline form in conditions of high relative humidity does not undergo changes in crystal structure under such conditions.

The salts for use in the combinations of the invention can be further characterised by infra-red spectroscopy, e.g. FTIR.

The infra-red spectrum of the lactate salt (KBr disc method) contains characteristic peaks at 3229, 2972 and 1660 cm$^{-1}$.

Accordingly, in a further embodiment, the invention provides combinations based on a (preferably substantially crystalline) lactic acid salt (particularly the L-lactate) of 1-cyclopropyl-3-[3-(5-morpholin-4-ylmethyl-1H-benzoimidazol-2-yl)-1H-pyrazol-4-yl]-urea that exhibits an infra-red spectrum, when analysed using the KBr disc method, that contains characteristic peaks at 3229, 2972 and 1660 cm$^{-1}$.

As will be evident from the foregoing paragraphs, the lactate salt (particularly the L-lactate) for use in the combinations of the invention can be characterised by a number of different physicochemical parameters. Accordingly, in a preferred case, the combinations of the invention are based on a L-lactate salt (particularly the L-lactate) of 1-cyclopropyl-3-[3-(5-morpholin-4-ylmethyl-1H-benzoimidazol-2-yl)-1H-pyrazol-4-yl]-urea which is crystalline and is characterised by any one or more (in any combination) or all of the following parameters, namely that the salt:

(a) has a crystal structure as set out in FIGS. 4 and 5; and/or
(b) has a crystal structure as defined by the coordinates in Table 4 in Example 71 of WO 2006/070195 (the content of which is incorporated herein by reference)herein; and/or
(c) has crystal lattice parameters at 97(2) K a=9.94(10), b=15.03(10), c=16.18(10) Å, α=β=γ=90°; and/or
(d) has crystal lattice parameters at room temperature a=10.08(10), b=15.22(10), c=16.22(10) Å, α=β=γ=90°; and/or
(e) has a crystal structure that belongs belong to an orthorhombic space group P2$_1$2$_1$2$_1$ (#19); and/or
(f) has an X-ray powder diffraction pattern characterised by the presence of major peaks at the diffraction angles (2θ) of 17.50, 18.30, 19.30, 19.60, and 21.85 degrees, more particularly 12.40, 15.20, 15.60, 17.50, 18.30, 18.50, 19.30, 19.60, 21.85, and 27.30 degrees, and/or interplanar spacings (d) of 5.06, 4.85, 4.60, 4.53, and 4.07, more particularly 7.13, 5.83, 5.68, 5.06, 4.85, 4.79, 4.60, 4.53, 4.07, and 3.26 angstrom; and/or
(g) exhibits peaks at the same diffraction angles as those of the X-ray powder diffraction pattern shown in FIG. 6 or Table 5 in Example 72 of WO 2006/070195 (the content of which is incorporated herein by reference) and optionally wherein the peaks have the same relative intensity as the peaks in FIG. 6; or Table 5 (as incorporated herein) and/or
(h) has an X-ray powder diffraction pattern substantially as shown in FIG. 6; and/or
(i) is anhydrous and exhibits onset at 190° C. and/or an endothermic peak at 194-197° C. when subjected to DSC; and/or
(j) exhibits an infra-red spectrum, when analysed using the KBr disc method, that contains characteristic peaks at 3229, 2972 and 1660 cm$^{-1}$.

Crystal Structures of 1-Cyclopropyl-3-[3-(5-morpholin-4-ylmethyl-1H-benzoimidazol-2-yl)-1H-pyrazol-4-yl]-urea Free Base The free base of 1-cyclopropyl-3-[3-(5-morpholin-4-ylmethyl-1H-benzoimidazol-2-yl)-1H-pyrazol-4-yl]-urea can also be amorphous or substantially crystalline. In one particular embodiment, the free base is substantially crystalline, the term "substantially crystalline" having the meaning defined above. In one embodiment, the free base of 1-cyclopropyl-3-[3-(5-morpholin-4-ylmethyl-1H-benzoimidazol-2-yl)-1H-pyrazol-4-yl]-urea exists in a dihydrate crystalline form.

The crystal structure of the free base dihydrate of 1-cyclopropyl-3-[3-(5-morpholin-4-ylmethyl-1H-benzoimidazol-2-yl)-1H-pyrazol-4-yl]-urea has been determined by X-ray crystallography.

In one embodiment, the invention provides combinations based on the dihydrate free base of 1-cyclopropyl-3-[3-(5-morpholin-4-ylmethyl-1H-benzoimidazol-2-yl)-1H-pyrazol-4-yl]-urea which is crystalline and (i) has a crystal structure as defined by the coordinates in Table 2 in Example 69 of WO 2006/070195 at pages 203 to 204 (the content of which is incorporated herein by reference); and/or (ii) wherein the crystals belong to a monoclinic space group P2$_1$/n (#14) with crystal lattice parameters a=7.66(10), b=15.18(10), c=17.71 (10) Å, β=98.53(2)°, α=γ=90°.

The free base forms of 1-cyclopropyl-3-[3-(5-morpholin-4-ylmethyl-1H-benzoimidazol-2-yl)-1H-pyrazol-4-yl]-urea have been characterised by XRPD. Therefore free base forms of 1-cyclopropyl-3-[3-(5-morpholin-4-ylmethyl-1H-benzoimidazol-2-yl)-1H-pyrazol-4-yl]-urea have X-ray powder diffraction patterns essentially as shown in FIG. 3, 6, 7 or 8 and/or Tables 3, 5 or 6 in Examples 70 and 72 of WO 2006/070195 (the content of which is incorporated herein by reference).

Accordingly, in one embodiment, the invention provides combinations based on crystals of 1-cyclopropyl-3-[3-(5-morpholin-4-ylmethyl-1H-benzoimidazol-2-yl)-1H-pyrazol-4-yl]-urea free base exhibiting X-ray powder diffraction patterns containing peaks at the same diffraction angles as those of the X-ray powder diffraction pattern shown in FIG. 3, 6, 7 or 8 and/or Table 3 and/or Table 5 and/or Table 6 in Examples 70-72 of WO 2006/070195 (the content of which is incorporated herein by reference).and wherein the peaks optionally have the same relative intensity.

The invention also provides combinations based on a crystal of 1-cyclopropyl-3-[3-(5-morpholin-4-ylmethyl-1H-benzoimidazol-2-yl)-1H-pyrazol-4-yl]-urea free base, which shows an X-ray powder diffraction pattern having characteristic peaks at a diffraction angle (2θ±1.0 degree such as ±0.2 degree, in particular ±0.1 degree) of Table 3 in Example 70 of WO 2006/070195 at pages 204 to 205 (the content of which is incorporated herein by reference).

In a further embodiment the invention provides combinations based on a crystal of 1-cyclopropyl-3-[3-(5-morpholin-4-ylmethyl-1H-benzoimidazol-2-yl)-1H-pyrazol-4-yl]-urea free base, which possess an X-ray powder diffraction pattern whose characteristic peaks appear as the lattice spacing (d) of Table 3 in Example 70 of WO 2006/070195 at pages 204 to 205 (the content of which is incorporated herein by reference).

The free base of 1-cyclopropyl-3-[3-(5-morpholin-4-ylmethyl-1H-benzoimidazol-2-yl)-1H-pyrazol-4-yl]-urea exhibits peaks at the same diffraction angles as those of the X-ray powder diffraction pattern shown in FIG. 3 and/or Table 3 (as incorporated herein) and further exhibits an exothermic peak accompanying decomposition in the vicinity of 193° C. according to thermal analysis (DSC).

In a further embodiment the invention provides combinations based on crystals of 1-cyclopropyl-3-[3-(5-morpholin-4-ylmethyl-1H-benzoimidazol-2-yl)-1H-pyrazol-4-yl]-urea free base, which possess an X-ray powder diffraction pattern whose characteristic peaks appear as the lattice spacing (d) of Table 3 in Example 70 of WO 2006/070195 at pages 204 to 205 (the content of which is incorporated herein by reference).

The free base of 1-cyclopropyl-3-[3-(5-morpholin-4-ylmethyl-1H-benzoimidazol-2-yl)-1H-pyrazol-4-yl]-urea exhibits peaks at the same diffraction angles as those of the X-ray powder diffraction pattern shown in FIG. 3 and/or Table 3 (as incorporated herein) and further exhibits an exothermic peak accompanying decomposition in the vicinity of 193° C. according to thermal analysis (DSC).

Biological Activity

Compounds for use in the combinations of of the invention are inhibitors of Aurora kinase. For example they inhibit Aurora A and/or Aurora B.

Compounds for use in the combinations of of the invention also have activity against cyclin dependent kinases. For example, they have activity against CDK2, CDK4, CDK5, CDK6 and CDK 9 kinases, and in particular CDK2. Compounds for use in the combinations of of the invention also have activity against glycogen synthase kinase-3 (GSK-3).

As a consequence of their activity in modulating or inhibiting CDK and Aurora kinases and glycogen synthase kinase, they will be useful as components in combinations which provide a means of arresting, or recovering control of, the cell cycle in abnormally dividing cells. The compounds will prove useful as components of combinations for treating or preventing proliferative disorders such as cancers. The components in the combinations of the invention they will also be useful in treating conditions such as viral infections, type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

Sub-groups of disease states and conditions where the compounds will be useful as components of the combinations of the invention include viral infections, autoimmune diseases and neurodegenerative diseases.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. RB−ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoacanthoma; thyroid follicular cancer; or Kaposi's sarcoma. In addition hematopoietic tumours of lymphoid lineage can include small cell lymphocytic lymphoma.

The cancers may be cancers which are sensitive to inhibition of any one or more cyclin dependent kinases.

Whether or not a particular cancer is one which is sensitive to inhibition by a cyclin dependent kinase or an Aurora kinase may be determined by means of a cell growth assay as set out in the examples below or by a method as set out in the section headed "Methods of Diagnosis".

CDKs are also known to play a role in apoptosis, proliferation, differentiation and transcription and therefore CDK inhibitors could also be useful as components of combinations for the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

It has also been discovered that some cyclin-dependent kinase inhibitors can be used in combination with other anti-cancer agents. For example, the cyclin-dependent kinase inhibitor flavopiridol has been used with other anticancer agents in combination therapy.

Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes breast cancer, ovarian cancer, colon cancer, prostate cancer, oesophageal cancer, squamous cancer and non-small cell lung carcinomas.

As the compounds for use in the combinations of the invention have activity against Aurora kinase, particular examples of cancers where Aurora kinase inhibiting compounds of the invention will be useful include: human breast cancers (e.g. primary breast tumours, node-negative breast cancer, invasive duct adenocarcinomas of the breast, non-endometrioid breast cancers); ovarian cancers (e.g. primary ovarian tumours); pancreatic cancers; human bladder cancers; colorectal cancers (e.g. primary colorectal cancers); gastric tumours; renal cancers; cervical cancers; neuroblastomas; melanomas; lymphomas; prostate cancers; leukemia; non-endometrioid endometrial carcinomas; gliomas; and non-Hodgkin's lymphoma.

Cancers which may be particularly amenable to Aurora inhibitors include breast, bladder, colorectal, pancreatic, ovarian, non-Hodgkin's lymphoma, gliomas and nonendometrioid endometrial carcinomas.

A particular sub-set of cancers which may be particularly amenable to Aurora inhibitors consist of breast, ovarian, colon, liver, gastric and prostate cancers.

Another subset of cancers that Aurora inhibitors may be particularly amenable to treat are hematological cancers, in particular leukemia. Therefore, in a further embodiment the compounds are used as components in combinations used to treat hematological cancers, in particular leukemia. Particular leukemias are selected from Acute Myelogenous Leukemia (AML), chronic myelogenous leukaemia (CML), B-cell lymphoma (Mantle cell), and Acute Lymphoblastic Leukemia (ALL—also known as acute lymphocytic leukemia). In one embodiment the leukemias are selected from relapsed or refractory acute myelogenous leukemia, myelodysplastic syndrome, acute lymphocytic leukemia and chronic myelogenous leukemia. Further leukemias include acute promyelocytic leukaemia.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma).

One particular cancer is chronic lymphocytic leukaemia.

Another particular cancer is mantle cell lymphoma.

Another particular cancer is diffuse large B cell lymphoma.

The combinations of the invention having Aurora kinase inhibitory activity, will be particularly useful in the treatment or prevention of cancers of a type associated with or characterised by the presence of elevated levels of Aurora kinases, for example the cancers referred to in this context in the introductory section of this application. Such cancers include medulloblastoma.

The compounds for use in the combinations of the invention are inhibitors of VEGFR activity. In addition they are inhibitors of EpH and FGFR activity. As such, they are useful in providing a means of preventing the growth or inducing apoptosis of neoplasias, particularly by inhibiting angiogenesis. The combinations of the invention are useful in treating or preventing proliferative disorders such as cancers. In particular tumours with activating mutants of VEGFR or upregulation of VEGFR and patients with elevated levels of serum lactate dehydrogenase may be particularly sensitive to the inhibitors. Patients with activating mutants of any of the isoforms of the specific VEGFR as discussed herein may also find treatment with VEGFR inhibitors particularly beneficial. For example, VEGFR overexpression in acute leukemia cells where the clonal progenitor may express VEGFR. Also particular tumours with activating mutants or upregulation or overexpression of any of the isoforms of FGFR such as FGFR2 or FGFR3 may be particularly sensitive to the combinations of the invention and thus patients as discussed herein with such particular tumours may also find treatment with the combinations of the invention particularly beneficial. It may be preferred that the treatment is related to or directed at a mutated form of a receptor tyrosine kinase, such as discussed above.

The compounds for use in the combinations of the invention having Flt3, JAK, C-abl, PDK1, Chk1, and Chk2 inhibitory activity, will be particularly useful as constituents of combinations in the treatment or prevention of the following diseases and leukemias: polycythemia vera; essential thrombocythemia; idiopathic myelofibrosis; juvenile myelomonocytic leukemia (JMML); Chronic Myelomonocytic Leukemias (CMML); megakaryocytic AML (AML M7); megakaryocytic leukaemia; Philadelphia chromosome-negative CML; Chronic Myeloid Leukaemia (CML); imatinib resistant CML; acute myeloid leukemias (AML); myelodysplastic syndromes (MDS); and acute lymphoblastic leukemia (ALL).

Therefore, in a further embodiment the combinations of the invention are used to treat polycythemia vera; essential thrombocythemia; idiopathic myelofibrosis; juvenile myelomonocytic leukemia (JMML); Chronic Myelomonocytic Leukemias (CMML); megakaryocytic AML (AML M7); megakaryocytic leukaemia; Philadelphia chromosome-negative CML; or imatinib resistant CML.

In a further embodiment the combinations of the invention are used to treat myeloproliferative disorders (MPD) such as polycythemia vera, essential thrombocythemia and idiopathic myelofibrosis including myelofibrosis with myeloid metaplasia (MMM).

In addition the combinations of the invention could be used in the treatment of diseases where malignancies are driven by BCR-abl in particular Philadelphia chromosome positive. In a further embodiment the lactate or citrate salts of compound of formula (I) are used to treat myeloproliferative syndrome, Philadelphia chromosome-positive leukamias such as Philadelphia chromosome positive CML and Philadelphia chromosome positive ALL. In particular the combination of the invention could be used to treat Philadelphia chromosome positive ALL.

The combination of the invention having VEGFR inhibitory activity, will be particularly useful in the treatment or prevention of ocular diseases such as age-related macular degeneration (AMD) in particular wet form of age-related macular degeneration, ischemic proliferative retinopathies such as retinopathy of prematurity (ROP) and diabetic retinopathy and hemangioma. Therefore, in a further embodiment combination of the invention are used to treat ocular diseases such as age-related macular degeneration in particular wet form of age-related macular degeneration, Ischemic proliferative retinopathies such as retinopathy of prematurity (ROP) and diabetic retinopathy and hemangioma.

It may be preferred that the treatment is related to or directed at a mutated form of a kinase, such as discussed herein. Diagnosis of tumours with such mutations could be performed using techniques known to a person skilled in the art and as described herein such as RTPCR and FISH.

The activity of the compounds for use in the combinations of the invention as inhibitors of cyclin dependent kinases, Aurora kinases, glycogen synthase kinase-3, VEGFR, Flt3, JAK, C-abl, PDK1, Chk1, and Chk2 can be measured using the assays set forth in the examples below and the level of activity exhibited by a given compound can be defined in terms of the $IC_{50}$ value.

The compounds for use in the combinations of the invention having FGFR such as FGFR3, Ret, Eph such as EphB2 or EphB4, or cSrc inhibitory activity, will be particularly useful in the treatment or prevention of the following diseases: papillary thyroid carcinoma; multiple endocrine neoplasia (MEN) types 2A and 2B; familial medullary thyroid carcinoma (FMTC); Hirschsprung's disease; Apert (AP) syndrome; Crouzon syndrome; Jackson-Weiss syndrome; Beare-Stevenson cutis gyrata syndrome; Pfeiffer Syndrome (PS); and multiple myelomas. In addition they will be particularly useful in the treatment of head and neck cancers and epithelial cancers.

Therefore, in a further embodiment the combinations of the invention are used to treat multiple myelomas, epithelial cancers, head and neck cancers, abnormalities in human skeletal development such as Apert (AP) syndrome, Crouzon syndrome, Jackson-Weiss syndrome, Beare-Stevenson cutis gyrata syndrome and Pfeiffer Syndrome (PS), thyroid cancers such as papillary thyroid carcinoma, familial medullary thyroid carcinoma (FMTC), multiple endocrine neoplasia (MEN) types 2A and 2B and Hirschsprung's disease.

As the combinations of the invention have activity against FGFR particular cancers include multiple myeloma, bladder, hepatocellular, oral squamous cell carcinoma, cervical, prostate and thyroid carcinomas, lung, breast, and colon cancers. The combinations fo the invention having FGFR such as FGFR1 inhibitory activity, will be particularly useful in the treatment or prevention of breast cancer in particular Classic Lobular Carcinomas (CLC). The combinations fo the invention having FGFR such as FGFR2 or FGFR3 inhibitory activity will be particularly useful in the treatment or prevention of the skeletal diseases.

Furthermore, the combinations fo the invention having FGFR such as FGFR1, FGFR2 or FGFR3 inhibitory activity, will be particularly useful in the treatment or prevention in pathologies in which progressive fibrosis is a symptom. Fibrotic conditions in which the compounds of the inventions may be useful in the treatment of in include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the combinations fo the invention may also be useful in the treatment of lung fibrosis in particular in idiopathic pulmonary fibrosis.

Since combinations fo the invention inhibit PDGFR they may also be useful in the treatment of a number of tumour and leukemia types including glioblastomas such as glioblastoma multiforme, prostate carcinomas, gastrointestinal stromal tumours, liver cancer, kidney cancer, chronic myeloid leukemia, chronic myelomonocytic leukemia (CMML) as well as hypereosinophilic syndrome, a rare proliferative hematological disorder and dermatofibrosarcoma protuberans, an infiltrative skin tumour.

The activity of the compounds for use in the combinations of the invention as inhibitors of FGFR such as FGFR3, Ret, Eph such as EphB2 or EphB4, or cSrc can be measured using the assays set forth in the examples below and the level of activity exhibited by a given compound can be defined in terms of the $IC_{50}$ value.

In further aspects, the invention provides:

A method for the prophylaxis or treatment of a disease state or condition mediated by VEGFR, Flt3, JAK, C-abl, PDK1, Chk1, or Chk2 which method comprises administering to a subject in need thereof a therapeutically effective amount of a combination of the invention.

A combination of the invention for use in the prophylaxis or treatment of a disease state or condition mediated by VEGFR, Flt3, JAK, C-abl, PDK1, Chk1, or Chk2.

The use of a combination of the invention for the manufacture of a medicament for the prophylaxis or treatment of a disease state or condition mediated by VEGFR, Flt3, JAK, C-abl, PDK1, Chk1, or Chk2.

A method for the prophylaxis or treatment of a disease state or condition mediated by FGFR such as FGFR3, Ret, Eph such as EphB2 or EphB4, or cSrc which method comprises administering to a subject in need thereof a therapeutically effective amount of a combination of the invention.

A combination of the invention for use in the prophylaxis or treatment of a disease state or condition mediated by FGFR such as FGFR3, Ret, Eph such as EphB2 or EphB4, or cSrc.

The use of a combination of the invention for the manufacture of a medicament for the prophylaxis or treatment of a disease state or condition mediated by FGFR such as FGFR3, Ret, Eph such as EphB2 or EphB4, or cSrc.

Mutated Kinases

Drug resistant kinase mutations that arise in patient populations treated with kinase inhibitors can occur, in part, in the regions of the protein that bind to or interact with the particular inhibitor used in therapy. Such mutations reduce the capacity of the inhibitor to bind to and inhibit the kinase in question. This can occur at any of the amino acid residues which interact with the inhibitor or are important for supporting the binding of said inhibitor to the target. Another inhibitor that binds to a target kinase without requiring the interaction with the mutated amino acid residue will likely be unaffected by the mutation and will remain an effective inhibitor of the enzyme (Carter et al, PNAS, 2005, 102, 31, 11011-110116).

One common site at which drug resistant mutations occur is the so-called gate keeper residue. This particular residue forms a key site of interaction for several kinase inhibitors and their respective targets. For example, imatinib (Gleevec) binds in part to threonine 315 the gate keeper residue in the abl kinase domain. T315I mutations are one of the major forms of drug resistance arising in imatinib treated CML patients and may also be seen in patients with acute lymphoblastic leukemia. Thus an inhibitor of BCR-abl which does not require an interaction with the T315 for effective target inhibition will still be an effective inhibitor of the T315I imatinib resistant mutation.

Imatinib inhibits the tyrosine kinase activity of the receptors c-kit and PDGF-R in addition to blocking abl activity. Thus the drug has found utility in gastrointestinal tumours and hypereosinophilic syndrome, conditions which are dependent on activation of c-kit and PDGFR respectively. PDGF-R activation is associated with other malignancies, which respond to imatinib under different molecular circumstances. These include chronic myelomonocytic leukemia (CMML). In another disorder, dermatofibrosarcoma protuberans, an infiltrative skin tumor, a reciprocal translocation involving the gene encoding the PDGF-B ligand results in constitutive secretion of the chimeric ligand and receptor activation. Gleevec has activity against all three of these diseases.

In addition to the T315I resistant disease observed in CML, resistance due to similar gate-keeper mutations has been observed in both c-kit and PDGFr in imatinib-treated patients. Thus the T670I mutation in KIT and the T674I mutation in PDGFR are homologous to the T315I mutation in BCR-abl, and all three mutations confer resistance to clinical-stage ATP-competitive kinase inhibitors including BMS-354825 (dasatanib) and AMN-107 (nilotinib). The clinical importance of this mutation may grow considerably, as to date it appears to represent the primary mechanism of resistance to src/Abl inhibitors in patients. There are currently no effective kinase-targeted treatments for patients with threonine gate-keeper mutations.

Further, the T790M mutation in EGFR is homologous to the T315I mutation in BCR-abl, and this mutation may also confer resistance to clinical-stage ATP-competitive kinase inhibitors. Other clinical-stage ATP-competitive kinase inhibitors therefore include the EGRF inhibitors Iressa (gefitinib), and Tarceva (erlotinib), and SU-11248 (Sunitinib maleate, Sutent), a PDGFr and c-Kit inhibitor and other PDGFR inhibitors such as sorafenib.

Aurora kinase does not contain a threonine in the gate keeper region of the kinase active site. Thus many Aurora kinase inhibitors, including those of the current invention do not depend on this interaction to support the inhibition of the kinase activity. Accordingly, Aurora kinase inhibitors with a cross reactivity against abl, kit PDGFR or other kinases will be inhibitory to the drug resistant gate-keeper mutations, in particular threonine gate-keeper mutations, as well as the wild type variants and to be effective in resistant disease arising because of mutations in the gate-keeper region.

The combination of the invention would therefore find particular application in relation to cancers which express a mutated molecular target such as BCRabl, c-kit, PDGF, EGF receptor, ErbB2. Diagnosis of tumours with such mutations could be performed using techniques known to a person skilled in the art and as described herein such as RTPCR and FISH.

Thus, since Aurora kinase does not represent a kinase harbouring a gatekeeper threonine, Aurora inhibitors may also be useful in the treatment of indications that are resistant to existing therapies by virtue of a mutation at that region of the protein. Such indications include gastrointestinal stromal tumors (GISTs), chronic myelomonocytic leukemia (CMML), the hypereosinophilic syndrome, a rare proliferative hematological disorder and dermatofibrosarcoma protuberans, an infiltrative skin tumour.

One aspect of the present invention is the use of combination of the invention for the inhibition of a kinase containing a mutation in a region of the protein that binds to or interacts with other cancer agents but does not bind to or interact with the compounds of formula (I).

A further aspect of the present invention is the method of treating a disease mediated by a kinase containing a mutation in a region of the protein that binds to or interacts with other cancer agents but does not bind to or interact with the compounds of formula (I), or formula (I') or formula (I$^0$) or sub-groups or examples thereof, with a combination of the invention.

Particular kinases for inhibition include c-abl, c-kit, PDGFR including PDGFR-beta and PDGFR-alpha, and ErbB family members such as EGFR (ErbB1), HER2 (ErbB2), ErbB3, and ErbB4, in particular c-abl, c-kit, and PDGFR.

Further kinases include those mentioned herein such as members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2.

Other cancer agents include ATP-competitive kinase inhibitors such as Gleevec, BMS-354825, AMN-107, SU-11248 (Sunitinib maleate, Sutent), sorafenib (BAY 43-9006), Iressa (gefitinib), Tarceva (erlotinib), in particular Gleevec, BMS-354825 (dasatinib), and AMN-107 (nilotinib). Further kinase inhibitors are discussed in Davies et al, Biochem. J. 2000, 351, 95-105 and McInnes C., Fischer P. M. Curr. Pharm. Des. 2005 11:14 (1845-1863).

Particular regions to bind to or interact with other cancer agents include the kinase active site, the ATP binding site, and the gate keeper region in particular threonine gate keeper residue including T315 in abl, T670 in KIT, T674 in PDGFR, and T790 in EGFR. Particular regions of the kinase active site including the ATP binding pocket are discussed in Vulpetti A., Bosotti R. Farmaco 2004 59:10 (759-765), Knight et al, Chemistry & Biology, 12, 621-637 and Cherry M., Williams D. H. Curr. Med. Chem. 2004 11:6 (663-673).

A further aspect of the invention relates to the use of a combination of the invention for the inhibition of c-abl, c-kit, and PDGFR containing a mutation in the threonine gate keeper residue (i.e. T315 in abl, T670 in KIT, T674 in PDGFR).

Thus in a further embodiment of the invention the combination of the invention are used to treat the gastrointestinal stromal tumors (GISTs), glioblastomas such as glioblastoma multiform, the hypereosinophilic syndrome or dermatofibrosarcoma protuberans.

It follows from the foregoing paragraphs that, in further aspects, the invention provides:

A combination of the invention as defined herein for use in the treatment of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T674I mutation in PDGFR.

A combination of the invention for use in the treatment of a cancer which expresses a mutated molecular target which is a mutated form of BCRabl, c-kit, PDGF, EGF receptor or ErbB2.

A combination of the invention for use in the treatment of gastrointestinal stromal tumours (GISTs), chronic myelomonocytic leukemia (CMML), the hypereosinophilic syndrome and dermatofibrosarcoma protuberans.

A combination of the invention for use in the treatment of a disease mediated by a kinase containing a mutation in a region of the protein that binds to or interacts with other cancer agents but does not bind to or interact with the compounds of formula (I), with a compound of formula (I), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, in particular c-abl, c-kit, PDGFR, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2.

The use of combination of the invention for the manufacture of a medicament for the treatment of a cancer in which the cancer cells thereof contain a drug resistant kinase mutation which is:
(a) a threonine gatekeeper mutation; or
(b) a drug-resistant gatekeeper mutation; or
(c) a T315I imatinib resistant mutation; or
(d) a T670I mutation in KIT; or
(e) a T674I mutation in PDGFR.

The use of a combination of the invention for the manufacture of a medicament for the treatment of a cancer which expresses a mutated molecular target which is a mutated form of BCRabl, c-kit, PDGF, EGF receptor or ErbB2.

The use of a combination of the invention for the manufacture of a medicament for the treatment of gastrointestinal stromal tumours (GISTs), chronic myelomonocytic leukemia (CMML), the hypereosinophilic syndrome and dermatofibrosarcoma protuberans.

The use of a combination of the invention for the manufacture of a medicament for the treatment of a disease mediated by a kinase containing a mutation in a region of the protein that binds to or interacts with other cancer agents but does not bind to or interact with the compounds of formula (I), with a compound of formula (I), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, in particular c-abl, c-kit, PDGFR, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2.

A method of treating a patient suffering from a cancer in which the cancer cells thereof contain a drug resistant kinase mutation which is:
  (a) a threonine gatekeeper mutation; or
  (b) a drug-resistant gatekeeper mutation; or
  (c) a T315I imatinib resistant mutation; or
  (d) a T670I mutation in KIT; or
  (e) a T674I mutation in PDGFR;
which method comprises administering to the patient a combination of the invention.

A method for the treatment of a cancer which expresses a mutated molecular target which is a mutated form of BCRabl, c-kit, PDGF, EGF receptor or ErbB2, which method comprises administering to a patient in need thereof a combination of the invention.

A method for the treatment of gastrointestinal stromal tumours (GISTs), chronic myelomonocytic leukemia (CMML), the hypereosinophilic syndrome and dermatofibrosarcoma protuberans, comprises administering to a patient in need thereof a combination of the invention.

A method for the treatment of a disease mediated by a kinase containing a mutation in a region of the protein that binds to or interacts with other cancer agents but does not bind to or interact with the compounds of formula (I), with a compound of formula (I), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, in particular c-abl, c-kit, PDGFR, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2, which method comprises administering to a patient in need thereof combination of the invention.

In a further aspect, the invention provides a combination of the invention use in the treatment of juvenile myelomonocytic leukemia (JMML) or Chronic Myelomonocytic Leukemias (CMML).

The invention further provides a combination of the invention for use in the treatment of polycythemia vera, essential thrombocythemia, or idiopathic myelofibrosis.

The invention further provides a combination of the invention for use in the treatment of megakaryocytic leukaemia including megakaryocytic AML (AML M7) or Philadelphia chromosome-negative or imatinib resistant CML.

In the treatment of polycythemia vera; essential thrombocythemia; idiopathic myelofibrosis; juvenile myelomonocytic leukemia (JMML); Chronic Myelomonocytic Leukemias (CMML); megakaryocytic leukaemia including megakaryocytic AML (AML M7); Philadelphia chromosome-negative CML or imatinib resistant CML, combination of the invention may be used.

Also provided are methods of treatment of polycythemia vera; essential thrombocythemia; idiopathic myelofibrosis; juvenile myelomonocytic leukemia (JMML); Chronic Myelomonocytic Leukemias (CMML); megakaryocytic leukaemia including megakaryocytic AML (AML M7); Philadelphia chromosome-negative CML or imatinib resistant CML by administering to a patient in need of such treatment a combination of the invention.

The invention also provides the combination of the invention for use in the treatment of nilotinib resistant CML or dasatinib resistant CML.

Advantages of 1-cyclopropyl-3-[3-(5-morpholin-4-ylmethyl-1H-benzoimidazol-2-yl)-1H-pyrazol-4-yl]-urea (The Compound of formula (I))

The compound of the formula (I) has a number of advantages over prior art compounds. For example, the compound of formula (I) is both more potent and more selective in its activities against different kinases including kinases implicated in cancer development and maintenance such as Jak 2, T315I abl and VEGFR kinases (see Table A), and demonstrate enhanced selectivity for and potency against Aurora A and B kinases in particular. Many of the other kinases targeted by the compound lie in oncogenic signaling pathways and have the potential to contribute in a positive way to the anti-tumor action of the compound (PDK1, Flt3, VEGFR2). In addition the potency against JAK2 and the c-abl T315I mutant could be of potential interest in leukemias and myeloproliferative diseases, including Gleevec resistant CML and polycythemia vera.

TABLE A

Inhibition of kinases in vitro

| Protein Kinase* | IC$_{50}$ (nM) |
|---|---|
| Aurora-A | 52% at 3 nM |
| Aurora-B | 58% at 3 nM |
| PDK1 | <10 |
| c-abl T315I mutant | <10 |
| JAK2 | <15 |
| Jak3$^c$ | <100 |
| Chk1 | <30 |
| c-abl | 57% at 30 nM |
| Chk2 | 41% at 30 nM |
| VEGFR2 (KDR) | <100 |
| Flt3 | <1000 |

In addition further kinases targeted by the compound could be of interest in particular in angiogenesis and thyroid cancers (Table B).

TABLE B

Inhibition of further kinases in vitro

| Protein Kinase | IC$_{50}$ (nM) |
|---|---|
| FGFR3 | <30 |
| cSrc | <100 |
| EphB2 | <100 |
| EphB4 | <100 |
| Ret | <100 |
| PDGFRb | 400 nM |
| EGFR | 380 nM |

The compound of formula (I) is also advantageous over prior art compounds in that it has different susceptibilities to P450 enzymes (Table C).

TABLE C

Inhibition of expressed cytochrome P450 isoforms in vitro.

| P450 isoform | IC50 (µM) |
|---|---|
| CYP1A2 | >10 |
| CYP2D6 | >10 |
| CYP3A4 | >10 |
| CYP2C9 | >10 |
| CYP2C19 | >10 |

In addition, compounds for use in the combinations of the invention are also advantageous over prior art compounds in that they exhibit improvements with regard to drug metabolism and pharmacokinetic properties. In particular the compounds have reduced plasma protein binding. The binding of the compound of Examples 24, 62, 63 and 64 to plasma proteins was comparably moderate across all species tested, ranging from 61% in rat to 82% in mouse plasma. This could confer the advantage of having more free drug available in the systemic circulation to reach the appropriate site of action to exert its therapeutic effect. Increased free fraction to exert pharmacological action in tumours potentially leads to improved efficacy which thereby allows reduced dosages to be administered.

Compound I for use in the combinations of the invention also demonstrates improved cell activity in proliferation and clonogenic assays (for example in the assay described in Examples 16 and 17), thereby indicating improved anti-cancer activity against a wide range of solid tumour and leukemic cell lines (Table D).

TABLE D

Inhibitory effect on tumour cell colony formation

| Origin | Origin | IC50 (nM) | p53 Status* |
|---|---|---|---|
| Colon | HCT 116 | 13 | + |
|  | HCT 116 N7 | 14 | − |
|  | HT-29 | 11 | − |
|  | SW620 | 14 | − |
| Ovarian | A2780 | 7.7 | + |
| Lung | A549 | 12 | + |
| Breast | MCF7 | 20 | + |
| Pancreatic | MIA-Pa-Ca-2 | 7.8 | − |

*+ indicates expression of wild type p53; − indicates no expression of p53 or that p53 is non-functional.

The compound of formula (I) has a reduced toxicity and therefore a greater therapeutic window. In vitro studies with primary human mammary epithelial cells have demonstrated that following treatment of normal cells, cf. tumor cells, fewer become multinucleated or die after treatment, but instead undergo reversible G2/M arrest before re-entering the cell cycle once treatment is stopped. Data indicates that compound-treatment has different effects on tumor cells compared with normal cells. In checkpoint compromised tumor cells compound treatment leads to multinucleation, due to disruption of mitosis, inhibition of cytokinesis and bypass of the spindle checkpoint through Aurora kinase inhibition. It is this multinucleation that appears to lead to cell death. In contrast, in normal checkpoint competent cells treated with compound, fewer cells become multinucleated or die after 24 h compound treatment, instead the greater proportion undergo reversible G2/M arrest and then re-enter the cell cycle once the compound is removed. These differences in effects could reflect the fact that normal cells have checkpoints in place to halt the cell cycle if accurate chromosomal segregation does not take place, such as the post-mitotic p53-dependent checkpoint. In tumor cells these checkpoints are absent allowing mitosis to proceed and multinucleation to occur.

Furthermore, salt forms of the compound of formula (I) demonstrate improved solubility in aqueous solution and better physicochemical properties, e.g. a lower log D.

Methods for the Preparation of Compounds of the Formula (I')

Compounds of the formula (I') can be prepared in accordance with synthetic methods well known to the skilled person.

These are as described in WO 2005/002552 and WO 2006/070195, the contents of which are incorporated herein by reference. In particular, the contents of WO 2005/002552 which relate to the relevant processes at pages 88 to 96 are hereby incorporated herein by reference. In particular, the contents of WO 2006/070195 which relate to the relevant processes at pages 90 to 101 are hereby incorporated herein by reference.

For example, compounds of the formula (I') may be prepared as described in WO 2005/002552, the contents of which are incorporated herein by reference. Thus, the disclosure of WO 2005/002552 at pages 88 to 96 is hereby incorporated herein by reference save that references to a "compound(s) of formula (I)" are to be read as references to "compound(s) of formula (I')".

Methods for the Preparation of Compounds of the Formula (I")

Compounds of the formula (I") can be prepared in accordance with synthetic methods well known to the skilled person.

For example, compounds of the formula (I") may be prepared as described in WO 2006/070195, the contents of which are incorporated herein by reference. In particular, the contents of WO 2006/070195 at pages 90 to 101 in relation to the preparation of the compounds of formula (I) of WO 2006/070195 can be applied to the compounds of formula (I") herein. Thus, the disclosure of WO 2006/070195 at pages 90 to 101 is hereby incorporated herein by reference save that references to a "compound(s) of formula (I)" are to be read as references to "compound(s) of formula (I")".

Processes for Preparing 1-Cyclopropyl-3-[3-(5-morpholin-4-ylmethyl-1H-benzoimidazol-2-yl)-1H-pyrazol-4-yl]-urea These are as described in WO 2006/070195, the contents of which are incorporated herein by reference. In particular, the contents of WO 2006/070195 which relate to the relevant processes at pages 102 to 109 are hereby incorporated herein by reference.

The invention contemplates methods for preparing the combinations of the invention which comprise the provision of 4-amino-1H-pyrazole-3-carboxylic acid (2-amino-4-morpholin-4-ylmethyl-phenyl)-amide or 4-amino-1H-pyrazole-3-carboxylic acid (2-amino-5-morpholin-4-ylmethyl-phenyl)-amide and protected forms thereof as chemical intermediates. One particular preferred chemical intermediate of formula ((XXVII) of WO 2006/070195 is [3-(2-amino-4-morpholin-4-ylmethyl-phenylcarbamoyl)-1H-pyrazol-4-yl]-carbamic acid tert-butyl ester. One particularly preferred chemical intermediate of Formula (XXVIII) of WO 2006/

070195 is [3-(2-amino-5-morpholin-4-ylmethylphenylcarbamoyl)-1H-pyrazol-4-yl]-carbamic acid tert-butyl ester.

The compound of formula ((XXVIIa) of WO 2006/070195in the process for preparing 3-(5-morpholin-4-ylmethyl-1H-benzoimidazol-2-yl)-1H-pyrazol-4-ylamine or a salt thereof or process for preparing 1-cyclopropyl-3-[3-(5-morpholin-4-ylmethyl-1H-benzoimidazol-2-yl)-1H-pyrazol-4-yl]-urea or a salt thereof above, can be prepared by a process which comprises:

(i) reaction of a compound of the formula (XXIX), where PG is an amine-protecting group which is removable with acid, APG;
(ii) with a compound of the formula (XXXI) in an organic solvent in the presence of a coupling agent such as EDC and HOBt.

Optionally the processes described herein have the further step of recrystallising the salt to give a crystalline form, e.g. a crystalline form as defined herein.

Methods of Purification

As described in WO 2006/070195, the contents of which are incorporated herein by reference. In particular, the contents of WO 2006/070195 which relate to purification at pages 109 to 110 are hereby incorporated herein by reference.

Recrystallisation

As described in WO 2006/070195, the contents of which are incorporated herein by reference. In particular, the contents of WO 2006/070195 which relate to recrystallisation at pages 110 to 111 are hereby incorporated herein by reference.

Ancillary Compounds for Use According to the Invention

Any of a wide variety of ancillary compounds may be used in the combinations of the invention. The ancillary compounds may be anti-cancer agents.

In this section, and in all other sections of this specification, unless the context indicates otherwise, references to formula (I') are to be understood to include references to formulae (I), (I") and all other sub-groups, preferences and examples thereof as defined herein (e.g. compounds of formulae (II") to (VIII")). Furthermore, and as explained below, any references to formula (I") herein shall also be taken to refer to formulae (II") to (VIII") and any other sub-group of compounds within formula (I") unless the context requires otherwise.

Preferably, the ancillary compounds for use in the combinations of the invention are selected from the following class lists:

List A
1. hormones, hormone agonists, hormone antagonists and hormone modulating agents (including corticosteroids, antiandrogens, antiestrogens and GNRAs);
2. cytokines and cytokine activating agents;
3. retinoids and rexinoids
4. monoclonal antibodies (including monoclonal antibodies to cell surface antigen(s));
5. camptothecin compounds and other topoisomerase I inhibitors;
6. antimetabolites;
7. vinca alkaloids and other tubulin targeting agents;
8. taxanes;
9. epothilones;
10. platinum compounds;
11. DNA binders and Topo II inhibitors (including anthracycline derivatives);
12. alkylating agents (including aziridine, nitrogen mustard and nitrosourea alkylating agents);
13. signalling inhibitors (including PKA/B inhibitors and PKB pathway inhibitors);
14. CDK inhibitors, including ancillary CDK inhibitors;
15. COX-2 inhibitors;
16. HDAC inhibitors;
17. Selective immunoresponse modulators;
18. DNA methyl transferase inhibitors;
19. proteasome inhibitors;
20. Aurora inhibitors, including ancillary Aurora inhibitors;
21. Hsp90 inhibitors;
22. Checkpoint targeting agents;
23. DNA repair inhibitors;
24. Inhibitors of G-protein coupled receptor inhibitors.

In embodiments where the combination of the invention comprises one or more ancillary compounds, the ancillary compound(s) are preferably independently selected from the classes (1) (in particular corticosteroids), (4), (6), (7), (8), (10), (11), (12), (13), (17), (18), (19), (23) and (24) of list A (above). Most preferably, the one or more ancillary compounds are independently selected from classes (1) in particular corticosteroids, (4), (6), (8), (10), (11), (12), (13), (18), (19), and (24) of list A (above).

In embodiments where the combination of the invention comprises two or more ancillary compounds, then the two or more ancillary compounds are preferably independently selected from the classes (1) to (24) of list A set out above.

In embodiments where the combination of the invention comprises two or more ancillary compounds, then the two or more ancillary compounds are preferably independently selected from the classes (1) (in particular corticosteroids), (2), (3), (17), (22), (23) and (24) of list A set out above.

List B

In some embodiments the ancillary compounds for use in the combination with the compounds of formula (I) may be selected from the following classes:

1. hormones, hormone agonists, hormone antagonists and hormone modulating agents (including antiandrogens, antiestrogens and GNRAs);
2. cytokines and cytokine activating agents;
3. retinoids;
4. monoclonal antibodies (e.g. monoclonal antibodies to cell surface antigen(s));
5. camptothecin compounds and other topoisomerase I inhibitors;
6. antimetabolites;
7. vinca alkaloids and other tubulin targeting agents;
8. taxanes;
9. epothilones;
10. platinum compounds;
11. DNA binders and Topo II inhibitors (including anthracycline derivatives);
12. alkylating agents (including aziridine, nitrogen mustard and nitrosourea alkylating agents);
13. signalling inhibitors (including PKA/B inhibitors and PKB pathway inhibitors);
14. CDK inhibitors;
15. COX-2 inhibitors;
16. HDAC inhibitors;
17. DNA methylase inhibitors;
18. proteasome inhibitors;
19. Aurora inhibitors (including ancillary Aurora inhibitors);
20. Hsp90 inhibitors;
21. Checkpoint targeting agents;
22. a combination of two or more of the foregoing classes (1) to (3);
23. a combination of two or more of the foregoing classes (6), (8) and/or (13);
24. a combination of two or more of the foregoing classes (5)-(11) and/or (13);

25. a combination of two or more of the foregoing classes (12) and/or (14)-(18);
26. a combination of two or more of the foregoing classes (1) and (4)-(18);
27. a combination of two or more of the foregoing classes (1), (4), (5), (6), (7), (8), (9), (10), (11), (12), (13) and (17);
28. a combination of two or more of the foregoing classes (1), (4), (5), (6), (7), (8), (9), (10) and (12);
29. a combination of two or more of the foregoing classes (5), (6), (7), (8), (9), (10), (11) and (12);
30. a combination of two or more of the foregoing classes (6), (8), (9) and (10);
31. a combination of two or more of the foregoing classes (18) and (19);
32. a combination of two or more of the foregoing classes (6), (7), (8), (9) and (10).

In embodiments where the combination of the invention comprises two or more ancillary compounds, then the two or more ancillary compounds are preferably independently selected from the classes 1 to 21 of list B set out above.

A reference to a particular ancillary compound herein is intended to include ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof).

The various compounds/compound classes described above are now described in more detail, wherein the numbering of the compound classes corresponds to that used in list A (above).

1. Hormones, Hormone Agonists Hormone Antagonists and Hormone Modulating Agents

Definition: The terms "corticosteroid", "antiandrogen", "antiestrogen", "antiandrogen agent" and "antiestrogen agent" as used herein refers to those described herein and analogues thereof, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological activity: The hormones, hormone agonists, hormone antagonists and hormone modulating agents (including the antiandrogens and antiestrogen agents) working via one or more pharmacological actions as described herein have been identified as suitable anti-cancer agents. The term 'hormonal therapies' is used to collectively to refer to hormones, hormone agonists, hormone antagonists and hormone modulating agents.

Technical background: Hormonal therapy plays an important role in the treatment of certain types of cancer where tumours are formed in tissues that are sensitive to hormonal growth control such as the breast and prostate. Thus, for example, estrogen promotes growth of certain breast cancers and testosterone promotes growth of prostate cancers. Since the growth of such tumours is dependent on specific hormones, considerable research has been carried out to investigate whether it is possible to affect tumour growth by increasing or decreasing the levels of certain hormones in the body. Hormonal therapy attempts to control tumour growth in these hormone-sensitive tissues by manipulating the activity of the hormones.

Cancers which are derived from either lymphocyte precursors or mature lymphocytes such as certain types of leukemia, Hodgkin's disease and non-Hodgkin's lymphoma often retain the sensitivity to treatment with corticosteroids including prednisolone, predisone and dexamethasone exhibited by mature lymphophocytes. As a consequence treatment with one or more corticosteroids is often incorporated into the treatment of these diseases. Thus contemplated for use with the invention are corticosteroids.

With regard to breast cancer, tumour growth is stimulated by estrogen, and antiestrogen agents have therefore been proposed and widely used for the treatment of this type of cancer. One of the most widely used of such agents is tamoxifen which is a competitive inhibitor of estradiol binding to the estrogen receptor (ER). When bound to the ER, tamoxifen induces a change in the three-dimensional shape of the receptor, inhibiting its binding to the estrogen responsive element on DNA. Under normal physiological conditions, estrogen stimulation increases tumour cell production of transforming growth cell b (TGF-b), an autocrine inhibitor of tumour cell growth. By blocking these pathways, the net effect of tamoxifen treatment is to decrease the autocrine stimulation of breast cancer growth. In addition, tamoxifen decreases the local production of insulin-like growth factor (IGF-1) by surrounding tissues: IGF-I is a paracrine growth factor for the breast cancer cell (Jordan and Murphy, Endocr. Rev., 1990, 11; 578-610). An alternative approach to disease control is to reduce circulating levels of estradiol by inhibition of aromatase—an enzyme which is critical for its production. Both Tamoxifen and aromatase inhibitors including anastrazole, letrozole and examestane are widely used in the treatment of post-menopausal women with breast cancer both in the adjuvant and metatsatic setting (e.g. metastatic breast cancer). Tamoxifen is also used in pre-menopausal women with ER-positive tumours. There are various potential side-effects of long-term tamoxifen treatment, for example the possibility of endometrial cancer and the occurrence of thrombo-embolic events. Although aromatase inhibitors are generally better tolerated than tamoxifen patients often experience musculoskeletal pain and significant bone loss leading to osteoporosis.

Other estrogen receptor antagonists (or selective estrogen receptor modulators (SERMs)) with broadly similar action to tamoxifen include toremifene and raloxifene. Toremifene is a non-steroidal SERM, which has the chemical name 2-(4-[(Z)-4-chloro-1,2-diphenyl-1-butenyl]-phenoxy)-N,N-dimethylethylamine, and is used for the treatment of metastatic breast cancer, side-effects including hot flushes, nausea and dizziness. Raloxifene is a benzothiophene SERM, which has the chemical name [6-hydroxy-2-(4-hydroxyphenyl)benzo[b]thien-3-yl]-[4-[2-(1-piperidinyl)ethoxy]-phenyl]-methanone hydrochloride, and is being investigated for the treatment of breast cancer, side-effects including hot flushes and leg cramps.

Fulvestrant, which acts by reducing the expression of the ER in tumour tissue has the chemical name 7-α-[9-(4,4,5,5,5-pentafluoropentylsulphinyl)-nonyl]estra-1,3,5-(10)-triene-3,17-beta-diol, is often used following treatment with tamoxifen and an aromatase inhibitor (e.g. as a second line treatment of advanced breast cancer). Treatment may be accompanied by hot flushes and endometrial stimulation.

Prostate cancer cells almost invariably overexpress the androgen receptor, and thus antiandrogens are widely used in the treatment of the disease. Antiandrogens are androgen receptor antagonists which bind to the androgen receptor and prevent dihydrotestosterone from binding. Dihydrotestosterone stimulates new growth of prostate cells, including cancerous prostate cells. An example of an antiadrogen is bicalutamide, which has the chemical name (R,S)—N-(4-cyano-3-(4-fluorophenylsulfonyl)-2-hydroxy-2-methyl-3-(trifluoromethyl)propanamide, and has been approved for use in combination with luteinizing hormone-releasing hormone (LHRH) analogs for the treatment of advanced prostate cancer, side effects including hot flushes, bone pain, hematuria and gastro-intestinal symptoms. An alternative means of reducing circulating levels of dihydrotestosterone is to directly inhibit its production from testosterone using flutamide.

In one embodiment the hormonal therapies include fulvestrant, toremifene and raloxifene. A further type of hormonal cancer treatment comprises the use of progestin analogs. Progestin is the synthetic form of progesterone, a hormone secreted by the ovaries and endometrial lining of the uterus. Acting with estrogen, progesterone promotes breast development and growth of endometrial cells during the menstrual cycle. It is believed that progestins may act by suppressing the production of estrogen from the adrenal glands (an alternate source particularly in post-menopausal women), lowering estrogen receptor levels, or altering tumour hormone metabolism.

Progestin analogs are used in the management of uterine cancer (e.g. advanced uterine cancer) or renal cancer. They can also be used for treating advanced breast cancer, although this use is less common, due to the numerous anti-estrogen treatment options available. Occasionally, progestin analogs are used as hormonal therapy for prostate cancer. An example of a progestin analog is megestrol acetate (a.k.a. megestrel acetate), which has the chemical name 17α-acetyloxy-6-methylpregna-4,6-diene-3,20-dione, and is a putative inhibitor of pituitary gonadotrophin production with a resultant decrease in estrogen secretion, The drug is used for the palliative treatment of advanced carcinoma of the breast or endometrium (i.e., recurrent, inoperable, or metastatic disease), side-effects including oedema and thromoembolic episodes.

Preferences and specific embodiments: A particularly preferred antiestrogen agent for use in accordance with the invention is tamoxifen. Tamoxifen is commercially available for example from AstraZeneca plc under the trade name Nolvadex, or may be prepared for example as described in U.K. patent specifications 1064629 and 1354939, or by processes analogous thereto.

Yet another preferred antiestrogen agent is droloxifene. Fulvestrant is commercially available for example from AstraZeneca plc under the trade name Faslodex, or may be prepared for example as described in European patent specification No.138504, or by processes analogous thereto. Raloxifene is commercially available for example from Eli Lilly and Company under the trade name Evista, or may be prepared for example as described in U.S. Pat. No. 4,418,068, or by processes analogous thereto. Toremifene is commercially available for example from Schering Corporation under the trade name Fareston, or may be prepared for example as described in U.S. Pat. No. 4,696,949, or by processes analogous thereto. The antiestrogen agent droloxifene, which may be prepared for example as described in U.S. Pat. No. 5,047,431, or by processes analogous thereto, can also be used in accordance with the invention.

A preferred antiandrogen for use in accordance with the invention is bicalutamide which is commercially available for example from AstraZeneca plc under the trade name Casodex, or may be prepared for example as described in European patent specification No. 100172, or by processes analogous thereto. Other preferred hormonal therapies for use in accordance with the invention include tamoxifen, fulvestrant, raloxifene, toremifene, droloxifene, letrazole, anastrazole, exemestane, bicalutamide, luprolide, megestrol/megestrel acetate, aminoglutethimide (alternatively spelt aminoglutethamide) and flutamide.

Other preferred hormonal therapies for use in accordance with the invention include tamoxifen, fulvestrant, raloxifene, toremifene, droloxifene, letrazole, anastrazole, exemestane, bicalutamide, luprolide, megestrol/megestrel acetate, aminoglutethimide and bexarotene.

A preferred progestin analog is megestrol/megestrel acetate which is commercially available for example from Bristol-Myers Squibb Corporation under the trade name Megace, or may be prepared for example as described in U.S. Pat. No. 2,891,079, or by processes analogous thereto.

Thus, specific embodiments of these anti-cancer agents for use in the combinations of the invention include: tamoxifen; toremifene; raloxifene; medroxyprogesterone; megestrol/megestrel; aminoglutethimide; letrozole; anastrozole; exemestane; goserelin; leuprolide; abarelix; fluoxymestrone; diethylstilbestrol; ketoconazole; fulvestrant; flutamide; bicalutimide; nilutamide; cyproterone and buserelin.

Thus, contemplated for use in the combinations of the invention are antiandrogens and antiestrogens.

In other embodiments, the hormone, hormone agonist, hormone antagonist or hormone modulating agent is fulvestrant, raloxifene, droloxifene, toremifene, megestrol/megestrel and flutamide.

In other embodiments, the hormone, hormone agonist, hormone antagonist or hormone modulating agent is fulvestrant, raloxifene, droloxifene, toremifene, megestrol/megestrel and bexarotene.

In one embodiment the hormones, hormone agonists, hormone antagonists and hormone modulating agents include corticosteroids, antiandrogens, antiestrogens and GNRAs. In another embodiment the hormones, hormone agonists, hormone antagonists and hormone modulating agents include antiandrogens, antiestrogens and GNRAs.

Posology: The antiandrogen or antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day (or 20 mg once a day), continuing the therapy for sufficient time to achieve and maintain a therapeutic effect.

With regard to the other preferred antiestrogen agents: fulvestrant is advantageously administered in the form of a 250 mg monthly injection (though doses of 250-750 mg per month may also be employed); toremifene is advantageously administered orally in a dosage of about 60 mg once a day, continuing the therapy for sufficient time to achieve and maintain a therapeutic effect; droloxifene is advantageously administered orally in a dosage of about 20-100 mg once a day; and raloxifene is advantageously administered orally in a dosage of about 60 mg once a day.

With regard to the preferred antiandrogen bicalutamide, this is generally administered in an oral dosage of 50 mg daily.

With regard to the preferred progestin analog megestrol/megestrel acetate, this is generally administered in an oral dosage of 40 mg four times daily.

The dosages noted above may generally be administered for example once, twice or more per course of treatment, which may be repeated for example daily or every 7, 14, 21 or 28 days in particular every 7, 14, 21 or 28 days.

Aromatase Inhibitors

Of the hormones, hormone agonists, hormone antagonists and hormone modulating agents for use in the combinations of the invention, preferred are aromatase inhibitors.

In post-menopausal women, the principal source of circulating estrogen is from conversion of adrenal androgens (androstenedione and testosterone) to estrogens (estrone and estradiol) by the aromatase enzyme in peripheral tissues. Estrogen deprivation through aromatase inhibition or inactivation is an effective and selective treatment for some post-menopausal patients with hormone-dependent breast cancer. Examples of such hormone modulating agents include aromatase inhibitors or inactivators, such as exemestane, anastrozole, letrozole and aminoglutethimide.

Exemestane, which has the chemical name 6-methylenandrosta-1,4-diene-3,17-dione, is used for the treatment of advanced breast cancer in post-menopausal women whose disease has progressed following tamoxifen therapy, side effects including hot flashes and nausea. Anastrozole, which has the chemical name, $\alpha,\alpha,\alpha',\alpha'$-tetramethyl-5-(1H-1,2,4-triazol-1-ylmethyl)-1,3-benzenediacetonitrile, is used for adjuvant treatment of post-menopausal women with hormone receptor-positive early breast cancer, and also for the first-line treatment of post-menopausal women with hormone receptor-positive or hormone receptor-unknown locally advanced or metastatic breast cancer, and for the treatment of advanced breast cancer in post-menopausal women with disease progression following tamoxifen therapy. Administration of anastrozole usually results in side-effects including gastrointestinal disturbances, musculoskeletal pain, rashes and headaches. Letrozole, which has the chemical name 4,4'-(1H-1,2,4-triazol-1-ylmethylene)-dibenzonitrile, is used for the adjuvant treatment of ER positive breast cancer, for first-line treatment of post-menopausal women with hormone receptor-positive or hormone receptor-unknown locally advanced or metastatic breast cancer, and for the treatment of advanced breast cancer in post-menopausal women with disease progression following antiestrogen therapy, possible side-effects including occasional transient thrombocytopenia and elevation of liver transaminases.

Aminoglutethimide which has the chemical name 3-(4-aminophenyl)-3-ethyl-2,6-piperidinedione, is also used for treating breast cancer but suffers from the side-effects of skin rashes and less commonly thrombocytopenia and leukopenia.

Preferred aromatase inhibitors include letrozole, anastrozole, exemestane and aminoglutethimide. Letrozole is commercially available for example from Novartis A.G. under the trade name Femara, or may be prepared for example as described in U.S. Pat. No. 4,978,672, or by processes analogous thereto. Anastrozole is commercially available for example from AstraZeneca plc under the trade name Arimidex, or may be prepared for example as described in U.S. Pat. No. 4,935,437, or by processes analogous thereto. Exemestane is commercially available for example from Pharmacia Corporation under the trade name Aromasin, or may be prepared for example as described in U.S. Pat. No. 4,978,672, or by processes analogous thereto. Aminoglutethimide is commercially available for example from Novartis A.G. under the trade name Cytadren, or may be prepared for example as described in U.S. Pat. No 2,848,455, or by processes analogous thereto. The aromatase inhibitor vorozole, which may be prepared for example as described in European patent specification No. 293978, or by processes analogous thereto, can also be used in accordance with the invention.

With regard to the preferred aromatase inhihibitors, these are generally administered in an oral daily dosage in the range 1 to 1000 mg, for example letrozole in a dosage of about 2.5 mg once a day; anastrozole in a dosage of about 1 mg once a day; exemestane in a dosage of about 25 mg once a day; and aminoglutethimide in a dosage of 250 mg 2-4 times daily.

Particularly preferred are aromatase inhibitors selected from the agents described herein, for example, letrozole, anastrozole, exemestane and aminoglutethimide.

GNRAs

Of the hormones, hormone agonists, hormone antagonists and hormone modulating agents for use in the combinations of the invention, preferred are agents of the GNRA class.

Definition: As used herein the term GNRA is intended to define gonadotropin-releasing hormone (GnRH) agonists and antagonists (including those described below), together with the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: When released from the hypothalamus in the brain, gonadotropin-releasing hormone (GnRH) agonists stimulate the pituitary gland to produce gonadotropins. Gonadotropins are hormones that stimulate androgen synthesis in the testes and estrogen synthesis in the ovaries. When GnRH agonists are first administered, they can cause an increase in gonadotropin release, but with continued administration, GnRH will block gonadotropin release, and therefore decrease the synthesis of androgen and estrogen. GnRH analogs are used to treat metastatic prostate cancer. They have also been approved for treatment of metastatic breast cancer in pre-menopausal women. Examples of GnRH analogs include goserelin acetate and leuprolide acetate. In contrast GnRH antagonists such as aberelix cause no initial GnRH surge since they have no agonist effects. However, due to their narrow therapeutic index, their use is currently limited to advanced prostate cancer that is refractory to other hormonal treatment such as GnRH agonists and anti-androgens.

Goserelin acetate is a synthetic decapeptide analog of LHRH or GnRH, and has the chemical structure of pyro-Glu-His-Trp-Ser-Tyr-D-Ser(Bu)-Leu-Arg-Pro-Azgly-NH$_2$ acetate (SEQ ID NO: 1), and is used for the treatment of breast and prostate cancers and also endometriosis, side effects including hot flashes, bronchitis, arrhythmias, hypertension, anxiety and headaches. Leuprolide acetate is a synthetic nonapeptide analog of GnRH or LHRH, and has the chemical name 5-oxo-L-prolyl-L-histidyl-L-tryptophyl-L-seryl-L-tyrosyl-D-leucyl-L-leucyl-L-arginyl-N-ethyl-L-prolinamide acetate (SEQ ID NO: 2. Leuprolide acetate is used for the treatment of prostate cancer, endometriosis, and also breast cancer, side effects being similar to those of goserelin acetate.

Abarelix is a synthetic decapeptide Ala-Phe-Ala-Ser-Tyr-Asn-Leu-Lys-Pro-Ala (SEQ ID NO: 3), and has the chemical name N-Acetyl-3-(2-naphthalenyl)-D-alanyl-4-chloro-D-phenylalanyl-3-(3-pyridinyl)-D-alanyl-L-seryl-N-methyl-L-tyrosyl-D-asparaginyl-L-leucyl-N6-(1-methylethyl)-L-lysyl-L-prolyl-D-alaninamide. Abarelix can be prepared according to R. W. Roeske, WO9640757 (1996 to Indiana Univ. Found.).

Preferences and specific embodiments: Preferred GnRH agonists and antagonists for use in accordance with the invention include any of the GNRAs described herein, including in particular goserelin, leuprolide/leuporelin, triptorelin, buserelin, abarelix, goserelin acetate and leuprolide acetate. Particularly preferred are goserelin and leuprolide. Goserelin acetate is commercially available for example from AstraZeneca plc under the trade name Zoladex, or may be prepared for example as described in U.S. Pat. No. 5,510,460, or by processes analogous thereto. Leuprolide acetate is commercially available for example from TAP Pharmaceuticals Inc. under the trade name Lupron, or may be prepared for example as described in U.S. Pat. No. 3,914,412, or by processes analogous thereto. Goserelin is commercially available from AstraZeneca under the trade name Zoladex and may be prepared for example as described in ICI patent publication U.S. Pat. No. 4,100,274 or Hoechst patent publication EP475184 or by processes analagous thereto. Leuprolide is commercially available in the USA from TAP Pharmaceuticals Inc. under the trade name Lupron and in Europe from Wyeth under the trade name Prostap and may be prepared for example as described in Abbott patent publication U.S. Pat. No. 4,005,063 or by processes analogous thereto. Triptorelin is commercially available from Watson Pharma under the trade name Trelstar and may be prepared for example as described in Tulane patent publication U.S. Pat. No. 5,003,011 or by processes analagous thereto. Buserelin is commercially available under the trade name Suprefact and may be prepared for example as described in Hoechst patent publication U.S. Pat. No. 4,024,248 or by processes analogous thereto. Abarelix is commercially available from Praecis Pharmaceuticals under the trade name Plenaxis and may be prepared for example as described by Jiang et al., J Med Chem (2001), 44(3), 453-467 or Polypeptide Laboratories patent publication WO2003055900 or by processes analogous thereto.

Other GnRH agonists and antagonists for use in accordance with the invention include, but are not limited to, Histrelin from Ortho Pharmaceutical Corp, Nafarelin acetate from Roche, and Deslorelin from Shire Pharmaceuticals.

Posology: The GnRH agonists and antagonists are advantageously administered in dosages of 1.8 mg to 100 mg, for example 3.6 mg monthly or 10.8 mg every three months for goserelin or 7.5 mg monthly, 22.5 mg every three months or 30 mg every four months for leuprolide.

With regard to the preferred GnRH analogs, these are generally administered in the following dosages, namely goserelin acetate as a 3.6 mg subcutaneous implant every 4 weeks, and leuprolide as a 7.5 mg intramuscular depot every month.

2. Cytokines and Cytokine-Activating Agents

Definition: The term "cytokine" is a term of art, and references to cytokines herein is intended to cover the cytokine perse together with the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. The term "cytokine-activating agent" is intended to cover any agent which (directly or indirectly) induces, potentiates, stimulates, activates or promotes endogenous cytokine production or the activity thereof in vivo, together with the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: Cytokines are a class of proteins or polypeptides predominantly produced by cells of the immune system which have the capacity to control the function of a second cell. In relation to anticancer therapy cytokines are used to control the growth or kill the cancer cells directly and to modulate the immune system more effectively to control the growth of tumours.

Cytokines, such as interferon (IFN) alpha and Interleukin-2, induce growth arrest or tumour cell death. IFN-alpha is used the treatment of malignant melanoma, chronic myelogenous leukemia (CML), hairy cell leukemia, and Kaposi's sarcoma. Interleukin-2 is used in the treatment of malignant melanoma and renal cell cancer either alone or in combination with IFN-alpha.

Cytokines exhibit antitumour activity through a variety of different mechanisms including the stimulation of immune cells to fight tumors For example, the T cell growth factor, IL-2 promotes T-cell and natural killer (NK) cell activation. Other cytokines such as the interferons and granulocyte-macrophage colony-stimulating factor (GM-CSF) act on antigen presenting cells to facilitate the activation of the key immune effector B cells and T cells.

Preferences and specific embodiments: Any of the cytokines and cytokine-modulating agents described herein may find application in the invention, including in particular interferons (such as interferon-y and interferon a) and interleukins (e.g. interleukin 2). Interferon α-2b (recombinant) is available commercially under the trade name of INTRON® A from Schering Plough.

Other preferred interferons include Interferon α-2a which is available under the trade name of ROFERON from Roche.

A particularly preferred interleukin is PROLEUKIN® IL-2 (aldesleukin) which is available from Chiron Corp.

Posology: The interferons are administered by injection in a schedule which is dependent on the particular indication. For IntronA treatment of malignant melanoma preferably in a schedule that includes induction treatment on 5 consecutive days per week for 4 weeks as an intravenous (IV) infusion at a dose of 20 million IU/m2, followed by maintenance treatment three times per week for 48 weeks as a subcutaneous (SC) injection, at a dose of 10 million IU/m2. For Intron A treatment of non-Hodgkin's Lymphoma preferably in a schedule of 5 million IU subcutaneously three times per week for up to 18 months in conjunction with an anthracycline-containing chemotherapy regimen.

The recommended initial dose of Roferon-A for CML is 9 MIU daily administered as a subcutaneous or intramuscular injection. Based on clinical experience short-term tolerance may be improved by gradually increasing the dose of Roferon-A over the first week of administration from 3 MIU daily for 3 days to 6 MIU daily for 3 days to the target dose of 9 MIU daily for the duration of the treatment period. The induction dose of Roferon-A for Hairy cell leukaemia is 3 MIU daily for 16 to 24 weeks, administered as a subcutaneous or intramuscular injection. Subcutaneous administration is particularly suggested for, but not limited to, thrombocytopenic patients (platelet count <50,000) or for patients at risk for bleeding. The recommended maintenance dose is 3 MIU, three times a week (tiw).

For PROLEUKIN the following schedule has been used to treat adult patients with metastatic renal cell carcinoma (metastatic RCC) or metastatic melanoma (each course of treatment consists of two 5-day treatment cycles separated by a rest period): 600,000 IU/kg (0.037 mg/kg) dose administered every 8 hours by a 15-minute IV infusion for a maximum of 14 doses. Following 9 days of rest, the schedule is repeated for another 14 doses, for a maximum of 28 doses per course, as tolerated.

Cytokine-activating agents: Preferred cytokine-activating agents include: (a) Picibanil from Chugai Pharmaceuticals, an IFN-gamma-inducing molecule for carcinoma treatment; (b) Romurtide from Daiichi which activates the cytokine network by stimulation of colony stimulating factor release; (c) Sizofiran from Kaken Pharmaceutical, a beta1-3, beta1-6 D-glucan isolated from suehirotake mushroom, which stimulates production of IFN-gamma and IL-2 by mitogen-stimulated peripheral blood mononuclear cells, and is useful in uterine cervix tumour and lung tumour treatment; (d) Virulizin from Lorus Therapeutics Inc, a NK agonist and cytokine release modulator which stimulates IL-17 synthesis and IL-12 release for the treatment of sarcoma, melanoma, pancreas tumours, breast tumours, lung tumours, and Kaposi sarcoma (e) Thymosin alpha 1, a synthetic 28-amino acid peptide with multiple biological activities primarily directed towards immune response enhancement for increased production of Th1 cytokines, which is useful in the treatment of non-small-cell lung cancer, hepatocellular carcinoma, melanoma, carcinoma, and lung brain and renal tumours.

3. Retinoids and Rexinoids

Definition: The term "retinoid" is a term of art used herein in a broad sense to include not only the specific retinoids disclosed herein, but also the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. The term 'rexinoids' refers to synthetic agents that bind specifically to retinoid X receptors.

Technical background: Tretinoin is an endogenous metabolite of retinol. It induces terminal differentiation in several hemopoietic precursor cell lines, including human myeloid cell lines. Acute Promyelocytic Leukemia (APL) is associated with a specific translocation between chromosomes 15 and 17; the retinoic acid receptor-α is located on chromosome 17. The translocation appears to inhibit differentiation and lead to carcinogenesis; tretinoin may overcome this when used in high doses. Tretinoin induces remissions in 64-100% of APL patients, with time to remission usually between 8 and 119 days of therapy. Acquired resistance during therapy is common especially with prolonged dosing (4-6 months).

Alitretinoin is a 9-cis-retinoic acid derivative which appears to be selective for the RXR subfamily of retinoid receptors. This selectivity may preserve therapeutic antineoplastic effects while reducing significant side effects of retinoid therapy including birth defects at fetal exposure, irritation of skin and mucosal surfaces or skeletal abnormalities. Topical alitretinoin is approved in the US for the treatment of Kaposi's Sarcoma. Oral and gel (topical) formulations of bexarotene (Targretin; LGD-1069), a retinoid X receptor (RXR)-selective antitumor retinoid, are available for the treatment of cutaneous T-cell lymphoma (CTCL).

U.S. Pat. No. 6,127,382, WO 01/70668, WO 00/68191, WO 97/48672, WO 97/19052 and WO 97/19062 (all to Allergan) each describe compounds having retinoid-like activity for use in the treatment of various hyperproliferative diseases including cancers.

Preferences and specific embodiments: Preferred retinoids for use in accordance with the invention include any of the retinoids disclosed herein, including in particular tretinoin (all-trans retinoic acid), alitretinoin and bexarotene. Tretinoin (Retacnyl, Aknoten, Tretin M) is commercially available from Roche under the trade name Vesanoid and may be prepared for example as described in D. A. van Dorp, J. R. Arens, Rec. Trav. Chim. 65, 338 (1946); C. D. Robeson et al., J. Am. Chem. Soc. 77, 4111 (1955); R. Marbet, DE 2061507; U.S. Pat. No. 3,746,730 (1971,1973 both to Hoffmann-La Roche), or by processes analogous thereto. Alitretinoin (9-cis-Tretinoin, Panrexin) is commercially available from Ligand Pharmaceuticals under the trade name Panretin and may be prepared for example as described in C. D. Robeson et al., J. Am. Chem. Soc. 77, 4111 (1955); M. Matsui et al., J. Vitaminol. 4, 178 (1958); M. F. Boehm et al., J. Med. Chem. 37, 408 (1994), or by processes analogous thereto. Bexarotene (Targrexin, Targret) is commercially available from Eisai Inc under the trade name Targretin and may be prepared for example as described in M. F. Boehm et al., WO 9321146 (1993 to Ligand Pharm.); M. L. Dawson et al., U.S. Pat. No. 5,466,861 (1995 to SRI Int.; La Jolla Cancer Res. Found.), or by processes analogous thereto.

Posology: Tretinoin is advantageously administered in dosages of 25 mg/m$^2$/day to 45 mg/m$^2$/day by mouth in two divided doses for 30 days after complete remission or up to a maximum of 90 days. Alitretinoin gel 0.1% is advantageously administered initially by application two (2) times a day to cutaneous KS lesions.

Bexarotene is advantageously administered initially as a single daily oral dose of 300 mg/m$^2$/day. The dose may be adjusted to 200 mg/m$^2$/day then to 100 mg/m$^2$/day, or temporarily suspended, if necessitated by toxicity. If there is no tumor response after eight weeks of treatment and if the initial dose of 300 mg/m2/day is well tolerated, the dose may be escalated to 400 mg/m$^2$/day with careful monitoring. Bexarotene gel is advantageously applied initially once every other day for the first week. The application frequency may be increased at weekly intervals to once daily, then twice daily, then three times daily and finally four times daily according to individual lesion tolerance.

4. Monoclonal Antibodies.

Any monoclonal antibody e.g. including but not limited to one or more cell surface antigen(s) may be used in the combinations of the invention. Antibody specificity may be assayed or determined using any of a wide variety of techniques well-known to those skilled in the art.

Definition: The term "monoclonal antibody" used herein refers to antibodies from any source, and so includes those that are fully human and also those which contain structural or specificity determining elements derived from other species (and which can be referred to as, for example, chimeric or humanized antibodies).

Technical background: The use of monoclonal antibodies is now widely accepted in anticancer chemotherapy as they are highly specific and can therefore bind and affect disease specific targets, thereby sparing normal cells and causing fewer side-effects than traditional chemotherapies.

One group of cells which have been investigated as targets for antibody chemotherapy for the treatment of various cancers are those bearing the cell-surface antigens comprising the cluster designation (CD) molecules which are over-expressed or aberrantly expressed in tumour cells, for example CD20, CD22, CD33 and CD52 which are over-expressed on the tumour cell surface, most notably in tumours of hematopoietic origin. Antibodies to these CD targets (anti-CD antibodies) include the monoclonal antibodies rituximab (a.k.a. rituxamab), tositumomab and gemtuzumab ozogamicin.

Rituximab/rituxamab is a mouse/human chimeric anti-CD20 monoclonal antibody which has been used extensively for the treatment of B-cell non-Hodgkin's lymphoma including relapsed, refractory low-grade or follicular lymphoma. The product is also being developed for various other indications including chronic lymphocytic leukaemia and rheumatoid arthritis. Side effects of rituximab/rituxamab may include hypoxia, pulmonary infiltrates, acute respiratory distress syndrome, myocardial infarction, ventricular fibrillation or cardiogenic shock. Tositumomab is a cell-specific anti-CD20 antibody labelled with iodine-131, for the treatment of non-Hodgkin's lymphoma and lymphocytic leukaemia. Possible side-effects of tositumomab include thrombocytopenia and neutropenia. Gemtuzumab ozogamicin is a cytotoxic drug (calicheamicin) linked to a human monoclonal antibody specific for CD33. Calicheamicin is a very potent antitumour agent, over 1,000 times more potent than adriamycin. Once released inside the cell, calicheamicin binds in a sequence-specific manner to the minor groove of DNA, undergoes rearrangement, and exposes free radicals, leading to breakage of double-stranded DNA, and resulting in cell apoptosis (programmed cell death). Gemtuzumab ozogamicin is used as a second-line treatment for acute myeloid leukaemia, possible side-effects including severe hypersensitivity reactions such as anaphylaxis, and also hepatotoxicity.

Alemtuzumab (Millennium Pharmaceuticals, also known as Campath) is a humanized monoclonal antibody against CD52 useful for the treatment of chronic lymphocytic leukaemia and Non-Hodgkin lymphoma which induces the secretion of TNF-alpha, IFN-gamma and IL-6.

Preferences: Preferred monoclonal antibodies for use according to the invention include anti-CD antibodies, including alemtuzumab, CD20, CD22 and CD33. Particularly preferred are monoclonal antibody to cell surface antigens, including anti-CD antibodies (for example, CD20, CD22, CD33) as described above. Other preferred monoclonal antibodies include those which target interleukin 6 (IL-6).

Specific embodiments: In one embodiment, the monoclonal antibody is an antibody to the cluster designation CD molecules, for example, CD20, CD22, CD33 and CD52. In another embodiment, the monoclonal antibody to cell surface antigen is selected from rituximab/rituxamab, tositumomab and gemtuzumab ozogamicin. Other monoclonal antibodies that may be used according to the invention include bevacizumab.

Exemplary formulations: Monoclonal antibodies to cell surface antigen(s) for use according to the invention include CD52 antibodies (e.g. alemtuzumab) and other anti-CD antibodies (for example, CD20, CD22 and CD33), as described herein. Preferred are therapeutic combinations comprising a monoclonal antibody to cell surface antigen(s), for example anti-CD antibodies (e.g. CD20, CD22 and CD33) which exhibit an advantageous efficacious effect, for example, against tumour cell growth, in comparison with the respective effects shown by the individual components of the combination.

CD52 selctivity has also been achieved through the combination of a specific ligand with diphtheria toxin which is released intracellularly (denileukin difitox; Ontak). This approach has been licensed for use in the treatment of cutaneous T-cell lymphoma and is under investigation for the treatment of other types of non-hodgkin's lymphoma.

In addition targeting structures other than tumour cells themselves have also been shown to be efficacious in cancer therapy. This approach has been most effective in inhibiting new blood vessel formation using bevacuzimab, a monoclonal antibody directed against circulating Vascular Endothelial Growth Factor. This approach may be useful in the treatment of a wide range of malignancies.

Preferred examples of monoclonal antibodies to cell surface antigens (anti-CD antibodies) include rituximab/rituxamab, tositumomab and gemtuzumab ozogamicin. Rituximab/rituxamab is commercially available from F Hoffman-La Roche Ltd under the trade name Mabthera, or may be obtained as described in PCT patent specification No. WO 94/11026. Tositumomab is commercially available from GlaxoSmithKline plc under the trade name Bexxar, or may be obtained as described in U.S. Pat. No. 5,595,721. Gemtuzumab ozogamicin is commercially available from Wyeth Research under the trade name Mylotarg, or may be obtained as described in U.S. Pat. No. 5,877,296.

Biological activity: Monoclonal antibodies (e.g. monoclonal antibodies to one or more cell surface antigen(s)) have been identified as suitable anti-cancer agents. Antibodies are effective through a variety of mechanisms. They can block essential cellular growth factors or receptors, directly induce apoptosis, bind to target cells or deliver cytotoxic payloads such as radioisotopes and toxins.

Posology: The anti-CD antibodies may be administered for example in dosages of 5 to 400 mg per square meter ($mg/m^2$) of body surface; in particular gemtuzumab ozogamicin may be administered for example in a dosage of about 9 $mg/m^2$ of body surface; rituximab/rituxamab may be administered for example in a dosage of about 375 $mg/m^2$ as an IV infusion once a week for four doses; the dosage for tositumomab must be individually quantified for each patient according to the usual clinical parameters such as age, weight, sex and condition of the patient to ensure appropriate delivery of the radioisotope.

These dosages may be administered for example once, twice or more per course of treatment, which may be repeated for example every 7, 14, 21 or 28 days.

5. Camptothecin Compounds

Definition: The term "camptothecin compound" as used herein refers to camptothecin per se or analogues of camptothecin as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: Camptothecin compounds are compounds related to or derived from the parent compound camptothecin which is a water-insoluble alkaloid derived from the Chinese tree Camptothecin acuminata and the Indian tree Nothapodytes foetida. Camptothecin has a potent inhibitory activity against DNA biosynthesis and has shown high activity against tumour cell growth in various experimental systems. Its clinical use in anti-cancer therapy is, however, limited significantly by its high toxicity, and various analogues have been developed in attempts to reduce the toxicity of camptothecin while retaining the potency of its anti-tumour effect. Examples of such analogues include irinotecan and topotecan.

These compounds have been found to be specific inhibitors of DNA topoisomerase I. Topoisomerases are enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme having a molecular weight of approximately 100,000. The enzyme binds to DNA and introduces a transient single-strand break, unwinds the double helix (or allows it to unwind) and subsequently reseals the break before dissociating from the DNA strand.

Irinotecan, namely 7-ethyl-10-(4-(1-piperidino)-1-piperidino)carbonyloxy-(20S)-camptothecin, and its hydrochloride, also known as CPT 11, have been found to have improved potency and reduced toxicity, and superior water-solubility. Irinotecan has been found to have clinical efficacy in the treatment of various cancers especially colorectal cancer. Another important camptothecin compound is topotecan, namely (S)-9-dimethylaminomethyl-10-hydroxy-camptothecin which, in clinical trials, has shown efficacy against several solid tumours, particularly ovarian and cervical cancer and small cell lung cancer or alternatively ovarian cancer and non-small cell lung carcinoma.

Exemplary formulations: A parenteral pharmaceutical formulation for administration by injection and containing a camptothecin compound can be prepared by dissolving 100 mg of a water soluble salt of the camptothecin compound (for example a compound as described in EP 0321122 and in particular the examples therein) in 10 ml of sterile 0.9% saline and then sterilising the solution and filling the solution into a suitable container.

Biological activity: The camptothecin compounds of the combinations of the invention are specific inhibitors of DNA topoisomerase I are described above and have activity against various cancers.

Prior art references: WO 01/64194 (Janssen) discloses combinations of farnesyl transferase inhibitors and camptothecin compounds. EP 137145 (Rhone Poulenc Rorer) discloses camptothecin compounds including irinotecan. EP 321122 (SmithKline Beecham) discloses camptothecin compounds including topotecan.

Problems: Although camptothecin compounds are widely used as chemotherapeutic agents in humans, they are not therapeutically effective in all patients or against all types of tumours. There is therefore a need to increase the inhibitory efficacy of camptothecin compounds against tumour growth and also to provide a means for the use of lower dosages of camptothecin compounds to reduce the potential for adverse toxic side effects to the patient.

Preferences: Preferred camptothecin compounds for use in accordance with the invention include irinotecan and topotecan referred to above. Irinotecan is commercially available for example from Rhone-Poulenc Rorer under the trade name "Campto" and may be prepared for example as described in European patent specification No.137145 or by processes analogous thereto. Topotecan is commercially available for example from SmithKline Beecham under the trade name "Hycamtin" and may be prepared for example as described in European patent number 321122 or by processes analogous thereto. Other camptothecin compounds may be prepared in conventional manner for example by processes analogous to those described above for irinotecan and topotecan.

Specific embodiments: In one embodiment, the camptothecin compound is irinotecan. In another embodiment, the camptothecin compound is a camptothecin compound other than irinotecan, for example a camptothecin compound such as topotecan.

Posology: The camptothecin compound is advantageously administered in a dosage of 0.1 to 400 mg per square metre (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment. These dosages may be administered for example once, twice or more per course of treatment, which may be repeated daily or every 7, 14, 21 or 28 days in particular every 7, 14, 21 or 28 days.

6. Antimetabolites

Definition: The terms "antimetabolic compound" and "antimetabolite" are used as synonyms and define antimetabolic compounds or analogues of antimetabolic compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. Thus, the antimetabolic compounds, otherwise known as antimetabolites, referred to herein consitute a large group of anticancer drugs that interfere with metabolic processes vital to the physiology and proliferation of cancer cells. Such compounds include nucleoside derivatives, either pyrimidine or purine nucleoside analogs, that inhibit DNA synthesis, and inhibitors of thymidylate synthase and/or dihydrofolate reductase enzymes.

Technical background: Antimetabolites (or antimetabolic compounds), constitute a large group of anticancer drugs that interfere with metabolic processes vital to the physiology and proliferation of cancer cells. Such compounds include nucleoside derivatives, either pyrimidine or purine nucleoside analogues, that inhibit DNA synthesis, and inhibitors of thymidylate synthase and/or dihydrofolate reductase enzymes. Anti-tumour nucleoside derivatives have been used for many years for the treatment of various cancers. Among the oldest and most widely used of these derivatives is 5-fluorouracil (5-FU) which has been used to treat a number of cancers such as colorectal, breast, hepatic and head and neck tumours.

In order to enhance the cytotoxic effect of 5-FU, leucovorin has been used to stabilise the resulting thymidylate synthase/5-FU complex thus further increasing its inhibiton . However, various factors limit the use of 5-FU, for example tumour resistance, toxicities, including gastrointestinal and haematological effects, and the need for intravenous administration. Various approaches have been taken to overcome these disadvantages including proposals to overcome the poor bioavailability of 5-FU and also to increase the therapeutic index of 5-FU, either by reducing systemic toxicity or by increasing the amount of active drug reaching the tumour.

One such compound which provides an improved therapeutic advantage over 5-FU is capecitabine, which has the chemical name [1-(5-deoxy-β-D-ribofuranosyl)-5-fluoro-1, 2-dihydro-2-oxo-4-pyrimidinyl]-carbamic acid pentyl ester. Capecitabine is a pro-drug of 5-FU which is well absorbed after oral dosing and delivers pharmacologically-active concentrations of 5-FU to tumours. As well as offering potentially superior activity to 5-FU, it can also be used for oral therapy with prolonged administration.

Gemcitabine is a nucleoside analogue which has the chemical name 2'-deoxy-2',2'-difluoro-cytidine, and which has been used in the treatment of various cancers including non-small cell lung cancer, breast, ovarian and pancreatic cancer in particular non-small cell lung cancer and pancreatic cancer. Further anti-tumour nucleosides include cytarabine and fludarabine. Cytarabine, also known as ara-C, which has the chemical name 1-β-D-arabinofuranosylcytosine, has been found useful in the treatment of acute leukemia, chronic myelocytic leukemia and erythroleukemia. Cytarabine, also known as ara-C, which has the chemical name 1-β-D-arabinofuranosylcytosine, has been found useful in the treatment of acute myelocytic leukemia, chronic myelocytic leukemia (blast phase), acute lymphocytic leukemia and erythroleukemia. Fludarabine is a DNA synthesis inhibitor, which has the chemical name 9-β-D-arabinofuranosyl-2-fluoro-adenine, and is used for the treatment of refractory B-cell chronic lymphocytic leukaemia. Other anti-folate antimetabolites used in anticancer chemotherapy include the enzyme inhibitors raltitrexed, pemetrexed, and methotrexate. Raltitrexed is a folate-based thymidylate synthase inhibitor, which has the chemical name N-[5-[N-[(3,4-dihydro-2-methyl-4-oxo-6-quinazolinyl)-methyl-N-methylamino]-2-thenoyl]-L-glutamic acid, and is used in the treatment of advanced colorectal cancer. Pemetrexed is a thymidylate synthase and transferase inhibitor, which has the chemical name N-[4-[2-(2-amino-4,7-dihydro-4-oxo-1H-pyrrolo[2,3-d]pyrimidin-5-yl)ethyl]benzoyl]-L-glutamic acid, disodium salt, and is used for the treatment of mesothelioma and locally advanced or metastatic non-small-cell lung cancer (SCLC) in previously treated patients. Methotrexate is an antimetabolite which interrupts cell division by inhibiting DNA replication through dihydrofolate reductase inhibition, resulting in cell death, and has the chemical name is N-[4-[[(2,4-diamino-6-pteridinyl)methyl]-ethylamino]benzoyl]-L-glutamic acid, and is used for the treatment of acute lymphocytic leukemia, and also in the treatment of breast cancer, epidermoid cancers of the head and neck, and lung cancer, particularly squamous cell and small cell types, and advanced stage non-Hodgkin's lymphomas, in particular in the treatment of breast cancer, epidermoid cancers of the head and neck, and advanced stage non-Hodgkin's lymphomas.

Biological activity: The antimetabolic compounds of the combinations of the invention interfere with metabolic processes vital to the physiology and proliferation of cancer cells as described above and have activity against various cancers.

Problems: These anticancer agents have a number of side-effects especially myelosuppression and in some cases nausea and diarrhoea. There is therefore a need to provide a means for the use of lower dosages to reduce the potential of adverse toxic side effects to the patient.

Preferences: Preferred antimetabolic compounds for use in accordance with the invention include anti-tumour nucleosides such as 5-fluorouracil, gemcitabine, capecitabine, cytarabine and fludarabine and enzyme inhibitors such as ralitrexed, pemetrexed and methotrexate referred to herein. Thus, preferred antimetabolic compounds for use in accordance with the invention are anti-tumour nucleoside derivatives including 5-fluorouracil, gemcitabine, capecitabine, cytarabine and fludarabine referred to herein. Other preferred antimetabolic compounds for use in accordance with the invention are enzyme inhibitors including ralitrexed, pemetrexed and methotrexate.

5-Fluorouracil is widely available commercially, or may be prepared for example as described in U.S. Pat. No. 2,802,005. Gemcitabine is commercially available for example from Eli Lilly and Company under the trade name Gemzar, or may be prepared for example as described in European patent specification No.122707, or by processes analogous thereto. Capecitabine is commercially available for example from Hoffman-La Roche Inc under the trade name Xeloda, or may be prepared for example as described in European patent specification No. 698611, or by processes analogous thereto. Cytarabine is commercially available for example from Pharmacia and Upjohn Co under the trade name Cytosar, or may be prepared for example as described in U.S. Pat. No. 3,116,282, or by processes analogous thereto. Fludarabine is commercially available for example from Schering AG under the trade name Fludara, or may be prepared for example as described in U.S. Pat. No.4,357,324, or by processes analogous thereto. Ralitrexed is commercially available for example from AstraZeneca plc under the trade name Tomudex, or may be prepared for example as described in European patent specification No.239632, or by processes analogous thereto. Pemetrexed is commercially available for example from Eli Lilly and Company under the trade name Alimta, or may be prepared for example as described in European patent specification No.432677, or by processes analogous thereto. Methotrexate is commercially available for example from Lederle Laboratories under the trade name Methotrexate-Lederle, or may be prepared for example as described in U.S. Pat. No. 2,512,572, or by processes analogous thereto. Other antimetabolites for use in the combinations of the invention include 6-mercaptopurine, 6-thioguanine, cladribine, 2'-deoxycoformycin and hydroxyurea.

Specific embodiments: In one embodiment, the antimetabolic compound is gemcitabine. In another embodiment, the antimetabolic compound is a antimetabolic compound other than 5-fluorouracil or fludarabine, for example an antimetabolic compound such as gemcitabine, capecitabine, cytarabine, ralitrexed, pemetrexed or methotrexate.

Posology: The antimetabolite compound will be administered in a dosage that will depend on the factors noted above. Examples of dosages for particular preferred antimetabolites are given below by way of example. With regard to anti-tumour nucleosides, these are advantageously administered in a daily dosage of 10 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of 800 to 1200 $mg/m^2$, for capecitabine in a dosage of 1000 to 1200 $mg/m^2$, for cytarabine in a dosage of 100-200 $mg/m^2$ and for fludarabine in a dosage of 10 to 50 $mg/m^2$.

For the following enzyme inhibitors, examples are given of possible doses. Thus, raltitrexed can be administered in a dosage of about 3 $mg/m^2$, pemetrexed in a dosage of 500 $mg/m^2$ and methotrexate in a dosage of 30-40 $mg/m^2$.

The dosages noted above may generally be administered for example once, twice or more per course of treatment, which may be repeated for example every 7, 14, 21 or 28 days.

7. Vinca Alkaloids

Definition: The term "vinca alkaloid" as used herein refers to vinca alkaloid compounds or analogues of vinca alkaloid compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: The vinca alkaloids for use in the combinations of the invention are anti-tumour vinca alkaloids related to or derived from extracts of the periwinkle plant (*Vinca rosea*). Among these compounds, vinblastine and vincristine are important clinical agents for the treatment of leukaemias, lymphomas and testicular cancer, and vinorelbine has activity against lung cancer and breast cancer.

Biological activity: The vinca alkaloid compounds of the combinations of the invention are tubulin targeting agents and have activity against various cancers.

Problems: Treatment with Vinca alkaloids is accompanied by significant toxicities. For example, vinblastine causes leukopenia which reaches a nadir in 7 to 10 days following drug administration, after which recovery ensues within 7 days, while vincristine demonstrates some neurological toxicity for example numbness and trembling of the extremities, loss of deep tendon reflexes and weakness of distal limb musculature.

Vinorelbine has some toxicity in the form of granulocytopenia but with only modest thrombocytopenia and less neurotoxicity than other vinca alkaloids. There is therefore a need to increase the inhibitory efficacy of anti-tumour vinca alkaloids against tumour growth and also to provide a means for the use of lower dosages of anti-tumour vinca alkaloids to reduce the potential of adverse toxic side effects to the patient.

Preferences: Preferred anti-tumour vinca alkaloids for use in accordance with the invention include vindesine, vinvesir, vinblastine, vincristine and vinorelbine. Particularly preferred anti-tumour vinca alkaloids for use in accordance with the invention include vinblastine, vincristine and vinorelbine referred to above. Vinblastine is commercially available for example as the sulphate salt for injection from Eli Lilly and Co under the trade name Velban, and may be prepared for example as described in German patent specification No. 2124023 or by processes analogous thereto. Vincristine is commercially available for example as the sulphate salt for injection from Eli Lilly and Co under the trade name Oncovin and may be prepared for example as described in the above German patent specification No. 2124023 or by processes analogous thereto. Vincristine is also available as a liposomal formulation under the name Onco-TCS™. Vinorelbine is commercially available for example as the tartrate salt for injection from Glaxo Wellcome under the trade name Navelbine and may be prepared for example as described in U.S. Pat. No. 4,307,100, or by processes analogous thereto. Other anti-tumour vinca alkaloids may be prepared in conventional manner for example by processes analogous to those described above for vinoblastine, vincristine and vinorelbine.

Another preferred vinca alkaloid is vindesine. Vindesine is a synthetic derivative of the dimeric catharanthus alkaloid vinblastine, is available from Lilly under the tradename Eldisine and from Shionogi under the tradename Fildesin. Details of the synthesis of Vindesine are described in Lilly patent DE2415980 (1974) and by C. J. Burnett et al., J. Med. Chem. 21, 88 (1978).

Specific embodiments: In one embodiment, the vinca alkaloid compound is selected from vinoblastine, vincristine and vinorelbine. In another embodiment, the vinca alkaloid compound is vinoblastine.

Posology: The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment. These dosages may be administered for example once, twice or more per course of treatment, which may be repeated for example every 1, 14, 21 or 28 days.

8. Taxanes (Taxoids)

Definition: The term "taxane compound" as used herein refers to taxane compounds or analogues of taxane compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: The taxanes are a class of compounds having the taxane ring system and related to or derived from extracts from certain species of yew (*Taxus*) trees. These compounds have been found to have activity against tumour cell growth and certain compounds in this class have been used in the clinic for the treatment of various cancers. Thus, for example, paclitaxel is a diterpene isolated from the bark of the yew tree, *Taxus brevifolia*, and can be produced by partial synthesis from 10-acetylbacctin, a precursor obtained from yew needles and twigs or by total synthesis, see Holton et al, J. Am. Chem. Soc. 116; 1597-1601 (1994) and Nicholau et al, Nature 367:630 (1994). Paclitaxel has shown anti-neoplastic activity and more recently it has been established that its antitumour activity is due to the promotion of microtubule polymerisation, Kumar N. J., Biol. Chem. 256: 1035-1041 (1981); Rowinsky et al, J. Natl. Cancer Inst. 82: 1247-1259 (1990); and Schiffet al, Nature 277: 655-667 (1979). Paclitaxel has now demonstrated efficacy in several human tumours in clinical trials, McGuire et al, Ann. Int. Med., 111:273-279 (1989); Holmes et al, J. Natl. Cancer Inst. 83: 1797-1805 (1991); Kohn et al J. Natl. Cancer Inst. 86: 18-24 (1994); and Kohn et al, American Society for Clinical Oncology, 12 (1993). Paclitaxel is used for the treatment of ovarian, breast and lung cancer, in particular has for example been used for the treatment of ovarian cancer and also breast cancer.

More recently a nanomolar formulation of paclitaxel complexed with albumin has been shown to be at least as efficacious and less myelosuppressive than paclitaxel alone. (APP; Abraxane). Paclitaxel mconjugates with glutamic acid are also in development.

Another taxane compound which has been used in the clinic is docetaxel which has been shown to have particular efficacy in the treatment of advanced breast cancer. Docetaxel has shown a better solubility in excipient systems than paclitaxel, therefore increasing the ease with which it can be handled and used in pharmaceutical compositions.

Biological activity: The taxane compounds of the combinations of the invention are tubulin targeting agents and have activity against various cancers.

Problems: Clinical use of taxanes has demonstrated a narrow therapeutic index with many patients unable to tolerate the side effects associated with its use. There is therefore a need to increase the inhibitory efficacy of taxane compounds against tumour growth and also to provide a means for the use of lower dosages of taxane compounds to reduce the potential of adverse toxic side effects to the patient. The development of taxanes with increased solubility in aqueous solutions would also be desirable.

Preferences: Preferred taxane compounds for use in accordance with the invention include paclitaxel Abraxane or docetaxel referred to herein. Paclitaxel is available commercially for example under the trade name Taxol from Bristol Myers Squibb and docetaxel is available commercially under the trade name Taxotere from Sanofi-Aventis (previously Rhone-Poulenc Rorer). Both compounds and other taxane compounds may be prepared in conventional manner for example as described in EP 253738, EP 253739 and WO 92/09589 or by processes analogous thereto.

Specific embodiments: In one embodiment, the taxane compound is paclitaxel. In another embodiment, the taxane compound is docetaxel.

Posology: The taxane compound is advantageously administered in a dosage of 50 to 400 mg per square metere (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment. These dosages may be administered for example once, twice or more per course of treatment, which may be repeated for example every 7,14, 21 or 28 days.

9. Epothilones

Definition: As used herein, the term "epothilone" is used to define a class of cytotoxic macrolides with a similar mechanism of action to paclitaxel but with the potential advantage of activity in taxane-resistant settings in preclinical models. The epothilones ixabepilone, patupilone, BMS-310705, KOS-862 and ZK-EPO are in early clinical trials for cancer treatment. Phase I studies have shown that dose-limiting toxicities of epothilones are generally neurotoxicity and neutropenia although initial studies with patupilone indicated that diarrhoea was dose limiting. Neuropathy induced by ixabepilone may be schedule dependent. Response rates in taxane-refractory metastatic breast cancer are relatively modest, but ixabepilone and patupilone have shown promising efficacy in hormone-refractory metastatic prostate cancer and in taxane-refractory ovarian cancer.

Technical Background; Epothilones A and B were originally isolated as anti-fungal fermentation products of the myxobacteria *Sorangium cellulosum*. Shortly thereafter these agents were demonstrated to stabilize microtubules and induce mitotic arrest. Though their cytotoxic activity relies on the same mechanism as that of the taxanes, the epothilones have a couple of key advantages. Firstly they are not substrates for the multi-drug resistance pump P-gylycoprotein. Secondly they are easier both to produce (because of their bacterial origin) and to manipulate. Chemical syntheses, either total or partial, of these molecules and their analogs allows for modification to enhance their efficacy Mani et al.

Anticancer Drugs 2004; 15(6):553-8). Several epothilones or epothilone-derivatives have been shown effective against cell lines and tumor xenografts and are now in clinical trials (Goodin et al. J Clin Oncol 2004;22(10): 2015-25). An unexpected source for the identification of microtubule stabilizing agents has been marine organisms. Laulimalide and isolaulimalide are natural products of the marine sponge *Cacospongia mycofijiensis* with strong paclitaxel-like activity, even against P-gp expressing cell lines. Eluetherobin, similar in both respects, is a product of the *Eleutherobia* species of soft coral.

Biological Activity; Formation of microtubules involves polymerization of heterodimeric α/β-tubulin subunits with multiple isoforms of both α- and β-tubulin present in human cells. Intact microtubule function is required for formation and functioning of the mitotic spindle, and cells treated with agents that bind either tubulin subunits or polymerized microtubules exhibit alterations in spindle formation, as well as arrest at the G2/M phase of the cell cycle, which is associated with induction of apoptosis. Compounds that target microtubules are potent cytotoxic agents, exemplified by the convergent evolution of microtubule-targeting compounds by a variety of plant and marine species. Published studies of three epothilones in current clinical development, epothilone B, aza-epothilone B, and desoxyepothilone B, indicate that these compounds exhibit broad spectrum antitumor activity in cell culture models and in xenografts. Furthermore, epothilones are generally more cytotoxic than paclitaxel in cell culture studies, with $IC_{50}$ values in the sub- or low nanomolar range in a variety of tumor cell lines (Bollag et al. Cancer Res 55:2325-2333, 1995; Lee et al. Clin Cancer Res 7:1429-1437, 2001; Chou et al. Proc Natl Acad Sci U S A 95:9642-9647, 1998; Newman et al. Cancer Chemother Pharmacol 48:319-326, 2001). Preclinical studies also demonstrated important differences with regard to drug resistance mechanisms between epothilones and taxanes. In particular, overexpression of P-glycoprotein minimally affects the cytotoxicity of epothilone B, aza-epothilone B, and desoxyepothilones in cell culture models. Comparison of the cytotoxic effects of epothilone B, aza-epothilone B, and desoxyepothilone B among P-glycoprotein-overexpressing cell lines suggests thatdesoxyepothilone B is least affected, whereas aza-epothilone B is most affected by P-glycoprotein expression. However, it should be noted that differences among the $IC_{50}$s of these compounds in P-glycoprotein-overexpressing cell lines are small compared with the differences between these values and $IC_{50}$s for paclitaxel in these cell lines. Although the significance of P-glycoprotein expression in clinical resistance to taxanes remains uncertain, these results suggest that epothilones may be more active than taxanes in patients with malignancies characterized by high levels of P-glycoprotein expression. In vivo studies indicate that epothilones are active in paclitaxel-sensitive and—resistant tumor models using a variety of schedules. When administered intravenously to mice using intermittent daily or weekly schedules, aza-epothilone B is highly active in ovarian, colon, and breast xenografts and induces cures in an ovarian xenograft model (Pat-7) that is resistant to paclitaxel. Notably, unlike paclitaxel, aza-epothilone B is effective when administered orally in preclinical models. This phenomenon likely relates to the expression of P-glycoprotein in intestinal mucosa, resulting in poor absorption of paclitaxel but not epothilones.

Problems; Sensory neuropathy and myelosuppression has been documented with epothilones Preferences; Existing structure-activity data provide some insight into the interaction between epothilones and microtubules. Results from several groups indicate that modifications at or near the C12-13 epoxide can affect microtubule-stabilizing activity (Wartmann and Altmann, Curr Med Chem Anti-Canc Agents 2:123-148, 2002). For example, addition of a methyl group to epothilone A at position C12 yields epothilone B, which is approximately twice as potent as epothilone A or paclitaxel in inducing tubulin polymerization in vitro (Kowalski et al. J Biol Chem 272: 2534-2541,1997; Nicolaou et al. Nature 387:268-272, 1997, abstr 428). In addition, it is clear that an epoxide at C12-13 is not required for microtubule-binding, because desoxyepothilone B (also known as epothilone D or KOS-862) lacks the C12-13 epoxide and is a more potent microtubule stabilizer in vitro than epothilone A or B. Less data are available regarding the effects of modifying other regions of epothilone. Despite attempts to improve microtubule binding by altering the C9-C12 region (on the basis of molecular modeling), alterations in this area resulted in loss of cytotoxic activity. By contrast, replacement of the lactone oxygen of epothilone B with a lactam (aza-epothilone B, also known as BMS-247550) does not impair microtubule-polymerizing activity or cytotoxicity. Although a variety of other epothilone analogs have been synthesized, it should be noted that increasing microtubule-stabilizing activity does not always result in increased cytotoxicity, presumably because of the importance of othervariables such as cellular accumulation and metabolic stability (Wartmann and Altmann, Curr Med Chem Anti-Canc Agents 2:123-148, 2002). Indeed, replacement of the methyl group at C12 position of desoxyepothilone B with a propanol group results in a compound that is as effective as desoxyepothilone B against the leukemic cell line CCRF-CEM but is significantly less active against a P-glycoprotein-overexpressing subline ($IC_{50}$ of 17 nmol/L for desoxyepothilone B v 167 nmol/L for the propanol derivative) (Chou et al. Proc Natl Acad Sci U S A 95:9642-9647,1998). Additional modifications of naturally occurring epothilones have been made in an effort to improve solubility, such as BMS-310705, which is a C-21-substituted derivative of epothilone B (Lee et al. Proc Am Assoc Cancer Res 43:a3928, 2002).

Specific embodiments: In one embodiment, the epothilone compound is BMS-247550. In another embodiment, the epothilone compound is Desoxyeopthilone and in another embodiment the epothilone compound is BMS-310705

Posology: BMS-247550 is dosed either 40 mg/m² over 3 hours every 21 days or 6 mg/m² administered over 1 hour daily times 5 days every 3 weeks. Because of the frequency of mucositis and neutropenia in the first 18 patients on the single-dose every-3-week schedule, the dose was reduced to 32 mg/m². EP0906 is dosed either at 2.5 mg/m² weekly for 3 weeks followed by 1 week of rest in one trial, and 6 mg/m² once every 3 weeks. KOS-862 is scheduled at either a single dose every 3 weeks, a daily dose times 3 every 3 weeks, a fixed rate dose every 3 weeks, and a weekly dose for 3 weeks with 1 week rest.

10. Platinum Compounds

Definition: The term "platinum compounds" as used herein refers to any tumour cell growth inhibiting platinum compound including platinum coordination compounds, compounds which provide platinum in the form of an ion and analogues of platinum compounds as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: In the chemotherapeutic treatment of cancers, cisplatin (cis-diaminodichloroplatinum (II)) has been used successfully for many years in the treatment of various human solid malignant tumours for example testicular cancer, ovarian cancer and cancers of the head and neck, bladder, oesophagus and lung.

More recently, other diamino-platinum complexes, for example carboplatin (diamino(1,1-cyclobutane-dicarboxylato)platinum (II)), have also shown efficacy as chemotherapeutic agents in the treatment of various human solid malignant tumours, carboplatin being approved for the treatment of ovarian and small cell lung cancer in particular in the treatment of ovarian cancer. A further antitumour platinum compound is oxaliplatin (L-OHP), a third generation diaminocyclohexane platinum-based cytotoxic drug, which has the chemical name (1,2-diaminocyclohexane)oxalato-platinum (II). Oxaliplatin is used, for example, for the treatment of metastatic colorectal cancer, based on its lack of renal toxicity and higher efficacy in preclinical models of cancer in comparison to cisplatin. Oxaliplatin is used in combination with 5-FU, for the treatment of metastatic colorectal cancer and is under investigation in the treatment of upper gastrointestinal cancer. An oral platinum derivative is under investigation for the treatment of prostate cancer.

Biological activity: The platinum compounds of the combinations of the invention have activity against various cancers.

Problems: Although cisplatin and other platinum compounds have been widely used as chemotherapeutic agents in humans, they are not therapeutically effective in all patients or against all types of tumours. Moreover, such compounds need to be administered at relatively high dosage levels which can lead to toxicity problems such as kidney damage, myelosuppression and neuropathy. Also, and especially with cisplatin, the compounds cause nausea and vomiting in patients to a varying extent, as well as leucopenia, anemia and thrombocytopenia. There is therefore a need to increase efficacy and also to provide a means for the use of lower dosages to reduce the potential of adverse toxic side effects to the patient.

Preferences: Preferred platinum compounds for use in accordance with the invention include cisplatin, carboplatin and oxaliplatin. Other platinum compounds include chloro(diethylenediamino)-platinum (II) chloride; dichloro(ethylenediamino)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; and tetraplatin. Cisplatin is commercially available for example under the trade name Platinol from Bristol-Myers Squibb Corporation as a powder for constitution with water, sterile saline or other suitable vehicle. Cisplatin may also be prepared for example as described by G. B. Kauffman and D. O. Cowan, Inorg. Synth. 7, 239 (1963), or by processes analogous thereto. Carboplatin is commercially available for example from Bristol-Myers Squibb Corporation under the trade name Paraplatin, or may be prepared for example as described in U.S. Pat. No. 4,140,707, or by processes analogous thereto. Oxaliplatin is commercially available for example from Sanofi-Synthelabo Inc under the trade name Eloxatin, or may be prepared for example as described in U.S. Pat. No. 4,169,846, or by processes analogous thereto. Other platinum compounds and their pharmaceutical compositions are commercially available and/or can be prepared by conventional techniques.

Specific embodiments: In one embodiment, the platinum compound is selected from chloro(diethylenediamino)-platinum (II) chloride; dichloro(ethylenediamino)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; tetraplatin, cisplatin, carboplatin and oxaliplatin. In another embodiment, the platinum compound is a platinum compound other than cisplatin, for example a platinum compound such as chloro(diethylenediamino)-platinum (II) chloride; dichloro(ethylenediamino)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato)platinum (II); onnaplatin; tetraplatin, carboplatin or oxaliplatin, preferably selected from carboplatin and oxaliplatin.

Posology: The platinum coordination compound is advantageously administered in a dosage of 1 to 500 mg per square meter ($mg/m^2$) of body surface area, for example 50 to 400 $mg/m^2$ or 500 $mg/m^2$ (e.g. 50 to 400 $mg/m^2$) particularly for cisplatin in a dosage of about 75 $mg/m^2$, for carboplatin in about 300-500 $mg/m^2$ e.g. 300 $mg/m^2$, and for oxaliplatin in about 50-100 $mg/m^2$. These dosages may be administered for example once, twice or more per course of treatment, which may be repeated for example every 7, 14, 21 or 28 days.

11. Topoisomerase 2 Inhibitors

Definition: The term "topoisomerase 2 inhibitor" as used herein refers to topoisomerase 2 inhibitor or analogues of topoisomerase 2 inhibitor as described above, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: An important class of anticancer drugs are the inhibitors of the enzyme topoisomerase 2 which causes double-strand breaks to release stress build-up during DNA transcription and translation. Compounds that inhibit the function of this enzyme are therefore cytotoxic and useful as anti-cancer agents.

Among the topoisomerase 2 inhibitors which have been developed and used in cancer chemotherapy are the podophyllotoxins. These drugs act by a mechanism of action which involves the induction of DNA strand breaks by an interaction with DNA topoisomerase 2 or the formation of free radicals. Podophyllotoxin, which is extracted from the mandrake plant, is the parent compound from which two glycosides have been developed which show significant therapeutic activity in several human neoplasms, including pediatric leukemia, small cell carcinomas of the lung, testicular tumours, Hodgkin's disease, and non-Hodgkin's lymphomas. Podophyllotoxin has activity in pediatric leukemia, small cell carcinomas of the lung, testicular tumours, Hodgkin's disease, and large cell lymphomas. These derivatives are etoposide (VP-16), which has the chemical name 4'-demethylepipodophyllotoxin 9-[4,6-O—(R)-ethylidene-β-D-glucopyranoside], and teniposide (VM-26), which has the chemical name 4'-demethylepipodophyllotoxin 9-[4,6-0-(R)-2-thenylidene-β-D-glucopyranoside].

Both etoposide and teniposide, however, suffer from certain toxic side-effects especially myelosuppression. Another important class of topoisomerase 2 inhibitors are the anthracycline derivatives which are important anti-tumour agents and comprise antibiotics obtained from the fungus *Streptomyces peuticus* var. *caesius* and their derivatives, characterized by having a tetracycline ring structure with an unusual sugar, daunosamine, attached by a glycosidic linkage. Among these compounds, the most widely used include daunorubicin, which has the chemical name 7-(3-amino-2,3,6-trideoxy-L-lyxohexosyloxy)-9-acetyl-7,8,9,10-tetrahydro-6,9,11-trihydroxy-4-methoxy-5,12-naphthacenequinone, doxorubicin, which has the chemical name 10-[(3-amino-2,3,6-trideoxy-α-L-lyxohexopyranosyl)oxy]-7,8,9,10-tetrahydro-6,8,11-trihydroxy-8-(hydroxylacetyl)-I-methoxy-5,12-naphthacenedione, and idarubicin (Zavedos™), which has the chemical name 9-acetyl-[(3-amino-2,3,6-trideoxy-α-L-lyxohexopyranosyl)oxy]-7,8,9,10-tetrahydro-6,9,11-trihydroxy-5,12-naphthacenedione.

Daunorubicin and idarubicin have been used primarily for the treatment of acute leukaemias whereas doxorubicin has been more widely tested against solid tumours particularly breast cancer. Another anthracycline derivative which is useful in cancer chemotherapy is epirubicin. Epirubicin, which has the chemical name (8S-cis)-10-[(3-amino-2,3,6-trideoxy-α-L-arabino-hexopyranosyl)oxy]-7,8,9,10-tetrahydro-6,8,11-trihydroxy-8-(hydroxyacetyl)-1-methoxy-5,12-naphthacenedione, is a doxorubicin analog having a catabolic pathway that involves glucuronidation, by uridine diphosphate-glucuronosyl transferase in the liver (unlike that for doxorubicin), which is believed to account for its shorter half-life and reduced cardiotoxicity. The compound has been used for the treatment of various cancers including cervical cancer, endometrial cancer, advanced breast cancer and carcinoma of the bladder but suffers from the side-effects of myelosuppression and cardiotoxicity. The latter side-effect is typical of anthracycline derivatives which generally display a serious cardiomyopathy at higher cumulative doses. A further type of topoisomerase 2 inhibitor is represented by mitoxantrone, which has the chemical name 1,4-dihydroxy-5,8-bis[[2-[(2-hydroxyethyl)amino]ethyl]amino]-9,10-anthracenedione, and is used for the treatment of multiple sclerosis, non-Hodgkin's lymphoma, acute myelogenous leukaemia, and breast, prostate and liver tumours. Others include losoxantrone and actinomycin D (the latter agent also known as Dactinomycin and Cosmegen Lyovac®).

Side-effects from administration of mitoxantrone include myelosuppression, nausea, vomiting, stomatitis and alopecia Biological activity: The topoisomerase 2 inhibitors of the combinations of the invention have activity against various cancers as described above.

Problems: This class of cytotoxic compound is associated with side effects, as mentioned above. Thus, there is a need to provide a means for the use of lower dosages to reduce the potential of adverse toxic side effects to the patient.

Preferences: Preferred topoisomerase 2 inhibitor compounds for use in accordance with the invention include anthracycline derivatives, mitoxantrone and podophyllotoxin derivatives as defined to herein.

Preferred anti-tumour anthracycline derivatives for use in accordance with the invention include daunorubicin, doxorubicin, idarubicin and epirubicin referred to above. Daunorubicin is commercially available for example as the hydrochloride salt from Bedford Laboratories under the trade name Cerubidine, or may be prepared for example as described in U.S. Pat. No. 4,020,270, or by processes analogous thereto. The therapeutic index of daunorubicin in acute myeloid leukemia may be improved by encapsulating the molecule in a liposome (Daunoxome; Gilead/Diatos). Doxorubicin is commercially available for example from Pharmacia and Upjohn Co under the trade name Adriamycin, or may be prepared for example as described in U.S. Pat. No. 3,803,124, or by processes analogous thereto. Doxorubicin derivatives include pegylated doxorubicin hydrochloride and liposome-encapsulated doxorubicin citrate. Pegylated doxorubicin hydrochloride is commercially available from Schering-Plough Pharmaceuticals under the trade name Caeylx; non-pegylated liposome-encapsulated doxorubicin citrate is commercially available for example from Cephalon Europe under the trade name Myocet. Idarubicin is commercially available for example as the hydrochloride salt from Pharmacia & Upjohn under the trade name Idamycin, or may be prepared for example as described in U.S. Pat. No. 4,046,878, or by processes analogous thereto. Epirubicin is commercially available for example from Pharmacia and Upjohn Co under the trade name Pharmorubicin, or may be prepared for example as described in U.S. Pat. No. 4,058,519, or by processes analogous thereto. Mitoxantrone is commercially available for example from OSI Pharmaceuticals, under the trade name Novantrone, or may be prepared for example as described in U.S. Pat. No. 4,197,249, or by processes analogous thereto.

Other anti-tumour anthracycline derivatives may be prepared in conventional manner for example by processes analogous to those described above for the specific anthracycline derivatives.

Preferred anti-tumour podophyllotoxin derivatives for use in accordance with the invention include etoposide and teniposide referred to above. Etoposide is commercially available for example from Bristol-Myers Squibb Co under the trade name VePesid, or may be prepared for example as described in European patent specification No111058, or by processes analogous thereto. Teniposide is commercially available for example from Bristol-Myers Squibb Co under the trade name Vumon, or may be prepared for example as described in PCT patent specification No. WO 93/02094, or by processes analogous thereto. Other anti-tumour podophyllotoxin derivatives may be prepared in conventional manner for example by processes analogous to those described above for etoposide and teniposide.

Specific embodiments: In one embodiment, the topoisomerase 2 inhibitor is an anthracycline derivative, mitoxantrone or a podophyllotoxin derivative. In another embodiment, the topoisomerase 2 inhibitor is selected from daunorubicin, doxorubicin, idarubicin and epirubicin. In a further embodiment, the topoisomerase 2 inhibitor is selected from etoposide and teniposide. Thus, in a preferred embodiment, the topoisomerase 2 inhibitor is etoposide. In another embodiment, the topoisomerase 2 inhibitor is an anthracycline derivative other than doxorubicin, for example a topoisomerase 2 inhibitor such as daunorubicin, idarubicin and epirubicin.

Posology: The anti-tumour anthracycline derivative is advantageously administered in a dosage of 10 to 150 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, for idarubicin in a dosage of about 10 to 15 $mg/m^2$ and for epirubicin in a dosage of about 100-120 $mg/m^2$.

Mitoxantrone is advantageously administered in a dosage of about 12 to 14 $mg/m^2$ as a short intravenous infusion about every 21 days.

The anti-tumour podophyllotoxin derivative is advantageously administered in a dosage of 30 to 300 $mg/m^2$ of body surface area, for example 50 to 250 mg/m particularly for etoposide in a dosage of about 35 to 100 mg/m, and for teniposide in about 50 to 250 $mg/m^2$.

The dosages noted above may generally be administered for example once, twice or more per course of treatment, which may be repeated for example every 7,14, 21 or 28 days.

12. Alkylating Agents

Definition: The term "alkylating agent" or "alkylating agents" as used herein refers to alkylating agents or analogues of alkylating agents as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: Alkylating agents used in cancer chemotherapy encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation, in particular DNA synthesis and cell division. The capacity of alkylating agents to interfere with DNA function and integrity in rapidly proliferating tissues provides the basis for their therapeutic applications and for many of their toxic properties. Alkylating agents as a class have therefore been investigated for their anti-tumour activity and certain of these compounds have been widely used in anti-cancer therapy although they tend to have in common a propensity to cause dose-limiting toxicity to bone marrow elements and to a lesser extent the intestinal mucosa.

Among the alkylating agents, the nitrogen mustards represent an important group of anti-tumour compounds which are characterised by the presence of a bis-(2-chloroethyl) grouping and include cyclophosphamide, which has the chemical name 2-[bis(2-chloroethyl)amino]tetrahydro-2H-1,3,2-oxazaphospholine oxide, and chlorambucil, which has the chemical name 4-[bis(2-chloroethyl)amino]-benzenebutoic acid. Cyclophosphamide has a broad spectrum of clinical activity and is used as a component of many effective drug combinations for non-Hodgkin's lymphoma, Hodgkin's disease, Burkitt's lymphoma and breast cancer. Cyclophosphamide has also been used as a component of combinations for malignant lymphomas.

Ifosfamide (a.k.a. ifosphamide) is a structural analogue of cyclophosphamide and its mechanism of action is presumed to be identical. It has the chemical name 3-(2-chloroethyl)-2-[(2-chloroethyl)amino]tetrahydro-2H-1,3,2-oxazaphosphorin-2-oxide, and is used for the treatment of cervical cancer, sarcoma, and testicular cancer but may have severe urotoxic effects. Chlorambucil has been used for treating chronic lymphocytic leukaemia and non-Hodgkin's lymphoma. Chlorambucil has also been used for treating CLL and malignant lymphomas including lymphosarcoma.

Another important class of alkylating agents are the nitrosoureas which are characterised by the capacity to undergo spontaneous non-enzymatic degradation with the formation of the 2-chloroethyl carbonium ion. Examples of such nitrosourea compounds include carmustine (BiCNU® or BCNU) which has the chemical name 1,3-bis(2-chloroethyl)-I-nitrosourea, and lomustine (CCNU) which has the chemical name 1-(2-chloroethyl)cyclohexyl-I-nitrosourea. Carmustine and lomustine each have an important therapeutic role in the treatment of brain tumours and gastrointestinal neoplasms although these compounds cause profound, cumulative myelosuppression that restricts their therapeutic value.

Another class of alkylating agent is represented by the bifunctional alkylating agents having a bis-alkanesulfonate group and represented by the compound busulfan which has the chemical name 1,4-butanediol dimethanesulfonate, and is used for the treatment of chronic myelogenous (myeloid, myelocytic or granulocytic) leukaemia. However, it can induce severe bone marrow failure resulting in severe pancytopenia. This property has led to its widespread usage as a conditioning agent prior to hematological stem cell transplantation.

Another class of alkylating agent are the aziridine compounds containing a three-membered nitrogen-containing ring which act as anti-tumour agents by binding to DNA, leading to cross-linking and inhibition of DNA synthesis and function. An example of such an agent is mitomycin, an antibiotic isolated from *Streptomyces caespitosus*, and having the chemical name 7-amino-9α-methoxymitosane.

Mitomycin is used to treat adenocarcinoma of stomach, pancreas, colon and breast, small cell and non-small cell lung cancer, and, in combination with radiation, head and neck cancer, side-effects including myelosuppression, nephrotoxicity, interstitial pneumonitis, nausea and vomiting.

Biological activity: One of the most important pharmacological actions of the alkylating agent in combination with the invention is its ability to disturb the fundamental mechanisms concerned with cell proliferation as herein before defined. This capacity to interfere with DNA function and integrity in rapidly proliferating tissues provides the basis for their therapeutic application against various cancers.

Problems: This class of cytotoxic compound is associated with side effects, as mentioned above. Thus, there is a need to provide a means for the use of lower dosages to reduce the potential of adverse toxic side effects to the patient.

Preferences: Preferred alkylating agents for use in accordance with the invention include the nitrogen mustard compounds cyclophosphamide, ifosfamide/ifosphamide and chlorambucil and the nitrosourea compounds carmustine and lomustine referred to above. Preferred nitrogen mustard compounds for use in accordance with the invention include cyclophosphamide, ifosfamide/ifosphamide and chlorambucil referred to above. Cyclophosphamide is commercially available for example from Bristol-Myers Squibb Corporation under the trade name Cytoxan, or may be prepared for example as described in U.K. patent specification No. 1235022, or by processes analogous thereto. Chlorambucil is commercially available for example from GlaxoSmithKline plc under the trade name Leukeran, or may be prepared for example as described in U.S. Pat. No. 3,046,301, or by processes analogous thereto. Ifosfamide/ifosphamide is commercially available for example from Baxter Oncology under the trade name Mitoxana, or may be prepared for example as described in U.S. Pat. No. 3,732,340, or by processes analogous thereto. Preferred nitrosourea compounds for use in accordance with the invention include carmustine and lomustine referred to above. Carmustine is commercially available for example from Bristol-Myers Squibb Corporation under the trade name BiCNU, or may be prepared for example as described in European patent specification No. 902015, or by processes analogous thereto. Lomustine is commercially available for example from Bristol-Myers Squibb Corporation under the trade name CeeNU, or may be prepared for example as described in U.S. Pat. No. 4,377,687, or by processes analogous thereto. Busulfan is commercially available for example from GlaxoSmithKline plc under the trade name Myleran, or may be prepared for example as described in U.S. Pat. No. 2,917,432, or by processes analogous thereto. Mitomycin is commercially available for example from Bristol-Myers Squibb Corporation under the trade name Mutamycin. Others include estramustine, mechlorethamine, melphalan, bischloroethylnitrosurea, cyclohexylchloroethylnitrosurea, methylcyclohexylchloroethylnitrosurea, nimustine, procarbazine, dacarbazine, temozolimide and thiotepa.

Specific embodiments: In one embodiment, the alkylating agent is a nitrogen mustard compound selected from cyclophosphamide, ifosfamide/ifosphamide and chlorambucil. In another embodiment, the alkylating agent is a nitrosurea selected from carmustine and lomustine. The alkylating agents further include Busulfan. In one embodiment, the alkylating agents are as herein before defined other than mitomycin C or cyclophosphamide.

Posology: The nitrogen mustard or nitrosourea alkylating agent is advantageously administered in a dosage of 100 to 9000 e.g. 100 to 2500 mg per square meter ($mg/m^2$) of body surface area, for example 100 to 5000, 100 to 2500 or 120 to 500 $mg/m^2$, particularly for cyclophosphamide in a dosage of about 100 to 5000 e.g. 100 to 500 $mg/m^2$, for ifosfamide/ifosphamide in a dosage of 500-9000 $mg/m^2$ e.g. 500-2500 $mg/m^2$, for chlorambucil in a dosage of about 0.1 to 0.2 mg/kg, for carmustine in a dosage of about 150 to 200 $mg/m^2$ and for lomustine in a dosage of about 100 to 150 $mg/m^2$. For bis-alkanesulfonate compounds such as busulphan a typical dose may be 1-2 $mg/m^2$, e.g. about 1.8 $mg/m^2$.

Aziridine alkylating agents such as mitomycin can be administered for example in a dosage of 15 to 25 $mg/m^2$ preferably about 20 $mg/m^2$.

The dosages noted above may be administered for example once, twice or more per course of treatment, which may be repeated for example every 7, 14, 21 or 28 days.

13. Signalling Inhibitors for Use According to the Invention

Definition: The term "signalling inhibitor" (or "signal transduction inhibitor") as used herein refers to signalling inhibitors or analogues of signalling inhibitors as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs.

One driver for growth is the epidermal growth factor (EGF), and the receptor for EGF (EGFR) has been implicated in the development and progression of a number of human solid tumours including those of the lung, breast, prostate, colon, ovary, head and neck. EGFR is a member of a family of four receptors, namely EGFR (HER1 or ErbB1), ErbB2 (HER2/neu), ErbB3 (HER3), and ErbB4 (HER4). These receptors are large proteins that reside in the cell membrane, each having a specific external ligand binding domain, a transmembrane domain and an internal domain which has tyrosine kinase enzyme activity. When EGF attaches to EGFR, it activates the tyrosine kinase, triggering reactions that cause the cells to grow and multiply. EGFR is found at abnormally high levels on the surface of many types of cancer cells, which may divide excessively in the presence of EGF. Inhibition of EGFR activity has therefore been a target for chemotherapeutic research in the treatment of cancer. Such inhibition can be effected by direct interference with the target EGFR on the cell surface, for example by the use of antibodies, or by inhibiting the subsequent tyrosine kinase activity.

Examples of antibodies which target EGFR are the monoclonal antibodies trastuzumab and cetuximab. Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor. In vitro and in vivo preclinical studies have shown that administration of trastuzumab alone or in combination with paclitaxel or carboplatin significantly inhibits the growth of breast tumour-derived cell lines that over-express the HER2 gene product. In clinical studies trastuzumab has been shown to have clinical activity in the treatment of breast cancer. The most common adverse effects of trastuzumab are fever and chills, pain, asthenia, nausea, vomiting, diarrhea, headache, dyspnea, rhinitis, and insomnia. Particularly troublesome is the onset of cardiomyopathy which may be reversible in the majority of patients. Trastuzumab has been approved for the treatment of early and metastatic breast cancer, in particular metastic breast cancer, exhibiting overexpression of the HER2 protein Cetuximab has been used for the treatment of irotecan-refractory colorectal cancer (CRC) and in combination with radiotherapy in the treatment of head and neck cancer. It is also being evaluated both as a single agent and in combination with other agents for use in the treatment of a variety of other cancers including metastatic pancreatic carcinoma, and non-small-cell lung cancer. The administration of cetuximab can cause serious side effects, which may include difficulty in breathing and low blood pressure.

Another suitable monoclonal antibody for use in the combinations of the invention is panitumumab. Amgen Inc (formerly Immunex and Abgenix Inc) is developing panitumumab (ABX-EGF), a fully human monoclonal antibody against the EGF receptor, for the potential treatment of cancer, such as monotherapy for renal cancer, non-small-cell lung cancer, and CRC in combination with standard chemotherapy as first-line treatment, as third-line monotherapy in advanced CRC, in particular to treat metastatic colorectal cancer (MCC) and in patients who failed standard chemotherapy. Thus ABX-EGF can be administered as a monotherapy or in association with chemotherapy and radiotherapy in order to complement independent approaches for the treatment of cancer.

ABX-EGF is a fully humanized IgG2 monoclonal antibody against the human EGFR. Fully humanized monoclonal antibodies such as ABX-EGF have several advantages over chimeric antibodies, which contain significant amounts of mouse protein. They do not generate human anti-mouse antibodies (HAMA); the risk of inducing hypersensitivity reactions in patients is therefore reduced and the antibodies should demonstrate an increased in vivo lifetime. Such considerations may be important for long-term administration.

It can be prepared as described in WO98/50433 and process analogous thereto.

Panitumumab may be dosed ranging from 0.01 to 5.0 mg/kg once per week, 6.0 mg/kg once every two weeks or 9.0 mg/kg once every three weeks administered by intravenous infusion.

In a Phase 3 pivotal study examining panitumumab as third-line monotherapy in colorectal cancer patients, patients received panitumumab every two weeks.

The farnesyltransferase inhibitor tipifarnib prevents signaling thru ras-mediated pathways and is under investigation for the treatment of myeloid leukemias.

Examples of agents which target EGFR tyrosine kinase activity include the tyrosine kinase inhibitors gefitinib and erlotinib. Gefitinib which has the chemical name 4-(3-chloro-4-fluoroanilino)-7-methoxy-6-(3-morpholinopropoxy)quinazoline, is used for the treatment of non-small-cell lung cancer. It has also been studied for other solid tumours that over-express EGF receptors such as breast and colorectal cancer. It has been found that patients receiving gefitinib may develop interstitial lung disease and eye irritation Erlotinib, which has the chemical name N-(3-ethynyl-phenyl)-6,7-bis(2-methoxyethoxy)-4-quinazoline, has also been used for the treatment of non-small-cell lung cancer, and is being developed for the treatment of various other solid tumours such as pancreatic cancer, the most common side effects being rash, loss of appetite and fatigue; a more serious side effect which has been reported is interstitial lung disease.

Another growth factor which has received attention as a target for anticancer research is the vascular endothelial growth factor (VEGF). VEGF is a key regulator of vasculogenesis during angiogenic processes including wound healing, retinopathy, psoriasis, inflammatory disorders, tumour growth and metastasis. Studies have shown that over-expression of VEGF is strongly associated with invasion and metastasis in human malignant disease.

An example of an antibody that targets the VEGF antigen on the surface of a cell is the monoclonal antibody bevacizumab which is a recombinant humanised monoclonal IgG1 antibody that binds to and inhibits VEGF. Bevacizumab has been used for the treatment of colorectal cancer, for example in combination with chemotherapy e.g. 5-fluorouracil. Bevacizumab also being developed as a potential treatment for other solid tumours such as metastatic breast cancer, metastatic non-small-cell lung cancer and renal cell carcinoma. The most serious adverse events associated with bevacizumab include gastrointestinal perforations, hypertensive crises, nephrotic syndrome and congestive heart failure. Other therapeutic agents in development which target the action of VEGF at alternate points in the signal transduction cascade intiated by this growth factor include sunitinib which is marketed under the trade name Sutent by Sugen/Pfizer and inhibits the kinase activity of the VEGF receptor. Sutent has demonstrated efficacy in Phase III trials in gastrointestinal stromal tumours.

Another growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment on chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. The most frequently reported drug-related adverse events were edema, nausea, vomiting, cramps and musculosketetal pain.

A further growth factor target for cancer chemotherapy is inhibition of Raf which is a key enzyme in the chain reaction of the body's chemistry that triggers cell growth. Abnormal activation of this pathway is a common factor in the development of most cancers, including two-thirds of melanomas. By blocking the action of Raf kinase, it may be possible to reverse the progression of these tumours. One such inhibitor is sorafenib (a.k.a. BAY 43-9006 and Nexavar) which has the chemical name 4-(4-(3-(4-chloro-3-(trifluoromethyl)phenyl)ureido)phenoxy)-N2-methylpyridine-2-carboxamide. Sorafenib targets both the Raf signalling pathway to inhibit cell proliferation and the VEGFR/PDGFR signalling cascades to inhibit tumour angiogenesis. Raf kinase is a specific enzyme in the Ras pathway. Mutations in the Ras gene occur in approximately 20 percent of all human cancers, including 90 percent of pancreatic cancers, 50 percent of colon cancers and 30 percent of non-small cell lung cancers. Sorafenib is being investigated for the treatment of a number of cancers including liver and kidney cancer. The most common side effects of sorafenib are pain, swelling, redness of the hands and/or feet, and also rash, fatigue and diarrhea.

Biological activity: The signalling inhibitors of the combinations of the invention are specific inhibitors of cell signalling proteins as described above and have activity against various cancers. Combinations of compounds of formula I with signalling inhibitors may be beneficial in the treatment and diagnosis of many types of cancer. Combination with a molecularly targeted agent such as a signalling inhibitor (e.g. Iressa, Avastin, herceptin, or Gleevec™) would find particular application in relation to cancers which express or have activated the relevant molecular target such as EGF receptor, VEGF receptor, ErbB2, BCRabl, c-kit, PDGF. Diagnosis of such tumours could be performed using techniques known to a person skilled in the art and as described herein such as RTPCR and FISH.

Problems: There is a need to increase the inhibitory efficacy of signalling inhibitors against tumour growth and also to provide a means for the use of lower dosages of signaling inhibitors to reduce the potential for adverse toxic side effects to the patient.

Preferences: Preferred signalling inhibitors for use in accordance with the invention include antibodies targeting EGFR such as monoclonal antibodies trastuzumab and cetuximab, EGFR tyrosine kinase inhibitors such as gefitinib and erlotinib, VEGF targeting antibody is bevacizumab, PDGFR inhibitor such as imatinib mesylate and Raf inhibitor such as sorafenib referred to herein.

Preferred antibodies targeting EGFR include the monoclonal antibodies trastuzumab and cetuximab. Trastuzumab is commercially available from Genentech Inc under the trade name Herceptin, or may be obtained as described in U.S. Pat. No. 5,821,337. Cetuximab is commercially available from Bristol-Myers Squibb Corporation under the trade name Erbitux, or may be obtained as described in PCT patent specification No. WO 96/40210.

Preferred EGFR tyrosine kinase inhibitors include gefitinib and erlotinib. Gefitinib is commercially available from AstraZeneca plc under the trade name Iressa, or may be obtained as described in PCT patent specification No. WO 96/33980. Erlotinib is commercially available from Genentech/Roche under the trade name Tarceva, or may be obtained as described in PCT patent specification No. WO 96/30347.

A preferred antibody targeting VEGF is bevacizumab which is commercially available from Genentech Inc under the trade name Avastin, or may be obtained as described in PCT patent specification No. WO 94/10202.

A preferred PDGFR inhibitor is imatinib mesylate which is commercially available from Novartis AG under the trade name Gleevec™ (a.k.a. Glivec®), or may be obtained as described in European patent specification No 564409.

A preferred Raf inhibitor is sorafenib which is available from Bayer AG, or may be obtained as described in PCT patent specification No. WO 00/42012.

Specific embodiments: In one embodiment, the signalling inhibitor is gefitinib (Iressa). In other embodiments the signalling inhibitor is selected from trastuzumab, cetuximab, gefitinib, erlotinib, bevacizumab, imatinib mesylate and sorafenib.

Further combinations of the invention include the following signalling inhibitors: dasatinib, lapatinib, nilotinib, vandetanib, vatalinib and CHIR-258, in particular dasatinib, lapatinib, nilotinib, vandetanib and vatalinib.

BMS is developing dasatinib (Sprycel or BMS-354825) an oral multitargeted kinase inhibitor, for the potential twice-daily treatment of chronic myelogenous leukemia (CML), Philadelphia chromosome-positive (Ph+) acute lymphoblastic leukemia (ALL) and solid tumors. The drug is also under investigation for multiple myeloma (MM) and other hematologic malignancies. Dasatanib has proved effective in Ph+ CML and AML in clinical trials given twice daily at 50-90 mg and also in imatinib resistant patients.

Thrombocytopenia and neutropenia were amongst the side effects observed during clinical evaluation of dasatinib.

The structure of dasatinib, a Src/Abl kinase inhibitor is below:

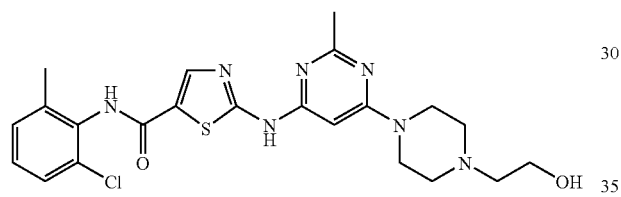

Dasatinib can be prepared by processes described in or analogous to WO 00/062778, WO 2005/076990 and WO 2005/077945.

Novartis is developing nilotinib (AMN-107), an orally available signal transduction inhibitor that targets BCR-ABL, c-kit and PDGF, for the potential treatment of leukemias. The compound is being investigated for chronic myeloid leukemia (CML) and relapsed or refractory acute lymphoblastic leukemia (ALL), systemic mastocytosis or chronic eosinophilic leukemia (hypereosinophilic syndrome), refractory gastrointestinal stromal tumor (GIST). Adverse events included hematological adverse events, headache, fatigue, muscle spasms, and nausea and vomiting. In early clinical studies doses of the order of 400 mg given twice daily have proved effective in treating CML, AML and ALL The structure of nilotinib is shown below. It can be prepared as described in or analogous to as described in WO 2004/005281 and WO 2005/049032.

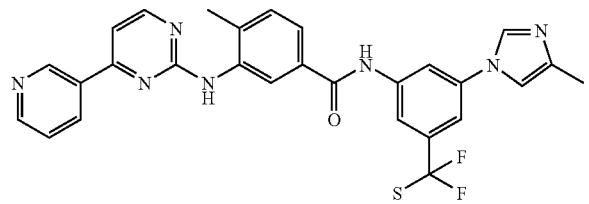 [SMILES: Cc1cn(-c2cc(NC(=O)c3ccc(C)c(Nc4nccc(-c5cccnc5)n4)c3)cc(C(F)(F)S)c2)cn1]

Vatalinib (PTK787/ZK222584) is a VEGF receptor tyrosine kinase angiogenesis inhibitor, under development by Novartis AG (formerly Ciba-Geigy) and Schering AG, for the potential treatment of colorectal cancer. The compound entered trials for colorectal cancer, the first- and second-line treatment of metastatic colorectal cancer (untreated and pre-treated metastatic colorectal patients). Schering and Novartis are also investigating vatalinib in other solid tumors e.g. non-small cell lung cancer (NSCLC), as a second-line monotherapy in patients with stage IIIb/IV disease who had relapsed or were refractory to first-line therapy, renal cell cancer and glioblastoma, and potentially prostate, ovarian, breast, pancreas and small cell lung cancers. In addition vatalanib is also investigated for wet age-related macular degeneration (AMD). Vatalanib has been evaluated at doses up to 1,250 mg daily in clinical studies. Adverse events include nausea/vomiting, fatigue, ataxia, lethargy, hypertension, headache, dizziness, diarrhoea, hypertension as well as syncope and neurotoxicity.

Vatalinib (structure shown below) can be prepared as described in or analogues to as described in WO 98/35958

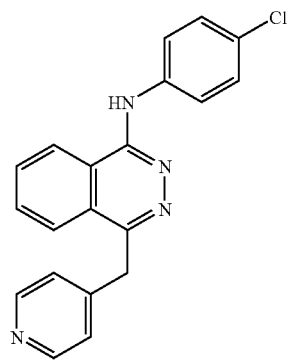 [SMILES: Clc1ccc(Nc2nnc(Cc3ccncc3)c3ccccc23)cc1]

Lapatinib ditosylate (Tykerb or GW2016/572016), an ErbB2 and EGFR dual tyrosine kinase inhibitor, is being developed by GlaxoSmithKline plc (GSK) for the potential treatment of solid tumors.

It is under investigation for various tumors including breast, lung, stomach, bladder and head and neck cancers, in particular for the treatment of patients with refractory advanced or metastatic breast cancer whose tumours express HER-2 and who have failed previous therapies both as a single agent and in combination with other therapies including capecitabine and paclitaxel. The compound had also entered trials for renal cell cancer, advanced and metastatic non-small cell lung cancer (NSCLC) and in the treatment of brain metastases associated with breast cancer. In early clinical evaluation Lapatinib has been evaluated on a twice daily and once daily schedule at doses over the range 500-1500 mg and at doses of 750-1250 mg given twice daily. Side effects include gastrointestinal gaseous symptoms, rash, headache and abnormal liver function tests.

Quinazoline compounds, and ditosylate salts, anhydrate or hydrate forms such as of the structure shown below (lapatinib) can be synthesised using the process described in WO 00/202552 and WO 99/35146 or process analogues thereto.

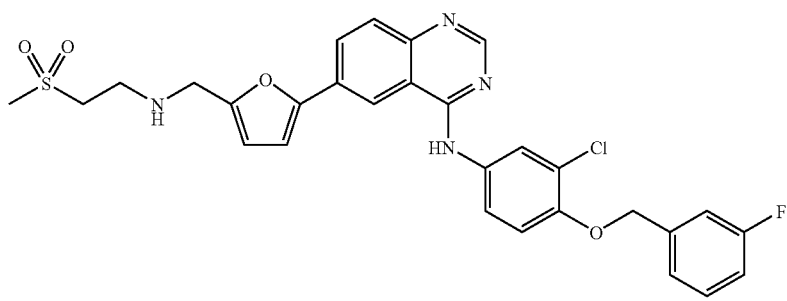 [SMILES: CS(=O)(=O)CCNCc1ccc(-c2ccc3ncnc(Nc4ccc(OCc5cccc(F)c5)c(Cl)c4)c3c2)o1]

Vandetanib (ZD-6474; Zactima; formerly AZD-6474) is under development by AstraZeneca for the potential once-daily oral treatment of solid and haematological tumors including thyroid, lung, breast, head and neck, brain (i.e. glioma) and multiple myeloma. It is one of a series of inhibitors of vascular endothelial growth factor (VEGF) receptor tyrosine kinase) that also has activity against the EGF and RET receptor tyrosine kinases. Clinical studies have investigated doses of vandetanib in the region of 100-300 mg daily as monotherapy and in combinations. Common adverse effects observed were rash, fatigue, nausea, diarrhea, asymptomatic QTc prolongation

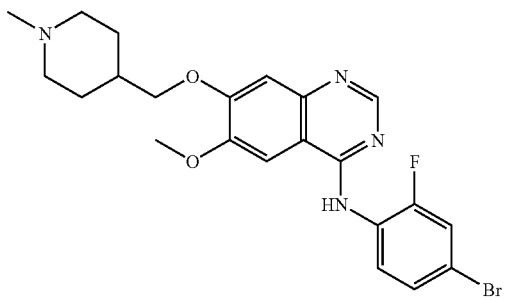 [SMILES: COc1cc2c(Nc3ccc(Br)cc3F)ncnc2cc1OCC1CCN(C)CC1]

ZD-6474 can be prepared as described in WO 01/32651 and processes analogous therein.

CHIR-258 (GFKI-258; structure shown), is a potent VEGF, FGF and PDGF receptor kinase inhibitor, for the potential oral treatment of various types of cancer. Novartis (formerly Chiron), had initiated a study in acute myelogenous leukemia (AML) patients and multiple myeloma (MM).

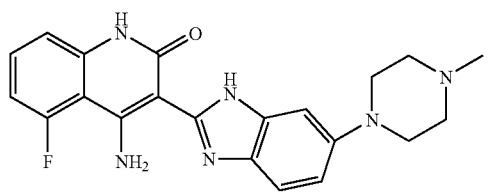 [SMILES: CN1CCN(c2ccc3nc(-c4c(N)c5c(F)cccc5[nH]c4=O)[nH]c3c2)CC1]

CHIR-258 can be prepared as described in WO 02/22598 and WO 2005/046590 and processes analogous therein.

Another suitable signalling inhibitor for use in the combinations of the invention is axitinib (AG-013736). Pfizer is developing axitinib (AG-13736, AG-013736), an oral inhibitor of the VEGF, PDGF and CSF-1 receptor tyrosine kinases which was discovered by Pfizer's wholly-owned subsidiary Agouron Pharmaceuticals, as an anti-angiogenic agent for the potential treatment of cancer. It is being studied for breast cancer, renal cell carcinoma (RCC), non-small cell lung cancer (NSCLC), melanoma, and carcinomas. The compound has also being investigated for the treatment of acute myeloid leukemia and myelodysplastic syndrome (MDS).

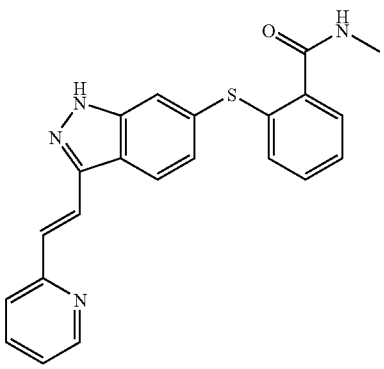 [SMILES: CNC(=O)c1ccccc1Sc1ccc2c(/C=C/c3ccccn3)n[nH]c2c1]

It can be prepared as described in WO 2004/087152, WO 2006/048746 and WO 2006/048745 and process analogous thereto. Axitinib may be dosed at 5 mg PO BID.

Posology: With regard to the EGFR antibodies, these are generally administered in a dosage of 1 to 500 mg per square meter (mg/m$^2$) of body surface area, trastuzumab being advantageously administered in a dosage of 1 to 5 mg/m$^2$ of body surface area, particularly 2 to 4 mg/m$^2$; cetuxumab is advantageously administered in a dosage of about 200 to 400 mg/m$^2$, preferably about 250 mg/m$^2$.

With regard to the EGFR tyrosine kinase inhibitors, these are generally administered in a daily oral dosage of 100 to 500 mg, for example gefitinib in a dosage of about 250 mg and erlotinib in a dosage of about 150 mg.

With regard to the VEGF monoclonal antibody bevacizumab, this is generally administered in a dosage of about 1 to 10 mg/kg for example about 5 mg/kg.

With regard to the PDGF inhibitor imatinib, this is generally administered in a dosage of about 400 to 800 mg per day preferably about 400 mg per day.

With regard to the Raf inhibitor sorafenib, this is administered at a dose of 800 mg daily.

These dosages may be administered for example once, twice or more per course of treatment, which may be repeated for example every 7, 14, 21 or 28 days.

PKA/B Inhibitors and PKB Pathway Inhibitors

Another preferred class of signaling inhibitor for use in the combinations of the invention are PKA/B inhibitors and PKB pathway inhibitors.

PKB pathway inhibitors are those that inhibit the activation of PKB, the activity of the kinase itself or modulate downstream targets, blocking the proliferative and cell survival effects of the pathway. Target enzymes in the pathway include phosphatidyl inositol-3 kinase (PI3K), PKB itself, mammalian target of rapamycin (MTOR), PDK-1 and p70 S6 kinase and forkhead translocation factor. Several components of the PI 3-kinase/PKB/PTEN pathway are implicated in oncogenesis. In addition to growth factor receptor tyrosine kinases, integrin-dependent cell adhesion and G-protein coupled receptors activate PI 3-kinase both directly and indirectly through adaptor molecules. Functional loss of PTEN (the most commonly mutated tumour-suppressor gene in cancer after p53), oncogenic mutations in PI 3-kinase, amplification of PI 3-kinase and overexpression of PKB have been established in many malignancies. In addition, persistent signaling through the PI 3-kinase/PKB pathway by stimulation of the insulin-like growth factor receptor is a mechanism of resistance to epidermal growth factor receptor inhibitors.

The discovery of non-random, somatic mutations in the gene encoding p110α in a range of human tumours suggests an oncogenic role for the mutated PI 3-kinase enzyme (Samuels, et al., Science, 304 554, April 2004). Mutations in p110α have since been detected in the following human tumours: colon (32%), hepatocellular (36%) and endometroid and clear cell cancer (20%). p110α is now the most commonly mutated gene in breast tumours (25-40%). Forkhead family translocations often occur in acute leukemia.

The PI 3-kinase/PKB/PTEN pathway is thus an attractive target for cancer drug development since such agents would be expected to inhibit proliferation and surmount resistance to cytotoxic agents in cancer cells.

Examples of PKB pathway inhibitors include PI3K Inhibitors such as Semaphore, SF1126 and MTOR inhibitors such as Rapamycin Analogues. RAD 001 (everolimus) from Novartis is an orally available derivative of the compound rapamycin. The compound is a novel macrolide, which is being developed as an antiproliferative drug with applications as an immunosuppressant and anticancer agent. RAD001 exerts its activity on growth-factor dependent proliferation of cells through its high affinity for an intracellular receptor protein, FKBP-12. The resulting FKBP-12/RAD001 complex then binds with mTOR to inhibit downstream signaling events. The compound is currently in clinical development for a wide variety of oncology indications. CCI 779 (temsirolemus) from Wyeth Pharmaceuticals and AP23573 from Ariad Pharmaceuticals are also rapamycin analogues. AP23841 and AP23573 from Ariad Pharmaceutical also target mTOR. Calmodulin inhibitors from Harvard are forkhead translocation inhibitors. (Nature Reviews drug discovery, Exploiting the PI3K/AKT Pathway for Cancer Drug Discovery; Bryan T. Hennessy, Debra L. Smith, Prahlad T. Ram, Yiling Lu and Gordon B. Mills; December 2005, Volume 4; pages 988-1004).

Definitions: The term "PKA/B inhibitor" is used herein to define a compound which has protein kinase B (PKB) and/or protein kinase A (PKA) inhibiting or modulating activity ity, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

The term "PKB pathway inhibitor" is used herein to define a compound which inhibits the activation of PKB, the activity of the kinase itself or modulate downstream targets, blocking the proliferative and cell survival effects of the pathway (including one or more of the target enzymes in the pathway as described herein, including phosphatidyl inositol-3 kinase (PI3K), PKB itself, mammalian target of rapamycin (MTOR), PDK-1 and p70 S6 kinase and forkhead translocation).

Technical background: KRX-0401 (Perifosine/NSC 639966) is a synthetic substituted heterocyclic alkylphosphocholine that acts primarily at the cell membrane targeting signal transduction pathways, including inhibition of PKB phosphorylation. KRX-0401 has been evaluated in phase 1 studies as a potential oral anticancer drug. Dose limiting toxicities included nausea, vomiting and fatigue. Gastrointestinal toxicities increased at higher doses. A phase II trial in refractory sarcoma is planned.

API-2/TCN is a small molecule inhibitor of PKB signaling pathway in tumour cells. Phase I and II clinical trials of API-2/TCN have been conducted on advanced tumours. API-2/TCN exhibited some side effects, which include hepatotoxicity, hypertriglyceridemia, thrombocytopenia, and hyperglycemia.

RX-0201 is being developed as an AKT protein kinase inhibitor for the treatment of solid tumours. In July 2004, a phase I trial was initiated in patients with advanced malignancies. Data from this showed RX-0201 inhibited overexpression of Akt and suppressed cancer growth in brain, breast, cervix, liver, lung, ovary, prostate and stomach tumours, and was well tolerated. By March 2005, US Orphan Drug status had been granted to RX-0201 for several solid tumour types.

Enzastaurin HCl (LY317615) suppresses angiogenesis and was advanced for clinical development based upon anti-angiogenic activity. It is described as a selective PKCβ inhibitor. It also has a direct anti-tumour effect, and suppresses GSK3β phosphorylation. It is currently being investigated for the treatment of glioma and non-Hodgkin's lymphoma.

SR-13668 is claimed to be an orally active specific AKT inhibitor that significantly inhibits phospho-AKT in breast cancer cells both in vitro and in vivo. In vivo assessment in mice showed no adverse effects at doses 10 times more than were needed for antitumour activity.

PX-316 is a D-3-deoxy-phosphatidyl-myo-inositol that binds to the PH domain of PKB, trapping it in the cytoplasm and thus preventing PKB activation. Anti-tumour activity was seen in early xenografts and was well tolerated.

Allosteric, selective inhibitors of PKB based on a 2,3-diphenylquinoxaline core or a 5,6-diphenylpyrazin-2(1H)-one core have been developed (Merck).

KRX-0401: In a Phase I weekly dosing study conducted in Europe, the recommended Phase II dose was 600/mg/week. Subsequent studies conducted in the U.S. have shown that much higher doses are well tolerated when the doses are divided and administered at 4 to 6 hour intervals. In addition, it has been shown that KRX-0401 has a very long half-life in the range of 100 hours. This makes the possibility of a relative non-toxic, intermittent dosing schedule very plausible.

A phase I trial of API-2 was conducted using a 5-day continuous infusion schedule. Dose levels ranged from 10 mg/sq m/day X 5 days to 40 mg/sq m/day X 5 days. Initially, courses were repeated every 3 to 4 weeks. As cumulative toxicity became manifested, the interval between courses was changed to every 6 weeks. Recommended schedule for Phase II studies is 20 mg/sq m/day for 5 days every 6 weeks. A Phase II trial of TCN-P was conducted in metastatic or recurrent squamous cell carcinoma of the cervix using a 5-day continuous infusion schedule. The starting dose was 35 mg/m$^2$×5 days and courses were repeated every 6 weeks.

Further PKB inhibitors include Perifosine from Keryx Biopharmaceuticals. Perifosine is an oral Akt inhibitor which exerts a marked cytotoxic effect on human tumour cell lines, and is currently being tested in several phase II trials for treatment of major human cancers. KRX-0401 (Perifosine/NSC 639966) has the structure:

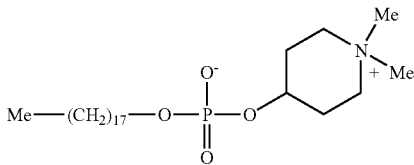

It can be prepared according to Aste Medica patent publication DE4222910 or Xenoport patent publication US2003171303.

API-2/TCN (Triciribine) has the structure:

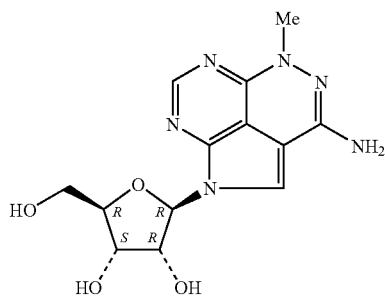

It can be prepared according to Bodor patent publication WO9200988 or Ribapharm patent publication WO2003061385.

Enzastaurin hydrochloride has the structure:

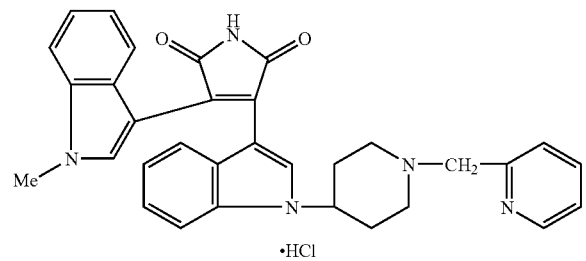 [SMILES: Cn1cc(C2=C(c3cn(C4CCN(Cc5ccccn5)CC4)c4ccccc34)C(=O)NC2=O)c2ccccc21 ; Cl]

It can be prepared according to Eli Lilly patent publication WO2004006928.

SR 13668 has the structure:

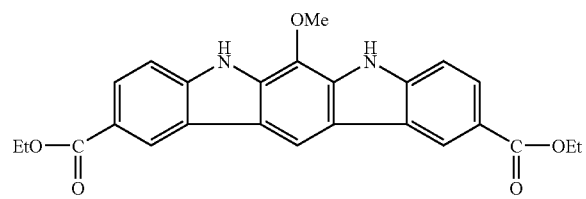 [SMILES: CCOC(=O)c1ccc2[nH]c3c(OC)c4[nH]c5ccc(C(=O)OCC)cc5c4cc3c2c1]

It can be prepared according to SRI International patent publication US2004043965.

NL-71-101 has the structure:

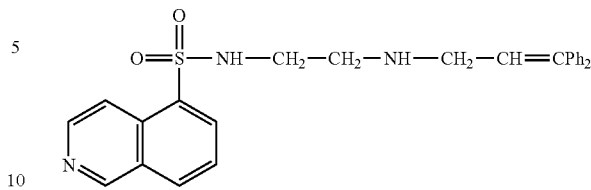

It can be prepared according to Biochemistry (2002), 41(32),10304-10314 or Peptor patent publication WO2001091754.

DeveloGen (formerly Peptor) is investigating NL-71-101, a protein kinase B (PKB) inhibitor, for the potential treatment of cancer [466579], [539004]. At the beginning of 2003, the compound was undergoing lead optimization [495463]. By February 2004, the company was seeking to outlicense certain development rights to its protein kinase B program [523638].

In 2002, data were published showing that NL-71-101 inhibited the activity of PKB over PKA, PKG and PKC with IC50 values of 3.7, 9, 36 and 104 microM, respectively. NL-71-101 induced apoptosis in OVCAR-3 tumour cells, in which PKB is amplified at concentrations of 50 and 100 microM [466579]. This compound has the structure:

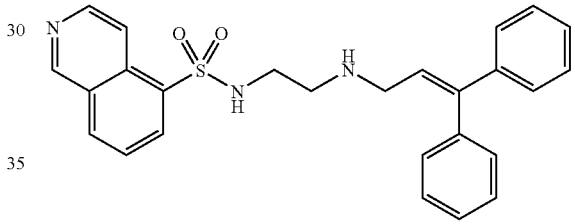

Specific embodiments: Embodiments contemplated include combinations in which the anti-cancer agent is a PKB inhibitor selected from one or more of the specific compounds described above.

14. CDK Inhibitors

Preferred CDK inhibitors for use as ancillary agents in the combinations of the invention are compounds of formula (I') as defined herein. However, CDK inhibitors for use in the combinations of the invention also include the ancillary CDK inhibitors described in more detail below that have cyclin dependent kinase inhibiting or modulating activity and/or glycogen synthase kinase-3 (GSK3) inhibiting or modulating activity. Thus, the combinations of the present invention may comprise (or consist essentially of) two or more compounds of formula (I') as defined herein.

In addition to the CDK compounds of formula (I') herein, the combinations of the present invention may include one or more ancillary CDK inhibitors or modulators. Such ancillary CDK inhibitors or modulators may be selected from the various CDK inhibitors described herein and preferred ancillary CDK inhibitors are discussed in more detail below.

Definition: The term "CDK inhibitor" as used herein refers to compounds that inhibit or modulate the activity of cyclin dependent kinases (CDK), including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

The term "ancillary CDK inhibitor" as used herein refers to a compound that inhibits or modulates the activity of cyclin dependent kinases (CDK) and which does not conform to the structure of formula (I') as defined herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical background: CDKs play a role in the regulation of the cell cycle, apoptosis, transcription, differentiation and CNS function. Therefore, CDK inhibitors may find application in the treatment of diseases in which there is a disorder of proliferation, apoptosis or differentiation such as cancer. In particular RB+ve tumours may be particularly sensitive to CDK inhibitors. RB−ve tumours may also be sensitive to CDK inhibitors.

Examples of CDK inhibitors which may be used in combinations according to the invention include seliciclib, alvocidib, 7-hydroxy-staurosporine, JNJ-7706621, BMS-387032 (a.k.a. SNS-032), PHA533533, PD332991, ZK-304709, and AZD-5438.

Seliciclib, which is the R isomer of roscovitine, and otherwise known as CYC 202, has the chemical name (2R)-2-[[9-(1-methylethyl)-6-[(phenylmethyl)-amino]-9H-purin-2-yl]amino]-1-butanol. It is being evaluated in clinical trials for the potential treatment of various cancers including lymphoid leukaemia, non-small-cell lung cancer, glomerulonephritis, mantle cell lymphoma, multiple myeloma, and breast cancer. Observed toxicities in clinical trials include nausea/vomiting and asthenia, skin rash and hypokalemia. Other toxicities included reversible renal impairment and transaminitis, and emesis.

Alvocidib, which is otherwise known as flavopiridol, HMR 1275 or L 86-8275, and which has the chemical name 5,7-dihydroxy-8-(4-N-methyl-2-hydroxypyridyl)-6'-chloroflavone, is being investigated in clinical trials for the potential treatment of various cancers including cancer of the esophagus, stomach, prostate, lung and colon, and also chronic lymphocytic leukaemia, and multiple myeloma, lymphoma; the most common toxicities observed were diarrhea, tumour pain, anemia, dyspnea and fatigue.

7-Hydroxystaurosporine, which is otherwise known as UCN-01 is being evaluated in clinical trials for the potential treatment of various cancers including chronic lymphocytic leukaemia, pancreas tumours and renal tumours; adverse events observed included nausea, headache and hyperglycemia.

JNJ-7706621, which has the chemical name N3-[4-(aminosulfonyl)-phenyl]-1-(2,6-difluorobenzoyl)-1H-1,2,4-triazole-3,5-diamine, is the subject of pre-clinical testing for the potential treatment of melanoma and prostate cancer. BMS-387032 which has the chemical name N-[5-[[[5-(1,1-dimethylethyl)-2-oxazolyl]-methyl]thio]-2-thiazolyl]-4-piperidinecarboxamide, has been evaluated in phase I studies as a potential anticancer drug for patients with metastatic solid tumours such as renal cell carcinomas, non-small-cell lung cancer, head and neck cancers and leiomyosarcoma The drug was well tolerated with transient neutropenia noted as the primary toxicity. Other side-effects included transient liver aminase elevations, gastrointestinal toxicity, nausea, vomiting, diarrhea and anorexia. PHA533533, which has the chemical name (αS)—N-(5-cyclopropyl-1H-pyrazol-3-yl)-α-methyl-4-(2-oxo-1-pyrrolidinyl)-benzene-acetamide, is the subject of pre-clinical testing for the potential treatment of various cancers such as tumours of the prostate, colon and ovary. PD332991, which has the chemical name 8-cyclohexyl-2-[[4-(4-methyl-1-piperazinyl)phenyl]amino]-pyrido[2,3-d]pyrimidin-7(8H)-one, is the subject of pre-clinical testing for the potential treatment of various cancers. Pre-clinical data suggests that it is a highly selective and potent CDK4 inhibitor, demonstrating marked tumour regression in vivo models.

ZK-304709 is an oral dual specificity CDK and VEGFR kinase inhibitor, described in PCT patent specification No. WO 02/096888, and is the subject of pre-clinical testing for the potential treatment of various cancers. AZD-5438 is a selective cyclin-dependent kinase (CDK) inhibitor, which is in pre-clinical development for the treatment of solid cancers. Seliciclib may be prepared for example as described in PCT patent specification No. WO 97/20842, or by processes analogous thereto. Alvocidib, may be prepared for example as described in U.S. Pat. No. 4,900,727 or by processes analogous thereto. 7-Hydroxystaurosporine may be prepared for example as described in U.S. Pat. No. 4,935,415, or by processes analogous thereto. JNJ-7706621 may be prepared for example as described in PCT patent specification No. WO 02/057240, or by processes analogous thereto. BMS-387032 may be prepared for example as described in PCT patent specification No. WO 01/44242, or by processes analogous thereto. PHA533533 may be prepared for example as described in U.S. Pat. No. 6,455,559, or by processes analogous thereto. PD332991, may be prepared for example as described in PCT patent specification No. WO 98/33798, or by processes analogous thereto. ZK-304709 may be prepared for example as described in PCT patent specification No. WO 02/096888, or by processes analogous thereto.

Preferences and specific embodiments: Embodiments contemplated include combinations in which the anti-cancer agent is a CDK inhibitor selected from one or more of the specific compounds described above. Thus, preferred CDK inhibitors for use in combinations according to the invention include seliciclib, alvocidib, 7-hydroxystaurosporine, JNJ-7706621, BMS-387032, PHA533533, PD332991 and ZK-304709. Particular CDK inhibitors for use in combinations according to the invention include seliciclib, alvocidib, 7-hydroxystaurosporine, JNJ-7706621, BMS-387032, PHA533533, PD332991 and ZK-304709.

Posology: The CDK inhibitor may be administered for example in a daily dosage of for example 0.5 to 2500 mg, more preferably 10 to 1000 mg, or alternatively 0.001 to 300 mg/kg, more preferably 0.01 to 100 mg/kg, particularly for seliciclib, in a dosage of 10 to 50 mg; for alvocidib, in a dosage in accordance with the above-mentioned U.S. Pat. No. 4,900,727; for 7-hydroxystaurosporine in a dosage of 0.01 to 20 mg/kg; for JNJ-7706621 in a dosage of 0.001 to 300 mg/kg; for BMS-387032 in a dosage of 0.001 to 100 mg/kg more preferably 0.01 to 50 mg/kg, and most preferably 0.01 to 20 mg/kg; for PHA533533 in a dosage of 10 to 2500 mg; for PD332991 in a dosage of 1 to 100 mg/kg; and for ZK-304709 in a dosage of 0.5 to 1000 mg preferably 50 to 200 mg.

These dosages may be administered for example once, twice or more per course of treatment, which may be repeated for example every 7, 14, 21 or 28 days.

15. COX-2 Inhibitors

Definition: The term "COX-2 inhibitor" is used herein to define compounds which inhibit or modulate the activity of the cyclo-oxygenase-2 (COX-2) enzyme, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological activity: The COX-2 inhibitors working via one or more pharmacological actions as described herein have been identified as suitable anti-cancer agents.

Technical background: Recently, research in cancer chemotherapy has focused on the role of the cyclo-oxygenase-2 (COX-2) enzyme in the aetiology of cancer. Epidemiological studies have shown that people who regularly take non-steroidal anti-inflammatory drugs (NSAIDs), for example aspirin and ibuprofen to treat conditions such as arthritis, have lower rates of colorectal polyps, colorectal cancer, and death due to colorectal cancer. NSAIDs block cyclooxygenase enzymes, which are produced by the body in inflammatory processes, and which are also produced by pre-cancerous tissues. For example in colon cancers, a dramatic increase of COX-2 levels is observed. One of the key factors for tumour growth is the supply of blood to support its increased size. Many tumours can harness chemical pathways that prompt the body to create a web of new blood vessels around the cancer, a process called angiogenesis. COX-2 is believed to have a role in this process. It has therefore been concluded that inhibition of COX-2 may be effective for treating cancer, and COX-2 inhibitors have been developed for this purpose. For example celecoxib, which has the chemical name 4-[5-(4-methylphenyl)-3-(trifluoromethyl)-1H-pyrazol-1-yl]benzenesulfonamide, is a selective COX-2 inhibitor that is being investigated for the treatment of various cancers including bladder and esophageal cancer, renal cell carcinoma, cervical cancer, breast cancer, pancreatic cancer non-Hodgkin's lymphoma and non-small cell lung cancer.

Posology: The COX-2 inhibitor (for example celecoxib) can be administered in a dosage such as 100 to 200 mg e.g. daily.

These dosages may also be administered for example once, twice or more per course of treatment, which may be repeated for example every 7, 14, 21 or 28 days.

Problems: The most common adverse effects are headache, abdominal pain, dyspepsia, diarrhea, nausea, flatulence and insomnia. There is a need to provide a means for the use of lower dosages of COX-2 inhibitors to reduce the potential for adverse toxic side effects to the patient.

Preferences and specific embodiments: In one embodiment the COX-2 inhibitor is celecoxib. Celecoxib is commercially available for example from Pfizer Inc under the trade name Celebrex, or may be prepared for example as described in PCT patent specification No. WO 95/15316, or by processes analogous thereto.

Two other commercially available COX-2 inhibitors are Arcoxia (etoricoxib from Merck) and Novartis Cox-2 inhibitor lumiracoxib (Prexige).

16. HDAC Inhibitors

Definition: The term "HDAC inhibitor" is used herein to define compounds which inhibit or modulate the activity of histone deacetylases (HDAC), including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological activity: The HDAC inhibitors working via one or more pharmacological actions as described herein have been identified as suitable anti-cancer agents.

Technical background: Reversible acetylation of histones is a major regulator of gene expression that acts by altering accessibility of transcription factors to DNA. In normal cells, histone deacetylase (HDAC) and histone acetyltrasferase (HDA) together control the level of acetylation of histones to maintain a balance. Inhibition of HDA results in the accumulation of hyperacetylated histones, which results in a variety of cellular responses. Inhibitors of HDA (HDAI) have been studied for their therapeutic effects on cancer cells. Recent developments in the field of HDAI research have provided active compounds, that are suitable for treating tumours.

Accruing evidence suggests that HDAI are more efficacious when used in combination with other chemotherapeutic agents. There are both synergistic and additive advantages, both for efficacy and safety. Therapeutic effects of combinations of chemotherapeutic agents with HDAI can result in lower safe dosage ranges of each component in the combination.

The study of inhibitors of histone deacetylases (HDAC) indicate that these enzymes play an important role in cell proliferation and differentiation. The inhibitor Trichostatin A (TSA) causes cell cycle arrest at both G1 and G2 phases, reverts the transformed phenotype of different cell lines, and induces differentiation of Friend leukaemia cells and others. TSA (and suberoylanilide hydroxamic acid SAHA) have been reported to inhibit cell growth, induce terminal differentiation, and prevent the formation of tumours in mice (Finnin et al., Nature, 401:188-193, 1999).

Trichostatin A has also been reported to be useful in the treatment of fibrosis, e.g. liver fibrosis and liver chirrhosis. (Geerts et al., European Patent Application EPO 827 742, published 11 Mar. 1998).

Preferences and specific embodiments: Preferred HDAC inhibitors for use in accordance with the invention are selected from TSA, SAHA, JNJ-16241199, LAQ-824, MGCD-0103 and PXD-101 (referred to above).

Thus, synthetic inhibitors of histone deacetylases (HDAC) which are suitable for use in the present invention include JNJ-16241199 from Johnson and Johnson Inc, LAQ-824 from Novartis, MGCD-0103 from MethylGene, and PXD-101 from Prolifix.

JNJ-16241199 has the following structure:

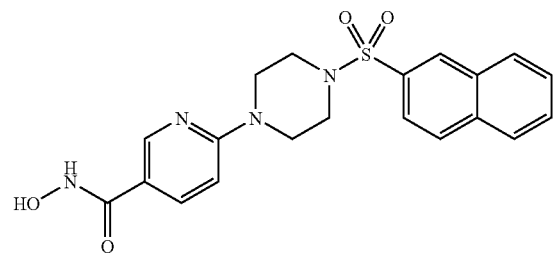 [SMILES: O=C(NO)c1ccc(N2CCN(S(=O)(=O)c3ccc4ccccc4c3)CC2)nc1]

MGCD-0103 has the structure:

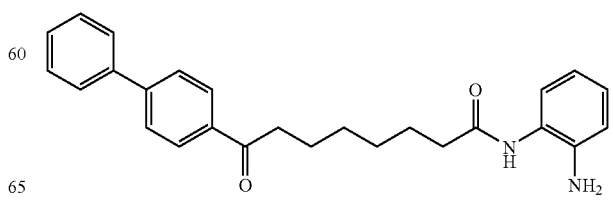

LAQ-824 has the structure:

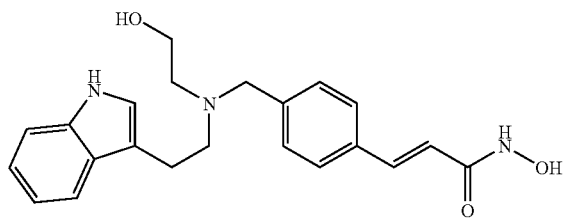 [SMILES: O=C(/C=C/c1ccc(CN(CCO)CCc2c[nH]c3ccccc23)cc1)NO]

Other inhibitors of histone deacetylases (HDAC) which are suitable for use in the present invention include, but are not limited to, the peptide chlamydocin, and A-173, also from Abbott Laboratories.

A-173 is a succinimide macrocyclic compound with the following structure:

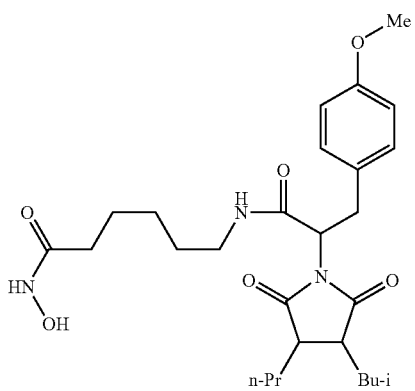

Posology: In general, for HDAC inhibitors it is contemplated that a therapeutically effective amount would be from 0.005 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

17. Selective Immunoresponse Modulators

Selective immunoresponse modulators include Lenalidomide and Thalidomide.

Lenalidomide (Revlimid) is an oral thalidomide derivative developed by Celgene which is a potent inhibitor of TNF-alpha and interleukin-1 beta which is being developed for the treatment of 5q-myelodysplastic syndrome multiple myeloma, chronic lymphocytic leukaemia gliomas, cutaneous T-cell lymphoma and epithelial ovarian cancer.

Lenalidomide (3-(4-amino-1-oxoisoindolin-2-yl)piperidine-2,6-dione) has the following structure:

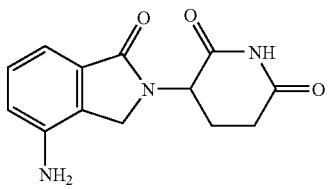 [SMILES: Nc1cccc2c1CN(C1CCC(=O)NC1=O)C2=O]

Thalidomide is a sedative and anti-emetic that became widely recognized as a result of reports of its teratogenic effects, most notably limb deformities in up to 12,000 children born to women who had received thalidomide in Europe and Canada during the 1960s. Celgene has developed and launched thalidomide as an oral TNF-alpha inhibitor (Sold to Pharmion). Extensive clinical evidence has accumulated with regard to the potential antitumor activity of thalidomide in several types of neoplasias, with notable activity in relapsed/refractory multiple myeloma, Waldenstrom's macroglobulinemia (WM) and myelodysplastic syndromes (MDS). There is also evidence of biological activity in acute myeloid leukemia, myelofibrosis with myeloid metaplasia, renal cell carcinoma, malignant gliomas, prostate cancer, Kaposi's sarcoma and colorectal carcinoma.

Thalidomide (1,3-dioxo-2-(2,6-dioxopiperidin-3-yl)isoindoline) has the following structure:

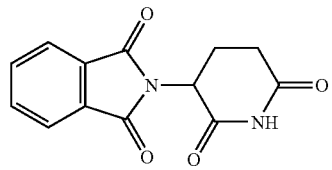 [SMILES: O=C1CCC(N2C(=O)c3ccccc3C2=O)C(=O)N1]

Posology: Thalidomide may be advantageously administered in dosages of 100 to 800 mg/day continuously as tolerated. Lenalidomide may be advantageously administered in 5- to 40-mg doses continuously as tolerated.

18. DNA Methylase Inhibitors

Definition: The term "DNA methylase inhibitor" or "DNA methyltransferase inhibitor" as used herein refers to a compound which directly or indirectly perturbs, disrupts, blocks, modulates or inhibits the methylation of DNA, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. They are also referred to as "hypomethylating agents".

Biological activity: The DNA methylase inhibitors working via one or more pharmacological actions as described herein have been identified as suitable anti-cancer agents.

Technical background: One target for cancer chemotherapy is DNA synthesis, which may depend on appropriate methylation of tumour DNA. Compounds which directly or indirectly perturb, disrupt, block, modulate or inhibit the methylation of DNA may therefore be useful anticancer drugs.

The DNA methylase inhibitor temozolomide is used for the treatment of glioblastoma multiforme, and first-line treatment of patients with advanced metastatic malignant melanoma (such as first-line treatment of patients with advanced metastatic malignant melanoma) and has also being investigated and used for the treatment of malignant glioma at first relapse. This compound undergoes rapid chemical conversion at physiological pH to the active compound, monomethyl triazeno imidazole carboxamide (MTIC) which is responsible for the methylation of DNA at the $O^6$ position of guanine residues (which appears to lead to a suppression in expression of DNA methyltransferase and so produce hypomethylation).

Problems: The most common side effects associated with temozolomide therapy are nausea, vomiting, headache, fatigue, thrombocytopenia and constipation. There is a need to increase the inhibitory efficacy of DNA\methylase inhibitors and to provide a means for the use of lower dosages of signaling inhibitors to reduce the potential for adverse toxic side effects to the patient.

Preferences and specific embodiments: In one embodiment, the DNA methylase inhibitor is temozolomide (3,4-dihydro-3-methyl-4-oxoimidazo[5,1-d]-as-tetrazine-8-carboxamide). Temozolomide is commercially available for example from Schering Corporation under the trade name Temodar, or may be prepared for example as described in German patent specification No. 3231255, or by processes analogous thereto.

A further DNA methyltransferase inhibitor for use in the combinations of the invention is Decitabine (a.k.a. Dacogen) having the structure shown below:

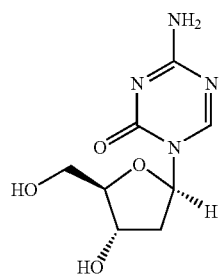 [SMILES: Nc1ncn([C@H]2C[C@H](O)[C@@H](CO)O2)c(=O)n1]

SuperGen Inc and MGI Pharma Inc have developed decitabine (Dacogen), an inhibitor of DNA methyltransferase, preventing methylation of cytosine residues on DNA and leading to hypomethylation of gene promoters, thereby reactivating silenced genes. Decitabine/Dacogen is cytotoxic to a broad range of malignant cells in vitro. It shows significant activity against acute myeloid leukemia (AML), chronic myeloid leukemia (CML) and myelodysplastic syndromes (MDS). Decitabine/Dacogen is indicated for the treatment of myelodysplastic syndromes (MDS) and secondary MDS (including chronic myelomonocytic leukemia, refractory anemia, refractory anemia with ringed sideroblasts, refractory anemia with excess blasts and refractory anemia with excess blasts in transformation).

Decitabine/Dacogen is an analog of deoxycytidine (beta-D-anomer of 2'-deoxy-5-azacytidine). It differs from deoxycytidine by substitution at position 5 of the pyrimidine ring with nitrogen. Decitabine contains deoxyribose, in contrast to the related analog, Pharmion Corp's 5-azacytidine (Vidaza), which contains a ribose sugar. Decitabine is, therefore, a deoxynucleoside and is incorporated into DNA, but not RNA, in contrast to 5-azacytidine which is incorporated into RNA. Decitabine and 5-azacytidine differ from other pyrimidine analogs, such as cytosine arabinoside and gemcitabine, by modification at position 5 of the pyrimidine ring. This distinctive feature, which is not present in these latter drugs, is responsible for inhibition of DNA methyltransferase. Pseudoisocytidine and 5-fluoro-2'-deoxycytidine, further analogs with modifications of the 5 position of the pyrimidine ring, also inhibit demethylation.

Decitabine/Dacogen is dosed at 15 mg/m2 over a three hour period every 8 hours for 3 days every 6 weeks as a cycle of therapy or on a daily dosing schedule with a one hour infusion usually delivered at 20 mg/m2 per day either for one week or two weeks every 6 weeks as a cycle At toxic doses decitabine/Dacogen produces leukopenia, thrombocytopenia and weight loss. The major toxicity of decitabine is myelosuppression, which is proportional to dose and duration of therapy. The effects are pronounced at high doses (>200 mg/m2/day), and myelosuppression is enhanced by concomitant administration of other cytotoxic drugs. Neutropenic infection and other complications of myelosuppression have proved fatal. Non-hematological side effects include nausea, vomiting, mucositis and alopecia.

Decitabine/Dacogen and other analogues thereof can be made as outlined in U.S. Pat. No. 03,432,549 and further discussed on WO 006/017278 and WO 2006/037024 to SuperGen Inc.

A further DNA methyltransferase inhibitor for use in the combinations of the invention is azacytidine (a.k.a. 5-azacitidine, 5-azacytidine or Vidaza) a sc administered hypomethylating agent and DNA methyltransferase inhibitor. It is indicated for the treatment of all myelodysplastic syndrome (MDS) subtypes, including refractory anemia (RA) or RA with ringed sideroblasts, RA with excess blasts, RA with excess blasts in transformation and chronic myelomonocytic leukemia.

5-azacitidine (Vidaza) can be administered twice-daily subcutaneously or via the iv route administration for MDS treatment.

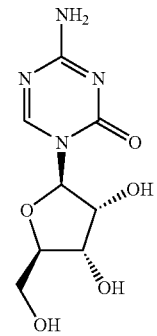 [SMILES: Nc1ncn([C@@H]2O[C@H](CO)[C@@H](O)[C@H]2O)c(=O)n1]

It can be prepared as described in DE 1922702, GB 1227691 and FR 2008048 from Ceskoslovenska Akademie Ved and WO 2004082618, WO 2004082619 and WO 2004082822 from Pharmion and process analogous thereto.

Posology: The DNA methylating agent (for example temozolomide) can be administered in a dosage such as 0.5 to 2.5 mg per square meter (mg/m$^2$) of body surface area, particularly about 1.3 mg/m$^2$. These dosages may be administered for example once, twice or more per course of treatment, which may be repeated for example every 7, 14, 21 or 28 days.

19. Proteasome Inhibitors

Definition: The term "proteasome inhibitor" as used herein refers to compounds which directly or indirectly perturb, disrupt, block, modulate or inhibit the half-life of many short-lived biological processes, such as those involved in the cell cycle. The term therefore embraces compounds which block the action of proteasomes (large protein complexes that are involved in the turnover of other cellular proteins). The term also embraces the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Biological activity: The proteasome inhibitors working via one or more pharmacological actions as described herein have been identified as suitable anti-cancer agents.

Technical background: Another class of anticancer agents are the proteasome inhibitors. Proteasomes control the half-life of many short-lived biological processes, such as those involved in the cell cycle. Therefore, proteasome malfunction can lead to abnormal regulation of the cell cycle and uncontrolled cell growth.

The cell cycle is controlled by both positive and negative signals. In a normal cell, proteasomes break down proteins that inhibit the cell cycle, such as cyclin-dependent kinase inhibitors. Inhibition of proteasome function causes cell cycle arrest and cell death. Tumour cells are more susceptible to these effects than normal cells, in part because they divide more rapidly and in part because many of their normal regulatory pathways are disrupted. The mechanism for the differential response of normal and cancer cells to proteasome inhibition is not fully understood. Overall, cancer cells are more susceptible to proteasome inhibitors and, as a result, these inhibitors may be an effective treatment for certain cancers.

One such proteasome inhibitor is bortezimib, which has the chemical name [(1R)-3-methyl-1-[[(2S)-1-oxo-3-phenyl-2-[(pyrazinylcarbonyl)amino]propyl]amino]butyl]-boronic acid.

Bortezimib specifically interacts with a key amino acid, namely threonine, within the catalytic site of the proteasome. Bortezimib is being used for the treatment of multiple myeloma and also for a number of other cancers, including leukemia and lymphoma, and prostate, pancreatic and colorectal carcinoma. In addition Velcade is useful for the treatment of non-Hodgkin's lymphoma.

Problems: The most common side effects with bortezimib are nausea, tiredness, diarrhea, constipation, decreased platelet blood count, fever, vomiting, and decreased appetite.

Bortezimib can also cause peripheral neuropathy.

Thus, there is a need to provide a means for the use of lower dosages to reduce the potential of adverse toxic side effects to the patient.

Preferences and specific embodiments: Preferred proteasome inhibitors for use in accordance with the invention include bortezimib. Bortezimib is commercially available for example from Millennium Pharmaceuticals Inc under the trade name Velcade, or may be prepared for example as described in PCT patent specification No. WO 96/13266, or by processes analogous thereto.

Posology: The proteasome inhibitor (such as bortezimib) can be administered in a dosage such as 100 to 200 mg/m². These dosages may be administered for example once, twice or more per course of treatment, which may be repeated for example every 7, 14, 21 or 28 days.

The antibiotic bleomycin may also be used as a cytotoxic agent as an anti-cancer agent according to the invention.

20. Aurora Inhibitors

In one embodiment of the invention, the ancillary compound is an inhibitor of Aurora kinase(s). Preferred Aurora inhibitors for use as ancillary agents in the combinations of the invention are compounds of formula (I') as defined herein. However, Aurora inhibitors for use in the combinations of the invention also include the ancillary Aurora inhibitors described in more detail below. Thus, the combinations of the present invention may comprise (or consist essentially of) two or more compounds of formula (I') as defined herein.

In addition to the Aurora inhibitors of formula (I') as defined herein, the combinations of the present invention may include one or more ancillary Aurora inhibitors or modulators. Such ancillary Aurora inhibitors or modulators may be selected from the various Aurora inhibitors described herein and preferred ancillary Aurora inhibitors are discussed in more detail below.

Definition: The term "Aurora kinase inhibitor" (or simply "Aurora inhibitor") as used herein refers to compounds that inhibit or modulate the activity of any of the Aurora kinase isoforms A, B and/or C as described herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

The term "ancillary Aurora inhibitor" as used herein refers to compounds that inhibit or modulate the activity of any of the Aurora kinase isoforms A, B and/or C and which do not conform to the structure of formula (I') as defined herein, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above.

Technical Background: Aurora kinases play a role in regulating the cell cycle and in particular in the process of cellular mitosis (they have an important role in the mitotic phase of the cell cycle). Therefore, Aurora kinase inhibitors may find application in the treatment of diseases in which there is a disorder of proliferation, cell division, differentiation such as cancer. In particular tumours with mitotic and or spindle defects may be particularly sensitive to CDK inhibitors.

Inhibition of the Aurora kinases has been shown to substantially disrupt the mitotic process leading to early mitotic effects from inhibition of Aurora A and late abnormalities of cytokinesis by inhibition of Aurora B. It is believed that combining Aurora kinase inhibitors with agents that activate, interfere with or modulate the mitotic or cell cycle checkpoint could sensitise cells to the cytotoxic effects and a beneficial combination effect could be observed (Anand S, Penrhyn-Lowe S, Venkitaraman A R. Cancer Cell. 2003 January;3(1): 51-62). In this context a combination of Aurora kinase inhibitors with the taxanes, epothilones or vinca alkaloids would be expected to be beneficial. Particular taxanes, epothilones and vinca alkaloids are described herein.

Examples of ancillary Aurora kinase inhibitors include AZD1152, MK0457 (VX680), PHA-739358, MLN-8054, MP-235 in particular MK0457 (VX680), PHA-739358, MLN-8054, MP-235. AZD1152 is undergoing clinical evaluation. AZD1152 is a pro-drug which is converted rapidly to the active moiety AZD1152-HQPA in the plasma (AZD-1152 hydroxy-QPA, structure shown below). In early studies in patients with advanced solid malignancies, AZD1152 given in a 2 hr infusion weekly, induces p53 independent cellular multinucleation and polyploidy, resulting in apoptosis. These early studies indicate neutropenia is the dose-limiting toxicology (ASCO 2006).

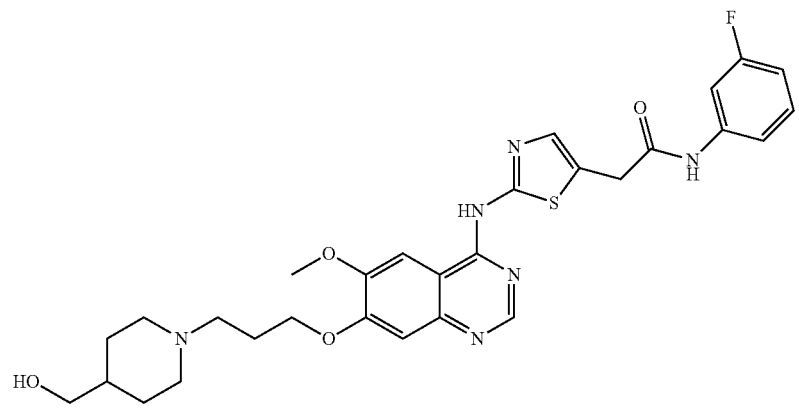 [SMILES: COc1cc2c(Nc3ncc(CC(=O)Nc4cccc(F)c4)s3)ncnc2cc1OCCCN1CCC(CO)CC1]

AZD1152 and AZD1152-HQPA can be synthesized as described in WO 02/00649 or by processes analogous thereto.

MK0457 (VX-680) is undergoing clinical evaluation. MK0457 has been given to patients with refractory malignancies in a continuous 5 day infusion every 28 days. These early studies indicate neutropenia is the dose-limiting toxicology (ASCO 2006).

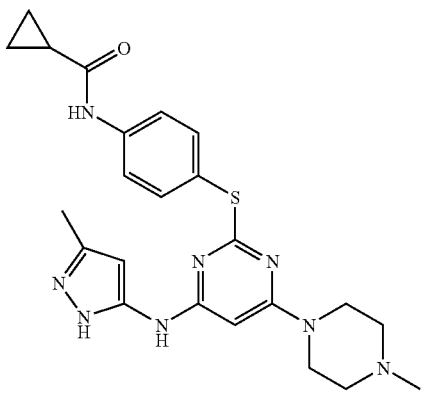 [SMILES: Cc1cc(Nc2cc(N3CCN(C)CC3)nc(Sc3ccc(NC(=O)C4CC4)cc3)n2)[nH]n1]

MK0457 can be synthesised as described in Harrington et al, *Nat Med.* 2004 March; 10(3):262-7 and WO 02/057259, WO 02/059111, WO 02/059112, WO 02/062789, WO 02/068415, WO 02/066461, WO 02/050065, WO 02/050066 and in particular WO 2004/000833, and by processes analogous thereto.

PHA-739358, the structure of which is shown below, is currently being evaluated by Nerviano Medical Sciences Srl in a multicenter phase 1 dose escalation clinical trials.

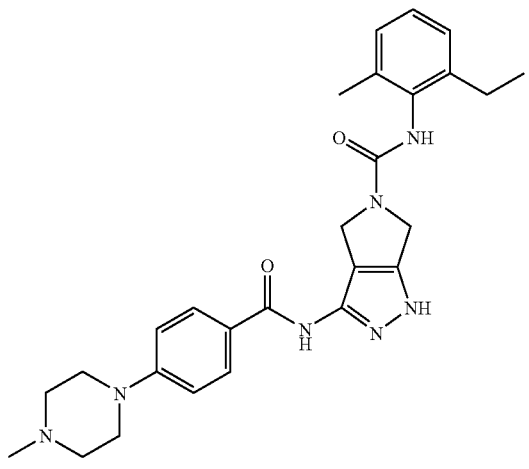 [SMILES: CCc1cccc(C)c1NC(=O)N1Cc2[nH]nc(NC(=O)c3ccc(N4CCN(C)CC4)cc3)c2C1]

PHA-739358 can be synthesised as described in Fancelli et al, Journal of Medicinal Chemistry (2005), 48(8), 3080-3084 and WO02/12242 and by processes analogous thereto.

MLN-8054 the chemical name of which is 4-[9-Chloro-7-(2,6-difluoro-phenyl)-5H-benzo[c]pyrimido[4,5-e]azepin-2-ylamino]-benzoic acid (structure shown below) is currently being evaluated in multicenter phase 1 dose escalation clinical trials in patients with refractory solid tumours including lymphomas.

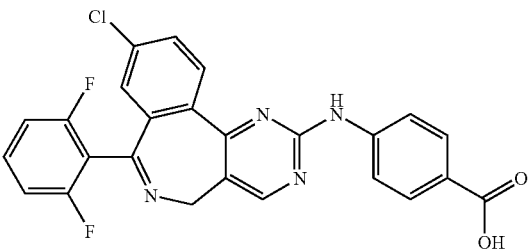 [SMILES: O=C(O)c1ccc(Nc2ncc3c(n2)-c2ccc(Cl)cc2C(c2c(F)cccc2F)=NC3)cc1]

MLN-8054 can be synthesised as described in WO 2005/111039, and by processes analogous thereto.

SuperGen, following the acquisition of Montigen in April 2006, is investigating a series of small molecule Aurora-2 kinase inhibitors that induce apoptosis and inhibit cell division, including MP-235 (HPK-62) (4-(6,7-Dimethoxy-9H-1,3,9-triaza-fluoren-4-yl)-piperazine-1-carbothioic acid [4-(pyrimidin-2-ylsulfamoyl)-phenyl]-amide, structure shown), for the potential treatment of various cancers, including pancreatic cancer. MP-235 can be synthesised as described in WO 2005/037825 and by processes analogous thereto

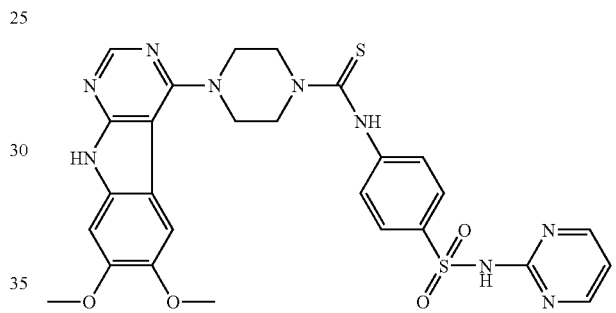

Further Aurora compounds include those described herein, including an additional compound of formula (I'), a further compound of the formula (I") and also includes those described in Formula (I) of WO2005/002552 (PCT/GB2004/002824). WO 2005/002552 is incorporated herein by reference and relates to compounds of Formula (I) as laid out therein.

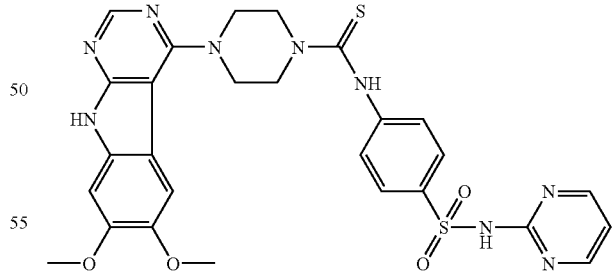

21. Hsp90 Inhibitors

Definition: The term Hsp90 inhibitor as used herein refers to compounds that inhibit or modulate the activity of Heat Shock Protein 90 as described herein.

Technical Background: In response to cellular stresses including heat, toxins, radiation, infection, inflammation, and oxidants, all cells produce a common set of heat shock proteins (Hsps) (Macario & de Macario 2000). Most heat shock proteins act as molecular chaperones. Chaperones bind and stabilize proteins at intermediate stages of folding and allow proteins to fold to their functional states. Hsp90 is the most abundant cytosolic Hsp under normal conditions. There are two human isoforms of Hsp90, a major form Hsp90α and minor form Hsp90β. Hsp90 binds proteins at a late stage of folding and is distinguished from other Hsps in that most of its protein substrates are involved in signal transduction. It has been shown that ATP bound at the N-terminal pocket of Hsp90 is hydrolysed. This ATPase activity results in a conformational change in Hsp90 that is required to enable conformational changes in the client protein.

Activation of Hsp90 is further regulated through interactions with a variety of other chaperone proteins and can be isolated in complex with other chaperones including Hsp70, Hip, Hop, p23, and p50cdc37. Many other co-chaperone proteins have also been demonstrated to bind Hsp90. There is some evidence that Hsp90 is found primarily within "activated" multichaperone complexes in the tumour cells as opposed to "latent" complexes in normal cells.

Increased genetic instability associated with the cancer phenotype leads to an increase in the production of non-native or mutant proteins. The ubiquitin pathway also serves to protect the cell from non-native or misfolded proteins, by targeting these proteins for proteasomal degradation. Mutant proteins are by their nature not native and therefore have the potential to show structural instability and an increased requirement for the chaperone system. (Giannini et al., Mol Cell Biol. 2004; 24(13):5667-76).

The number of reported Hsp90 client proteins now exceeds 100. Since many of its client proteins are involved in cell signalling proliferation and survival, Hsp90 has received major interest as an oncology target. Hsp90 protein kinase client proteins implicated in cell proliferation and survival include the following; Cellular Src (c-Src), ErbB2 (Her2/neu), Polo-like kinases (Plks), Akt (PKB), c-Raf, B-RAF, Mek, epidermal growth factor receptor (EGFR), FMS-like tyrosine kinase 3 (FLT3), c-met, Cdk1, Cdk2, Cdk4, and Cdk6, Wee-1, Mutant p53, Hypoxia inducible factor-1a (HIF-1a)

Examples of Hsp90 inhibitors include herbimycin, geldanamycin (GA), 17-AAG e.g. Kos-953 and CNF-1010, 17-DMAG (Kos-1022), CNF-2024 (an oral purine), and IPI-504, in particular 17-AAG e.g. Kos-953 and CNF-1010, 17-DMAG (Kos-1022), CNF-2024, and IPI-504. Preferred compounds are geldanamycin analogs such as 17-AAG e.g. Kos-953 and CNF-1010, 17-DMAG (Kos-1022), and IPI-504.

Ansamycin antibiotics herbimycin, geldanamycin (GA) and 17-allylamino-17-desmethoxygeldanamycin (17-AAG) are ATP binding site inhibitors that block the binding of ATP and prevent conversion to the mature complex (Grenert et. al, 1997. J Biol Chem., 272:23834-23850). Despite Hsp90 being ubiquitously expressed, GA and its analogues have a higher binding affinity for Hsp90 derived from tumour vs. normal cell lines (Kamal et. al., Nature 2003; 425: 407-410). GA also shows more potent cytotoxic activity in tumour cells and is sequestered at higher concentrations within tumours in xenograft mouse models (Brazidec J. Med. Chem. 2004, 47, 3865-3873). Furthermore the ATP-ase activity of Hsp90 is elevated in cancer cells and is an indication of the increased level of stress in these cells. Hsp90 gene amplification has also been reported to occur in the later stages of cancer (Jolly and Morimoto JNCI Vol. 92, No.19, 1564-1572, 2000).

17-AAG (NSC-330507, 17-allylaminogeldanamycin) is an injectable semisynthetic derivative of geldanamycin and a polyketide inhibitor of Hsp90 identified at the University of Maryland under development by Kosan Biosciences, in collaboration with the National Cancer Institute (NCI) and the UK Institute of Cancer Research, for the potential treatment of cancer. Studies of 17-AAG have been initiated in melanoma, multiple myeloma, non-Hodgkin's lymphoma (NHL) and Hodgkin's lymphoma (HL) and as a combination therapy with imatinib (qv) for chronic myelogenous leukemia (CML).

The structure of 17-AAG is outlined below. It can be prepared as described in WO 02/36574 and processes analogous those described therein.

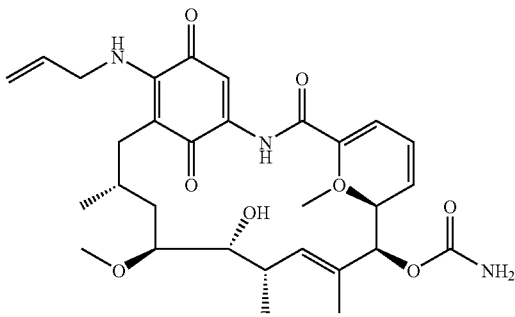

KOS-953 is a 17-AAG formulation developed by Kosan that replaces the DMSO-egg lecithin vehicle used in the original formulation, with the aim of improving patient tolerability and providing greater stability. This can be prepared as described in WO 2005/110398 and processes analogous those described therein.

Conforma is developing CNF-1010, an organic solvent-free lipid-based formulation of 17-AAG (qv) for the potential iv treatment of cancer. This can be prepared as described in WO 03/026571, WO 02/069900 and WO 2006/050333 and processes analogous those described therein. An oral formulation of 17-AAG is described by Conforma in US 2006/0067953.

17-DMAG (17-dimethylaminoethylamino-17-demethoxygeldanamycin hydrochloride, NSC-707545; structure shown) is an analog of 17-AAG (qv). It is a water-soluble geldanamycin derivative and it is being investigated for advanced solid tumors. Kosan, under license from the National Cancer Institute (NCI), is developing an iv formulation of KOS-1022 (17-DMAG), for the potential treatment of solid tumors. Kosan is also developing an oral formulation of KOS-1022 (qv) for the same indication.

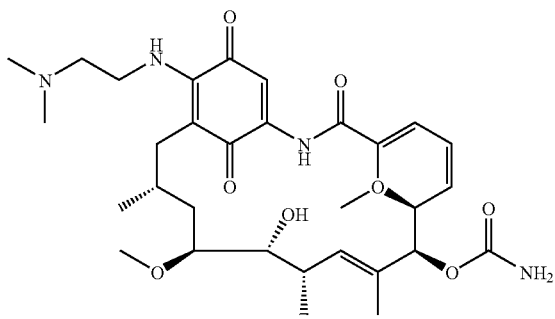

It can be prepared as described in WO 03/013430 and processes analogous to those described therein.

Infinity is developing the Hsp90 inhibitor IPI-504, a further analog of 17-AAG (qv) that is soluble in aqueous formulations for iv administration, for the potential treatment of cancer. Infinity started studies of IPI-504 in multiple myeloma (MM), and gastrointestinal stromal tumors (GIST), and the compound has potential for other haematological cancers and solid tumors.

The structure of IPI-504, a reduced form of 17-AAG called 18,21-didehydro-17-demethoxy-18,21-dideoxo-18,21-dihydroxy-17-(2-propenylamino)-geldanamycin monohydrochloride, is shown below. It can be prepared as described in WO 2005/063714 and processes analogous those described therein.

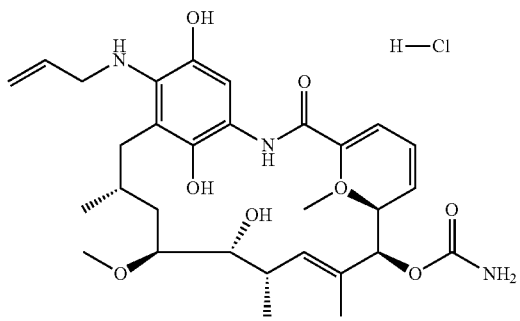

Conforma Therapeutics is developing CNF-2024, a synthetic oral Hsp 90 inhibitor, for the potential treatment of cancer. CNF-2024 is an oral purine analogue.

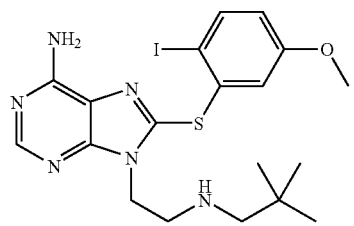 [SMILES: COc1ccc(I)c(Sc2nc3c(N)ncnc3n2CCNCC(C)(C)C)c1]

It can be prepared as described in J Med Chem (2006) 49: 817-828.

22. Checkpoint Targeting Agents

The cell proliferation cycle is a complex process during which the cell first replicates its chromosomes and then undergoes cell division or cytokinesis. At various stages of the cycle, mechanisms exist to prevent further progression through the cycle until all appropriate events have occurred. This ensures the integrity of the DNA of the cell as it progresses through the cycle in the required sequential manner. One such checkpoint is known to occur in mitosis. This is variously referred to as the mitotic or spindle checkpoint. Cells are held at this checkpoint until all chromosomes are appropriately attached to the mitotic spindle via their centrosomes. Defects in this checkpoint lead to either aneuploid phenotypes, typical of cancer cells or an imbalance of chromosomes in daughter cells. Some cancer therapies are known to act by disruption of this checkpoint causing chromosome mis-alignment or premature cytokinesis leading to activation of a checkpoint that results in preferential death of the tumour cell. For example the taxanes and epothilones are classes of agents which cause stabilisation of spindle microtubules preventing the normal spindle contraction process. The vinca alkaloids are another class of agents which act to prevent spindle formation via an action on tubulin the principal protein in the microtubules. Agents which cause DNA damage or disrupt DNA replication including platinum compounds and nucleoside analogues such as 5-FU lead to cell arrest at checkpoints and subsequent cell death. They thus require a functional checkpoint for their therapeutic action.

The Aurora kinases have an important role in the mitotic phase of the cell cycle. Inhibition of the Aurora kinases has been shown to substantially disrupt the mitotic process leading to early mitotic effects from inhibition of Aurora A and late abnormalities of cytokinesis by inhibition of Aurora B. It is believed that combining Aurora kinase inhibitors with agents that activate, interfere with or modulate the mitotic or cell cycle checkpoint could sensitise cells to the cytotoxic effects and a beneficial combination effect could be observed (Anand S, Penrhyn-Lowe S, Venkitaraman A R. Cancer Cell. 2003 January;3(1):51-62). In this context a combination of Aurora kinase inhibitors with the taxanes, epothilones or vinca alkaloids would be expected to be beneficial. Particular taxanes, epothilones and vinca alkaloids are described herein.

Further checkpoint targeting agents are those that cause DNA damage or disrupt DNA replication including platinum compounds such as cisplatin and nucleoside analogues such as 5-FU leading to cell arrest at checkpoints and subsequent cell death. In this context a combination of Aurora kinase inhibitors with the platinum compounds and nucleoside analogues would be expected to be beneficial as they could sensitise cells to the cytotoxic effects. Particular platinum compounds and nucleoside analogues are described herein.

Further checkpoint targeting agents that activate, interfere with or modulate the cell cycle checkpoints which would also be expected to be particularly beneficial for use in combination with the Aurora inhibitors of the invention include polo-like kinase inhibitors (Plks), CHK kinase inhibitors, inhibitors of the BUB kinase family and kinesin inhibitors. Polo-like kinases are important regulators of cell cycle progression during M-phase. Plks are involved in the assembly of the mitotic spindle apparatus and in the activation of CDK/cyclin complexes. Plk1 regulates tyrosine dephosphorylation of CDKs through phosphorylation and activation of Cdc25C. CDK1 activation in turn leads to spindle formation and entry into M phase. The importance of Checkpoint kinases such as Chk1 and Chk2 is described herein.

Thus other agents in development which act to disrupt the mitotic checkpoint and therefore could be combined beneficially with the compounds of the invention include polo-like kinase inhibitors (e.g. BI-2536), CHK kinase inhibitors (e.g. Irofulven (a CHK2 inhibitor), 7-hydroxystaurosporine (UCN-01, an inhibitor of both CHK1 and PKC) and PD-321852), inhibitors of the BUB kinase family, and kinesin inhibitors (also known as mitotic kinesin spindle protein (KSP) inhibitors) such as CK0106023, CK-0060339 and SB-743921 (structures shown below).

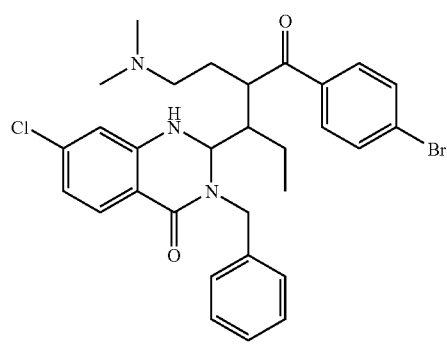

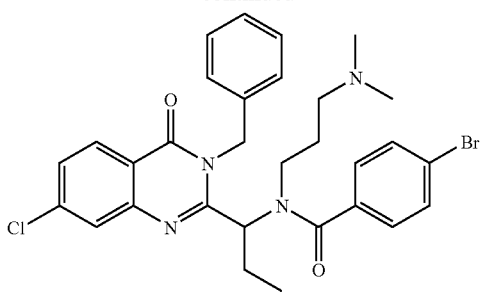

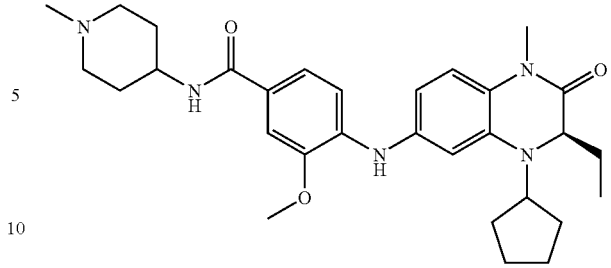

CK0106023, CK-0060339 and SB-743921 can be prepared and used as described in WO 01/30768 and WO 01/98278 and processes analogous thereto.

CHK kinase inhibitors include irofulven, UCN-01 and PD-321852. Irofulven (structure shown) is a semisynthetic compound derived from illudin S, a toxin from the Omphalotus illudens mushroom, for the potential treatment of refractory and relapsed tumors, including ovarian, prostate, hepatocellular, breast, lung and colon cancers, and gliomas. This can be synthesised as described in WO 98/05669 or processes analogous thereto.

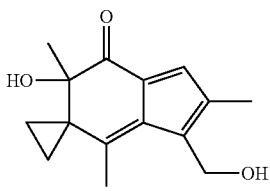 [SMILES: CC1=C(CO)C2=C(C)C3(CC3)C(C)(O)C(=O)C2=C1]

PD-321852, a checkpoint kinase Chk I inhibitor, (structure shown), is being investigated by Pfizer for the potential treatment of cancer.

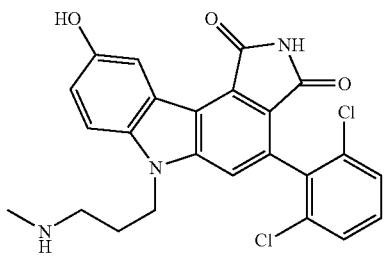 [SMILES: CNCCCn1c2ccc(O)cc2c2c3c(c(-c4c(Cl)cccc4Cl)cc21)C(=O)NC3=O]

It can be prepared and used as described in WO 01/53274, WO 01/53268 and in particular WO 03/091255 or processes analogous thereto.

BI-2536 (structure shown below) an inhibitor of the serine-threonine kinase polo-like kinase-1 (PLK-1), for the potential treatment of solid tumors. It can be prepared and used as described in WO2004/076454, WO 2006/018220, WO 2006/018221 and WO 2006/018222 or processes analogous thereto.

In addition, checkpoint targeting agents that arrest cells in G2/M phase could also be combined with the Aurora kinase inhibitors of the invention to have a similar beneficial effect. Therefore Platinum compounds and CDK inhibitors would be therefore be expected to be beneficial in combination with the combinations of the invention and are thus further Checkpoint Targeting Agents. Particular Platinum compounds and CDK inhibitors are described herein.

Thus, examples of Checkpoint Targeting Agents for use according to the invention include Platinum compounds, nucleoside analogues, CDK inhibitors, Taxanes, Vinca alkaloids, polo-like kinase inhibitors, CHK kinase inhibitors, inhibitors of the BUB kinase family and kinesin inhibitors, in particular Platinum compounds, nucleoside analogues, Taxanes and Vinca alkaloids more particularly checkpoint targeting agents which target the mititoic checkpoint such as Taxanes and Vinca alkaloids. Particular combinations of the invention include cisplatin or vinblastine or taxol or 5FU, in particular taxol.

23. DNA Repair Inhibitors

DNA repair inhibitors include PARP inhibitors.

Definition: The term "PARP inhibitor" is used herein to define compounds which inhibit or modulate the activity of the family of Poly adenosine diphosphate ribose (poly(ADP-Ribose)) nuclear enzymes, including the ionic, salt, solvate, isomers, tautomers, N-oxides, ester, prodrugs, isotopes and protected forms thereof (preferably the salts or tautomers or isomers or N-oxides or solvates thereof, and more preferably, the salts or tautomers or N-oxides or solvates thereof), as described above. They may also be referred to as "DNA repair inhibitors".

Biological activity: PARP inhibitors have a role as chemosensitizing agents (for example by preventing DNA repair after anticancer therapy) and may have a role in enhancing overall patient response to anti-cancer treatments. PARP inhibitors may also act in isolation as anti cancer agents in patients whose tumours have intrinsic deficiencies in DNA repair.

Technical background: The PARP enzyme synthesizes poly(ADP-ribose), a branched polymer that can consists of over 200 ADP-ribose units. The protein acceptors of poly (ADP-ribose) are directly or indirectly involved in maintaining DNA integrity. They include histones, topoisomerases, DNA and RNA polymerases, DNA ligases, and Ca 2'- and Mg 2, -dependent endonucleases. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold.

PARP is activated by damaged DNA fragments and, once activated, catalyzes the attachment of up to 100 ADP-ribose units to a variety of nuclear proteins, including histones and PARP itself. It is also known that PARP inhibitors, such as 3-amino benzamide, affect overall DNA repair in response, for example, to hydrogen peroxide or ionizing radiation. The pivotal role of PARP in the repair of DNA strand breaks is well established, especially when caused directly by ionizing radiation or, indirectly after enzymatic repair of DNA lesions induced by methylating agents, especially temozolamide, topoisomerases I inhibitors and other chemotherapeutic agents as cisplatin and bleomycin. A variety of studies using knockout mice, trans-dominant inhibition models (over-expression of the DNA-binding domain), antisense and small molecular weight inhibitors have demonstrated the role of PARP in repair and cell survival after induction of DNA damage. The inhibition of PARP enzymatic activity should lead to an enhanced sensitivity of tumor cells towards DNA damaging treatments.

PARP inhibitors have been reported to be effective in radiosensitizing (hypoxic) tumor cells and effective in preventing tumor cells from recovering from potentially lethal and sublethal damage of DNA after radiation therapy, presumably by their ability to prevent DNA strand break rejoining and by affecting several DNA damage signaling pathways. PARP inhibitors have been used to treat cancer. A recent comprehensive review of the state of the art has been published by Li and Zhang in IDrugs 2001, 4(7): 804.

Preferences and specific embodiments: Preferred PARP inhibitors for use in accordance with the invention are selected from Bendamustine (5-[Bis(2-chloroethyl)amino]-1-methyl-2-benzimidazolebutyric acid or α-[1-Methyl-5-[bis(.beta.-chloroethyl)amino]-2-benzimidazolyl]butyric acid), available from Bayer, INO-1001 (Pardex) from Inotek Pharmaceuticals, BSI-201 from BiPar Sciences, AG-014699 from Pfizer, and ONO-2231 (N-[3-(3,4-dihydro-4-oxo-1-phthalazinyl)phenyl]-4-morpholinebutanamide methanesulfonate) from Ono Pharmaceutical.

Posology: The PARP inhibitors are advantageously administered in daily dosages of 20-100 mg, for example 80-120 mg/m2 iv over a 30 to 60 min infusion over a 21 day cycle for Bendamustine.—The key PARP inhibitor is a Pfizer product which is in phase III combination trials in metastatic melanoma. It is administered intravenously on days one thru five of a twenty-one day cycle dose?

24. Inhibitors of G-Protein Coupled Receptors (GPCR)

A preferred GPCR is Atrasentan (3-Pyrrolidinecarboxylic acid, 4-(1,3-benzodioxol-5-yl)-1-[2-(dibutylamino)-2-oxoethyl]-2-(4-methoxyphenyl)-, [2R-(2.alpha.,3.beta.,4.alpha.)]-). Atrasentan, from Abbott Laboratories, is a potent and selective endothelin A receptor antagonist for the treatment of prostate tumors. There is also evidence of biological activity in other cancer types such as glioma, breast tumor, lung tumor, brain tumor, ovary tumor, colorectal tumor and renal tumor.

Posology: Atrasentan may be advantageously administered orally in dosages of e.g. 10 mg daily.

Anti-Cancer Agent Combinations

The combinations of the invention may comprise two or more ancillary compounds. In such embodiments, the ancillary compounds may be anti-cancer agents. In such embodiments, the two or more anticancer agents may be independently selected from carboplatin, cisplatin, taxol, taxotere, gemcitabine, and vinorelbine. Preferably the two or more further anti-cancer agents are carboplatin, taxol and vinorelbine, or carboplatin and taxol.

Combinations of compounds of formula (I) or (I') with carboplatin, taxol and vinorelbine or combinations of compounds of formula (I) or (I') with carboplatin and taxol, are particularly suitable for treating Non-Small cell lung cancer.

Alternatively, combinations of compounds of formula (I) or (I') with platinum agents, taxol, taxotere, gemcitabine, pemetrexed, mitomycin, ifosfamide, vinorelbine, erlotinib and bevacizumab or combinations of compounds of formula (I) or (I') with carboplatin and taxol or cisplatin and gemcitabine are particularly suitable for treating Non-Small cell lung cancer.

In one embodiment, the two or more anti-cancer agents are independently selected from 5-FU, leucovorin, oxaliplatin, CPT 11, and bevacizumab. Preferably, the two or more anti-cancer agents are 5-FU, leucovorin and CPT 11 or 5-FU, leucovorin and oxaliplatin.

Combinations of compounds of formula (I) or (I') with 5-FU, leucovorin and CPT 11 or a combination of compounds of formula (I) or (I') with 5-FU, leucovorin and oxaliplatin, are particularly suitable for treating colon cancer. In addition, combinations of compounds of formula (I) or (I') with 5-FU, leucovorin and CPT 11 or a combination of compounds of formula (I) or (I') with 5-FU, leucovorin and oxaliplatin, each with bevacizumab, are particularly suitable for treating colon cancer.

In one embodiment, the two or more anti-cancer agents are independently selected from methotrexate, taxanes, anthracyclines e.g. doxorubicin, herceptin, lapatinib, bevacizumab, mitozantrone, epothilones, 5-FU, and cyclophosphamide. In another embodiment, the two or more anti-cancer agents are independently selected from methotrexate, taxanes, anthracyclines e.g. doxorubicin, herceptin, 5-FU, and cyclophosphamide. In one embodiment, the two or more anti-cancer agents are independently selected from taxanes, anthracyclines e.g. doxorubicin, herceptin, 5-FU, and cyclophosphamide. In one embodiment, the two or more anti-cancer agents are independently selected from 5-FU, methotrexate, cyclophosphamide and doxorubicin. Preferably the two or more anti-cancer agents are 5-FU, methotrexate and cyclophosphamide or 5-FU, doxorubicin and cyclophosphamide or doxorubicin and cyclophosphamide.

Combinations of compounds of formula (I) or (I') with 5-FU, methotrexate and cyclophosphamide, or a combination of compounds of formula (I) or (I') with 5-FU, doxorubicin and cyclophosphamide, or combinations of compounds of formula (I) or (I') with doxorubicin and cyclophosphamide, are particularly suitable for treating breast cancer.

In one embodiment, the two or more anti-cancer agents are independently selected from cyclophosphamide, doxorubicin (hydroxydaunorubicin), vincristine, and prednisone. In another embodiment, the two or more anti-cancer agents are independently selected from cyclophosphamide, doxorubicin (hydroxydaunorubicin), vincristine, bortezomib, rituximab and prednisone. Preferably the two or more anti-cancer agents are cyclophosphamide, doxorubicin (hydroxydaunorubicin), vincristine and prednisone, or cyclophosphamide, vincristine and prednisone, with or without rituximab. Preferably the two or more anti-cancer agents are cyclophosphamide, doxorubicin (hydroxydaunorubicin), vincristine and prednisone, or cyclophosphamide, vincristine and prednisone.

Combinations of compounds of formula (I) or (I') with cyclophosphamide, doxorubicin (hydroxydaunorubicin), vincristine and prednisone are particularly suitable for treating non Hodgkin's lymphoma (and in particular high grade non Hodgkin's lymphoma). Combinations of compounds of formula (I) with cyclophosphamide, doxorubicin (hydroxydaunorubicin), vincristine, rituximab, and prednisone are also particularly suitable for treating non Hodgkin's lymphoma (and in particular high grade non Hodgkin's lymphoma).

Combinations of compounds of formula (I) or (I') with cyclophosphamide, vincristine and prednisone are particularly suitable for treating non Hodgkin's lymphoma (and in particular low grade non Hodgkin's lymphoma). Combinations of compounds of formula (I) with cyclophosphamide, vincristine, rituximab, and prednisone are also particularly suitable for treating non Hodgkin's lymphoma (and in particular low grade non Hodgkin's lymphoma).

In one embodiment, the two or more anti-cancer agents are independently selected from vincristine, doxorubicin, and dexamethasone. In another embodiment, the two or more anti-cancer agents are independently selected from vincristine, thalidomide, doxorubicin, bortezomib and dexamethasone. Preferably the two or more anti-cancer agents are vincristine, doxorubicin and dexamethasone.

Combinations of compounds of formula (I) or (I') with vincristine, doxorubicin, thalidomide and dexamethasone are particularly suitable for treating multiple myeloma. In addition, combinations of compounds of formula (I) or (I') with vincristine, doxorubicin and dexamethasone are particularly suitable for treating multiple myeloma.

In one embodiment, the two or more anti-cancer agents are independently selected from: (a) fludarabine and rituxamab or (b) fludarabine, almentuzamab and rituxamab. Preferably the two or more anti-cancer agents are fludarabine and rituxamab.

Combinations of compounds of formula (I) or (I') with fludarabine and rituxamab are particularly suitable for treating chronic lymphocytic leukemia.

In one embodiment the combination of the invention optionally excludes combination of two or more of the following anti-cancer agents selected from a topoisomerase inhibitor, an alkylating agent, a antimetabolite, DNA binders, monoclonal antibodies, signal transduction inhibitors and microtubule inhibitors (tubulin targeting agents), such as cisplatin, cyclophosphamide, doxorubicin, irinotecan, fludarabine, 5FU, taxanes and mitomycin C.

In one embodiment the combination of the invention includes at least one anti-cancer agent selected from an anti-androgen, a histone deacetylase inhibitor (HDAC), cylcooxygenase-2 (COX-2) inhibitor, proteasome inhibitor, DNA methylation inhibitor and a CDK inhibitor.

Disease-Specific Anti-Cancer Agent Combinations
Multiple Myeloma

Particularly suitable for treating multiple myeloma are combinations of compounds of formula (I) with: (a) monoclonal antibodies (e.g. those targeting Interleukin 6); (b) proteasome inhibitors (e.g. bortezomib); (c) proteasome inhibitors and corticosteroids (e.g. velcade and dexamethasone); and (d) corticosteroids, alkylating agents and lenolidamide/thalidomide (e.g. prednisolone, melphalan and thalidomide).

Melanoma

Particularly suitable for treating melanoma are combinations of compounds of formula (I) with: (a) DNA methylase inhibitors/hypomethylating agents (e.g. temozolamide); (b) alkylating agents (e.g. dacarbazine or fotemustine); and (c) DNA methylase inhibitors/hypomethylating agents (e.g. temozolamide) and DNA repair inhibitors/PARP inhibitors.

Breast Cancer

Particularly suitable for treating breast cancer are combinations of compounds of formula (I) with: (a) monoclonal antibodies (e.g. trastuzumab and bevicizamab); (b) monoclonal antibodies (e.g. trastuzumab and bevicizamab) and taxanes; and (c) antimetabolites (e.g. capecitabine) and signalling inhibitors (e.g. lapatinib).

Prostate Cancer

Particularly suitable for treating prostate cancer are combinations of compounds of formula (I) with hormones and G-protein coupled receptor inhibitors.

Non Small Cell Lung Cancer (NSCLC)

Particularly suitable for treating NSCLC are combinations of compounds of formula (I) with: (a) platinum compounds and taxanes; and (b) platinum compounds and antimetabolites.

Specific Combinations of the Invention

Particular combinations according to the invention include compounds of formula (I) or (I') and subgroups thereof as defined herein with the following two or more anti-cancer agents:

For cancer (and in particular acute myeloid leukemia) treatment, two or more anti-cancer agents independently selected from two or more of anthracycline, Ara C (a.k.a. Cytarabine), 6-mercaptopurine, thiopurine, methotrexate, mitoxantrone, daunorubicin, idarubicin, gemtuzumab ozogamicin and granulocyte colony stimulating factors. In addition, for cancer (and in particular acute myeloid leukemia) treatment, two or more anti-cancer agents independently selected from two or more of anthracycline, Ara C (a.k.a. Cytarabine), 6-mercaptopurine, methotrexate, mitoxantrone, daunorubicin, idarubicin, gemtuzumab ozogamicin and granulocyte colony stimulating factors. Alternatively, the two or more anti-cancer agents may be independently selected from two or more of anthracycline, Ara C (a.k.a. Cytarabine), daunorubicin, idarubicin, gemtuzumab ozogamicin and granulocyte colony stimulating factors.

For cancer (and in particular breast cancer) treatment, two or more anti-cancer agents independently selected from bevacizumab, taxanes, methotrexate, paclitaxel, docetaxel, gemcitabine, anastrozole, exemestane, letrozole, tamoxifen, doxorubicin, herceptin, 5-fluorouracil, cyclophosphamide, epirubicin and capecitabine, particularly 5-FU, methotrexate and cyclophosphamide; 5FU, doxorubicin and cyclophosphamide; or doxorubicin and cyclophosphamide. Preferably, for cancer (and in particular breast cancer) treatment, the two or more anti-cancer agents may also be independently selected from taxanes, methotrexate, paclitaxel, docetaxel, gemcitabine, anastrozole, exemestane, letrozole, tamoxifen, doxorubicin, herceptin, 5-fluorouracil, cyclophosphamide, epirubicin and capecitabine, particularly 5-FU, methotrexate and cyclophosphamide; 5FU, doxorubicin and cyclophosphamide; or doxorubicin and cyclophosphamide.

Typical dosing regimens include:
Cyclophosphamide at 100 mg/m$^2$ PO Daily×14 days, Doxorubicin at 30 mg/m$^2$ IV Day 1 & day 8 and fluorouracil at 500 mg/m$^2$ IV Day 1 & day 8, repeated every 28 days e.g. for up to 6 cycles
Cyclophosphamide at 600 mg/m$^2$ IV Day 1 and Doxorubicin at 60 mg/m$^2$ IV Day 1, repeated every 21 days e.g. for up to 4 cycles For cancer (and in particular chronic lymphocytic leukemia (CLL)) treatment, two or more anti-cancer agents independently selected from alemtuzumab, chlorambucil, cyclophosphamide, vincristine, predinisolone, fludarabine, mitoxantrone and rituximab/rituxamab, particularly fludarabine and rituxamab. Preferably, for cancer (and in particular chronic lymphocytic leukemia (CLL)) treatment, the two or more anti-cancer agents are independently selected from chlorambucil, cyclophosphamide, vincristine, predinisolone, fludarabine, mitoxantrone and rituximab/rituxamab, particularly fludarabine and rituxamab.

For cancer (and in particular chronic myeloid leukemia (CML)) treatment, two or more anti-cancer agents independently selected from hydroxyurea, cytarabine, and imatinib. In addition, for cancer (and in particular chronic myeloid leukemia (CML)) treatment, the two or more anti-cancer agents are independently selected from hydroxyurea, cytarabine, Interferon-alpha and imatinib. Alternatively for cancer (and in particular chronic myeloid leukemia (CML)) treatment, two or more anti-cancer agents independently selected from hydroxyurea, cytarabine, dasatinib, nilotinib and imatinib.

For cancer (and in particular Colon Cancer treatment), two or more anti-cancer agents independently selected from cetuximab, 5-Fluorouracil, pantuzumab, leucovorin, irinotecan, oxaliplatin, raltirexed, capecitabine, bevacizumab, oxaliplatin, CPT 11. Alternatively for cancer (and in particular Colon Cancer treatment), two or more anti-cancer agents independently selected from cetuximab, 5-Fluorouracil, leucovorin, irinotecan, oxaliplatin, raltirexed, capecitabine, bevacizumab, oxaliplatin, CPT 11, particularly 5-Fluorouracil, Leucovorin and CPT 11 or Fluorouracil, Leucovorin and Oxaliplatin.

Alternatively, for cancer (and in particular Colon Cancer treatment), two or more anti-cancer agents independently selected from 5-Fluorouracil, leucovorin, irinotecan, oxaliplatin, raltirexed, capecitabine, bevacizumab, oxaliplatin, CPT 11 and Avastin, particularly 5-Fluorouracil, Leucovorin and CPT 11 or Fluorouracil, Leucovorin and Oxaliplatin.

Typical dosing regimens include:
Fluorouracil at 400-425 mg/m$^2$ IV Days 1 to 5 and Leucovorin at 20 mg/m$^2$ IV Days 1 to 5, repeated every 28 days, e.g. for 6 cycles
Irinotecan at 100-125 mg/m$^2$ IV over 90 minutes Days 1, 8, 15 & 22, Folinic acid at 20 mg/m2 IV Days 1, 8,15 & 22, and Fluorouracil at 400-500 mg/m2 IV Days 1, 8, 15 & 22, repeated every 42 days until disease progression
Oxaliplatin at 85 mg/m2 IV in 500mL of D5W over 120 minutes Day 1, Folinic acid at 200 mg/m2 IV over 120 minutes Days 1 & 2, Fluorouracil at 400 mg/m2 IV bolus, after Folinic Acid, Days 1 & 2, then Fluorouracil at 600 mg/m2 CIV over 22 hours Days 1 & 2, repeated every 12 days for up to 12 cycles For cancer (and in particular multiple myeloma treatment), two or more anti-cancer agents independently selected from vincristine, doxorubicin, thalidomide, dexamethasone, melphalan, prednisone, cyclophosphaimde, etoposide, pamidronate, zoledronate and bortezomib, particulary vincristine, doxorubicin and, dexamethasone. Alternatively, for cancer (and in particular multiple myeloma treatment), two or more anti-cancer agents independently selected from vincristine, doxorubicin, dexamethasone, melphalan, prednisone, cyclophosphaimde, etoposide, pamidronate, zoledronate and bortezomib, particulary vincristine, doxorubicin and dexamethasone.

For cancer (and in particular Non-Hodgkin's lymphoma treatment), two or more anti-cancer agents independently selected from cyclophosphamide, doxorubicin/hydroxydaunorubicin, vincristine/Onco-TCS (V/O), prednisolone, methotrexate, cytarabine, bleomycin, etoposide, rituximab/rituxamab, fludarabine, cisplatin, and ifosphamide, particularly cyclophosphamide, doxorubicin (hydroxydaunorubicin), vincristine and prednisone for high grade NHL or cyclophosphamide, vincristine and prednisone for low grade NHL.

For cancer (and in particular Non Small Cell Lung Cancer (NSCLC)) treatment, two or more anti-cancer agents may be independently selected from bevacizumab, gefitinib, erlotinib, cisplatin, carboplatin, etoposide, mitomycin, vinblastine, paclitaxel, docetaxel, gemcitabine and vinorelbine, especially taxol, vinorelbine and carboplatin or taxol and carboplatin. Alternatively for cancer (and in particular Non Small Cell Lung Cancer (NSCLC)) treatment, two or more anti-cancer agents may be independently selected from bevacizumab, gefitinib, erlotinib, cisplatin, carboplatin, mitomycin, vinblastine, paclitaxel, docetaxel, gemcitabine and vinorelbine. Particularly preferred for cancer (and in particular Non Small Cell Lung Cancer (NSCLC)) treatment, two or more anti-cancer agents are independently selected from cisplatin, carboplatin, etoposide, mitomycin, vinblastine, paclitaxel, docetaxel, gemcitabine and vinorelbine, especially taxol, vinorelbine and carboplatin or taxol and carboplatin. In particular the two or more anti-cancer agents are independently selected from gemcitabine and cisplatin.

Typical dosing regimens include:
Gemcitabine at 1000 mg/m$^2$ IV Days 1, 8 & 15, and Cisplatin at 75-100 mg/m$^2$ IV Day 1, repeated every 28 days for 4-6 cycles
Paclitaxel at 135-225 mg/m$^2$ IV over 3 hrs Day 1 and Carboplatin at AUC 6.0 IV Day 1, repeated every 21 days for 4-6 cycles
Docetaxel at 75 mg/m$^2$ IV Day 1, and Carboplatin at AUC 5 or 6 IV Day 1, repeated every 21 days for 4-6 cycles
Docetaxel at 75 mg/m$^2$ IV Day 1, and Cisplatin at 75 mg/m$^2$ IV Day 1, repeated every 21 days for 4-6cycles For cancer (and in particular ovarian cancer) treatment, two or more anti-cancer agents independently selected from platinum compounds (for example Cisplatin, Carboplatin), taxol, doxorubicin, liposomal doxorubicin, paclitaxel, docetaxel, gemcitabine, melphalan and mitoxantrone.

For cancer (and in particular prostate cancer) treatment, two or more anti-cancer agents independently selected from mitoxantrone, prednisone, buserelin, goserelin, bicalutamide, nilutamide, flutamide, cyproterone acetate, megestrol/megestrel, diethylstilboestrol, docetaxel, paclitaxel, zoledronic acid and taxotere. Alternatively, for cancer (and in particular prostate cancer) treatment, two or more anti-cancer agents independently selected from mitoxantrone, prednisone, buserelin, goserelin, bicalutamide, nilutamide, flutamide, cyproterone acetate, megestrol/megestrel, diethylstilboestrol, docetaxel, paclitaxel, zoledronic acid, prednisolone and taxotere.

Pharmaceutical Formulations

While it is possible for the active compounds in the combinations (e.g. a compound of the formula (I) or 1-cyclopropyl-3-[3-(5-morpholin-4-ylmethyl-1H-benzoimidazol-2-yl)-1H-pyrazol-4-yl]-urea or all salts thereof (such as the lactate or citrate salt) to be administered alone, it is preferable to present them as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents; for example agents that reduce or alleviate some of the side effects associated with chemotherapy. Particular examples of such agents include antiemetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF).

Thus, the present invention further provides pharmaceutical compositions, as defined above, and methods of making a pharmaceutical composition comprising admixing at a compound of the formula (I) or (I') or 1-cyclopropyl-3-[3-(5- morpholin-4-ylmethyl-1H-benzoimidazol-2-yl)-1H-pyrazol-4-yl]-urea or all salts thereof such as the lactate or citrate salt, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Accordingly, in a further aspect, the invention provides combinations comprising the lactate or citrate salt or mixtures thereof of 1-cyclopropyl-3-[3-(5-morpholin-4-ylmethyl-1H-benzoimidazol-2-yl)-1H-pyrazol-4-yl]-urea as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Examples of these are described in R. G. Strickly, Solubilizing Excipients in oral and injectable formulations, Pharmaceutical Research, Vol 21(2) 2004, p 201-230. In addition, they may contain co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

A drug molecule that is ionizable can be solubilized to the desired concentration by pH adjustment if the drug's pKa is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins Liposomes are closed spherical vesicles composed of outer lipid bilayer membranes and an inner aqueous core and with an overall diameter of <100 µm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer. A typical liposome formulation contains water with phospholipid at 5-20 mg/ml, an isotonicifier, a pH 5-8 buffer, and optionally cholesterol.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of the formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt thereof as defined herein. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediamietetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/ or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

Pharmaceutical compositions of the present invention for parenteral injection can also comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If a compound not stable in aqueous media or has low solubility in aqueous media it can be formulated as a concentrate in organic solvents. The concentrate can then be diluted to a lower concentration in an aqueous system, and can be sufficiently stable for the short period of time during dosing. Therefore in another aspect, there is provided a pharmaceutical composition comprising a non aqueous solution composed entirely of one or more organic solvents, which can be dosed as is or more commonly diluted with a suitable IV excipient (saline, dextrose; buffered or not buffered) before administration (Solubilizing excipients in oral and injectable formulations, Pharmaceutical Research, 21(2), 2004, p 201-230). Examples of solvents and surfactants are propylene glycol, PEG300, PEG400, ethanol, dimethylacetamide (DMA), N-methyl-2-pyrrolidone (NMP, Pharmasolve), Glycerin, Cremophor EL, Cremophor RH 60 and polysorbate. Particular non aqueous solutions are composed of 70-80% propylene glycol, and 20-30% ethanol. One particular non aqueous solution is composed of 70% propylene glycol, and 30% ethanol. Another is 80% propylene glycol and 20% ethanol. Normally these solvents are used in combination and usually diluted at least 2-fold before IV bolus or IV infusion. The typical amounts for bolus IV formulations are ~50% for Glycerin, propylene glycol, PEG300, PEG400, and ~20% for ethanol. The typical amounts for IV infusion formulations are ~15% for Glycerin, 3% for DMA, and ~10% for propylene glycol, PEG300, PEG400 and ethanol.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing a compound of the formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastrointestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient.

Pharmaceutical compositions according to the invention may be, for example, in unit dose form, such as in the form of ampoules, vials, suppositories, dragees, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The combination or its constituent components (e.g. the compound of the formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt) will generally be presented in unit dosage form and, as such, will typically contain sufficient compound to provide a desired level of biological activity. For example, a formulation intended for oral administration may contain from 0.1 milligrams to 2 grams of active ingredient, or 1 nanogram to 2 milligrams of active ingredient. Within this range, particular sub-ranges of compound are 0.1 milligrams to 2 grams of active ingredient (more usually from 10 milligrams to 1 gram, for example, 50 milligrams to 500 milligrams or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

The combinations of the invention will be useful in the prophylaxis or treatment of a range of disease states or conditions mediated by cyclin dependent kinases, glycogen synthase kinase-3 and Aurora kinases. Examples of such disease states and conditions are set out above.

The combination is generally administered to a subject in need of such administration, for example a human or animal patient, preferably a human.

The combination will typically be administered in amounts that are therapeutically or prophylactically useful and which generally are non-toxic. However, in certain situations (for example in the case of life threatening diseases), the benefits of administering a combination of the invention may outweigh the disadvantages of any toxic effects or side effects, in which case it may be considered desirable to administer the combination in amounts that are associated with a degree of toxicity.

The constituent compounds of the combinations of the invention may be administered over a prolonged term to maintain beneficial therapeutic effects or may be administered for a short period only. Alternatively they may be administered in a pulsatile or continuous manner.

A typical daily dose of the compound of formula (I) or (I') present in the combination can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, such as 1 micrograms to 10 milligrams) per kilogram of bodyweight although higher or lower doses may be administered where required. The compound can be administered on a daily basis or on a repeat basis every 2, or 3, or 4, or 5, or 6, or 7, or 10 or 14, or 21, or 28 days for example.

The constituent compounds of the combinations of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compounds may be administered once or more than once each day. The compounds can be administered continuously (i.e. taken every day without a break for the duration of the treatment regimen). Alternatively, the compounds can be administered intermittently, i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

An example of a daily dose of the compound comprises administering a compound of the formula (I) or (I') as defined herein, for example the lactate salt of compound I at a starting dosage of 1 mg/m$^2$/day-100 mg/m$^2$/day, in particular 1 mg/m$^2$/day-10 mg/m$^2$/day more particularly 3-6 mg/m$^2$/day (equivalent to 2.5-5 mg free base/m$^2$/day) or at an efficacious dose of the lactate salt of compound I of 2.5 mg/m$^2$/day-1.5 g/m$^2$/day, in particular 25 mg/m$^2$/day-600 mg/m$^2$/day, more particularly 200-500 mg/m$^2$/day such as 250 mg/m$^2$/day or 45-200 mg/m$^2$/day such as 45-150 mg/m$^2$/day or 56-185 mg/m$^2$/day (equivalent to 45-150 mg free base/m$^2$/day) although higher or lower doses may be administered where required.

In one particular dosing schedule, a patient will be given a continuous IV infusion of the compound or a salt thereof, for example the compound of formula (I), for periods of 2 hour to 120 hour, for example 2 to 96 hour in particular for 24 to 72 hour and the treatment repeated at a desired interval such as every one to three weeks.

More particularly, a patient may be given a continuous IV infusion of the compound or a salt thereof for periods of 24 hour daily for 5 days and the treatment repeated every week, or for periods of 24 hour and the treatment repeated every week, or for periods of 48 hour and the treatment repeated every two weeks or for periods of 72 hour and the treatment repeated every three weeks.

In another particular dosing schedule, a patient is given an infusion of the compound as an IV bolus over 2 hour once a day for a week every 1, 2, or 3 weeks or over 2 hour once every 1, 2, or 3 weeks.

Higher doses such as 1.5 g/m$^2$/day could be administered using a dosing regimen with frequent off-treatment periods such as 24 to 48 hour continuous IV fusion every one to two weeks. Lower dosages such could be administered using a dosing regimens with more sustained dosing (but still cyclical on/off) such as 48 to 72 hour continuous IV fusion every two to three weeks.

In particular, compounds of the formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt in particular the lactate salt could be administered to a patient at 250 mg/m$^2$/day for 72 hours by continuous IV infusion every 3 weeks.

In another embodiment, compounds of the formula (I') or 1-cyclopropyl-3-[3-(5-morpholin-4-ylmethyl-1H-benzoimidazol-2-yl)-1H-pyrazol-4-yl]-urea or all salts thereof such as the lactate or citrate salt in particular the lactate salt could be administered to a patient over a five day treatment cycle.

Ultimately, the quantity of compound administered, dosing regimen and type of composition used will be commensurate with the nature of the disease or physiological condition being treated and will be at the discretion of the physician.

Accordingly, a person skilled in the art would know through their common general knowledge the dosing regimes and combination therapies to use. It will be appreciated that the preferred method and order of administration and the respective dosage amounts and regimes for each component of the combination will depend on the particular compounds of formula (I') and two or more further anti-cancer agents being administered, their route of administration, the particular tumour being treated and the particular host being treated. The optimum method and order of administration and dosage amounts and regime can be readily determined by those skilled in the art using conventional methods and in view of the information set out herein.

The combinations of the invention as defined herein can be further combined and/or administered with one of more other compounds for treatment of a particular disease state, for example a neoplastic disease such as a cancer as hereinbefore defined. Examples of other therapeutic agents or treatments that may be administered together (whether concurrently or at different time intervals) with the combinations of the invention include but are not limited to:
Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and,
Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromoembolic episodes.

Each of the compounds present in the combinations of the invention may be given in individually varying dose schedules and via different routes.

The compound of the formula (I) and ancillary compound may be simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The combinations of the invention may also be administered in conjunction with non-chemotherapeutic treatments such as radiotherapy, photodynamic therapy, gene therapy; surgery and controlled diets.

For use in combination therapy with an ancillary compound, the compound of the formula (I) and one, two, three, four or more ancillary compounds can be, for example, formulated together in a dosage form containing two, three, four or more ancillary compounds. In an alternative, the constituent compounds of the combination of the invention may be formulated separately and presented together in the form of a kit, optionally with instructions for their use.

A person skilled in the art would know through his or her common general knowledge the dosing regimes and combination therapies to use.

Methods of Diagnosis

Prior to administration of the combination of the invention, a patient may be screened to determine whether a disease or condition from which the patient is or may be suffering is one which would be susceptible to treatment with a compound having activity against Aurora and/or cyclin dependent kinases.

For example, a biological sample taken from a patient may be analysed to determine whether a condition or disease, such as cancer, that the patient is or may be suffering from is one which is characterised by a genetic abnormality or abnormal protein expression which leads to over-activation of CDKs or to sensitisation of a pathway to normal CDK activity. Examples of such abnormalities that result in activation or sensitisation of the CDK2 signal include up-regulation of cyclin E, (Harwell R M, Mull B B, Porter D C, Keyomarsi K.; J Biol Chem. 2004 Mar. 26;279(13):12695-705) or loss of p21 or p27, or presence of CDC4 variants (Rajagopalan H, Jallepalli P V, Rago C, Velculescu V E, Kinzler K W, Vogelstein B, Lengauer C.; Nature. 2004 Mar. 4;428(6978):77-81). Tumours with mutants of CDC4 or up-regulation, in particular over-expression, of cyclin E or loss of p21 or p27 may be particularly sensitive to CDK inhibitors. Alternatively or in addition, a biological sample taken from a patient may be analysed to determine whether a condition or disease, such as cancer, that the patient is or may be suffering from is one which is characterised by upregulation of Aurora kinase and thus may be particularly sensitive to Aurora inhibitors. The term up-regulation includes elevated expression or over-expression, including gene amplification (i.e. multiple gene copies) and increased expression by a transcriptional effect, and hyperactivity and activation, including activation by mutations.

Thus, the patient may be subjected to a diagnostic test to detect a marker characteristic of over-expression, up-regulation or activation of Aurora kinase or the patient may be subjected to a diagnostic test to detect a marker characteristic of up-regulation of cyclin E, or loss of p21 or p27, or presence of CDC4 variants. The term diagnosis includes screening. By marker we include genetic markers including, for example, the measurement of DNA composition to identify mutations of Aurora or CDC4. The term marker also includes markers which are characteristic of up regulation of Aurora or cyclin E, including enzyme activity, enzyme levels, enzyme state (e.g. phosphorylated or not) and mRNA levels of the aforementioned proteins. Tumours with upregulation of cyclin E, or loss of p21 or p27 may be particularly sensitive to CDK inhibitors. Tumours may preferentially be screened for upregulation of cyclin E, or loss of p21 or p27 prior to treatment. Thus, the patient may be subjected to a diagnostic test to detect a marker characteristic of up-regulation of cyclin E, or loss of p21 or p27.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

It has been found, see Ewart-Toland et al., (Nat Genet. 2003 August;34(4):403-12), that individuals forming part of the sub-population possessing the Ile31 variant of the STK gene (the gene for Aurora kinase A) may have an increased susceptibility to certain forms of cancer. Therefore, such individuals suffering from cancer will benefit from the administration of compounds having Aurora kinase inhibiting activity. A patient suffering from, or suspected of suffering from, a cancer may therefore be screened to determine whether he or she forms part of the Ile31 variant sub-population. In addition, it has been found, Rajagopalan et al (Nature. 2004 Mar. 4;428(6978):77-81), that there were mutations present in CDC4 (also known as Fbw7 or Archipelago) in human colorectal cancers and endometrial cancers (Spruck et al, Cancer Res. 2002 Aug. 15;62(16):4535-9). Identification of individual carrying a mutation in CDC4 may mean that the patient would be particularly suitable for treatment with a CDK inhibitor. Tumours may preferentially be screened for presence of a CDC4 variant prior to treatment. The screening process will typically involve direct sequencing, oligonucleotide microarray analysis, or a mutant specific antibody.

Tumours with activating mutants of Aurora or up-regulation of Aurora including any of the isoforms thereof, may be particularly sensitive to Aurora inhibitors. Tumours may preferentially be screened for up-regulation of Aurora or for Aurora possessing the Ile31 variant prior to treatment (Ewart-Toland et al., Nat Genet. 2003 August;34(4):403-12). Ewart-Toland et al identified a common genetic variant in STK15 (resulting in the amino acid substitution F31I) that is preferentially amplified and associated with the degree of aneuploidy in human colon tumors. These results are consistent with an important role for the Ile31 variant of STK15 in human cancer susceptibility. In particular, this polymorphism in Aurora A has been suggested to be a genetic modifier for developing breast carcinoma (Sun et al, Carcinogenesis, 2004, 25(11), 2225-2230).

The Aurora A gene maps to the chromosome 20q13 region that is frequently amplified in many cancers e.g. breast, bladder, colon, ovarian, pancreatic. Patients with a tumour that has this gene amplification might be particularly sensitive to treatments targeting Aurora kinase inhibition Methods of identification and analysis of mutations and up-regulation of protein e.g. Aurora isoforms and chromosome 20q13 amplification are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of cyclin E, or loss of p21 or p27, or detection of CDC4 variants, Aurora up-regulation and mutants of Aurora could be applicable in the present case.

Therefore, all of these techniques could also be used to identify tumours particularly suitable for treatment with the compounds of the invention.

Tumours with mutants of CDC4 or up-regulation, in particular over-expression, of cyclin E or loss of p21 or p27 may be particularly sensitive to CDK inhibitors as a compenent of the combination of the invention. Tumours may preferentially be screened for up-regulation, in particular over-expression, of cyclin E (Harwell R M, Mull B B, Porter D C, Keyomarsi K.; J Biol Chem. 2004 Mar. 26;279(13):12695-705) or loss of p21 or p27 or for CDC4 variants prior to treatment (Rajagopalan H, Jallepalli P V, Rago C, Velculescu V E, Kinzler K W, Vogelstein B, Lengauer C.; Nature. 2004 Mar. 4;428(6978): 77-81).

Patients with mantle cell lymphoma (MCL) could be selected for treatment with a compound of the invention using diagnostic tests outlined herein. MCL is a distinct clinicopathologic entity of non-Hodgkin's lymphoma, characterized by proliferation of small to medium-sized lymphocytes with co-expression of CD5 and CD20, an aggressive and incurable clinical course, and frequent t(11; 14)(q13;q32) translocation. Over-expression of cyclin D1 mRNA, found in mantle cell lymphoma (MCL), is a critical diagnostic marker. Yatabe et al (Blood. 2000 Apr. 1;95(7):2253-61) proposed that cyclin D1-positivity should be included as one of the standard criteria for MCL, and that innovative therapies for this incurable disease should be explored on the basis of the new criteria. Jones et al (J Mol Diagn. 2004 May;6(2):84-9) developed a real-time, quantitative, reverse transcription PCR assay for cyclin D1 (CCND1) expression to aid in the diagnosis of mantle cell lymphoma (MCL). Howe et al (Clin Chem. 2004 January;50(1):80-7) used real-time quantitative RT-PCR to evaluate cyclin D1 mRNA expression and found that quantitative RT-PCR for cyclin D1 mRNA normalized to CD19 mRNA can be used in the diagnosis of MCL in blood, marrow, and tissue. Alternatively, patients with breast cancer could be selected for treatment with a combination of the invention using diagnostic tests outline above. Tumour cells commonly overexpress cyclin E and it has been shown that cyclin E is over-expressed in breast cancer (Harwell et al, Cancer Res, 2000, 60, 481-489). Therefore breast cancer may in particular be treated with a CDK inhibitor as provided herein.

Prior to administration of the combination of the invention, a patient may be screened to determine whether a disease or condition from which the patient is or may be suffering is:

A. a disease state or condition mediated by a kinase which is BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. csrc); or B. a cancer in which the cancer cells thereof contain a drug resistant kinase mutation which is:
 (a) a threonine gatekeeper mutation; or
 (b) a drug-resistant gatekeeper mutation; or
 (c) an imatinib resistant mutation; or
 (d) a nilotinib resistant mutation; or
 (e) a dasatinib resistant mutation; or
 (f) a T6701 mutation in KIT; or
 (g) a T6741 mutation in PDGFR; or
 (h) T790M mutation in EGFR; or
 (i) a T315I mutation in abl; or C. a cancer which expresses a mutated molecular target which is a mutated form of BCRabl, c-kit, PDGF, EGF receptor or ErbB2; or D. a disease mediated by a kinase containing a mutation in a region of the protein that binds to or interacts with other cancer agents but does not bind to or interact with the compounds of formula (I) or (I'), for example a mutated kinase selected from c-abl, c-kit, PDGFR including PDGFR-beta and PDGFR-alpha, and ErbB family members such as EGFR (ErbB1), HER2 (ErbB2), ErbB3, and ErbB4, members of the Ephrin receptor family including EphA1, EphA2, EphA3, EphA4, EphA5, EphA8, EphA10, EphB1, EphB2, EphB3, EphB5, EphB6, c-Src and kinases of the JAK family such as TYK2;

and is a disease state or condition which would be susceptible to treatment with a combination of the invention.

In a particular embodiment, prior to administration of a combination of the invention, a patient may be screened to determine whether a disease or condition from which the patient is or may be suffering is one which would be susceptible to treatment with a combination of the invention having activity against BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases.

A biological sample taken from a patient may be analysed to determine whether a condition or disease, such as cancer, that the patient is or may be suffering from is one which is characterised by a genetic abnormality (e.g. contains a mutated form of a kinase as described above) or abnormal protein expression which leads to over-activation of a kinase or to sensitisation of a pathway to normal kinase activity. Alternatively or in addition, a biological sample taken from a patient may be analysed to determine whether a condition or disease, such as cancer, that the patient is or may be suffering from is one which is characterised by upregulation of a particular kinase and thus may be particularly sensitive to an inhibitor of that kinase. The term up-regulation includes elevated expression or over-expression, including gene amplification (i.e. multiple gene copies) and increased expression by a transcriptional effect, and hyperactivity and activation, including activation by mutations.

In the case of the kinases BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, a biological sample taken from a patient may be analysed to determine whether a condition or disease, such as cancer, that the patient is or may be suffering from is one which is characterised by a genetic abnormality or abnormal protein expression which leads to up-regulation of the levels or activity of the kinase or to sensitisation of a pathway to normal kinase activity, or to upregulation of the kinase signalling pathways such as kinase ligand levels or kinase ligand activity or to upregulation of a biochemical pathway downstream of kinase activation.

Examples of such abnormalities that result in activation or sensitisation of the kinase signal include loss of, or inhibition of apoptotic pathways, up-regulation of the receptors or ligands, or presence of mutant variants of the receptors or ligands e.g PTK variants.

Tumours with mutants of FGFR1, FGFR2 or FGFR3 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions (Lemonnier, et al., J. Bone Miner. Res., 16, 832-845 (2001)). In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas (Powers, C. J., et al., Endocr. Rel. Cancer, 7,165 (2000)). A particular mutation T6741 of the PDGF receptor has been identified in imatinib-treated patients.

In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. Clin Cancer Res. 2006 12(22): 6652-6662.

Alternatively, a biological sample taken from a patient may be analysed for loss of a negative regulator or suppressor of a particular kinase (e.g. BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases). In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

Thus, the patient may be subjected to a diagnostic test to detect a marker characteristic of over-expression, up-regulation or activation of a kinase. The term diagnosis includes screening. By marker we include genetic markers including, for example, the measurement of DNA composition to identify mutations of a particular kinase. The term marker also includes markers which are characteristic of up regulation of the activity of a kinase, including enzyme activity, enzyme levels, enzyme state (e.g. phosphorylated or not) and mRNA levels of the aforementioned proteins. The term up-regulation includes elevated expression or over-expression, including gene amplification (i.e. multiple gene copies) and increased expression by a transcriptional effect, and hyperactivity and activation, including activation by mutations.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

More specifically, the patient may be subjected to a diagnostic test to detect a marker characteristic of up-regulation of BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases. The term diagnosis includes screening. By marker we include genetic markers including, for example, the measurement of DNA composition to identify mutations of the kinases. The term marker also includes markers which are characteristic of up regulation of the kinases including enzyme activity, enzyme levels, enzyme state (e.g. phosphorylated or not) and mRNA levels of the aforementioned proteins.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in a kinase such as BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases may mean that the patient would be particularly suitable for treatment with an inhibitor of the kinase in question. Tumours may preferentially be screened for presence of a kinase variant prior to treatment. The screening process will typically involve direct sequencing, oligonucleotide microarray analysis, or a mutant specific antibody or by using the RT-PCR and FISH techniques described above.

In addition, mutant forms of, for example a kinase such as BCR-abl, VEGFR, PDGFR, EGFR, Flt3, JAK (e.g. JAK2 or JAK3), C-abl, PDK1, Chk (e.g. Chk1 or Chk2), FGFR (e.g. FGFR3), Ret, Eph (e.g. EphB2 or EphB4), or Src (e.g. cSrc) or a mutated form thereof as defined herein, and in particular C-abl and JAK kinases, can be identified by direct sequencing of, for example, tumour biopsies using PCR and methods to sequence PCR products directly as hereinbefore described. The skilled person will recognize that all such well-known techniques for detection of the over expression, activation or mutations of the aforementioned proteins could be applicable in the present case.

In particular, prior to administration of a combination of the invention, a patient may be screened to determine whether a disease or condition from which the patient is or may be suffering is one which would be susceptible to treatment with a compound having activity against Flt3, JAK, C-abl, PDK1, Chk1, and Chk2. These techniques may also be used for screening for diseases or conditions caused by the up-regulation or mutants of Flt3, JAK, C-abl, PDK1, Chk1, and Chk2 kinases. These techniques may also be used for screening for diseases or conditions caused by the up-regulation or mutants of VEGFR kinases, include, but are not limited to, standard methods such as reverse-transcriptase polymerase chain reaction (RT-PCR) or in-situ hybridisation.

In another embodiment of the invention, prior to administration of a combination of the invention, a patient may be screened to determine whether a disease or condition from which the patient is or may be suffering is one which would be susceptible to treatment with a combination of the invention having activity against FGFR, ret, Eph, cSRC, VEGFR, PDGFR kinases. These techniques may also be used for screening for diseases or conditions caused by the up-regulation or mutants of GFR, ret, Eph, cSRC, VEGFR, PDGFR kinases.

In addition, mutant forms of, for example, VEGFR2 can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

Abnormal levels of proteins such as VEGFR can be measured using standard enzyme assays, for example, those assays described herein. Activation or overexpression could also be detected in a tissue sample, for example, a tumour tissue, by measuring the tyrosine kinase activity with an assay such as that available from Chemicon International. The tyrosine kinase of interest would be immunoprecipitated from the sample lysate and its activity measured.

Alternative methods for the measurement of the over expression or activation of VEGFR including the isoforms thereof, include the measurement of microvessel density. This can for example be measured using methods described by Orre and Rogers (Int J Cancer 1999 84(2) 101-8). Assay methods also include the use of markers, for example, in the case of VEGFR these include CD31, CD34 and CD105 (Mineo et al. J Clin Pathol. 2004 57(6) 591-7).

Activating mutations of FLT3 are frequently observed in acute myeloid leukaemia, myelodysplastic syndromes (MDS) and some cases with acute lymphoblastic leukemia (ALL). Cancer patients with activating mutants of FLT3 can be screened for presence of the length mutations or internal tandem duplication mutations as an indication of those most sensitive to inhibitors of FLT3.

Activating mutations in the tyrosine kinase JAK2 has been observed in polycythemia vera, essential thrombocythemia and myeloid metaplasia with myelofibrosis. The methods described herein could be used to identify patients harbouring these mutations.

Patients with tumours harbouring cells expressing the resistance mutants of BCR-abl e.g. T315I can be identified using the methods described herein.

Therefore in addition the methods described herein could be used to diagnose mutations of JAK2 e.g. V617F, activating mutations of FLT3, mutants of C-Abl e.g. T315I.

In a further embodiment the combination of the invention could be used to treat patients and/or tumours and/or leukemias which are Philadelphia chromosome positive (Ph+). This is a translocation which occurs between chromosomes 9 and 22 resulting in an altered chromosome 22. The translocation, often referred to as the BCR-abl translocation, can be distinguished by cytogenetic methods such as those known to the skilled person including those described herein, in particular FISH, and used to identify patients suitable for treatment with the combination of the invention.

As the combination of the invention, contain inhibitors of aurora kinase which is directly related to mitotic checkpoint defects, the combination of the invention may be particularly suitable for treating patients suffering from a leukaemia exhibiting polyploidy as a manifestation of loss of chromosomal integrity, mitotic spindle defects or disease progression.

Genetic instability is a common feature in many leukemias resulting in aneuploidy. Centrosome aberrations have recently been described in several different hematological malignancies including acute myeloid leukemias, myelodysplastic syndromes, Hodgkin's as well as non-Hodgkin's lymphomas, chronic lymphocytic leukemias and multiple myelomas. Analagous to many solid tumors a correlation between centrosome abnormalities on the one hand and karyotype aberrations as well as clinical aggressiveness on the other hand seems to exist in myeloid malignancies, chronic lymphocytic leukemias and at least some types of non-Hodgkin's lymphomas.

Complex chromosomal aberrations are present in up to 30% of patients with primary myelodysplastic syndrome (MDS) or acute myeloid leukemia (AML) and are associated with a poor prognosis. Specific alterations in complex karyotypes are difficult to define by conventional cytogenetics alone. A more comprehensive view of the recurrent aberrations can be obtained when spectral karyotyping (SKY) and fluorescence in situ hybridization (FISH) with selected probes on bone marrow samples are used (Cancer Genet. Cytogenet., 2006,165(1), 51-63, Trost D et al). A detailed analysis of specific breakpoints and deletions can reveal recurrent involvement of specific chromosomal bands harboring known tumor suppressor genes or oncogenes. Analysis of a large number of MDS and AML cases in a similar detailed manner with SKY and FISH will reveal whether new subgroups can be identified according to their genetic alterations. Correlation with clinical parameters may reveal the prognostic significance of these genetic subgroups. In MDS for example, the International Prognostic Scoring System combines blast percentage, karyotype, and number of cytopenias to generate a scoring system that reliably estimates survival and risk of transformation to acute myeloid leukemia for patients with MDS. This universally accepted scoring system is often combined with FAB or World Health Organization morphologic criteria to provide a more complete clinical picture and the most accurate prognostic assessment possible (Semin Oncol. 2005 August;32(4 Suppl 5):S3-10, Bennett).

Genetic instability is a common feature of acute myeloid leukemia (AML) (Blood, 2003, 101(1), 289-91, Neben et al) and centrosome aberrations have been described as a possible cause of aneuploidy in many human tumors. To investigate whether centrosome aberrations correlate with cytogenetic findings in AML, a set of AML samples were examined using a centrosome-specific antibody to pericentrin. The AML samples analyzed displayed numerical and structural centrosome aberrations as compared with peripheral blood mononuclear cells. In comparison to AML samples with normal chromosome count, the extent of numerical and structural centrosome aberrations was higher in samples with numerical chromosome changes. When the frequency of centrosome aberrations was analyzed within cytogenetically defined risk groups, a correlation was found between the extent of centrosome abnormalities in all 3 risk groups. These results indicate that centrosome defects may contribute to the acquisition of chromosome aberrations and thereby to the prognosis in AML.

Thus a number of techniques known to the skilled person could be used to determine whether a tumour or leukaemia was associated with chromosomal aberrations.

Therefore an aspect of the invention is a method of detecting whether a patient is suffering from a disease, in particular cancer, exhibiting chromosomal aberrations and treating them with a combination of the invention.

The invention further provides a method of diagnosing whether a patient as suffering from a leukaemia exhibiting a chromosomal aberration and then administering a combination of the invention.

A further aspect of the invention is a method for the prophylaxis or treatment of (or alleviating or reducing the incidence of) cancer in a patient suffering from or suspected of suffering from cancer; which method comprises (i) subjecting a patient to a diagnostic test to determine whether the patient possesses chromosomal aberrations; and (ii) where the patient does possess the said chromosomal aberrations, thereafter administering to the patient a combination of the invention as defined herein having aurora kinase inhibiting activity.

Antifungal Use

In a further aspect, the invention provides the use of the combinations comprising (or consisting essentially of) an ancillary compound and a compound of the formula (I) or (I') and sub-groups thereof as defined herein as antifungal agents.

The combinations of the invention may be used in animal medicine (for example in the treatment of mammals such as humans), or in the treatment of plants (e.g. in agriculture and horticulture), or as general antifungal agents, for example as preservatives and disinfectants.

In one embodiment, the invention provides a combination as defined herein for use in the prophylaxis or treatment of a fungal infection in a mammal such as a human.

Also provided is the use of a combination as defined herein for the manufacture of a medicament for use in the prophylaxis or treatment of a fungal infection in a mammal such as a human.

For example, combination of the invention may be administered to human patients suffering from, or at risk of infection by, topical fungal infections caused by among other organisms, species of *Candida, Trichophyton, Microsporum* or *Epidermophyton*, or in mucosal infections caused by *Candida albicans* (e.g. thrush and vaginal candidiasis). The combinations of the invention can also be administered for the treatment or prophylaxis of systemic fungal infections caused by, for example, *Candida albicans, Cryptococcus neoformans, Aspergillus flavus, Aspergillus fumigatus, Coccidiodies, Paracoccidioides*, Histoplasma or Blastomyces.

In another aspect, the invention provides an antifungal composition for agricultural (including horticultural) use, comprising a compound of the formula (I) or (I') and sub-groups thereof as defined herein together with an ancillary agent and an agriculturally acceptable diluent or carrier.

The invention further provides a method of treating an animal (including a mammal such as a human), plant or seed having a fungal infection, which comprises treating said animal, plant or seed, or the locus of said plant or seed, with an effective amount of a combination as defined herein.

The invention also provides a method of treating a fungal infection in a plant or seed which comprises treating the plant or seed with an antifungally effective amount of a fungicidal composition containing a combination as defined herein.

Differential screening assays may be used to select for those compounds with specificity for non-human CDK enzymes. Compounds which act specifically on the CDK enzymes of eukaryotic pathogens can be used as anti-fungal or anti-parasitic agents. Inhibitors of the Candida CDK kinase, CKSI, can be used in the treatment of candidiasis. Antifungal agents can be used against infections of the type hereinbefore defined, or opportunistic infections that commonly occur in debilitated and immunosuppressed patients such as patients with leukemias and lymphomas, people who are receiving immunosuppressive therapy, and patients with predisposing conditions such as diabetes mellitus or AIDS, as well as for non-immunosuppressed patients.

Assays described in the art can be used to screen for agents which may be useful for inhibiting at least one fungus implicated in mycosis such as candidiasis, aspergillosis, mucormycosis, blastomycosis, geotrichosis, cryptococcosis, chromoblastomycosis, coccidiodomycosis, conidiosporosis, histoplasmosis, maduromycosis, rhinosporidosis, nocardiosis, para-actinomycosis, penicilliosis, monoliasis, or sporotrichosis. The differential screening assays can be used to identify anti-fungal agents which may have therapeutic value in the treatment of aspergillosis by making use of the CDK genes cloned from yeast such as *Aspergillus fumigatus, Aspergillus flavus, Aspergillus niger, Aspergillus nidulans*, or *Aspergillus terreus*, or where the mycotic infection is muconnycosis, the CDK assay can be derived from yeast such as *Rhizopus arrhizus, Rhizopus oryzae, Absidia corymbifera, Absidia ramosa*, or *Mucorpusillus*. Sources of other CDK enzymes include the pathogen *Pneumocystis carinii*.

By way of example, in vitro evaluation of the antifungal activity of the compounds can be performed by determining the minimum inhibitory concentration (M.I.C.) which is the concentration of the test compounds, in a suitable medium, at which growth of the particular microorganism fails to occur. In practice, a series of agar plates, each having the test compound incorporated at a particular concentration is inoculated with a standard culture of, for example, *Candida albicans* and each plate is then incubated for an appropriate period at 37° C. The plates are then examined for the presence or absence of growth of the fungus and the appropriate M.I.C. value is noted. Alternatively, a turbidity assay in liquid cultures can be performed and a protocol outlining an example of this assay can be found in the Examples below.

The in vivo evaluation of the compounds can be carried out at a series of dose levels by intraperitoneal or intravenous injection or by oral administration, to mice that have been inoculated with a fungus, e.g., a strain of *Candida albicans* or *Aspergillus flavus*. The activity of the compounds can be assessed by monitoring the growth of the fungal infection in groups of treated and untreated mice (by histology or by retrieving fungi from the infection). The activity may be measured in terms of the dose level at which the compound provides 50% protection against the lethal effect of the infection ($PD_{50}$).

For human antifungal use, the combinations as defined herein can be administered alone or in admixture with a pharmaceutical carrier selected in accordance with the intended route of administration and standard pharmaceutical practice. Thus, for example, they may be administered orally, parenterally, intravenously, intramuscularly or subcutaneously by means of the formulations described above in the section headed "Pharmaceutical Formulations".

For oral and parenteral administration to human patients, the daily dosage level can be from 0.01 to 10 mg/kg (in divided doses), depending on inter alia the potency of the combination when administered by either the oral or parenteral route. Tablets or capsules of the combination or its constituent compounds may contain, for example, from 5 mg to 0.5 g of active compound for administration singly or two or more at a time as appropriate. The physician in any event will determine the actual dosage (effective amount) which will be most suitable for an individual patient and it will vary with the age, weight and response of the particular patient.

Alternatively, the antifungal combinations can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

In addition to the therapeutic uses described above, antifungal agents developed with such differential screening assays can be used, for example, as preservatives in foodstuff, feed supplement for promoting weight gain in livestock, or in disinfectant formulations for treatment of non-living matter, e.g., for decontaminating hospital equipment and rooms. In similar fashion, side by side comparison of inhibition of a mammalian CDK and an insect CDK, such as the *Drosophilia* CDK5 gene (Hellmich et al. (1994) FEBS Lett 356:317-21), will permit selection amongst the compounds herein of inhibitors which discriminate between the human/mammalian and insect enzymes. Accordingly, the present invention expressly contemplates the use and formulation of the combinations of the invention in insecticides, such as for use in management of insects like the fruit fly.

In yet another embodiment, certain of the subject CDK inhibitors can be selected for use in the combinations of the invention on the basis of inhibitory specificity for plant CDK's relative to the mammalian enzyme. For example, a plant CDK can be disposed in a differential screen with one or more of the human enzymes to select those compounds of greatest selectivity for inhibiting the plant enzyme. Thus, the present invention specifically contemplates formulations of the subject CDK inhibitors for agricultural applications, such as in the form of a defoliant or the like.

For agricultural and horticultural purposes the combinations of the invention may be used in the form of a composition formulated as appropriate to the particular use and intended purpose. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they can be manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack. By way of example, the compositions may contain from 0.01 to 1 wt. % of the active ingredient. For field use, likely application rates of the active ingredient may be from 50 to 5000 g/hectare.

The invention also contemplates the use of the combinations of the invention in the control of wood decaying fungi and in the treatment of soil where plants grow, paddy fields for seedlings, or water for perfusion. Also contemplated by the invention is the use of the combinations as defined herein to protect stored grain and other non-plant loci from fungal infestation.

EXAMPLES

Figure 1:
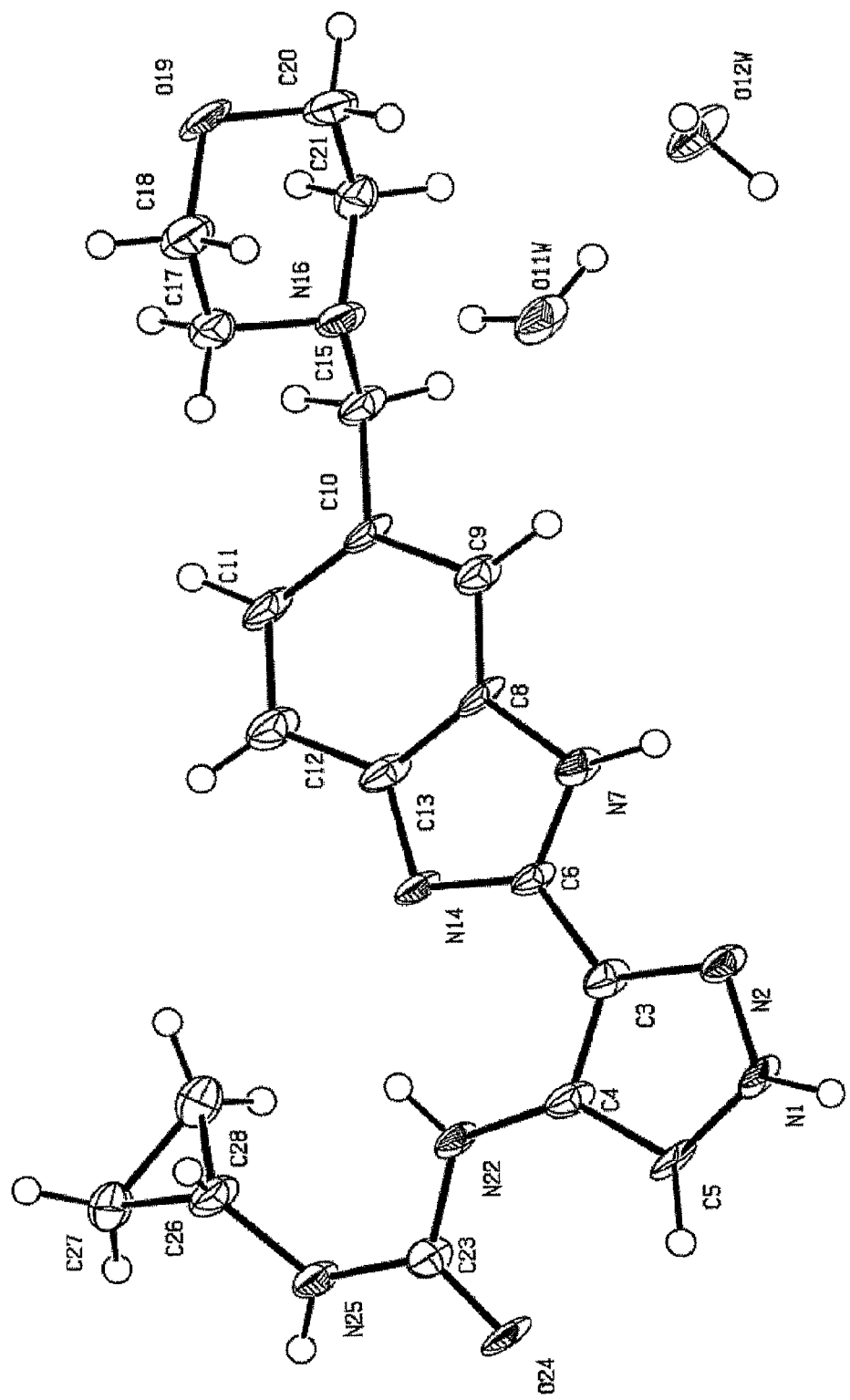
FIG. 1 is a thermal ellipsoid plot of the free base dihydrate of 1-cyclopropyl-3-[3-(5-morpholin-4-ylmethyl-1H-benzoimidazol-2-yl)-1H-pyrazol-4-yl]-urea as described in Example 69 of WO 2006/070195 (the content of which is incorporated herein by reference).
Figure 2:
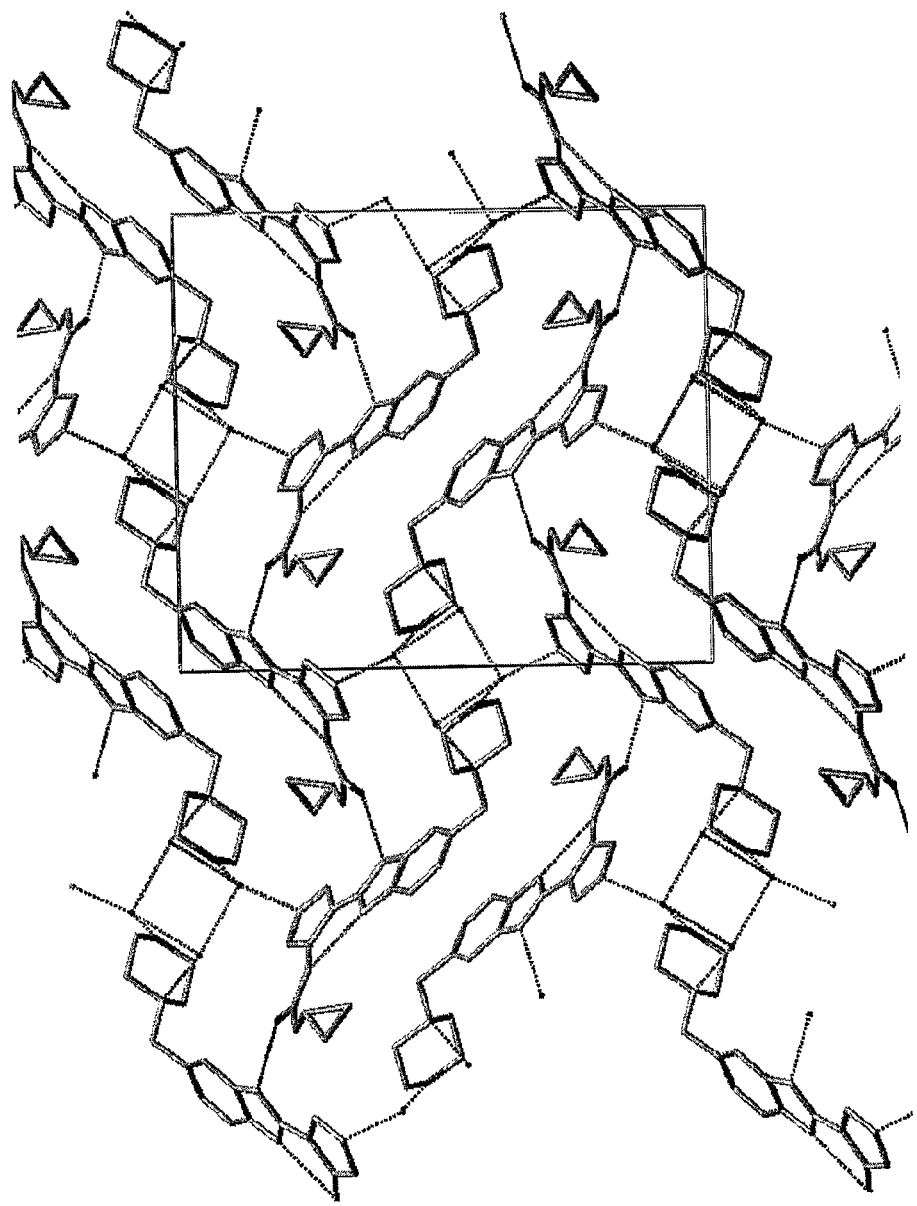
FIG. 2 shows a packing diagram of the free base dihydrate of 1-cyclopropyl-3-[3-(5-morpholin-4-ylmethyl-1H-benzoimidazol-2-yl)-1H-pyrazol-4-yl]-urea as described in Example 69 of WO 2006/070195 (the content of which is incorporated herein by reference).
Figure 3:
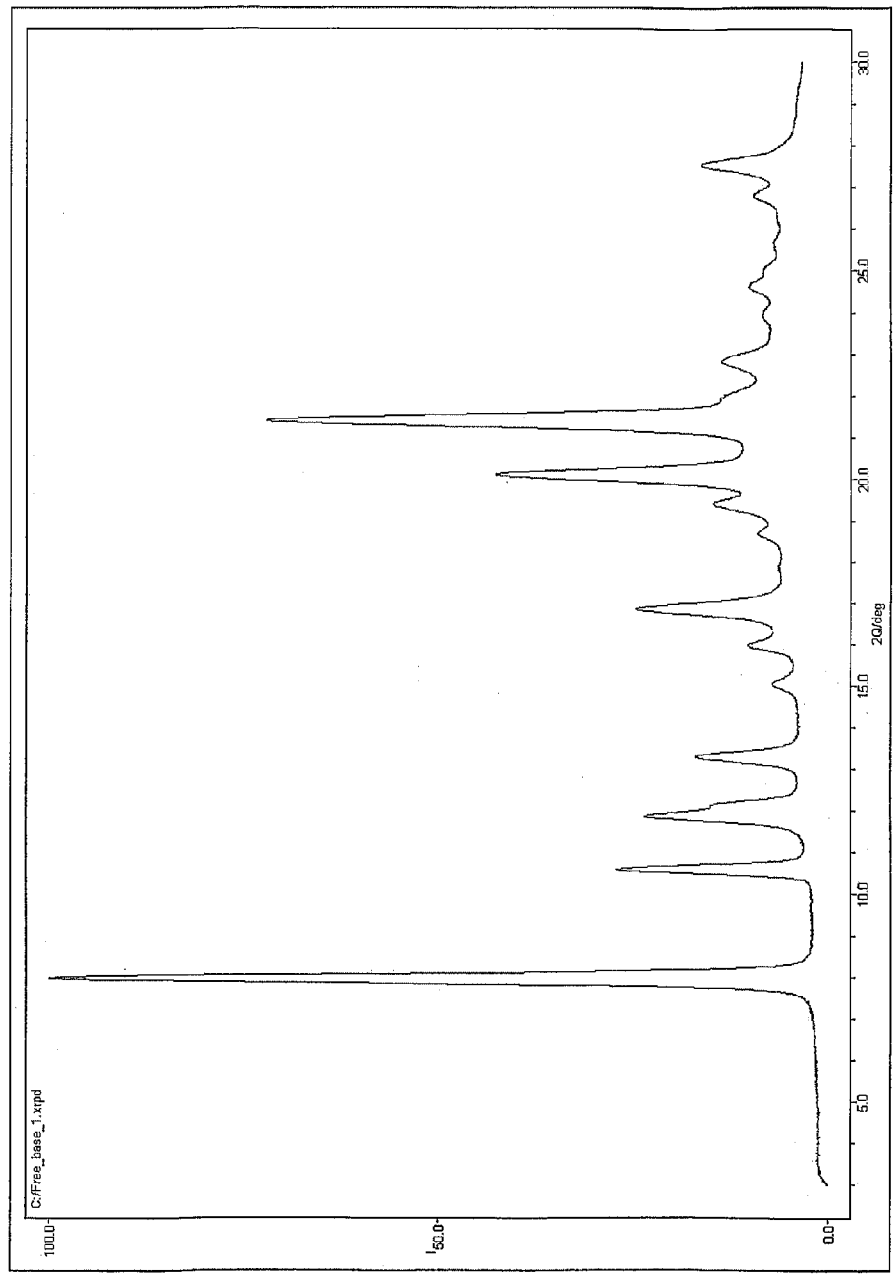
FIG. 3 shows the XRPD pattern of the free base of 1-cyclopropyl-3-[3-(5-morpholin-4-ylmethyl-1H-benzoimidazol-2-yl)-1H-pyrazol-4-yl]-urea as described in Example 70 of WO 2006/070195 (the content of which is incorporated herein by reference).
Figure 4:
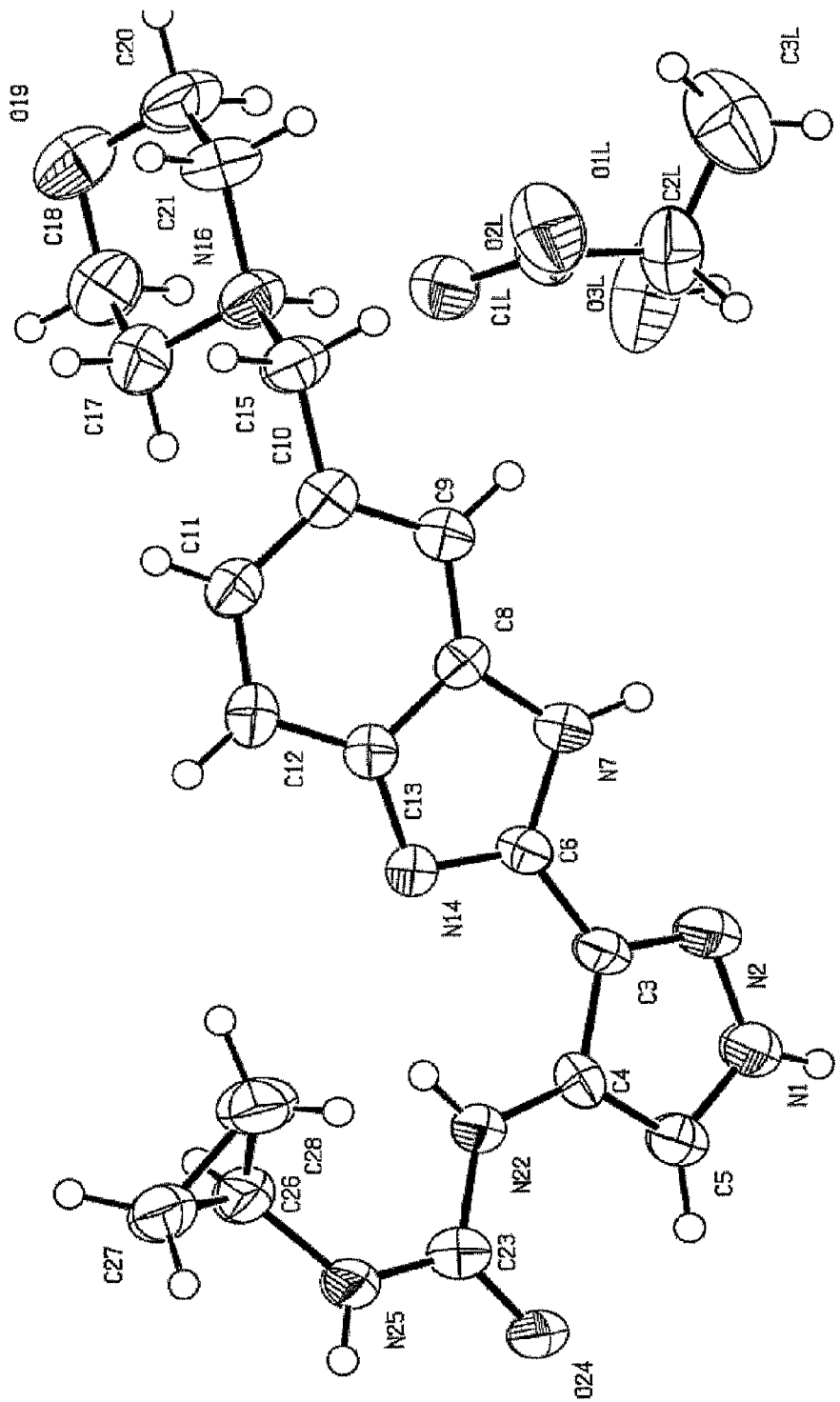
FIG. 4 shows a thermal ellipsoid plot of the L-lactate salt of 1-cyclopropyl-3-[3-(5-morpholin-4-ylmethyl-1H-benzoimidazol-2-yl)-1H-pyrazol-4-yl]-urea as described in Example 71 of WO 2006/070195 at pages 205 to 209 (the content of which is incorporated herein by reference).
Figure 5:
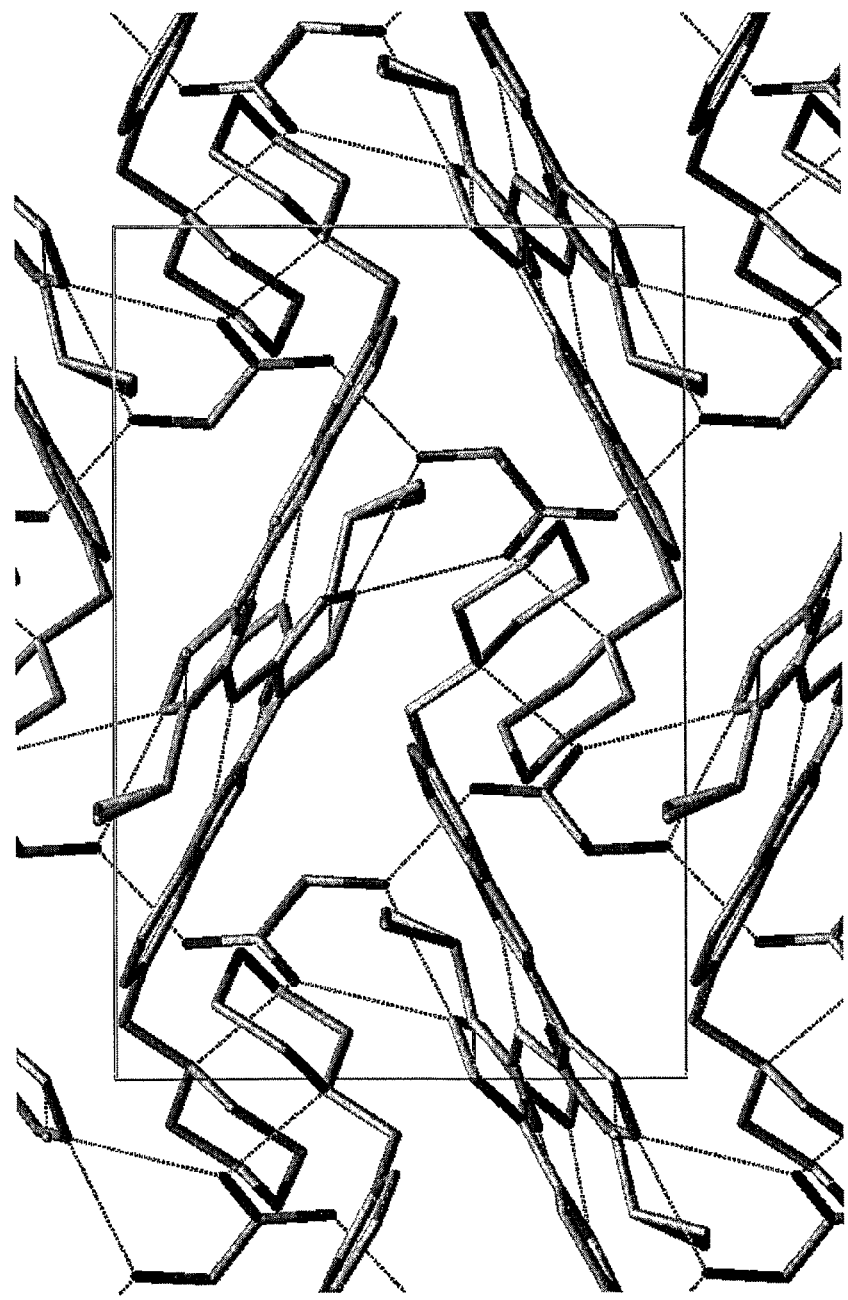
FIG. 5 shows a packing diagram of the L-lactate salt of 1-cyclopropyl-3-[3-(5-morpholin-4-ylmethyl-1H-benzoimidazol-2-yl)-1H-pyrazol-4-yl]-urea as described in Example 71 of WO 2006/070195 at pages 205 to 209 (the content of which is incorporated herein by reference).
Figure 6:
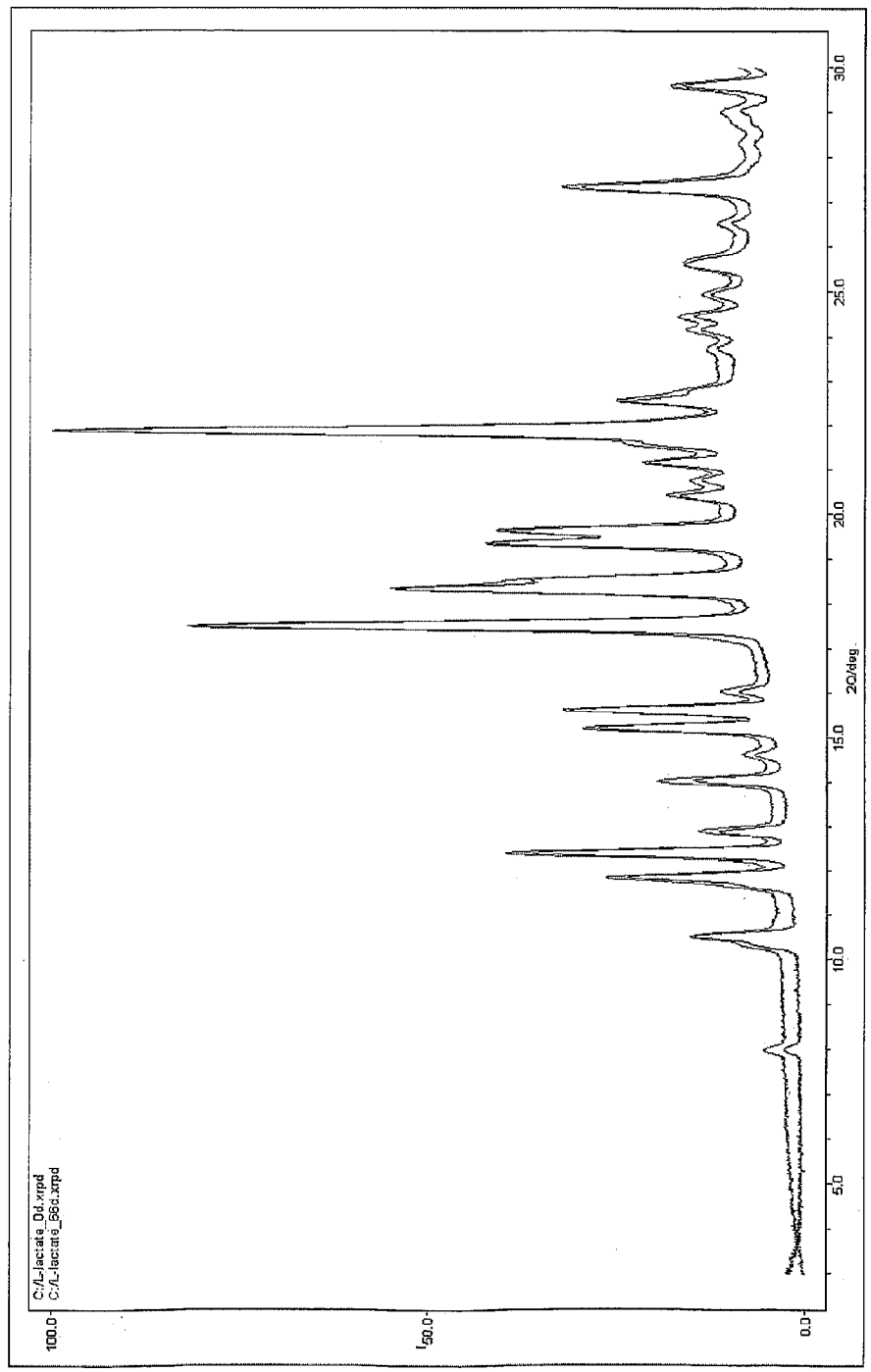
FIG. 6 shows the XRPD patterns of starting and stability tested samples of the L-lactate salt of 1-cyclopropyl-3-[3-(5-morpholin-4-ylmethyl-1H-benzoimidazol-2-yl)-1H-pyrazol-4-yl]-urea as described in Example 72 of WO 2006/070195 at pages 209 to 211 (the content of which is incorporated herein by reference).
Figure 7:
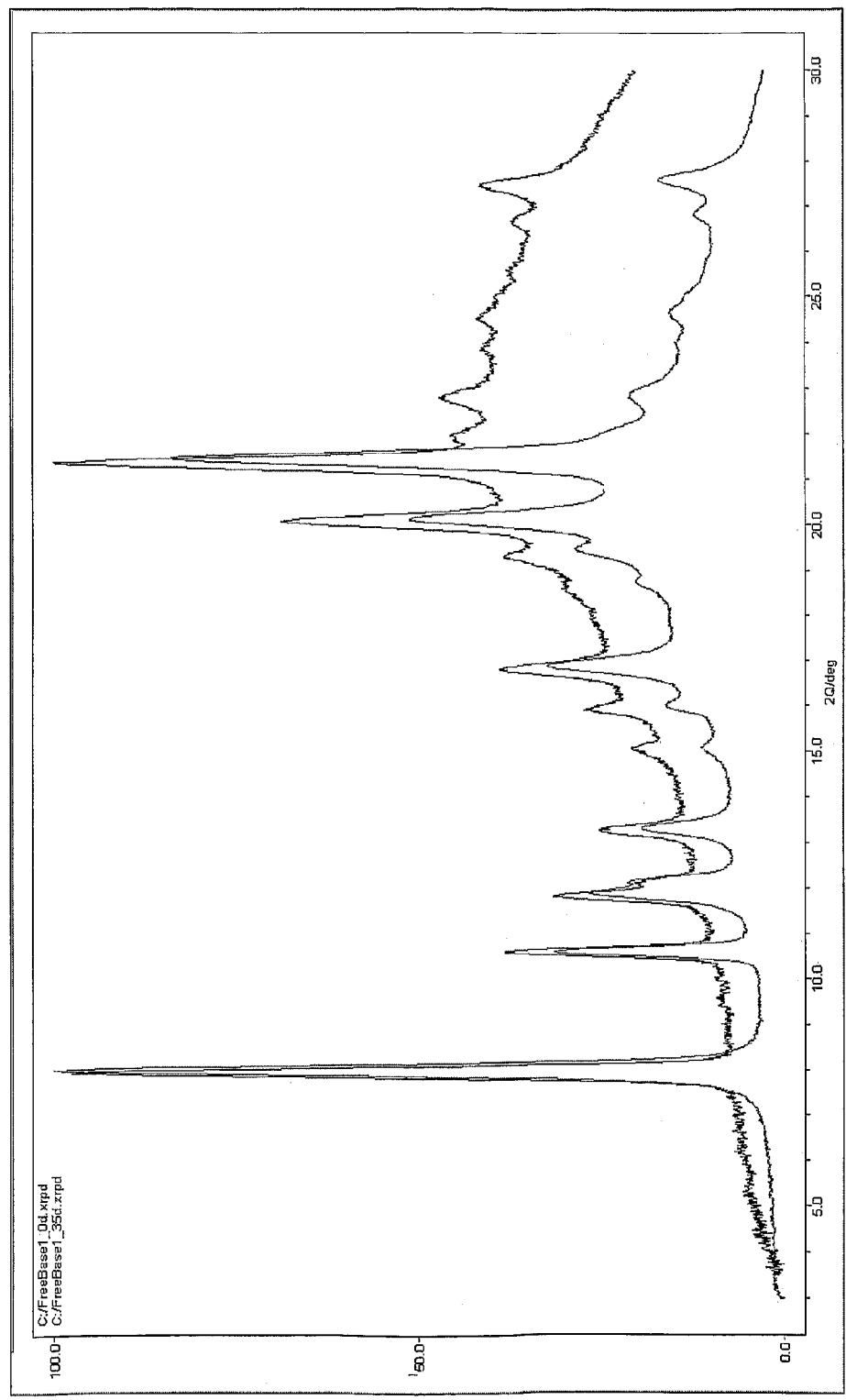
FIG. 7 shows the XRPD patterns of starting and stability tested samples of the free base (FB1) of 1-cyclopropyl-3-[3-(5-morpholin-4-ylmethyl-1H-benzoimidazol-2-yl)-1H-pyrazol-4-yl]-urea as described in Example 72 of WO 2006/070195 at pages 209 to 211 (the content of which is incorporated herein by reference).
Figure 8:
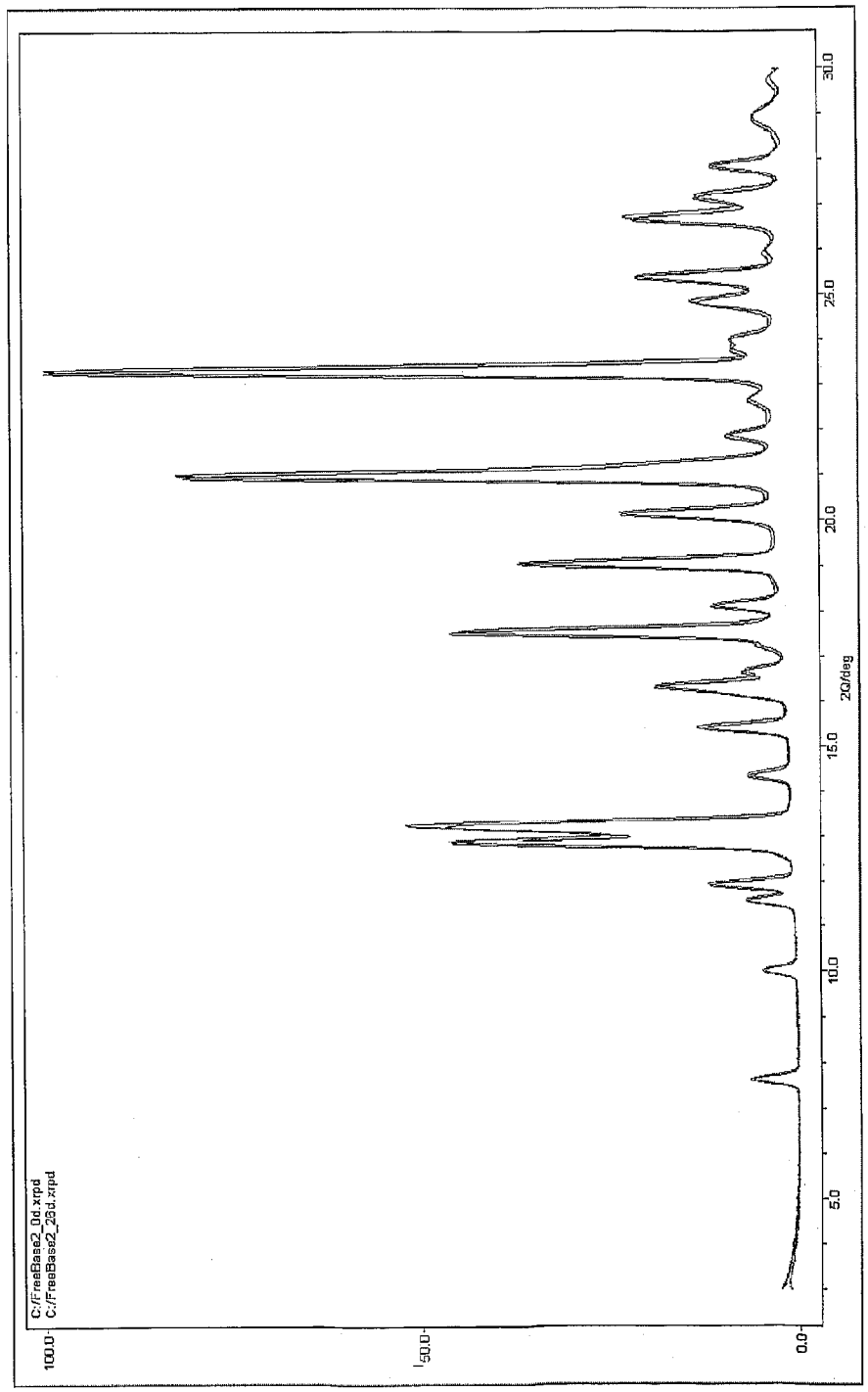
FIG. 8 shows the XRPD patterns of starting and stability tested samples of the free base dihydrate (FB2) of 1-cyclopropyl-3-[3-(5-morpholin-4-ylmethyl-1H-benzoimidazol-2-yl)-1H-pyrazol-4-yl]-urea as described in Example 72 of WO 2006/070195 at pages 209 to 211 (the content of which is incorporated herein by reference).

The invention will now be illustrated, but not limited, by reference to the specific embodiments described in the following examples.

In the examples, the abbreviations described in WO 2006/070195 (the contents of which are incorporated herein by reference) are used (see in particular pages 136-137).

Analytical LC-MS System and Method Description

The compounds prepared were characterised by liquid chromatography and mass spectroscopy using the systems and operating conditions set out in WO 2006/070195 (the contents of which are incorporated herein by reference). The operating conditions used are also described in WO 2006/070195 (see in particular pages 137 to 144).

The starting materials for each of the Examples are commercially available unless otherwise specified.

Various exemplary compounds of the formula (I') may be prepared as described in WO 2006/070195, the contents of which are incorporated herein by reference. In particular, the contents of WO 2006/070195 which relate to the synthesis of the compounds as described in Examples 1 to 77 at pages 136 to 214 are hereby incorporated herein by reference, so that examples of the preparation of the following compounds are specifically described herein:

5-cyano-2-methoxy-N-[3-(5-morpholin-4-ylmethyl-1H-benzoimidazol-2-yl)-1H-pyrazol-4-yl]-benzamide
6-methyl-imadazol[2.1-b]thiazole-5-carboxylic acid[3-(5-morpholin-4-vlmethyl-1H-benzoimidazol-2-yl)-1H-pyrazol-4-yl]-amide
2-cyano-N-[3-(5-morpholin-4-ylmethyl-1H-benzoimidaxol-2-yl)-1H-pyrazol-4-yl]-acetamide
2-Cyano-2-cyclopropyl-N-[3-(5-morpholin-4-ylmethyl-1H-benzoimidazol-2-yl)-1H-pyrazol-4-yl]-acetamide
N-[3-(5,6-dimethoxy-1H-benzimidazol-2-yl)-1H-pyrazol-4-yl]-rac-2-morpholine carboxamide-trifluoroacetate salt
N-[3-(5,6-dimethoxy-1H-benzimidazol-2-yl)-1H-pyrazol-4-yl]-rac-4 isopropyl-2-morpholine carboxamide
N-[3-(5,6-dimethoxy-H-benzimidazol-2-yl)-1H-pyrazol-4-yl]-rac-1-methyl-piperidine 3-carboxamide
3-chloro-N-(5,6-dimethoxy-1H-benzoimidazol-2-yl)-1H-pyrazol-4-yl-5-(4-methyl-piperazin-1-yl)-benzamide
5-chloro-2-methoxy-N-{3-[5-(4-methyl-piperazin-1-ylmethyl)-1H-benzoimidazol-2-yl]-1H-pyrazol-4-yl}-benzamide
1-(2,6-Difluoro-benzyl-3-[3-(5-morpholin-4-ylmethyl-1H-benzoimidazol-2-yl)-1H-pyrazol-4-yl]-urea
1-[3-(5 morpholin-4-ylmethyl-1H-benzoimidazol-2-yl)-1H-pyrazol-4-vl]-3-pyridin-3-yl-urea
Thiomorpholine-4-carboxylic acid[3-(5-morpholin-4-ylmethyl-1H-benzoimidazol-2-yl)-1H-pyrazol-4-yl]-amide
1-(4-fluorophenyl)-1-methyl-3-[3-(5-morpholin-4-ylmethyl-1H-benzimadazol-2-yl)-1H-pyrazol-4-yl]-urea
1-(4-fluorophenyl)-N-[3-(5-morpholin-4-ylmethyl-1H-benzimidazol-2-yl)-1H-pyrazol-4-yl]-urea
1-(2,6-difluorophenyl)-N-[3-(5-morpholin-4-ylmethyl-1H-benzimidazol-2-yl)-1H-pyrazol-4-yl]-urea-hydrochloride salt
Free Base and Salts of 1-Cyclopropyl-3-[3-(5-morpholin-4-ylmethyl-1H-benzoimidazol-2-yl)-1H-pyrazol-4-yl]-urea
1-Cyclopropyl-3-[3-(5-Morpholin-4-ylmethyl-1H-Benzoimidazol-2-yl)-1H-Pyrazol-4-yl]-Urea lactate salt
L-lactate salt of 1-cyclopropyl-3-[3-(5-morpholin-4-ylmethyl-1H-benzoimidazol-2-yl)-1H-pyrazol-4-yl]-urea
Crystalline Free Base And Crystalline Salt Forms Of 1-Cyclopropyl-3-[3-(5-Morpholin-4-ylmethyl-1H-Benzoimidazol-2-yl)-1H-Pyrazol-4-yl]-Urea The compounds shown in the table below:

| Structure | LC/MS |
|---|---|
| 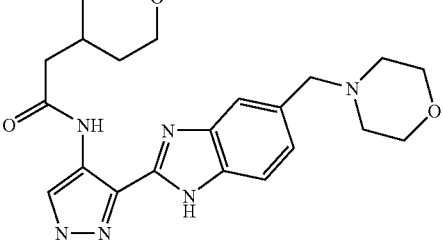 | [M + H]$^+$ 425 R$_t$ 1.77 Acidic |
| 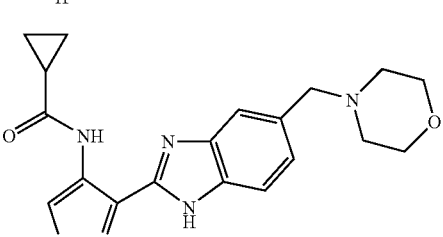 | [M + H]$^+$ 365 R$_t$ 2.45 Basic |
| 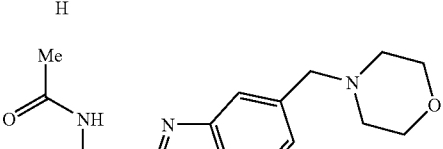 | [M + H]$^+$ 339 R$_t$ 2.21 Basic |

-continued

| Structure | LC/MS |
|---|---|
| (structure) | [M + H]+ 399<br>R_t 1.74<br>Acidic |
| (structure) | [M + H]+ 397<br>R_t 1.64<br>Acidic |
| (structure) | [M + H]+ 381<br>R_t 1.85<br>Acidic |
| (structure) | [M + H]+ 397<br>R_t 1.76<br>Acidic |
| (structure) | [M + H]+ 397<br>R_t 1.76<br>Acidic |

-continued
| Structure | LC/MS |
|---|---|
| 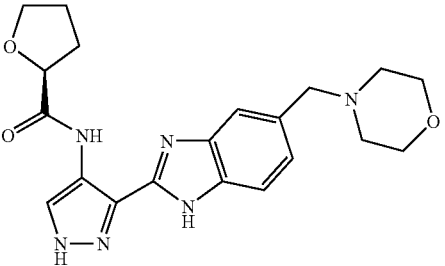 [SMILES: O=C(Nc1c[nH]nc1-c1nc2cc(CN3CCOCC3)ccc2[nH]1)C1CCCO1] | [M + H]+ 397.24 R<sub>t</sub> 1.79 Acidic |
| 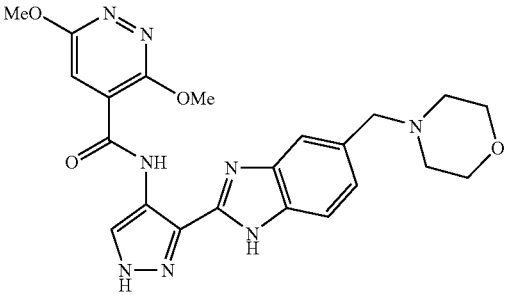 [SMILES: COc1cc(C(=O)Nc2c[nH]nc2-c2nc3cc(CN4CCOCC4)ccc3[nH]2)c(OC)nn1] | [M + H]+ 465.3 R<sub>t</sub> 1.99 Acidic |
| 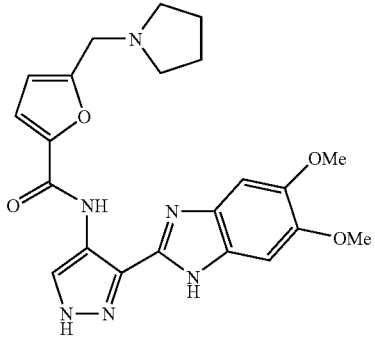 [SMILES: COc1cc2nc(-c3n[nH]cc3NC(=O)c3ccc(CN4CCCC4)o3)[nH]c2cc1OC] | [M + H]+ 437 R<sub>t</sub> 2.62 Basic |
| 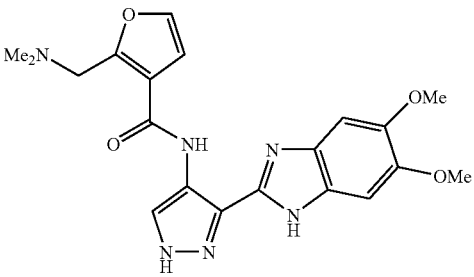 [SMILES: COc1cc2nc(-c3n[nH]cc3NC(=O)c3ccoc3CN(C)C)[nH]c2cc1OC] | [M + H]+ 411 R<sub>t</sub> 1.6 Acidic |
| 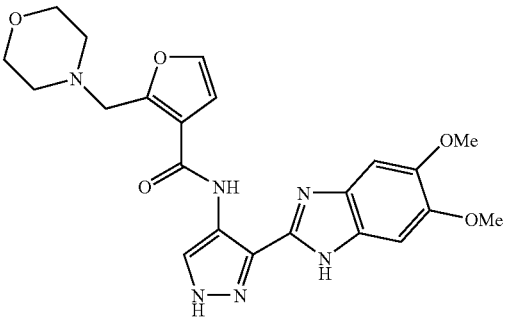 [SMILES: COc1cc2nc(-c3n[nH]cc3NC(=O)c3ccoc3CN3CCOCC3)[nH]c2cc1OC] | [M + H]+ 453.17 R<sub>t</sub> 1.75 Acidic |

| Structure | LC/MS |
|---|---|
| (cyclopropyl urea pyrazole benzimidazole morpholinomethyl) | [M + H]+ 382.24 R_t 1.59 Acidic |
| (cis-2,6-dimethylmorpholine carboxamide pyrazole benzimidazole morpholinomethyl) | [M + H]+ 440.31 R_t 1.84 Acidic |
| (tetrahydropyran-4-ylmethyl urea pyrazole benzimidazole morpholinomethyl) | [M + H]+ 440.34 R_t 2.20 Polar |
| (tetrahydropyran-4-yl urea pyrazole benzimidazole morpholinomethyl) | [M + H]+ 426.27 R_t 1.57 Acidic |
| (isoindoline-2-carboxamide pyrazole benzimidazole morpholinomethyl) | [M + H]+ 444 R_t 6.67 Acidic |

-continued
| Structure | LC/MS |
|---|---|
| 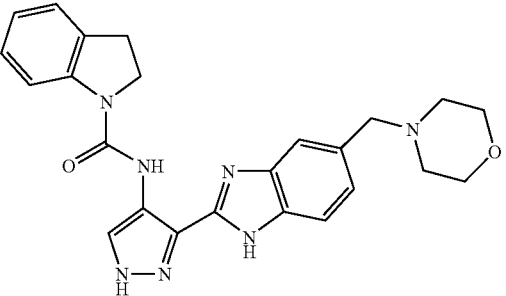 [SMILES: O=C(Nc1c[nH]nc1-c1nc2cc(CN3CCOCC3)ccc2[nH]1)N1CCc2ccccc21] | [M + H]+ 444<br>R_t 6.98<br>Acidic |
| 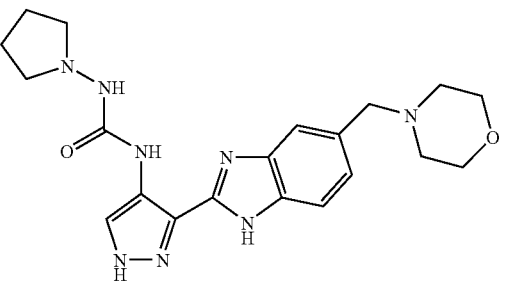 [SMILES: O=C(Nc1c[nH]nc1-c1nc2cc(CN3CCOCC3)ccc2[nH]1)NN1CCCC1] | [M + H]+ 411<br>R_t 2.45<br>Basic |
| 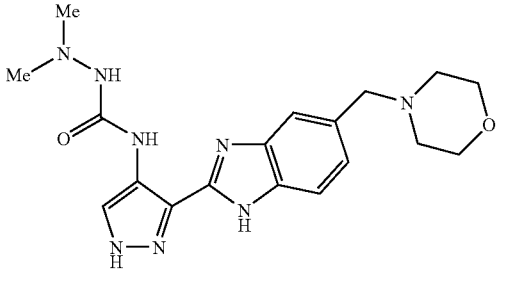 [SMILES: CN(C)NC(=O)Nc1c[nH]nc1-c1nc2cc(CN3CCOCC3)ccc2[nH]1] | [M + H]+ 385<br>R_t 1.60<br>Acidic |
| 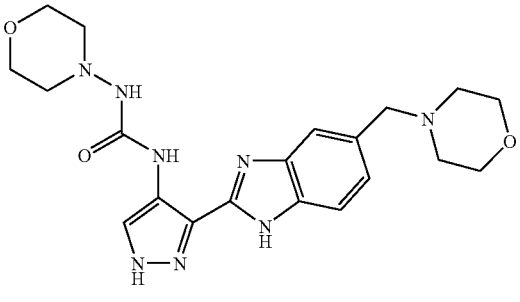 | [M + H]+ 427<br>R_t 1.69<br>Acidic |
| 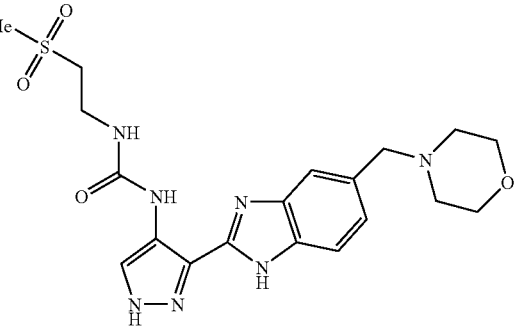 | [M + H]+ 448<br>R_t 2.07<br>Basic |

-continued

| Structure | LC/MS |
|---|---|
| (cyclopropylmethyl-NH-C(=O)-NH-pyrazole-benzimidazole-CH2-morpholine) | [M + H]+ 396<br>R$_t$ 1.74<br>Basic |
| (PhC(Me)2-NH-C(=O)-NH-pyrazole-benzimidazole-CH2-morpholine) | [M + H]+ 460<br>R$_t$ 2.03<br>Acidic |
| (N-methyl-2-oxopyridin-3-yl-NH-C(=O)-NH-pyrazole-benzimidazole-CH2-morpholine) | [M + H]+ 449<br>R$_t$ 2.32<br>Polar |
| (thiomorpholine-1,1-dioxide-C(=O)-NH-pyrazole-benzimidazole-CH2-morpholine) | [M + H]+ 460<br>R$_t$ 222<br>Basic |

| Structure | LC/MS |
|---|---|
| 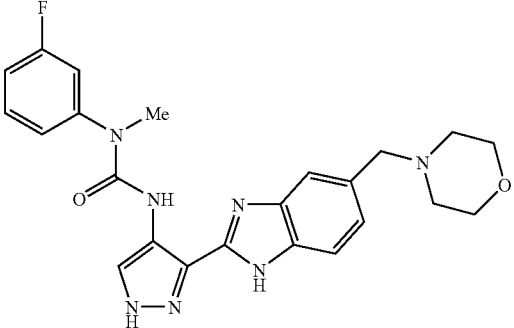 [SMILES: CN(C(=O)Nc1c[nH]nc1-c1nc2cc(CN3CCOCC3)ccc2[nH]1)c1cccc(F)c1] | [M + H]+ 450.24<br>R_t 2.09<br>Acidic |
| 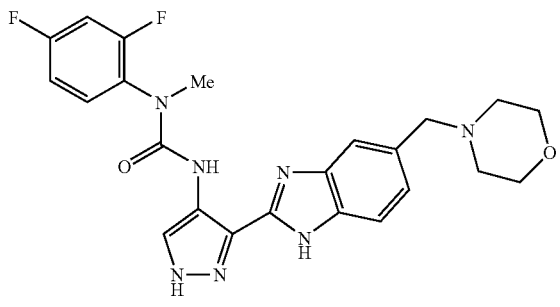 [SMILES: CN(C(=O)Nc1c[nH]nc1-c1nc2cc(CN3CCOCC3)ccc2[nH]1)c1ccc(F)cc1F] | [M + H]+ 468.38<br>R_t 1.99<br>Acidic |
| 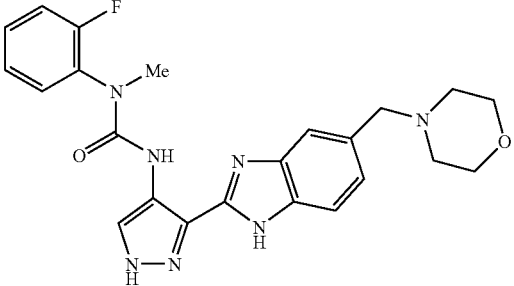 [SMILES: CN(C(=O)Nc1c[nH]nc1-c1nc2cc(CN3CCOCC3)ccc2[nH]1)c1ccccc1F] | [M + H]+ 450.41<br>R_t 2.68<br>Basic |
| 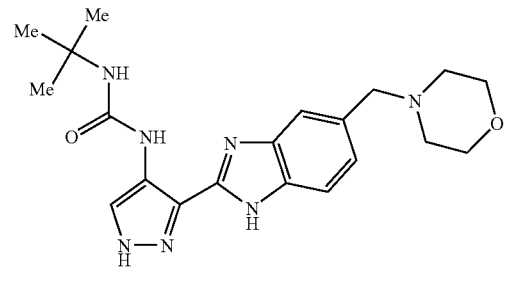 [SMILES: CC(C)(C)NC(=O)Nc1c[nH]nc1-c1nc2cc(CN3CCOCC3)ccc2[nH]1] | [M + H]+ 398<br>R_t 1.79<br>Acidic |
| 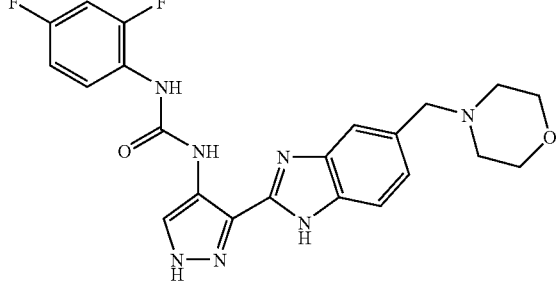 | [M + H]+ 454<br>R_t 1.95<br>Acidic |

| Structure | LC/MS |
|---|---|
| 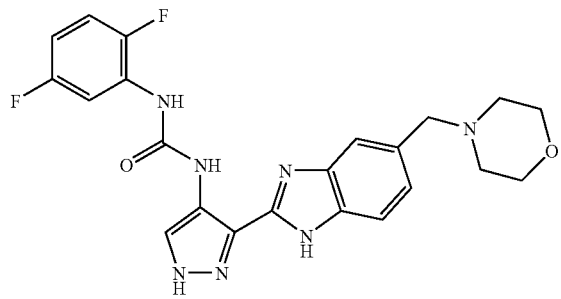 [SMILES: O=C(Nc1cc(F)ccc1F)Nc1c[nH]nc1-c1nc2cc(CN3CCOCC3)ccc2[nH]1] | |
| 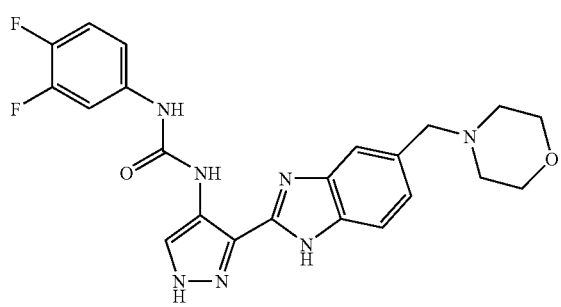 [SMILES: O=C(Nc1ccc(F)c(F)c1)Nc1c[nH]nc1-c1nc2cc(CN3CCOCC3)ccc2[nH]1] | [M + H]+ 452 R$_t$ 2.09 Acidic |
| 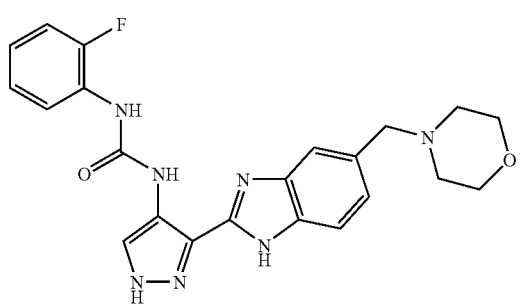 [SMILES: O=C(Nc1ccccc1F)Nc1c[nH]nc1-c1nc2cc(CN3CCOCC3)ccc2[nH]1] | [M + H]+ 4.36 R$_t$ 2.68 Basic |
| 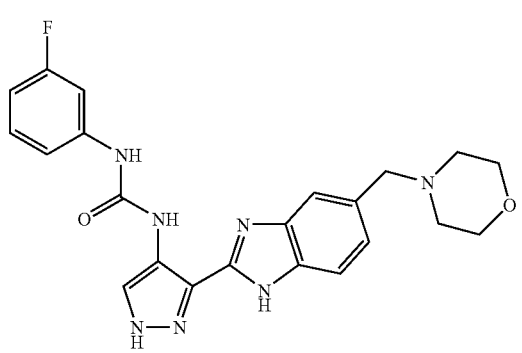 [SMILES: O=C(Nc1cccc(F)c1)Nc1c[nH]nc1-c1nc2cc(CN3CCOCC3)ccc2[nH]1] | [M + H]+ 436 R$_t$ 2.77 Basic |
| 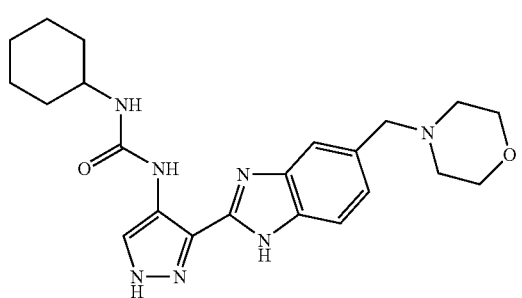 [SMILES: O=C(Nc1c[nH]nc1-c1nc2cc(CN3CCOCC3)ccc2[nH]1)NC1CCCCC1] | [M + H]+ 422 R$_t$ 1.89 Acidic |

-continued

| Structure | LC/MS |
|---|---|
| (furan-2-ylmethyl urea pyrazole benzimidazole morpholinomethyl) | [M + H]+ 422<br>R_t 1.65<br>Acidic |
| (3,5-difluorophenyl urea pyrazole benzimidazole morpholinomethyl) | [M + H]+ 452<br>R_t 2.21<br>Acidic |
| (2,4,6-trifluorophenyl urea pyrazole benzimidazole morpholinomethyl) | [M + H]+ 472<br>R_t 1.89<br>Acidic |
| (2-methoxyphenyl urea pyrazole benzimidazole morpholinomethyl) | [M + H]+ 448<br>R_t 6.28<br>Acidic |
| (5-chloro-2-methoxyphenyl urea pyrazole benzimidazole morpholinomethyl) | [M + H]+ 482<br>R_t 7.28<br>Acidic |

-continued

| Structure | LC/MS |
|---|---|
| | [M − H⁺]⁻ 368<br>R$_t$ 2.39<br>(Basic method) |
| | [M + H⁺]⁺ 396<br>R$_t$ 2.48<br>(Basic method) |
| | [M + H⁺]⁺ 384<br>R$_t$ 2.40<br>(Basic method) |

Determination of the Solubilities of Acid Addition Salts of 1-(2,6-difluorophenyl)-N-[3-(5-morpholin-4-ylmethyl-1H-benzimidazol-2-yl)-1H-pyrazol-4-yl]-urea This was carried out as described in Example 61 of WO 2006/070195 at pages 173 to 175 (the content of which is incorporated herein by reference).

Determination of the Solubilities of the Free Base and Salts of 1-Cyclopropyl-3-[3-(5-morpholin-4-ylmethyl-1H-benzimidazol-2-yl)-1H-pyrazol-4-yl]-urea This was carried out as described in Example 63 of WO 2006/070195 at pages 176 to 178 (the content of which is incorporated herein by reference).

Example A

Preparation of 1-Cyclopropyl-3-[3-(5-Morpholin-4-ylmethyl-1H-Benzoimidazol-2-yl)-1H-Pyrazol-4-yl]-Urea lactate salt To a solution of 1-cyclopropyl-3-[3-(5-morpholin-4-ylmethyl-1H-benzoimidazol-2-yl)-1H-pyrazol-4-yl]-urea (0.7 g, 1.83 mmol) in EtOAc-MeOH was added L-lactic acid (166 mg, 1.85 mmol). The mixture was stirred at ambient temperature then reduced in vacuo. This solid was purified by recrystallisation from boiling EtOH (20 mL) to give after drying 1-cyclopropyl-3-[3-(5-morpholin-4-ylmethyl-1H-benzoimidazol-2-yl)-1H-pyrazol-4-yl]-urea, L-lactate salt (0.48 g).

Example B
Synthesis of the L-lactate salt of 1-cyclopropyl-3-[3-(5-morpholin-4-ylmethyl-1H-benzoimidazol-2-yl)-1H-pyrazol-4-yl]-urea
The L-lactate salt of 1-cyclopropyl-3-[3-(5-morpholin-4-ylmethyl-1H-benzoimidazol-2-yl)-1H-pyrazol-4-yl]-urea may be prepared by the synthetic route shown in the Scheme below.
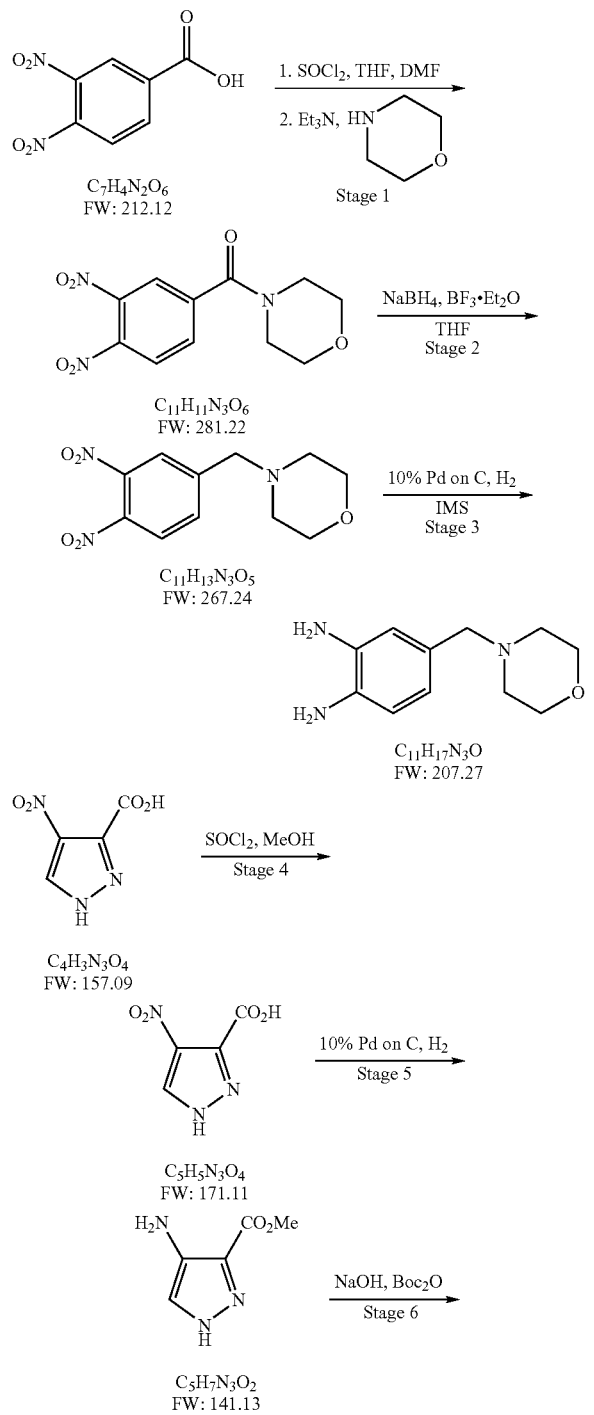
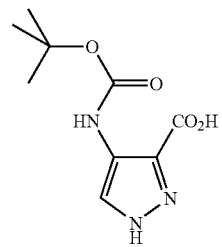
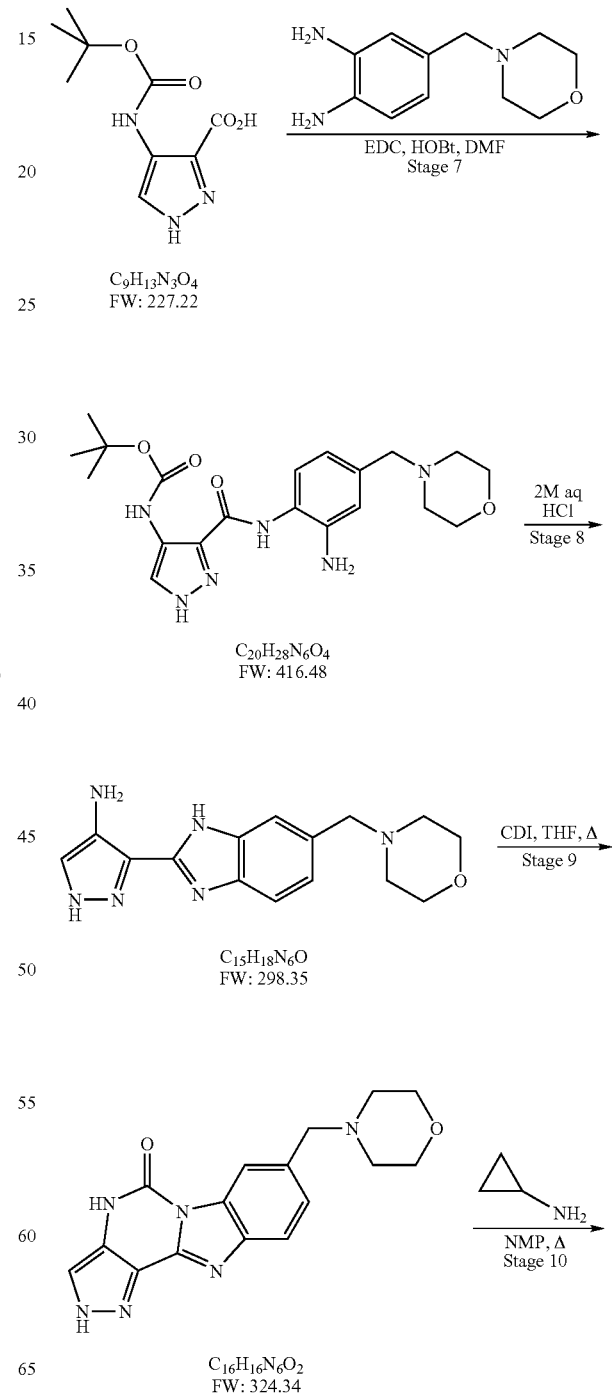

-continued

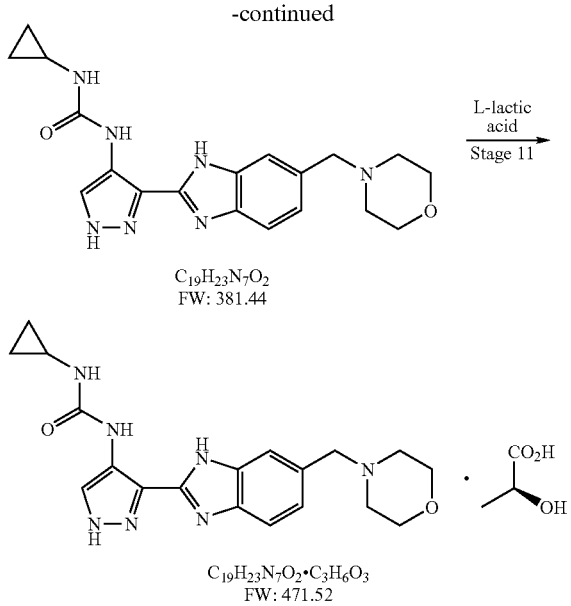

C<sub>19</sub>H<sub>23</sub>N<sub>7</sub>O<sub>2</sub>
FW: 381.44

L-lactic acid
Stage 11

C<sub>19</sub>H<sub>23</sub>N<sub>7</sub>O<sub>2</sub>·C<sub>3</sub>H<sub>6</sub>O<sub>3</sub>
FW: 471.52

Stage 1: Synthesis of (3,4-dinitro-phenyl)-morpholin-4-yl-methanone

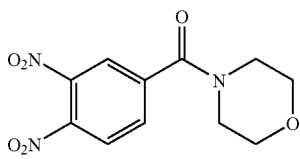

A solution of 3,4-dinitrobenzoic acid (10 g, 47 mmol, 1 eq.) and DMF (0.1 mL) in THF (100 mL) was treated with thionyl chloride (4.5 mL, 62 mmol, 1.3 eq.) then heated to reflux for 2.5 h. The mixture was cooled in ice then triethylamine (10 mL, 71 mmol, 1.1 eq.) was added over 20 min, keeping internal temperature <5° C. Morpholine (6.2 mL, 71 mmol, 1.5 eq) was added to the resulting thick yellow suspension over 15 min, keeping internal temperature <10° C. The ice-bath was removed and the mixture allowed to warm to r.t. After 15 min, a further portion of morpholine (1 mL, 11 mmol, 0.24 eq.) was added and the mixture stirred overnight.

The mixture was diluted with water (250 mL) and cooled in ice. A beige solid was filtered off under suction, washed with a further portion of cold water (25 mL) and dried in vacuo to afford the title compound (12.7 g, 96%).

Stage 2: Synthesis of 4-(3,4-dinitro-benzyl)-morpholine

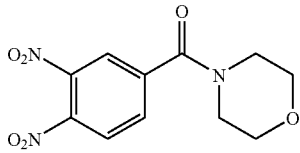 [SMILES: O=C(c1ccc([N+](=O)[O-])c([N+](=O)[O-])c1)N1CCOCC1]

Sodium borohydride (3.36 g, 89 mmol, 2.1 eq.) was ground, placed in a nitrogen-flushed flask and suspended in THF (120 mL). After cooling to ~0° C., boron trifluoride etherate (11.3 mL, 89 mmol, 2.1 eq.) was added via syringe. This reaction is mildly exothermic and some hydrogen evolution was noted. 4-(3,4-Dinitrobenzoyl)morpholine (11.91 g, 42 mmol, 1.0 eq.) was added as a solid in one portion, the vessel being rinsed with an additional portion of THF (20 mL). The ice-bath was removed and the suspension stirred at r.t. for 3 h before cooling again in ice. Methanol (100 mL) was added cautiously (hydrogen evolution) then the mixture was brought to reflux for 1 h. The mixture was concentrated in vacuo then the residue was partitioned between ethyl acetate (100 mL) and 1:1 saturated sodium bicarbonate solution/water (100 mL). The organic phase was separated, washed with water (50 mL) then brine (100 mL) and dried (MgSO<sub>4</sub>). The initial bicarbonate wash was extracted a second time with ethyl acetate (50 mL), this extract then being washed with the same aqueous washes used for the first extract before drying (MgSO<sub>4</sub>), combination and concentration to afford 10.97 g of crude material. Recrystallisation from methanol (45 mL, 10 mL wash) gave the title compound (9.34 g, 83%).

Stage 3: Synthesis of 4-morpholin-4-ylmethyl-benzene-1,2-diamine

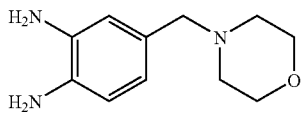 [SMILES: Nc1ccc(CN2CCOCC2)cc1N]

4-(3,4-Dinitrobenzyl)morpholine (21 g, 101 mmol) was suspended in ethanol (0.9 L) and the vessel purged with nitrogen. 10% Palladium on charcoal (1.05 g) was suspended in ethanol (25 mL) and added to the substrate. The mixture was cooled in ice then the atmosphere exchanged for hydrogen. The mixture was allowed to warm to 15-20° C. and hydrogenation continued at ambient pressure for 2 days. The vessel was purged with nitrogen then the mixture was filtered through Celite, rinsing with ethanol (0.3 L) in portions. Concentration afforded the title compound (15.8 g, 97%).

Stage 4: Synthesis of 4-nitro-1H-pyrazole-3-carboxylic acid methyl ester

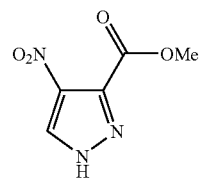 [SMILES: COC(=O)c1n[nH]cc1[N+](=O)[O-]]

A 20 L reaction vessel equipped with a digital thermometer and stirrer was charged with 4-nitro-1H-pyrazole-3-carboxylic acid (1.117 Kg, 7.11 mol, 1 wt) and methanol (8.950 L, 8 vol). The reaction mixture was stirred under nitrogen, cooled to 0 to 5° C., thionyl chloride (0.581 L, 8.0 mol, 0.52 vol) added over 180 minutes and the resultant mixture allowed to warm to and stir at 18 to 22° C. overnight after which time <sup>1</sup>H NMR analysis (d<sub>6</sub>-DMSO) indicated reaction completion. The reaction mixture was concentrated under reduced pressure at 40 to 45° C., the residue treated with toluene and re-concentrated (3×2.250 L, 3×2 vol) under reduced pressure at 40 to 45° C. to give 4-nitro-1H-pyrazole-3-carboxylic acid methyl ester as an off-white solid (1.210 Kg, 99.5% th).

Stage 5: Synthesis of 4-amino-1H-pyrazole-3-carboxylic acid methyl ester

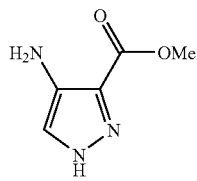

A 20 L reaction vessel equipped with a digital thermometer and stirrer was charged with palladium on carbon (10% wet paste, 0.170 Kg, 0.14 wt) under nitrogen. In a separate vessel, a slurry of 4-nitro-1H-pyrazole-3-carboxylic acid methyl ester (1.210 Kg, 7.07 mol, 1 wt) in ethanol (12.10 L, 10 vol) was warmed to 30 to 35° C. to effect dissolution and the solution added to the catalyst under nitrogen. Following a nitrogen-hydrogen purge sequence an atmosphere of hydrogen was introduced and the reaction mixture maintained at 28 to 30° C. until reaction completion (5 to 10 hours) was noted by $^1$H NMR analysis ($d_6$-DMSO). Following a purge cycle, the reaction mixture under nitrogen was filtered and the liquors concentrated under reduced pressure to give 4-amino-1H-pyrazole-3-carboxylic acid methyl ester (0.987 Kg, 98.9% th).

Stage 6: Synthesis of 4-tert-butoxycarbonylamino-1H-pyrazole-3-carboxylic acid

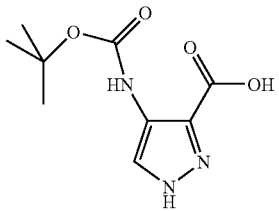 [SMILES: CC(C)(C)OC(=O)Nc1c[nH]nc1C(=O)O]

To a mixture of 4-amino-1H-pyrazole-3-carboxylic acid methyl ester (50.0 g, 355 mmol) in dioxane (500 mL) was added 2M aqueous NaOH solution (213 mL, 426 mmol), the mixture heated to 50° C. and stirred for 5 h. To this mixture was then added (BOC)$_2$O (81.4 g, 373 mmol), using a dioxane rinse (100 mL) and the mixture heated at 50° C. for a further 5 h, then stirred at ambient for 14 h. The dioxane was removed in vacuo and water (1 L) added. The mixture was taken to pH~2 using conc. aqueous HCl solution and the solid formed collected by filtration and dried on the filter. The solid was dried further through azeotrope with toluene (×3) and in the vacuum oven to give 4-tert-butoxycarbonylamino-1H-pyrazole-3-carboxylic acid (70.0 g, 87%) as a violet solid.

Stage 7: Synthesis of [3-(2-amino-4-morpholin-4-ylmethyl-phenvlcarbamoyl)-1H-pyrazol-4-yl]-carbamic acid tert-butyl ester

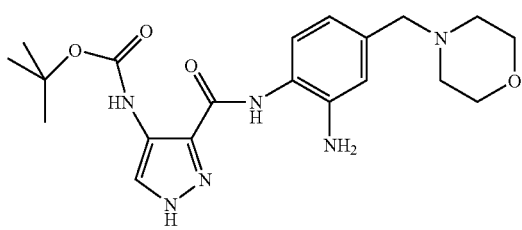 [SMILES: CC(C)(C)OC(=O)Nc1c[nH]nc1C(=O)Nc1ccc(CN2CCOCC2)cc1N]

A mixture of 4-tert-butoxycarbonylamino-1H-pyrazole-3-carboxylic acid (10.0 g, 44.1 mmol), 4-morpholin-4-ylmethyl-benzene-1,2-diamine (10.0 g, 48.5 mmol), EDC (10.14 g, 52.9 mmol) and HOBt (7.15 g, 52.9 mmol) in DMF (150 mL) was stirred at ambient temperature for 20 h and then the majority of the solvent removed in vacuo. The residue was partitioned between EtOAc (150 mL) and saturated aqueous NaHCO$_3$ (150 mL), the layers separated and the organic portion washed with brine, dried over MgSO$_4$ and reduced in vacuo to give [3-(2-amino-4-morpholin-4-ylmethyl-phenylcarbamoyl)-1H-pyrazol-4-yl]-carbamic acid tert-butyl ester (17.6 g, 96%) as a brown solid. LC/MS analysis indicates product contains ~15% of the di-amide. This shows at approx. 5% level in $^1$H NMR. Di-amide is cleaved in subsequent step.

Stage 8: Synthesis of 3-(5-morpholin-4-ylmethyl-1H-benzoimidazol-2-yl)-1H-pyrazol-4-ylamine

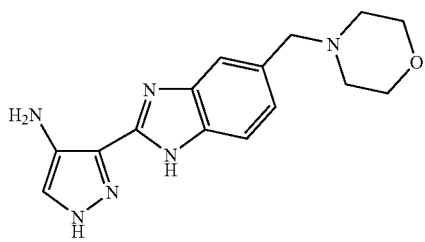 [SMILES: Nc1c[nH]nc1-c1nc2cc(CN3CCOCC3)ccc2[nH]1]

A mixture of [3-(2-amino-4-morpholin-4-ylmethyl-phenylcarbamoyl)-1H-pyrazol-4-yl]-carbamic acid tert-butyl ester (12.0 g, 28.8 mmol) and 2M aqueous HCl solution (50 mL) was heated at 85° C. for 14 h, then allowed to cool to ambient temperature. Solid Na$_2$CO$_3$ was carefully added until mixture was pH~8.5 and solution was saturated. A dark coloured gummy liquid was formed. The mixture was allowed to settle and the solvent decanted. To the remaining residue was added EtOH (60 mL), the mixture heated at reflux for 1 h and then hot filtered, washing with EtOH (2×20 mL), to remove inorganic residues. The filtrate was reduced in vacuo to give a glassy solid which was then stirred in Et$_2$O (60 mL) for 1 h and the resultant purple coloured powder collected by filtration and dried in vacuo to give 3-(5-morpholin-4-ylmethyl-1H-benzoimidazol-2-yl)-1H-pyrazol-4-ylamine (6.8 g, 80%, ~90% purity).

Stage 9: Synthesis of 7-morpholin-4-ylmethyl-2,4-dihydro-1,2,4,5a,10-pentaaza-cyclopenta[a]fluoren-5-one

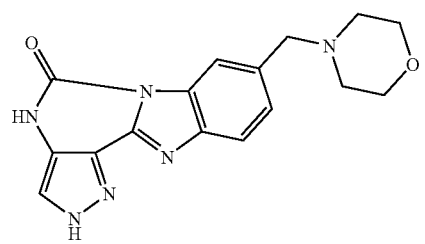 [SMILES: O=c1[nH]c2c[nH]nc2c2nc3ccc(CN4CCOCC4)cc3n12]

To a mixture of 3-(5-morpholin-4-ylmethyl-1H-benzoimidazol-2-yl)-1H-pyrazol-4-ylamine (3.2 g, 10.7 mmol) in anhydrous THF (50 mL) stirring at ambient temperature was added 1,1'-carbonyldiimidazole (1.78 g, 11 mmol). The mixture was heated at reflux for 14 h and then cooled to ambient. The solid formed was collected by filtration, washed with THF (20 mL) and dried in vacuo to give 7-morpholin-4-ylmethyl-2,4-dihydro-1,2,4,5a,10-pentaaza-cyclopenta[a]fluoren-5-one (2.34 g, 67%) as a pink solid.

Stage 10: Synthesis of 1-cyclopropyl-3-[3-(5-morpholin-4-ylmethyl-1H-benzoimidazol-2-yl)-1H-pyrazol-4-yl]-urea.

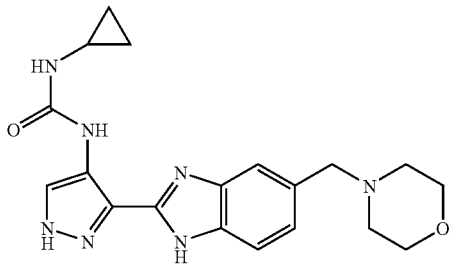 [SMILES: O=C(Nc1c[nH]nc1-c1nc2cc(CN3CCOCC3)ccc2[nH]1)NC1CC1]

To a mixture of 7-morpholin-4-ylmethyl-2,4-dihydro-1,2,4,5a,10-pentaaza-cyclopenta[a]fluoren-5-one (10.7 g, 32.9 mmol) in NMP (65 mL) was added cyclopropylamine (6.9 mL, 99 mmol). The mixture was heated at 100° C. for 5 h. LC/MS analysis indicated ~75% conversion to product, therefore a further portion of cyclopropylamine (2.3 mL, 33 mmol) was added, the mixture heated at 100° C. for 4 h and then cooled to ambient. The mixture was diluted with water (100 mL) and extracted with EtOAc (100 mL). The organic portion was washed with sat. aq. $NH_4Cl$ (2×50 mL) and brine (50 mL) and then the aqueous portions re-extracted with EtOAc (3×100 mL). The combined organic portions were dried over $MgSO_4$ and reduced in vacuo to give 1-cyclopropyl-3-[3-(5-morpholin-4-ylmethyl-1H-benzoimidazol-2-yl)-1H-pyrazol-4-yl]-urea as an orange glassy solid (9.10 g).

Stage 11: Synthesis of 1-cyclopropyl-3-[3-(5-morpholin-4-ylmethyl-1H-benzoimidazol-2-yl)-1H-pyrazol-4-yl]-urea, L-lactate salt

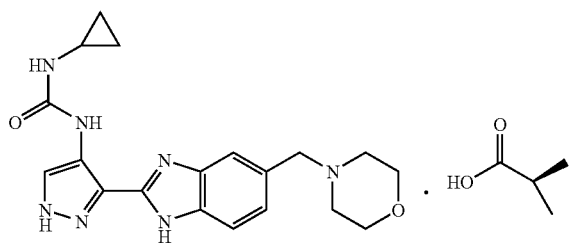

To a solution of 1-cyclopropyl-3-[3-(5-morpholin-4-ylmethyl-1H-benzoimidazol-2-yl)-1H-pyrazol-4-yl]-urea (9.10 g, 24 mmol) in EtOAc-iPrOH (1:1, 90 mL) was added L-lactic acid (2.25 g, 25 mmol). The mixture was stirred at ambient temperature for 24 h then reduced in vacuo. The residue was given consecutive slurries using toluene (100 mL) and $Et_2O$ (100 mL) and the resultant solid collected and dried (8.04 g).

This solid was purified by recrystallisation from boiling iPrOH (200 mL) to give after drying 1-cyclopropyl-3-[3-(5-morpholin-4-ylmethyl-1H-benzoimidazol-2-yl)-1H-pyrazol-4-yl]-urea, L-lactate salt (5.7 g) as a beige solid.

Example C

Stage 1: Preparation of (3,4-dinitrophenyl)-morpholin-4-yl-methanone

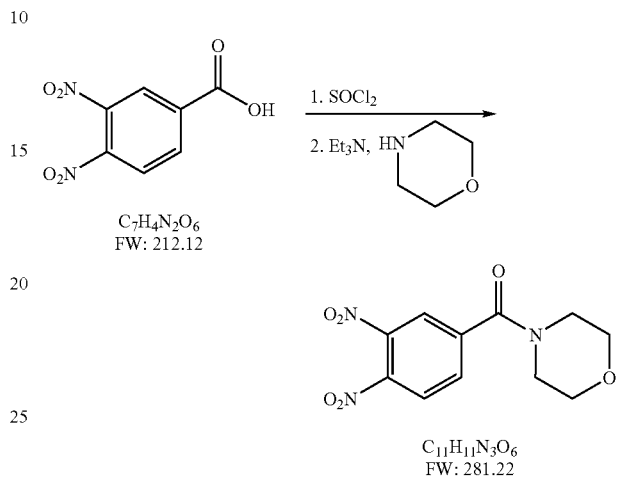

3,4-Dinitrobenzoic acid (1.000 Kg, 4.71 mol, 1.0 wt), tetrahydrofuran (10.00 L, 10.0 vol), and dimethylformamide (0.010 L, 0.01 vol) were charged to a flask under nitrogen. Thionyl chloride (0.450 L, 6.16 mol, 0.45 vol) was added at 20 to 30° C. and the reaction mixture was heated to 65 to 70° C. Reaction completion was determined by $^1$H NMR analysis ($d_6$-DMSO), typically in 3 hours. The reaction mixture was cooled to 0 to 5° C. and triethylamine (1.25 L, 8.97 mol, 1.25 vol) was added at 0 to 10° C. Morpholine (0.62 L, 7.07 mol, 0.62 vol) was charged to the reaction mixture at 0 to 10° C. and the slurry was stirred for 30 minutes at 0 to 10° C. Reaction completion was determined by $^1$H NMR analysis ($d_6$-DMSO). The reaction mixture was warmed to 15 to 20° C. and water (4.00 L, 4.0 vol) was added. This mixture was then charged to a 40 L flange flask containing water (21.00 L, 21.0 vol) at 15 to 25° C. to precipitate the product. The flask contents were cooled to and aged at 0 to 5° C. for 1 hour and the solids were collected by filtration. The filter-cake was washed with water (4×5.00 L, 4×5.0 vol) and the pH of the final wash was found to be pH 7. The wet filter-cake was analysed by $^1$H NMR for the presence of triethylamine hydrochloride. The filter-cake was dried at 40 to 45° C. under vacuum until the water content by KF<0.2% w/w, to yield (3,4-dinitrophenyl)-morpholin-4-yl-methanone (1.286 Kg, 97.0%, KF 0.069% w/w) as a yellow solid.

Stage 2: Preparation of 4-(3,4-dinitro-benzyl)-morpholine

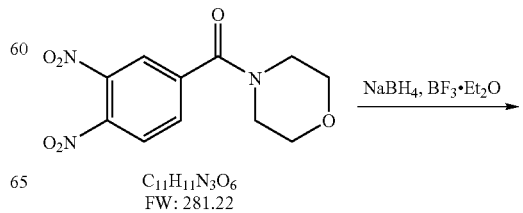

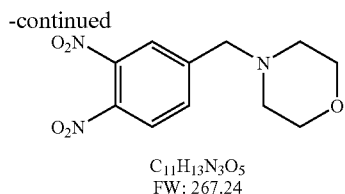

C₁₁H₁₃N₃O₅
FW: 267.24

(3,4-Dinitrophenyl)-morpholin-4-yl-methanone (0.750 Kg, 2.67 mol, 1.0 wt) and tetrahydrofuran (7.50 L, 10.0 vol) were charged to a flask under nitrogen and cooled to 0 to 5° C. Borontrifluoride etherate (0.713 L, 5.63 mol, 0.95 vol) was added at 0 to 5° C. and the suspension was stirred at this temperature for 15 to 30 minutes. Sodium borohydride (0.212 Kg, 5.60 mol, 0.282 wt) was added in 6 equal portions over 90 to 120 minutes. (A delayed exotherm was noted 10 to 15 minutes after addition of the first portion. Once this had started and the reaction mixture had been re-cooled, further portions were added at 10 to 15 minute intervals, allowing the reaction to cool between additions). The reaction mixture was stirred at 0 to 5° C. for 30 minutes. Reaction completion was determined by $^1$H NMR analysis (d$_6$-DMSO). Methanol (6.30 L, 8.4 vol) was added dropwise at 0 to 10° C. to quench the reaction mixture (rapid gas evolution, some foaming). The quenched reaction mixture was stirred at 0 to 10° C. for 25 to 35 minutes then warmed to and stirred at 20 to 30° C. (exotherm, gas/ether evolution on dissolution of solid) until gas evolution had slowed. The mixture was heated to and stirred at 65 to 70° C. for 1 hour. The mixture was cooled to 30 to 40° C. and concentrated under vacuum at 40 to 45° C. to give crude 4-(3,4-dinitro-benzyl)-morpholine (0.702 Kg, 98.4%) as a yellow/orange solid.

4-(3,4-Dinitro-benzyl)-morpholine (2.815 kg, 10.53 mol, 1.0 wt) and methanol (12.00 L, 4.3 vol) were charged to a flask under nitrogen and heated to 65 to 70° C. The temperature was maintained until complete dissolution. The mixture was then cooled to and aged at 0 to 5° C. for 1 hour. The solids were isolated by filtration. The filter-cake was washed with methanol (2×1.50 L, 2×0.5 vol) and dried under vacuum at 35 to 45° C. to give 4-(3,4-dinitro-benzyl)-morpholine (2.353 Kg, 83.5% based on input Stage 2, 82.5% overall yield based on total input Stage 1 material,) as a yellow solid.

Stage 3: Preparation of
4-morpholin-4-yl-methyl-benzene-1,2-diamine

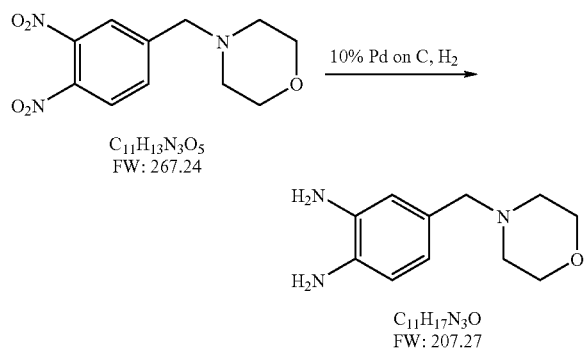

4-(3,4-Dinitro-benzyl)-morpholine (0.800 Kg, 2.99 mol, 1.0 wt), and ethanol (11.20 L, 14.0 vol) were charged to a suitable flask and stirred at 15 to 25° C. and a vacuum/nitrogen purge cycle was performed three times. 10% Palladium on carbon (10% Pd/C, 50% wet paste, 0.040 Kg, 0.05 wt wet weight) was slurried in ethanol (0.80 L, 1.0 vol) and added to the reaction. The mixture was cooled to 10 to 20° C. and a vacuum/nitrogen purge cycle was performed three times. A vacuum/hydrogen purge cycle was performed three times and the reaction was stirred under a hydrogen atmosphere at 10 to 20° C. Reaction completion was determined by $^1$H NMR analysis (d$_6$-DMSO), typically 14 to 20 hours. A vacuum/nitrogen purge cycle was performed three times and the reaction mixture was filtered through glass microfibre paper under nitrogen. The filter-cake was washed with ethanol (3×0.80 L, 3×1.0 vol) and the combined filtrate and washes were concentrated to dryness under vacuum at 35 to 45° C. to give 4-morpholin-4-yl-methyl-benzene-1,2-diamine (0.611 Kg 98.6%) as a brown solid.

Stage 4: Preparation of
4-nitro-1H-pyrazole-3-carboxylic acid methyl ester

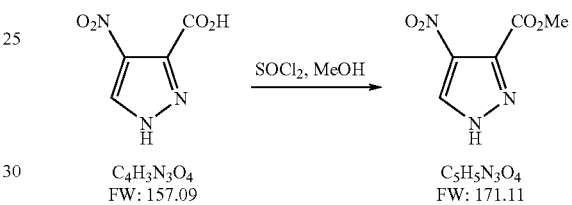

4-Nitro-1H-pyrazole-3-carboxylic acid (1.00 kg, 6.37 mol, 1.0 wt) and methanol (8.00 L, 8.0 vol) were charged to a flange flask equipped with a mechanical stirrer, condenser and thermometer. The suspension was cooled to 0 to 5° C. under nitrogen and thionyl chloride (0.52 L, 7.12 mol, 0.52 vol) was added at this temperature. The mixture was warmed to 15 to 25° C. over 16 to 24 hours. Reaction completion was determined by $^1$H NMR analysis (d$_6$-DMSO). The mixture was concentrated under vacuum at 35 to 45° C. Toluene (2.00 L, 2.0 vol) was charged to the residue and removed under vacuum at 35 to 45° C. The azeotrope was repeated twice using toluene (2.00 L, 2.0 vol) to give 4-nitro-1H-pyrazole-3-carboxylic acid methyl ester (1.071 Kg, 98.3%) as an off white solid.

Stage 5: Preparation of
4-amino-1H-pyrazole-3-carboxylic acid methyl ester

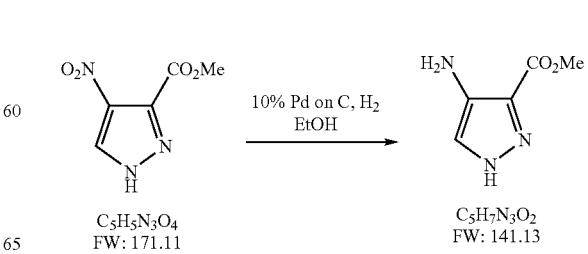

A suspension of 4-nitro-1H-pyrazole-3-carboxylic acid methyl ester (1.084 Kg, 6.33 mol, 1.0 wt) and ethanol (10.84 L, 10.0 vol) was heated to and maintained at 30 to 35° C. until complete dissolution occurred. 10% Palladium on carbon (10% Pd/C wet paste, 0.152 Kg, 0.14 wt) was charged to a separate flask under nitrogen and a vacuum/nitrogen purge cycle was performed three times. The solution of 4-nitro-1H-pyrazole-3-carboxylic acid methyl ester in ethanol was charged to the catalyst and a vacuum/nitrogen purge cycle was performed three times. A vacuum/hydrogen purge cycle was performed three times and the reaction was placed under an atmosphere of hydrogen. The reaction mixture was stirred at 28 to 30° C. until deemed complete by $^1$H NMR analysis (d$_6$-DMSO). The mixture was filtered under nitrogen and concentrated under vacuum at 35 to 45° C. to give 4-amino-1H-pyrazole-3-carboxylic acid methyl ester (0.883 Kg, 98.9%) as a purple solid.

Stage 6: Preparation of 4-tert-butoxycarbonylamino-1H-pyrazole-3-carboxylic acid

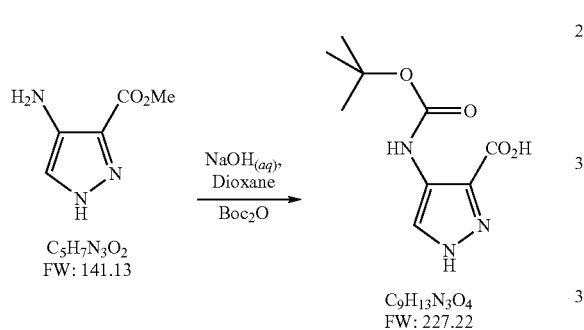

4-Amino-1H-pyrazole-3-carboxylic acid methyl ester (1.024 Kg, 7.16 mol, 1.0 wt) and dioxane (10.24 L, 10.0 vol) were charged to a flange flask equipped with a mechanical stirrer, condenser and thermometer. 2M aq. Sodium hydroxide solution (4.36 L, 8.72 mol, 4.26 vol) was charged at 15 to 25° C. and the mixture was heated to 45 to 55° C. The temperature was maintained at 45 to 55° C. until reaction completion, as determined by $^1$H NMR analysis (d$_6$-DMSO). Di-tert-butyl dicarbonate (Boc anhydride, 1.667 Kg, 7.64 mol, 1.628 wt) was added at 45 to 55° C. and the mixture was stirred for 55 to 65 minutes. $^1$H NMR IPC analysis (d$_6$-DMSO) indicated the presence of 9% unreacted intermediate. Additional di-tert-butyl dicarbonate (Boc anhydride, 0.141 Kg, 0.64 mol, 0.14 wt) was added at 55° C. and the mixture was stirred for 55 to 65 minutes. Reaction completion was determined by $^1$H NMR analysis (d$_6$-DMSO). The dioxane was removed under vacuum at 35 to 45° C. and water (17.60 L, 20.0 vol) was added to the residue. The pH was adjusted to pH 2 with 2M aq. hydrochloric acid (4.30 L, 4.20 vol) and the mixture was filtered. The filter-cake was slurried with water (10.00 L, 9.7 vol) for 20 to 30 minutes and the mixture was filtered. The filter-cake was washed with heptanes (4.10 L, 4.0 vol) and pulled dry on the pad for 16 to 20 hours. The solid was azeodried with toluene (5×4.00 L, 5×4.6 vol) then dried under vacuum at 35 to 45° C. to give 4-tert-butoxycarbonylamino-1H-pyrazole-3-carboxylic acid (1.389 Kg, 85.4%) as a purple solid.

Stage 7: Preparation of [3-(2-amino-4-morpholin-4-ylmethyl-phenylcarbamoyl)-1H-pyrazol-4-yl]-carbamic acid tert-butyl ester

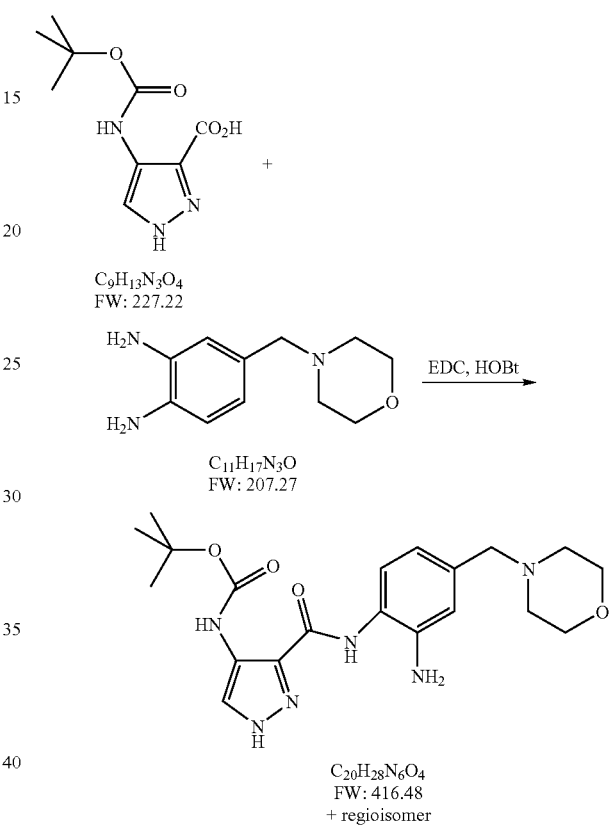

4-tert-Butoxycarbonylamino-1H-pyrazole-3-carboxylic acid (0.750 Kg, 3.30 mol, 1.0 wt), 4-morpholin-4yl-methyl-benzene-1,2-diamine (0.752 Kg, 3.63 mol, 1.0 wt) and N,N'-dimethylformamide (11.25 L, 15.0 vol) were charged under nitrogen to a flange flask equipped with a mechanical stirrer and thermometer. 1-Hydroxybenzotriazole (HOBT, 0.540 Kg, 3.96 mol, 0.72 wt) was added at 15 to 25° C. N-(3-Dimethylaminopropyl)-N'-ethylcarbodiimide (EDC, 0.759 Kg, 3.96 mol, 1.01 wt) was added at 15 to 25° C. and the mixture was stirred at this temperature for 16 to 24 hours. Reaction completion was determined by $^1$H NMR analysis. The reaction mixture was concentrated under vacuum at 35 to 45° C. The residue was partitioned between ethyl acetate (7.50 L, 10.0 vol) and sat. aq. sodium hydrogen carbonate solution (8.03 L, 10.7 vol) and the layers were separated. The organic phase was washed with brine (3.75 L, 5.0 vol), dried over magnesium sulfate (1.00 Kg, 1.33 wt) and filtered. The filter-cake was washed with ethyl acetate (1.50 L, 2.0 vol). The combined filtrate and wash were concentrated under vacuum at 35 to 45° C. to give [3-(2-amino-4-morpholin-4-ylmethyl-phenylcarbamoyl)-1H-pyrazol-4-yl]-carbamic acid tert-butyl ester (1.217 Kg, 88.6%) as a dark brown solid.

Stage 8: Preparation of 3-(5-morpholin-4-ylmethyl-1H-benzoimidazol-2-yl)-1H-pyrazol-4-ylamine

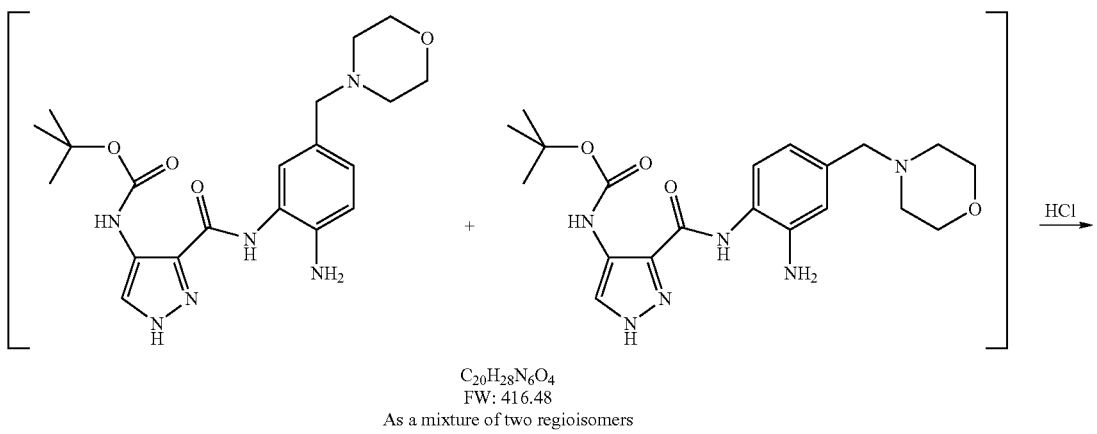

C20H28N6O4
FW: 416.48
As a mixture of two regioisomers

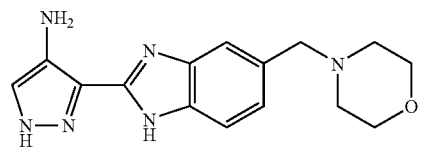

C15H18N6O
FW: 298.35

[3-(2-Amino-4-morpholin-4-ylmethyl-phenylcarbamoyl)-1H-pyrazol-4-yl]-carbamic acid tert-butyl ester (1.350 Kg, 3.24 mol, 1.0 wt) and ethanol (6.75 L, 5.0 vol) were charged to a flange flask equipped with a mechanical stirrer, condenser and thermometer. Conc. aq. hydrochloric acid (1.10 L, 13.2 mol, 0.80 vol) was added at 15 to 30° C. under nitrogen and the contents were then heated to 70 to 80° C. and maintained at this temperature for 16 to 24 hours. A second portion of hydrochloric acid (0.11 L, 1.32 mol, 0.080 vol) was added at 70 to 80° C. and the reaction was heated for a further 4 hours. Reaction completion was determined by HPLC analysis. The reaction mixture was cooled to 10 to 20° C. and potassium carbonate (1.355 Kg, 9.08 mol, 1.0 wt) was charged portionwise at this temperature. The suspension was stirred until gas evolution ceased and was then filtered. The filter-cake was washed with ethanol (1.35 L, 1.0 vol) and the filtrates retained. The filter-cake was slurried with ethanol (4.00 L, 3.0 vol) at 15 to 25° C. for 20 to 40 minutes and the mixture was filtered. The filter-cake was washed with ethanol (1.35 L, 1.0 vol) and the total combined filtrates were concentrated under vacuum at 35 to 45° C. Ethanol (4.00 L, 3.0 vol) was charged to the residue and removed under vacuum at 35 to 45° C. Tetrahydrofuran (5.90 L, 4.4 vol) was added to the residue and stirred for 10 to 20 minutes at 15 to 25° C. The resulting solution was filtered, the filter-cake was washed with tetrahydrofuran (1.35 L, 1.0 vol) and the combined filtrates were concentrated under vacuum at 35 to 45° C. Tetrahydrofuran (5.40 L, 4.0 vol) was charged to the concentrate and removed under vacuum at 35 to 45° C. Tetrahydrofuran (5.40 L, 4.0 vol) was charged to the concentrate and removed under vacuum at 35 to 45° C. to give the desired product, 3-(5-morpholin-4-ylmethyl-1H-benzoimidazol-2-yl)-1H-pyrazol-4-ylamine (0.924 Kg, 95.5%, 82.84% by HPLC area) as a purple foam.

Stage 9: Preparation of 7-morpholin-4-ylmethyl-2,4-dihydro-1,2,4,5a,10-pentaaza-cyclopenta[a]fluoren-5-one

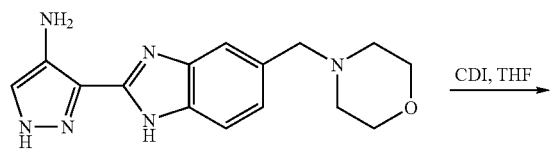

C15H18N6O
FW: 298.35

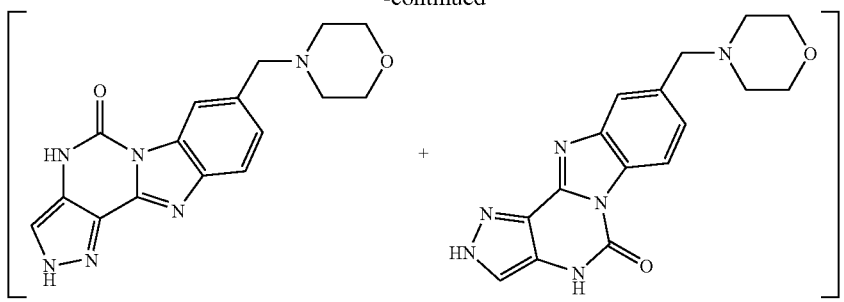

C₁₆H₁₆N₆O₂
FW: 324.34
As a mixture of two regioisomers 3-(5-Morpholin-4-ylmethyl-1H-benzoimidazol-2-yl)-1H-pyrazol-4-ylamine (0.993 Kg, 3.33 mol, 1.0 wt) and tetrahydrofuran (14.0 L, 15.0 vol) were charged to a flange flask equipped with a mechanical stirrer, condenser and thermometer. The contents were stirred under nitrogen at 15 to 25° C. and 1,1'-carbonyldiimidazole (0.596 Kg, 3.67 mol, 0.60 wt) was added. The contents were then heated to 60 to 70° C. and stirred at this temperature for 16 to 24 hours. Reaction completion was determined by TLC analysis. The mixture was cooled to 15 to 20° C. and filtered. The filter-cake was washed with tetrahydrofuran (4.00 L, 4.0 vol) and pulled dry for 15 to 30 minutes. The solid was dried under vacuum at 35 to 45° C. to yield 7-morpholin-4-ylmethyl-2,4-dihydro-1,2,4,5a,10-pentaaza-cyclopenta[a]fluoren-5-one (0.810 Kg, 75.0% th, 92.19% by HPLC area) as a purple solid.

Stage 10: Preparation of 1-cyclopropyl-3-[3-(5-morpholin-4-ylmethyl-1H-benzoimidazol-2-yl)-1H-pyrazol-4-yl]-urea

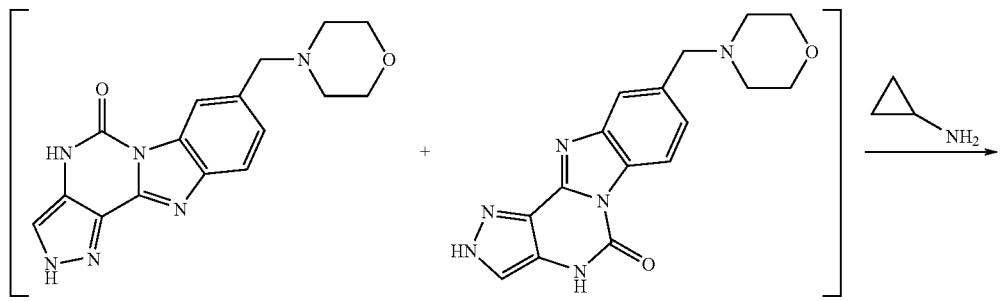

C₁₆H₁₆N₆O₂
FW: 324.34
As a mixture of two regioisomers

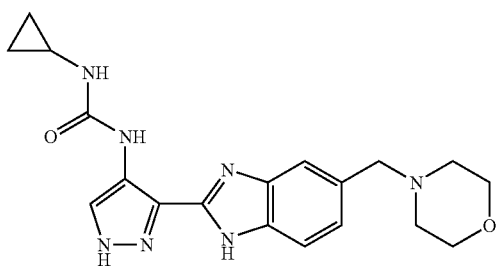

C₁₉H₂₃N₇O₂
FW: 381.44

7-Morpholin-4-ylmethyl-2,4-dihydro-1,2,4,5a,10-pentaaza-cyclopenta[a]fluoren-5-one (0.797 Kg, 2.46 mol, 1.0 wt) and 1-methyl-2-pyrrolidinone (2.40 L, 3.0 vol) were charged to a flange flask equipped with a mechanical stirrer, condenser and thermometer. Cyclopropylamine (0.279 Kg, 4.88 mol, 0.351 wt) was added at 15 to 30° C. under nitrogen.

The contents were heated to 95 to 105° C. and stirred at this temperature for 16 to 24 hours. Reaction completion was determined by $^1$H NMR analysis. The reaction mixture was cooled to 10 to 20° C. and ethyl acetate (8.00 L, 10.0 vol) and sat. aq. sodium chloride (2.50 L, 3.0 vol) were charged, the mixture was stirred for 2 to 5 minutes and the layers separated. The organic phase was stirred with sat. aq. sodium chloride (5.00 L, 6.0 vol) for 25 to 35 minutes, the mixture filtered and the filter-cake washed with ethyl acetate (0.40 L, 0.5 vol). The filter-cake was retained and the filtrates were transferred to a separating funnel and the layers separated. The procedure was repeated a further 3 times and the retained solids were combined with the organic phase and the mixture concentrated to dryness under vacuum at 35 to 45° C. The concentrate was dissolved in propan-2-ol (8.00 L, 10.0 vol) at 45 to 55° C. and activated carbon (0.080 Kg, 0.1 wt) was charged. The mixture was stirred at 45 to 55° C. for 30 to 40 minutes and then hot filtered at 45 to 55° C. The filter-cake was washed with propan-2-ol (0.40 L, 0.5 vol). Activated carbon (0.080 L, 0.1 wt) was charged to the combined filtrates and wash and the mixture stirred at 45 to 55° C. for 30 to 40 minutes. The mixture was hot filtered at 45 to 55° C. and the filter-cake washed with propan-2-ol (0.40 L, 0.5 vol). The filtrates and wash were concentrated under vacuum at 35 to 45° C. Ethyl acetate (8.00, 10.0 vol) and water (2.20 L, 3.0 vol) were charged to the concentrate at 25 to 35° C. and the mixture stirred for 1 to 2 minutes. The layers were separated and the organic phase was concentrated under vacuum at 35 to 45° C. Ethyl acetate (4.00 L, 5.0 vol) was charged to the residue and concentrated under vacuum at 35 to 45° C. Ethyl acetate (4.00 L, 5.0 vol) was charged to the residue and the mixture was stirred for 2 to 20 hours at 15 to 25° C. The mixture was cooled to and aged at 0 to 5° C. for 90 to 120 minutes and then filtered. The filter-cake was washed with ethyl acetate (0.80 L, 1.0 vol) and pulled dry for 15 to 30 minutes. The solid was dried under vacuum at 35 to 45° C. to yield 1-cyclopropyl-3-[3-(5-morpholin-4-ylmethyl-1H-benzoimidazol-2-yl)-1H-pyrazol-4-yl]-urea (0.533 Kg, 56.8%, 93.20% by HPLC area) as a brown solid.

Several batches of Stage 9 product were processed in this way and the details of the quantities of starting material and product for each batch are set out in Table 1A.

Stage 11: Preparation of 1-cyclopropyl-3-[3-(5-morpholin-4-ylmethyl-1H-benzoimidazol-2-yl)-1H-pyrazol-4-yl]-urea L-lactic acid salt

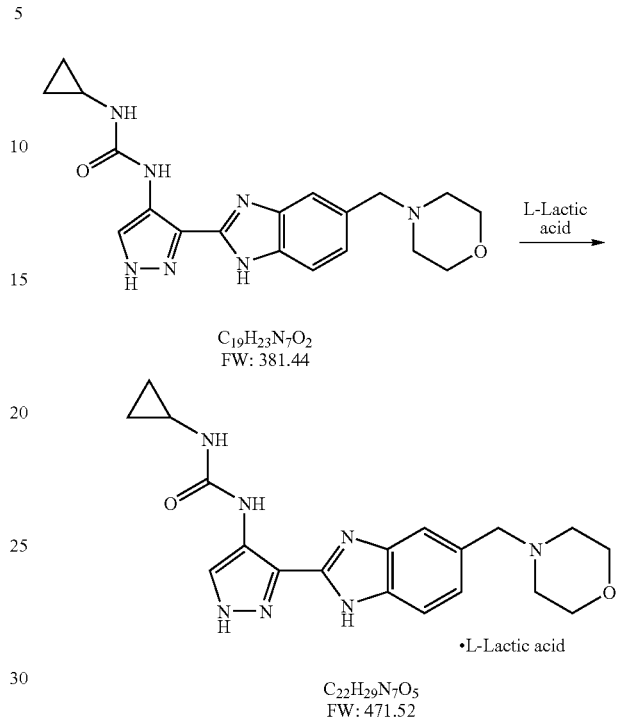

1-Cyclopropyl-3-[3-(5-morpholin-4-ylmethyl-1H-benzoimidazol-2-yl )-1H-pyrazol-4-yl]-urea (1.859 Kg, 4.872 mol, 1.0 wt), propan-2-ol (9.00 L, 5.0 vol) and ethyl acetate (8.00 L, 4.5 vol) were charged to a flange flask equipped with a mechanical stirrer and thermometer. The contents were stirred under nitrogen and L-lactic acid (0.504 Kg, 5.59 mol, 0.269 wt) was added at 15 to 25° C. followed by a line rinse of ethyl acetate (0.90 L, 0.5 vol). The mixture was stirred at 15 to 25° C. for 120 to 140 minutes. The solid was isolated by filtration, the filter-cake washed with ethyl acetate (2×2.00 L, 2×1.0 vol) and pulled dry for 20 to 40 minutes. The filter-cake was dissolved in ethanol (33.00 L, 17.7 vol) at 75 to 85° C., cooled to 65 to 70° C. and the solution clarified through glass microfibre paper. The filtrates were cooled to and aged at 15 to 25° C. for 2 to 3 hours. The crystallised solid was isolated

TABLE 1A

Yields from urea formation step - Stage 10

| Batch | Input (g) of 7-Morpholin-4-ylmethyl-2,4-dihydro-1,2,4,5a,10-pentaaza-cyclopenta[a]fluoren-5-one | Input (g) of 1-cyclopropyl-3-[3-(5-morpholin-4-ylmethyl-1H-benzoimidazol-2-yl)-1H-pyrazol-4-yl]-urea | Chemical purity by HPLC area |
|---|---|---|---|
| 1 | 680 | 442 | 91.80 |
|   |     | 55.2% th, 64.9% w/w |   |
| 2 | 882 | 487 | 91.21 |
|   |     | 47.0% th, 56.6% w/w |   |
| 3 | 879 | 445 | 91.66 |
|   |     | 43.0% th, 50.6% w/w |   |
| 4 | 797 | 533 | 93.20 |
|   |     | 56.8% th, 66.8% w/w |   | by filtration, the filter-cake washed with ethanol (2×1.00 L, 2×0.5 vol) and pulled dry for at least 30 minutes. The solid was dried under vacuum at 35 to 45° C. to yield 1-cyclopropyl-3-[3-(5-morpholin-4-ylmethyl-1H-benzoimidazol-2-yl)-1H-pyrazol-4-yl]-urea L-lactic acid salt (1.386 Kg, 58.7% th, 99.47% by HPLC area,) as a dark pink uniform solid.

$^1$H NMR data (400 MHz, CD$_3$OD) δ 8.08 (s,1H, pyrazole-CH), 7.66 (s,1H, aryl-CH), 7.60 (d, J=8.0 Hz, 1H, aryl-CH), 7.29 (d, J=8.5 Hz, 1H, aryl-CH), 4.15 (q, J=7.0 Hz, 1H, lactate-CH), 3.96 (s, 2H, benzyl-CH$_2$), 3.79-3.77 (m, 4H, morpholino-(CH$_2$)$_2$), 2.82-2.80 (m, 4H, morpholino-(CH$_2$)$_2$), 2.74-2.68 (m, 1H, cyclopropyl-CH), 1.38 (d, J=7.0 Hz, 3H, lactate-CH$_3$), 0.98 (br s, 2H, cyclopropyl-CH$_2$), 0.68 (br s, 2H, cyclopropyl-CH$_2$).

Example D

The preparation of 1-cyclopropyl-3-[3-(5-morpholin-4-ylmethyl-1H-benzoimidazol-2-yl)-1H-pyrazol-4-yl]-urea L-lactic acid salt as described in Example 66 of WO 2006/070195 and outlined above can be completed using the revised procedures outlined below in Example (i) and (ii).

Example (i)

Further to Example 66 of WO 2006/070195, the preparation of 1-cyclopropyl-3-[3-(5-morpholin-4-ylmethyl-1H-benzoimidazol-2-yl)-1H-pyrazol-4-yl]-urea L-lactic acid salt can be completed using the revised procedures outlined below.

Stage 1: Preparation of 1-cyclopropyl-3-[3-(5-morpholin-4-ylmethyl-1H-benzoimidazol-2-yl)-1H-pyrazol-4-yl]-urea

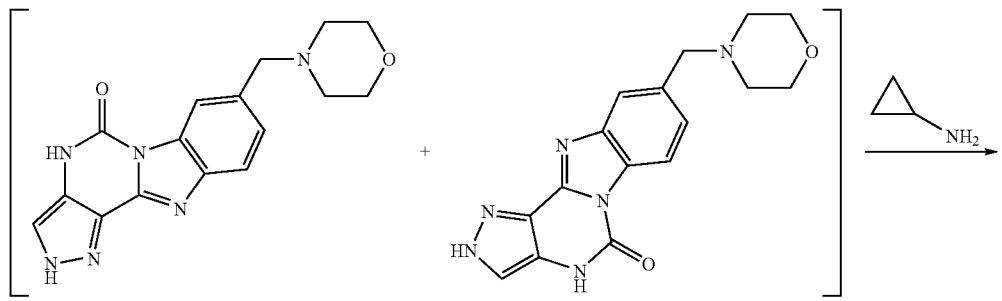

C$_{16}$H$_{16}$N$_6$O$_2$
FW: 324.34
As a mixture of two regioisomers

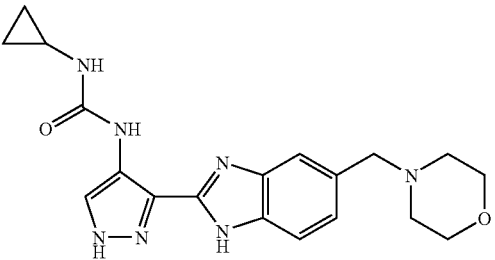

C$_{19}$H$_{23}$N$_7$O$_2$
FW: 381.44

The infra-red spectrum of the lactate salt (KBr disc method) included characteristic peaks at 3229, 2972 and 1660 cm$^{-1}$.

Without wishing to be bound by any theory, it is believed that the infra red peaks can be assigned to structural components of the salt as follow:

| Peak: | Due to: |
|---|---|
| 3229 cm$^{-1}$ | N—H |
| 2972 cm$^{-1}$ | aliphatic C—H |
| 1660 cm$^{-1}$ | urea C=O |

7-Morpholin-4-ylmethyl-2,4-dihydro-1,2,4,5a,10-pentaaza-cyclopenta[a]fluoren-5-one (1.0 wt, prepared as outlined in Example 66 of WO 2006/070195) and a solvent such as n-butanol, butyronitrile, glycol or toluene (3.0 vol) can be charged to a flange flask equipped with a mechanical stirrer, condenser and thermometer. Cyclopropylamine (0.351 wt) can be added at temperature such as 15 to 30° C. under an inert atmosphere e.g. nitrogen. The contents can be heated to 40 to 105° C., in particular 40-80° C. and stirred at this temperature for 16 to 24 hours. Reaction completion can be determined by $^1$H NMR analysis. The reaction mixture can then be cooled to 10 to 20° C. The product can then be isolated by organic-aqueous extraction method as outlined above in Example 66, or an alternative method of isolation may be employed such as the addition of an anti-solvent, for example n-heptanes, to the reaction mixture. This could allow the reaction product to precipitate with subsequent isolation by filtration. The solid can then be dried under vacuum at 35 to 45° C. to yield 1-cyclopropyl-3-[3-(5-morpholin-4-ylmethyl-1H-benzoimidazol-2-yl)-1H-pyrazol-4-yl]-urea. At this stage the solid can be purified by recrystallisation from an appropriate solvent, preferably a Class 2 or 3 solvent[1]. In addition, alternative methods of purification aside from recrystallisation may be employed for purification of the product such as flash column chromatography or filtration through a plug of silica gel or reverse-phase silica gel.

[1] Class 3 and Class 2 solvents are as outlined Q3C - Tables and List in Guidance for Industry Q3C Impurities: Residual Solvents (November 2003, CDER, CBER, FDA, ICH) and as further outlined in Impurities: Guideline for Residual Solvents (1997, ICH).

Stage 2: Preparation of 1-cyclopropyl-3-[3-(5-morpholin-4-ylmethyl-1H-benzoimidazol-2-yl)-1H-pyrazol-4-yl]-urea L-lactic acid salt

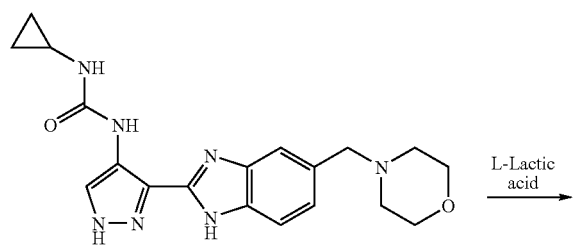

$C_{19}H_{23}N_7O_2$
FW: 381.44

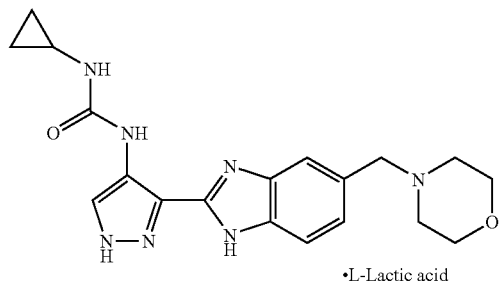

•L-Lactic acid $C_{22}H_{29}N_7O_5$
FW: 471.52

1-Cyclopropyl-3-[3-(5-morpholin-4-ylmethyl-1H-benzoimidazol-2-yl )-1H-pyrazol-4-yl]-urea (1.0 wt), in a Class 2 or Class 3 solvent in particular a Class 3 solvent such as aqueous ethanol (5.0-10.0 vol), can be charged to a flange flask equipped with a mechanical stirrer and thermometer. The contents are stirred under an inert atmosphere e.g. nitrogen and L-lactic acid (0.269 wt) can be added at 15 to 25° C. followed by a line rinse of the appropriate solvent such as aqueous ethanol (0.5 vol). The mixture can be stirred at 15 to 25° C. for 120 to 140 minutes. The solid may be isolated by filtration or by use of addition of anti-solvent such as n-butanol to bring the salt out of solution and then isolated by filtration. The filter-cake can be washed with the appropriate solvent (2×2.00 L, 2×1.0 vol) and pulled dry for 20 to 40 minutes. The filter-cake can then be dissolved in a Class 2 or Class 3 solvent in particular a Class 3 solvent (~3-60 vol) at 40 to 150° C., cooled to 40 to 70° C. and the solution clarified through glass microfibre paper. The filtrates can be cooled to and aged at 15 to 25° C. for 2 to 3 hours. The crystallised solid can be isolated by filtration, the filter-cake washed with the appropriate solvent (2×0.5-2 vol) and pulled dry for at least 30 minutes. The solid can then be dried under vacuum at 35 to 45° C. to yield 1-cyclopropyl-3-[3-(5-morpholin-4-ylmethyl-1H-benzoimidazol-2-yl)-1H-pyrazol-4-yl]-urea L-lactic acid salt. In addition, alternative methods of purification aside from recrystallisation may be employed for purification of the product such as flash column chromatography or filtration through a plug of silica gel or reverse-phase silica gel.

Example (ii)

Further to Example 66 of WO 2006/070195, the preparation of 1-cyclopropyl-3-[3-(5-morpholin-4-ylmethyl-1H-benzoimidazol-2-yl)-1H-pyrazol-4-yl]-urea L-lactic acid salt can be completed using the revised procedures outlined below.

Stage 1: Preparation of 1-cyclopropyl-3-[3-(5-morpholin-4-ylmethyl-1H-benzoimidazol-2-yl)-1H-pyrazol-4-yl]-urea

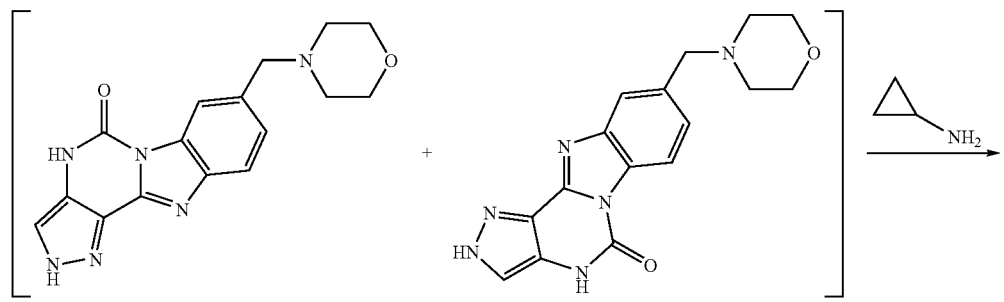

$C_{16}H_{16}N_6O_2$
FW: 324.34
As a mixture of two regioisomers

-continued

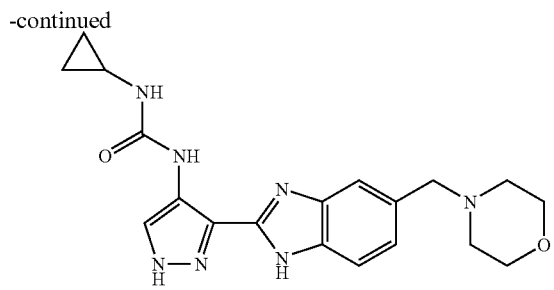

C₁₉H₂₃N₇O₂
FW: 381.44

7-Morpholin-4-ylmethyl-2,4-dihydro-1,2,4,5a,10-pentaaza-cyclopenta[a]fluoren-5-one (1.0 wt, prepared as outlined above in Example 66 of WO 2006/070195) and 1-methyl-2-pyrrolidinone (3.0 vol) are charged to a suitably sized flange flask equipped with a mechanical stirrer, condenser and thermometer. Cyclopropylamine (0.351 wt) is added at 15 to 30° C. under nitrogen. The contents are then heated to 95 to 105° C. and stirred at this temperature until the reaction is judged complete by $^1$H NMR analysis. Once complete, the reaction mixture is cooled to 16 to 25° C. and added slowly (approximately 2 to 3 hours) to stirred ca. 13% w/w sodium chloride solution (11.5 vol) whilst maintaining the mixture at 16 to 25° C. A precipitate is formed. The transfer of the reaction mixture is completed with a 1-methyl-2-pyrrolidinone (0.5 vol) rinse at 16 to 25° C. The precipitated solid is collected by filtration, washed with water (0.5 vol) and pulled dry on the filter until deemed suitable for handling. The solid is suspended in ethyl acetate (5.0 vol) and water (6.0 vol) and stirred at 16 to 25° C. for 60 to 70 minutes. The solid is collected by filtration, sequentially washed with ethyl acetate (1.0 vol) and mixed heptanes (2×2.0 vol) and dried on the filter until deemed suitable for handling. The solid is suspended in ethyl acetate (4.0 vol) and stirred at 15 to 25° C. for at least 60 minutes. The solid is collected by filtration, washed with ethyl acetate (1.0 vol) and pulled dry on the filter to yield crude 1-cyclopropyl-3-[3-(5-morpholin-4-ylmethyl-1H-benzoimidazol-2-yl)-1H-pyrazol-4-yl]-urea (60 to 80% w/w) as a dark brown/red solid.

Crude 1-cyclopropyl-3-[3-(5-morpholin-4-ylmethyl-1H-benzoimidazol-2-yl)-1H-pyrazol-4-yl]-urea (1.0 wt) is dissolved in propan-2-ol (15 vol) at 45 to 55° C. and activated carbon (DARCO KB) (0.2 wt) is charged. The mixture is stirred at 45 to 55° C. for 60 to 70 minutes and then hot filtered at 45 to 55° C. The filter-cake is washed with propan-2-ol (2.5 vol). Activated carbon (DARCO KB) (0.2 wt) is charged to the combined filtrate and wash and the mixture stirred at 45 to 55° C. for 60 to 70 minutes. The mixture is hot filtered at 45 to 55° C. and the filter-cake is washed with propan-2-ol (2.5 vol). The combined filtrate and wash are concentrated under vacuum at 35 to 45° C. to yield the desired product, 1-cyclopropyl-3-[3-(5-morpholin-4-ylmethyl-1H-benzoimidazol-2-yl)-1H-pyrazol-4-yl]-urea, as a brown foam in 65 to 100% w/w yield.

Stage 2: Preparation of 1-cyclopropyl-3-[3-(5-morpholin-4-ylmethyl-1H-benzoimidazol-2-yl)-1H-pyrazol-4-yl]-urea L-lactic acid salt Using material generated from the alternative procedure in Example B Stage 1 (above), the salt formation procedure can be performed as in Example 66A Stage 11 of WO 2006/070195, to give 1-cyclopropyl-3-[3-(5-morpholin-4-ylmethyl-1H-benzoimidazol-2-yl)-1H-pyrazol-4-yl]-urea L-lactic acid salt as an off-white solid.

Synthesis of Crystalline Free Base And Crystalline Salt Forms Of 1-Cyclopropyl-3-[3-(5-Morpholin-4-ylmethyl-1H-Benzoimidazol-2-yl)-1H-Pyrazol-4-yl]-Urea A. Preparation of 1-Cyclopropyl-3-[3-(5-Morpholin-4-ylmethyl-1H-Benzoimidazol-2-yl)-1H-Pyrazol-4-yl]-Urea free base A sample of crude 1-cyclopropyl-3-[3-(5-morpholin-4-ylmethyl-1H-benzoimidazol-2-yl)-1H-pyrazol-4-yl]-urea free base was prepared as outlined in Example 60 and initially purified by column chromatography on silica gel, eluting with EtOAc-MeOH (98:2-80:20). A sample of the free base obtained was then recrystallised from hot methanol to give crystalline material of 1-cyclopropyl-3-[3-(5-morpholin-4-ylmethyl-1H-benzoimidazol-2-yl )-1H-pyrazol-4-yl]-urea free base.

B. Preparation of 1-Cyclopropyl-3-[3-(5-Morpholin-4-ylmethyl-1H-Benzoimidazol-2-yl)-1H-Pyrazol-4-yl]-Urea free base dihydrate A sample of crude 1-cyclopropyl-3-[3-(5-morpholin-4-ylmethyl-1H-benzoimidazol-2-yl)-1H-pyrazol-4-yl]-urea free base was dissolved in THF and then concentrated in vacuo to a minimum volume (~4 volumes). To the solution was added water dropwise (2-4 volumes) until the solution became turbid. A small amount of THF was added to re-establish solution clarity and the mixture left to stand overnight to give a crystalline material which was air-dried to give 1-cyclopropyl-3-[3-(5-morpholin-4-ylmethyl-1H-benzoimidazol-2-yl)-1H-pyrazol-4-yl]-urea free base dihydrate.

C. Preparation of 1-Cyclopropyl-3-[3-(5-Morpholin-4-ylmethyl-1H-Benzoimidazol-2-yl)-1H-Pyrazol-4-yl]-Urea hydrochloride salt A sample of crude 1-cyclopropyl-3-[3-(5-morpholin-4-ylmethyl-1H-benzoimidazol-2-yl)-1H-pyrazol-4-yl]-urea free base was dissolved in the minimum amount of MeOH and then diluted with EtOAc. To the solution at 0° C. was slowly added 1.1 equivalents of HCl (4M solution in dioxane). Following addition, solid precipitated from solution which was collected by filtration. To the solid was added MeOH and the mixture reduced in vacuo. To remove traces of residual MeOH the residue was evaporated from water and then dried at 60° C./0.1 mbar to give the hydrochloride salt.

D. Preparation of 1-Cyclopropyl-3-[3-(5-Morpholin-4-ylmethyl-1H-Benzoimidazol-2-yl)-1H-Pyrazol-4-yl]-Urea ethanesulfonate salt To a solution of 1-cyclopropyl-3-[3-(5-morpholin-4-ylmethyl-1H-benzoimidazol-2-yl)-1H-pyrazol-4-yl]-urea free base in MeOH-EtOAc was added 1 equivalent of ethanesulfonic acid. The mixture was stirred at ambient temperature and then reduced in vacuo. The residue was taken up in MeOH and to the solution was added Et$_2$O. Mixture left to stand for 72 h and the solid formed collected by filtration and dried to give 1-cyclopropyl-3-[3-(5-morpholin-4-ylmethyl-1H-benzoimidazol-2-yl)-1H-pyrazol-4-yl]-urea ethanesulfonate salt.

E. Preparation of 1-Cyclopropyl-3-[3-(5-Morpholin-4-ylmethyl-1H-Benzoimidazol-2-yl)-1H-Pyrazol-4-yl]-Urea methanesulfonate salt To a solution of 1-cyclopropyl-3-[3-(5-morpholin-4-ylmethyl-1H-benzoimidazol-2-yl)-1H-pyrazol-4-yl]-urea free base (394 mg) in MeOH-EtOAc was added 1 equivalent of methanesulfonic acid (67 μl). A solid was formed which was collected by filtration, washing with EtOAc. The solid was dissolved in the minimum amount of hot MeOH, allowed to cool and then triturated with Et$_2$O. The solid was left to stand for 72 h and then collected by filtration, washing with MeOH, to give 1-cyclopropyl-3-[3-(5-morpholin-4-ylmethyl-1H-benzoimidazol-2-yl)-1H-pyrazol-4-yl]-urea methanesulfonate salt.

Characterisation of 1-Cyclopropyl-3-[3-(5-Morpholin-4-ylmethyl-1H-Benzoimidazol-2-yl)-1H-Pyrazol-4-yl]-Urea Free Base and Salts Various forms of 1-cyclopropyl-3-[3-(5-morpholin-4-ylmethyl-1H-benzoimidazol-2-yl)-1H-pyrazol-4-yl]-urea were characterised. The forms selected for characterisation were identified from studies which primarily investigated extent of polymorphism and salt stability. The salts selected for further characterisation were the L-lactate salt, Free base dihydrate, Esylate salt, Free base and Hydrochloride salt.

A1. Differential Scanning Calorimetry (DSC):

Thermograms were collected on a TA instrument Q1000 equipped with a 50 position auto-sampler. The energy and temperature calibration standard was indium. Samples were heated at a rate of 10° C./minute from 10 to 250° C. A nitrogen purge of 30 ml/min was maintained over the sample. Between 2 and 10 mg of sample was used (unless otherwise stated) and all samples were enclosed in an aluminium pan with a pinhole in the lid.

| Identity | Melting Point (° C.) |
| --- | --- |
| L-lactate salt | Onset at 190° C. |
| | Minimum at 194.6° C. |
| Free base dihydrate | Desolvates (peaking at 110° C.) |
| Esylate salt | None seen (up to 350° C.) |
| Free base | 193° C. |
| Hydrochloride salt | 190° C. |

A2. Further Differential Scanning Calorimetry (DSC):

Thermograms were collected on a Mettler Toledo 821e Differential Scanning Calorimeter. Samples were heated at a rate of 10° C./minute from 40° C. to 300° C. A nitrogen purge of 80 ml/min was maintained over the sample. Approximately 5-10 mg of sample was used and all samples were enclosed in a suitable high pressure pan (e.g. small aluminum, medium pressure aluminum or high pressure gold plated pan).

| Identity | Melting Point (° C.) |
| --- | --- |
| L-lactate salt (as prepared from Example 66) | Minimum at 195.7° C. |
| L-lactate salt (as prepared from Example 66) | Minimum at 196.3° C. |

B. Thermogravimetric Analysis (TGA):

Thermograms were collected on a TA Instruments Q500. Samples were heated at a rate of 10° C./minute. A nitrogen purge of 100 ml/minute was maintained over the sample. Typically 5-20 mg of sample was loaded into a tared, open aluminium pan.

| Identity | Observation |
| --- | --- |
| L-lactate salt | Loss of 1.7% unbound solvent, melt with degradation at 190° C. |
| Free base dihydrate | Weight loss (prior to degradation) of 4.1% w/w (corresponds to 1 equivalent of water) |
| Esylate salt | Loss of 4% unbound solvent, no other clearly identifiable features. |
| Free base | Loss of 1.7% unbound solvent, melt with degradation at 193° C. |
| Hydrochloride salt | Loss of 5.4% unbound solvent, melt with degradation at 190° C. |

C. Polarised Light Microscopy

Samples were studied on a Leica LM/DM microscope with a digital camera for image capture. A small amount of sample was mounted in immersion oil on a glass slide and covered with a glass cover slip. The individual particles were separated as well as possible and viewed with 50-500× magnification and partially crossed polars, coupled to a λ wave-plate.

| Identity | Observation |
| --- | --- |
| L-lactate salt | Irregular crystalline particles |
| Free base dihydrate | Irregular crystalline particles |
| Esylate salt | Irregular crystalline particles |
| Free base | Acicular crystalline particles |
| Hydrochloride salt | Irregular crystalline particles |

D. XRPD (X-Ray Powder Diffraction)
D5000

An XRPD study was carried out on a Siemens D5000 diffractometer using CuK radiation (40 kV, 40 mA), θ-θ goniometer, automatic divergence and receiving slits, a graphite secondary monochromator and a scintillation counter. The data were collected over an angular range of 2° to 30° 2θ in continuous scan mode using a step size of either 0.02° 2θ or 0.005° 2θ and a step time of 1 second.

Samples, run under ambient conditions, were prepared as flat plate specimens using powder as received without grinding. Approximately 25-50 mg of the sample was gently packed into 12 mm diameter, 0.5 mm deep cavity cut into a polished, zero-background (510) silicon wafer (The Gem Dugout, 1652 Princeton Drive, Pennsylvania State College, Pa. 16803, USA).

All XRPD analyses were performed using the Diffrac Plus XRD Commander software v2.3.1.

Bruker AXS C2 GADDS Diffractometer (Used for Samples Recovered from GVS)

X-ray powder diffraction patterns for the samples were acquired on a Bruker AXS C2 GADDS diffractometer using Cu K radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm.

Beam divergence, i.e. the effective size of the X-ray beam on the sample, was approximately 4 mm. A θ-θ continuous scan mode was employed with a sample to detector distance of 20 cm which gives an effective 2θ range of 3.2-29.8°. A typical exposure time of a sample would be 120 s.

Samples were prepared as flat plate specimens using powder as received without grinding. Approximately 1-2 mg of the sample was lightly pressed on a glass slide to obtain a flat surface.

The XRPD trace was recorded for the L-lactate salt and the free base. The traces show good signal to noise ratio, and indicate crystalline material.

E. Gravimetric Vapour Sorption (GVS):

All samples were run on a Hiden IGASorp moisture sorption analyser running CFRSorp software. The sample size was ca. 10-25 mg. A moisture adsorption/desorption isotherm was performed as outlined below. The sample was loaded and unloaded at room humidity and temperature (ca. 40% RH, 25° C.) and analysed afterwards by XRPD (using a Bruker AXS C2 GADDS system).

The standard isotherm run was a single cycle starting at 40% RH.

The humidity was stepped as follows:
40, 50, 60, 70, 80, 90
85, 75, 65, 55, 45, 35, 25,15, 5,0
10, 20, 30, 40

(i) L-Lactate Salt

The GVS isotherm for the L-lactate salt indicates that the sample does not display hygroscopic behaviour and does not form a hydrate. The XRPD trace for the sample following the GVS experiment is concordant with that of the input material, indicating that no phase change occurred during the experiment.

(ii) Free Base

During the experiment the sample weight differs by approximately 9% between 0% R.H and 95% R.H. This indicates that the sample is hygroscopic in nature.

Determination of the crystal structure of 1-Cyclopropyl-3-[3-(5-Morpholin-4-ylmethyl-1H-Benzoimidazol-2-yl)-1H-Pyrazol-4-yl]-Urea dihydrate free base by X-ray diffraction This was carried out as described in Example 69 of WO 2006/070195 at pages 201 to 204 (the content of which is incorporated herein by reference).

Determination of the XRPD pattern of 1-cyclopropyl-3-[3-(5-morpholin-4-ylmethyl-1H-benzoimidazol-2-yl)-1H-pyrazol-4-yl]-urea free base This was carried out as described in Example 70 of WO 2006/070195 at pages 204 to 205 (the content of which is incorporated herein by reference).

Determination of the crystal structure of 1-Cyclopropyl-3-[3-(5-Morpholin-4-ylmethyl-1H-Benzoimidazol-2-yl)-1H-Pyrazol-4-yl]-Urea lactate salt This was carried out as described in Example 71 of WO 2006/070195 at pages 205 to 209 (the content of which is incorporated herein by reference).

1-Cyclopropyl-3-[3-(5-Morpholin-4-ylmethyl-1H-Benzoimidazol-2-yl)-1H-Pyrazol-4-yl]-Urea salt stability at 40° C. 75% RH This was carried out as described in Example 72 of WO 2006/070195 at pages 209 to 211 (the content of which is incorporated herein by reference).

Biological Activity

Measurement of Activated CDK2/CyclinA Kinase Inhibitory Activity Assay ($IC_{50}$)

Compounds of the invention were tested for kinase inhibitory activity using the protocol described in Example 73 of WO 2006/070195 at pages 211 to 212 (the content of which is incorporated herein by reference).

Measurement of Activated CDK1/CyclinB Kinase Inhibitory Activity Assay ($IC_{50}$)

As described in Example 74 of WO 2006/070195 at pages 212 to 213 (the content of which is incorporated herein by reference).

Aurora A Kinase Assays

As described in Example 75 of WO 2006/070195 at page 213 (the content of which is incorporated herein by reference).

Aurora B Kinase Assays

As described in Example 76 of WO 2006/070195 at page 214 (the content of which is incorporated herein by reference).

GSK3-B Kinase Inhibitory Activity Assay

As described in Example 77 of WO 2006/070195 at page 214 (the content of which is incorporated herein by reference).

A. Other Kinase Inhibitory Activity Assays

The inhibitory activity against these enzymes was assayed at Upstate Discovery Ltd. Enzymes were prepared at 10× final concentration in enzyme buffer (as described in table below). Enzymes were then incubated in assay buffer with various substrates and $^{33}$P-ATP (~500 cpm/pmol) as described in the table.

The reaction was initiated by the addition of Mg/ATP. The reaction was allowed to proceed for 40 minutes at room temperature before being stopped with 5 μl of a 3% phosphoric acid solution. Ten μl of the reaction mix was transferred to either a filtermat A or P30 filtermat and washed three times in 75 mM phosphoric acid and once in methanol before being dried for scintillation counting.

Compounds were tested at the concentrations detailed below in duplicate against all kinases and the percent activity compared to control was calculated. Where inhibition was high an IC50 was determined.

| Enzyme | Enzyme Buffer | Assay Buffer | Substrate | ATP Concentration (μM) |
|---|---|---|---|---|
| c-abl | A | A | 50 μM EAIYAAPFAKKK (SEQ ID NO: 4) | 45 |
| c-abl (T315I) | A | A | 50 μM EAIYAAPFAKKK (SEQ ID NO: 4) | 10 |
| Cdk3 | A | A | 0.1 mg/ml Histone H1 | 200 |
| Cdk6 | A | A | 0.1 mg/ml Histone H1 | 200 |
| Cdk7 | A | A | 500 μM peptide | 90 |
| Cdk9 | A | A | 100 μM KTFCGTPEYLAPEVRREPRILSEEEQEMFRDFDYIADWC (SEQ ID NO: 5) | 45 |
| Chk1 | A | A | 200 μM KKKVSRSGLYRSPSMPENLNRPR (SEQ ID NO: 6) | 90 |
| Chk2 | A | A | 200 μM KKKVSRSGLYRSPSMPENLNRPR (SEQ ID NO: 6) | 70 |
| Flt3 | A | A | 50 μM EAIYAAPFAKKK (SEQ ID NO: 4) | 200 |
| Jak2 | A | A | 100 μM KTFCGTPEYLAPEVRREPRILSEEEQEMFRDFDYIADWC (SEQ ID NO: 5) | 45 |
| PDK1 | B | B | 100 μM KTFCGTPEYLAPEVRREPRILSEEEQEMFRDFDYIADWC (SEQ ID NO: 5) | 10 |
| VEGFR2 (KDR) | A | A | 0.33 mg/ml myelin basic protein | 90 |

Enzyme buffers were:
A: 20 mM MOPS pH 7.0, 1 mM EDTA, 0.1% β-mercaptoethanol, 0.01% Brij-35, 5% glycerol, 1 mg/ml BSA
B: 50 mM Tris pH 7.5, 0.05% β-mercaptoethanol, 1 mg/ml BSA
Assay buffers were:
A: 8 mM MOPS pH 7.0, 0.2 mM EDTA, 10 mM Mg acetate
B: 50 mM Tris pH 7.5, 0.1% β-mercaptoethanol, 10 mM Mg acetate B. Further Kinase Inhibitory Activity Assays The inhibitory activity against these enzymes was assayed at Upstate Discovery Ltd. Enzymes were prepared at 10× final concentration in enzyme buffer (as described in table below). Enzymes were then incubated in assay buffer with various substrates and $^{33}$P-ATP (~500 cpm/pmol) as described in the table.

The reaction was initiated by the addition of Mg/ATP. The reaction was allowed to proceed for 40 minutes at room temperature before being stopped with 5 μl of a 3% phosphoric acid solution. Ten μl of the reaction mix was transferred to either a filtermata or P30 filtermat and washed three times in 75 mM phosphoric acid and once in methanol before being dried for scintillation counting.

Compounds were tested at the concentrations detailed below in duplicate against allkinases and the percent activity compared to control was calculated.

C. EGFR and PDGFR Kinase Inhibitory Activity Assays

The inhibitory activity against the EGFR and PDGFR-beta enzymes was determined. Enzymes (from Upstate) were prepared at 2× final concentration in 1× kinase assay buffer (as described below). Enzymes were then incubated with test compounds, biotinylated Flt3 substrate (biotin–DNEYFYV) (SEQ ID NO:10) (Cell Signalling Technology Inc.) and ATP. The 60 ul reaction was allowed to proceed for 60 minutes (EGFR) or 2.5 hrs (PDGFR-beta) at room temperature on a plate shaker at 900 rpm before being stopped with 20 μl 55 mM EDTA, pH 8. Twenty μl of 5× detection mix (50 mM HEPES, pH 7.5, 0.5 M KF, 0.1% BSA, 11.34 nM Eu-anti-pY (PT66) (PerkinElmer), 94 nM SA-XL665 (Cisbio)) was then added to each well and the plate sealed and incubated at room temperature for one hour on a plate shaker at 900 rpm. The plate was then read on a Packard Fusion plate reader in TRF mode.

| Enzyme | Enzyme Buffer | Assay Buffer | Substrate | ATP Concentration (μM) |
|---|---|---|---|---|
| cSRC | A | A | 250 μM KVEKIGEGTYGVVYK ((SEQ ID NO: 7) | 200 |
| EphB2 | A | C | 0.1 mg/ml poly(Glu, Tyr) 4:1 | 10 |
| EphB4 | A | C | 0.1 mg/ml poly(Glu, Tyr) 4:1 | 10 |
| FGFR3 | A | C | 0.1 mg/ml Poly (Glu, Tyr) | 15 |
| Jak3 | A | A | 500 μM GGEEEEYFELVKKKK (SEQ ID NO: 8) | 10 |
| Ret | A | A | 250 μM KKKSPGEYVNIEFG (SEQ ID NO: 9) | 70 |

Enzyme buffers were:
A: 20 mM MOPS pH 7.0, 1 mM EDTA, 0.1% β-mercaptoethanol, 0.01% Brij-35, 5% glycerol, 1 mg/ml BSA
Assay buffers were:
A: 8 mM MOPS pH 7.0, 0.2 mM EDTA, 10 mM Mg acetate
C: 8 mM MOPS, pH 7, 0.2 mM EDTA, 10 mM MnCl$_2$, 10 mM Mg acetate

| Enzyme | 1 × Assay Buffer | Flt3 substrate concentration | ATP concentration |
|---|---|---|---|
| EGFR | A | 0.15 uM | 0.9 uM |
| PDGFR-beta | B | 0.15 uM | 30 uM |

Kinase Assay buffers were:
A: 20 mM HEPES pH 7.5, 10 mM $MnCl_2$, 0.1 mg/ml BSA, 0.01% Triton X-100, 1 mM DTT, 0.1 mM Sodium orthovanadate
B: 20 mM MOPS pH 7.0, 10 mM $MnCl_2$, 0.01% Triton X-100, 1 mM DTT, 0.1 mM Sodium orthovanadate Determination of Potency against Cytochrome P450

As described in Example 81 of WO 2006/070195 at pages 220 to 221 (the content of which is incorporated herein by reference).

Anti-Proliferative Activity

As described in Example 79 of WO 2006/070195 at pages 217 to 218 (the content of which is incorporated herein by reference).

A. General Colony Forming Assay Protocol

As described in Example 80 of WO 2006/070195 at page 218 (the content of which is incorporated herein by reference).

B. Colony Forming Assay Protocol for 1-Cyclopropyl-3-[3-(5-morpholin-4-ylmethyl-1H-benzoimidazol-2-yl)-1H-pyrazol-4-yl]-urea As described in Example 80 of WO 2006/070195 at pages 218 to 220 (the content of which is incorporated herein by reference).

Inhibitory Effect on Tumour Cell Colony Formation

| Origin | Origin | IC50 (nM) | p53 Status* |
|---|---|---|---|
| Colon | HCT 116 | 13 | + |
| | HCT 116 N7 | 14 | − |
| | HT-29 | 11 | − |
| | SW620 | 14 | − |
| Ovarian | A2780 | 7.7 | + |
| Lung | A549 | 12 | + |
| Breast | MCF7 | 20 | + |
| Pancreatic | MIA-Pa-Ca-2 | 7.8 | − |

*+ indicates expression of wild type p53; − indicates no expression of p53 or that p53 is non-functional.

Determination of Antifungal Activity

As described in Example 83 of WO 2006/070195 at pages 224 to 225 (the content of which is incorporated herein by reference).

Protocol for the Biological Evaluation of Control of In Vivo Whole Plant Fungal Infection As described in Example 84 of WO 2006/070195 at page 225 (the content of which is incorporated herein by reference).

Western Blotting Assay to Determine the Inhibition of Phosporylation of the Downstream Substrates of JAK2 (e.g. Stat5) and Bcr-Abl (e.g. CRKL) in Erythroleukemia (HEL) and Chronic Myelogenous Leukaemia (K562) Cells Following compound treatment at a final concentration of 0.1% DMSO, cells were harvested and lysed in ice cold triton lysis buffer. Lysates were cleared by centrifugation and a sample of the supernatant removed for protein determination. Equivalent amounts of protein lysate had SDS sample buffer and DTT added and were boiled for 5 minutes.

Samples were resolved by SDS PAGE, blotted onto nitrocellulose filters, blocked with 5% non-fat milk or equivalent blocking buffer and incubated overnight with the specific antibodies to phosphorylated and non-phosphorylated proteins at 4° C. Secondary antibodies used were anti-rabbit and anti-mouse IgG, HRP linked (Cell SignallingTechnology) and detection achieved using ECLPLUs reagents (Amersham Bioscience).

Alternatively secondary antibodies used were IRDye® conjugated and detection achievedusing the Odyssey Infrared Imaging System (LI-COR Biosciences).

Using this protocol, it was shown that the phosphorylation of direct downstream substrates of JAK2 (e.g. Stat5) and Bcr-Abl (e.g. CRKL) in erythroleukemia (HEL) and chronic myelogenous leukaemia (K562) cells respectively is inhibited when cells are treated with 1-cyclopropyl-3-[3-(5-morpholin-4-ylmethyl-1H-benzoimidazol-2-yl)-1H-pyrazol-4-yl]-urea. The results are set out in the table below.

| Downstream substrates | Kinase | 1-Cyclopropyl-3-[3-(5-morpholin-4-ylmethyl-1H-benzoimidazol-2-yl)-1H-pyrazol-4-yl]-urea |
|---|---|---|
| Histone H3 phosphorylation | Aurora | 10-30 nM |
| crkl phosphorylation | BCR-abl | ~10000 nM |
| STAT5 phosphorylation | JAK2 | 100-300 nM |

Pharmaceutical Formulations (i) Tablet Formulation

A tablet composition containing a compound of the formula (I) or (I') is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) or (I') with 100 mg lactose and filling the resulting mixture into standard opaque hard gelatin capsules.

(iii) Injectable Formulation I

A parenteral composition for administration by injection can be prepared by dissolving a compound of the formula (I) or (I') (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) or (I') (e.g. in salt form) (2 mg/ml) and mannitol (50 mg/ml), sterile filtering the solution and filling into sealable 1 ml vials or ampoules.

(v) Injectable Formulation III

A formulation for i.v. delivery by injection or infusion can be prepared by dissolving the compound of formula (I) or (I') (e.g. in a salt form) in water at 20 mg/ml. The vial is then sealed and sterilised by autoclaving.

(vi) Injectable Formulation IV

A formulation for i.v. delivery by injection or infusion can be prepared by dissolving the compound of formula (I) or (I') (e.g. in a salt form) in water containing a buffer (e.g. 0.2 M acetate pH 4.6) at 20 mg/ml. The vial is then sealed and sterilised by autoclaving.

(viii) Lyophilised Formulation I

Aliquots of formulated compound of formula (I) or (I') or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps iftemperature to 50° C. The pressure during primary and secondary drying is set at 80 millitor.

(viii) Lyophilised Formulation II

Aliquots of formulated compound of formula (I) or (I') or s salt thereof as defined herein areput into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation for Use in i.v. Administration III

An aqueous buffered solution is prepared by dissolving 1-cyclopropyl-3-[3-(5-morpholin-4-ylmethyl-1H-benzoimidazol-2-yl)-1H-pyrazol-4-yl]-urea L-lactic acid salt at a concentration of 12.86 mg/ml in a 0.02M citric acid buffer corrected to a pH of 4.5 with sodium hydroxide or hydrochloric acid.

The buffered solution is filled, with filtration to remove particulate matter, into a container(such as class 1 glass vials) which is then partially sealed (e.g. by means of a Florotec stopper). If the compound and formulation are sufficiently stable, the solution issterilised by autoclaving at 121° C. for a suitable period of time. If the formulation is not stable to autoclaving, it can be sterilised using a suitable filter and filled under sterileconditions into sterile vials. The solution is freeze dried using a suitable cycle: for example Freezing—freeze to −40° C. over 2 hours and hold at −40° C. for 3 hours.

Primary drying—ramp −40° C. to −30° C. over 8 hours and hold at −30° C. for 7 hours.

Secondary drying—ramp to +30° C. over 4 hours and hold at +30° C. for 8-10 hours On completion of the freeze drying cycle the vials are back filled with nitrogen toatmospheric pressure, stoppered and secured (e.g. with an aluminium crimp). Forintravenous administration, the freeze dried solid can be reconstituted into apharmaceutically acceptable excipient, such as 0.9% saline or 5% dextrose. The solution can be dosed as is, or can be injected into an infusion bag (containing a pharmaceutically-acceptable excipient, such as 0.9% saline or 5% dextrose), before administration.

(x) Subcutaneous Injection Formulation

A composition for sub-cutaneous administration is prepared by mixing a compound of theformula (I) or (I'), or a salt thereof as defined herein, with pharmaceutical grade corn oil togive a concentration of 5 mg/ml. The composition is sterilised and filled into a suitable container.

(xi) Lyophilsed Formulation for Use in i.v. Administration IV

An aqueous buffered solution is prepared by dissolving 13 mg/ml of 1-cyclopropyl-3-[3-(5-morpholin-4-ylmethyl-1H-benzoimidazol-2-yl)-1H-pyrazol-4-yl]-urea L-lactic acid salt (equivalent to 10 mg of free base) in 20 mg/ml citric acid anhydrous buffer corrected to a pH of 4.5 with 2M aqueous sodium hydroxide or 2M aqueous hydrochloric acid. 5 ml of the solution of 1-cyclopropyl-3-[3-(5-morpholin-4-ylmethyl-1H-benzoimidazol-2-yl)-1H-pyrazol-4-yl]-urea L-lactic acid salt (containing 65.9 mg of the L-lactate salt which equates to 52 mg the free base) in approximately 100 mM (e.g. 104 mM) citrate buffer pH 4.5 was filled into 20 ml type I glass vials and lyophilised. The solution is freeze dried usinga suitable cycle for example:

| Step | Cycle stage | Temperature (° C.) | Pressure (mbar) | Time (min) |
|---|---|---|---|---|
| 1 | Ramp | −40 | n/a | 120 |
| 2 | Freezing | −40 | n/a | 110 |
| 3 | Hold | −40 | 0.133 | 60 |
| 4 | Ramp | 0 | 0.133 | 90 |
| 5 | Primary drying | 0 | 0.133 | 1380 |
| 6 | Ramp | 35 | 0 | 150 |
| 7 | Secondary drying | 35 | 0 | 360 |
| 8 | Ramp | 45 | 0 | 45 |
| 9 | Secondary drying | 45 | 0 | 360 |
| 10 | Finish | | Vials stoppered to 95% atmosphere with (pure) nitrogen. | |

On completion of the freeze drying cycle the vials are back filled with nitrogen to aroundatmospheric pressure (e.g. just below (95%)), stoppered and secured (e.g. with analuminium crimp). For intravenous administration, the freeze dried solid can bereconstituted into a pharmaceutically acceptable excipient, such as 0.9% saline or 5% dextrose. The solution can be dosed as is, or can be injected into an infusion bag (containing a pharmaceutically acceptable excipient, such as 0.9% saline or 5% dextrose), before administration.

Assay for Therapeutic Efficacy

The effect of a compound of formula (I) or (I') (Compound I) in combination with anancillary compound (Compound II) can be assessed using the following technique:

$IC_{50}$ Shift Assay

Cells from human cells lines (e.g. HCT116, U87MG, A549) were seeded onto 96-well tissue culture plates at a concentration of $2.5\times10^3$, $6.0\times10^3$, or $4.0\times10^3$ cells/well respectively. Cells were allowed to recover for 48 hours prior to addition of compound(s) or vehicle control (0.35% DMSO) as follows:

Compounds were added concurrent for 96 hours.

Following a total of 96 hours compound incubation, cells were fixed with ice-cold 10% (w/v) trichloroacetic acid for 1 hour on ice and then washed four times with $dH_2O$ using a platewasher (Labsystems Wellwash Ascent) and air-dried. Cells were then stained with 0.4% (w/v) Sulforhodamine B (Sigma) in 1% acetic acid for 20 min at room temperature and then washed four times with 1% (v/v) acetic acid and air-dried before the addition of 10 mM Tris buffer to solubilise the dye. Colourmetric product was quantified by reading at Abs490 nm on a Wallac Victor² plate reader (1420 multilabel counter, Perkin Elmer Life Sciences). The$IC_{50}$ for Compound II in the presence of varying doses of Compound I was determined. Synergy was determined when the $IC_{50}$ shifted down in the presence of sub-effective doses of Compound I. Additivity was determined when the response to Compound II andCompound I together resulted in an effect equivalent to the sum of the two compoundsindividually. Antagonistic effects were defined as those causing the $IC_{50}$ to shift upwards, i.e. those where the response to the two compounds was less than the sum of the effect ofthe two compounds individually.

|  | Conc | Compound I | | | | | | Compound I | | | | | |
|---|---|---|---|---|---|---|---|---|---|---|---|---|---|
|  |  | a | b | c | d | e | Control | a | b | c | d | e | Control |
| Compound II | a | | | | | | | | | | | | |
|  | b | | | | | | | | | | | | |
|  | c | | | | | | | | | | | | |
|  | d | | | | | | | | | | | | |
|  | e | | | | | | | | | | | | |
|  | f | | | | | | | | | | | | |
|  | g | | | | | | | | | | | | |
|  | Control | | | | | | | | | | | | |

General Method for the Assessment of the Effect of Combination

The effect of the compound 1-cyclopropyl-3-[3-(6-morpholin-4-ylmethyl-1H-benzoimidazol-2-yl)-1H-pyrazol-4-yl]-urea, L-lactate salt ("Compound I") in combination with any ancillary agent (Compounds II-IV) can be assessed using the following technique:

1. Combination Screen Assay

Human colon carcinoma cell line HCT 116 (ECACC No. 91091005) cells were seeded onto 96-well tissue culture plates at a concentration of $2\times10^4$ cells/ml and 200 µl per well. Cells were allowed to recover overnight prior to addition of compound(s) or vehicle control (0.2% DMSO) as follows;

Following a total of 72 hours compound incubation, Alamar Blue™ was added to a finalconcentration of 10% (v/v) and incubated at 37° C. for 6 hours. Fluorescent product was quantified by reading at d535/25x (excitation) and d590/20m (emission) on a Fusion Reader (Perkin Elmer).

The fluorescence as a percentage of vehicle control (0.2% DMSO) was determined for cell samples treated with Compound II, III or IV, in the presence of varying concentrations ofCompound I. The data were analysed using the method of multiplicity which assumes thateach individual agent demonstrates a linear dose response curve. This assumption allowsfor the generation of a theoretical curve, termed the line of multiplicity, that represents theexpected additive response.

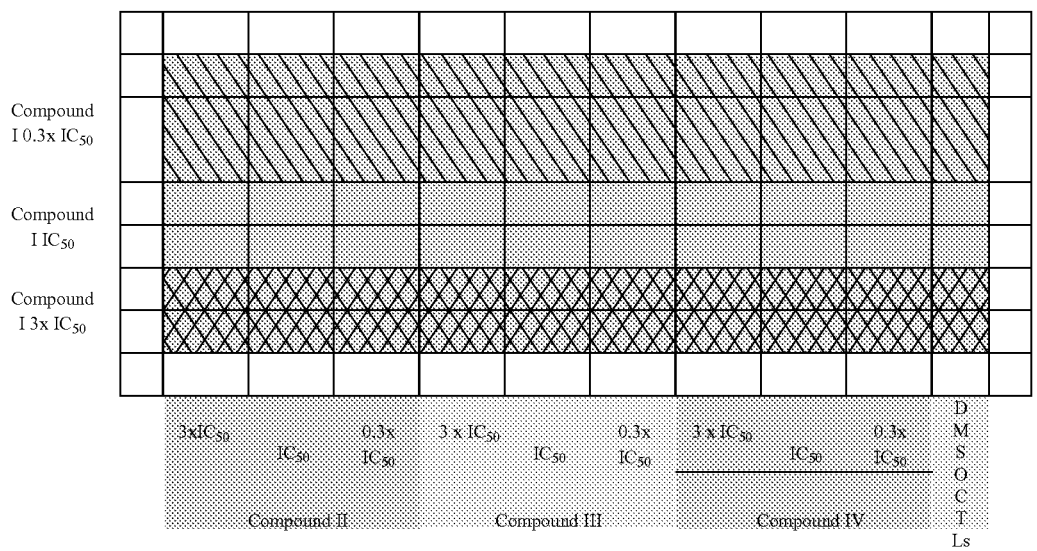

Compounds were added according to one of the following schedules;
a) Concurrent for 72 hours.
b) Compound I for 24 hours, followed by the addition of Compound II, III or IV for afurther 48 hours.
c) Compound II, III or IV for 24 hours, followed by the addition of Compound I for a further 48 hours.

Additivity was determined when the response to Compounds II, III or IV and Compound Itogether resulted in an effect approximately equivalent to the theoretical line of multiplicitycalculated from the product of the two compounds individually. Synergy was determined when the observed response to the combined agents was greater than the theoretical lineof multiplicity. Antagonism was determined when the observed response to the combined agents was less than the theoretical line of multiplicity.

Effect of the compound 1-cyclopropyl-3-[3-(6-morpholin-4-ylmethyl-1H-benzoimidazol-2-yl)-1H-pyrazol-4-yl]-urea, L-lactate salt ("Compound I") in combination with various ancillary Compounds The effect of the compound 1-cyclopropyl-3-[3-(6-morpholin-4-ylmethyl-1H-benzoimidazol-2-yl)-1H-pyrazol-4-yl]-urea, L-lactate salt ("Compound I") in combination with 5FU, Vinblastine, Paclitaxel, and Cisplatin. In this example the use of paclitaxel is considered representative of the other taxol derived therapeutics and the use of cisplatin is considered representative of other platinum based therapeutic agents. Further the use of taxanes and platins is considered representative of other checkpoint targeting agents as described herein.

1. Combination Screen Assay

Human colon carcinoma cell line HCT 116 (ECACC No. 91091005) cells were seeded onto 96-well tissue culture plates at a concentration of $2 \times 10^4$ cells/ml and 200 µl per well. Cells were allowed to recover overnight prior to addition of compound(s) or vehicle control (0.2% DMSO) as follows:

Additivity was determined when the response to Compounds II, III or IV and Compound I together resulted in an effect approximately equivalent to the theoretical line of multiplicity calculated from the product of the two compounds individually. Synergy was determined when the observed response to the combined agents was greater than the theoretical line of multiplicity. Antagonism was determined when the observed response to the combined agents was less than the theoretical line of multiplicity.

1. Taxol

Figure 9:
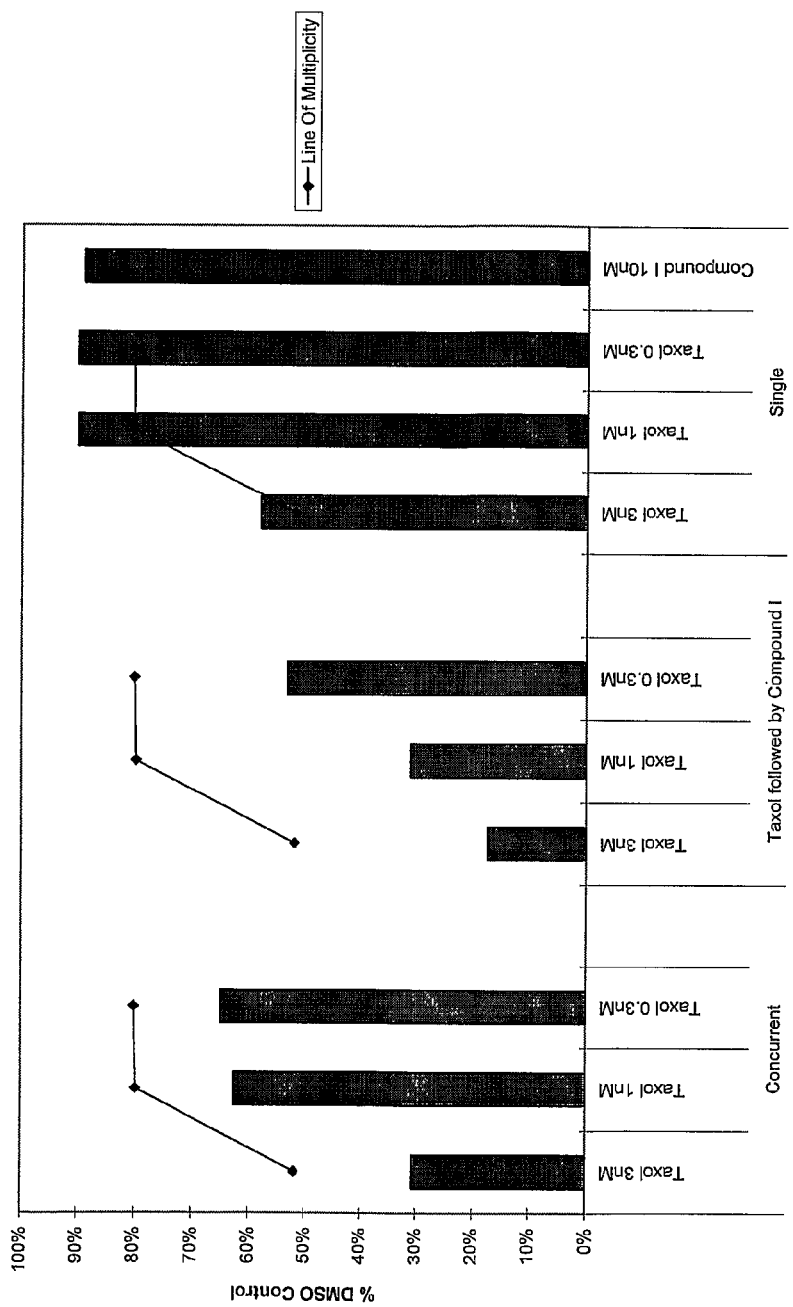
FIG. 9 shows the results of a combination Screen assay performed in HCT 116 cells for 3 concentrations of Taxol in the presence and absence of 0.01 μM Compound I as described in the example herein. The calculated theoretical line of multiplicity is shown for comparison.

Combinations of Compound I and Taxol were shown to be additive or synergistic dependent on schedule but not antagonistic in the Combination Screen assay performed in HCT 116 cells. An example is shown in FIG. 9 for 3 concentrations of Taxol in the presence and absence of 0.01 µM Compound I. The calculated theoretical line of multiplicity is shown for comparison.

2. Cisplatin

Figure 10:
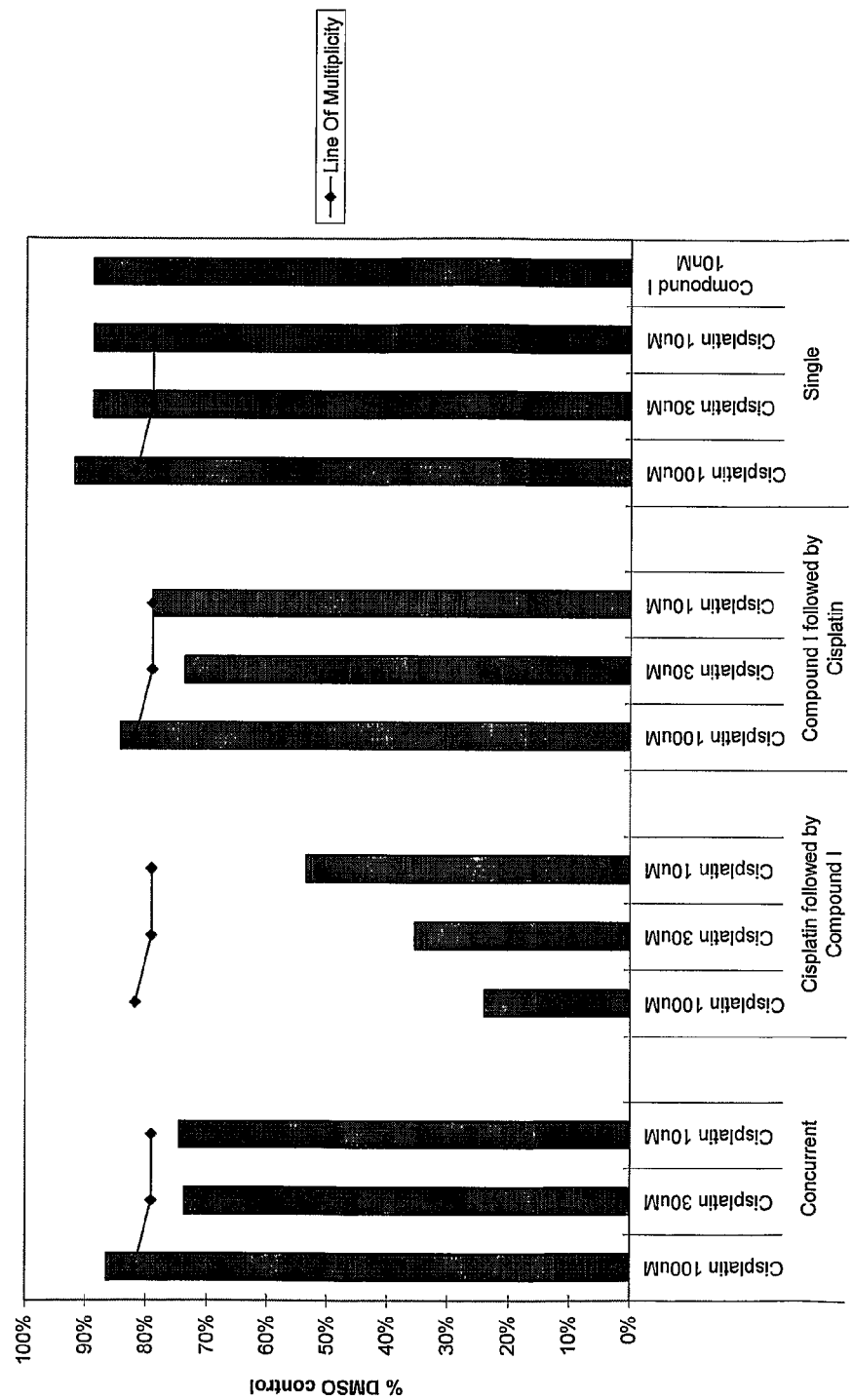
FIG. 10 shows the results of a combination Screen assay performed in HCT 116 cells for 3 concentrations of Cisplatin in the presence and absence of 0.01 μM Compound I as described in the example herein. The calculated theoretical line of multiplicity is shown for comparison.

Combinations of Compound I and Cisplatin were shown to be additive or synergistic dependent on schedule but not antagonistic in the Combination Screen assay performed in HCT 116 cells. An example is shown in FIG. 10 for 3

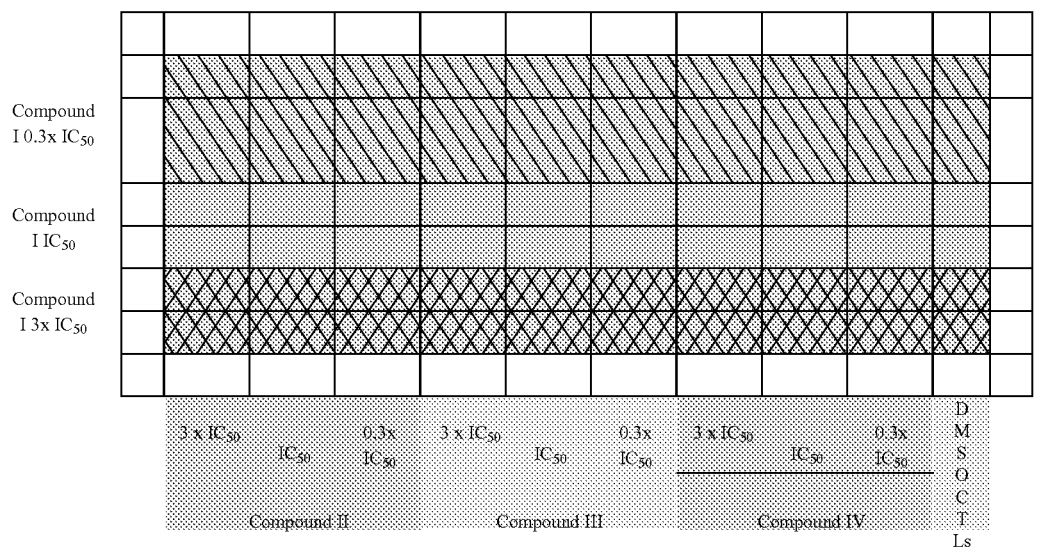

Compounds were added according to one of the following schedules;
d) Concurrent for 72 hours.
e) Compound I for 24 hours, followed by the addition of Compound II, III or IV for a further 48 hours.
f) Compound II, III or IV for 24 hours, followed by the addition of Compound I for a further 48 hours.

Following a total of 72 hours compound incubation, Alamar Blue™ was added to a final concentration of 10% (v/v) and incubated at 37° C. for 6 hours. Fluorescent product was quantified by reading at d535/25x (excitation) and d590/20m (emission) on a Fusion Reader (Perkin Elmer).

The fluorescence as a percentage of vehicle control (0.2% DMSO) was determined for cell samples treated with Compound II, III or IV, in the presence of varying concentrations of Compound I. The data were analysed using the method of multiplicity which assumes that each individual agent demonstrates a linear dose response curve. This assumption allows for the generation of a theoretical curve, termed the line of multiplicity, that represents the expected additive response.

concentrations of Cisplatin in the presence and absence of 0.01 µM Compound I. The calculated theoretical line of multiplicity is shown for comparison.

3. 5FU

Figure 11:
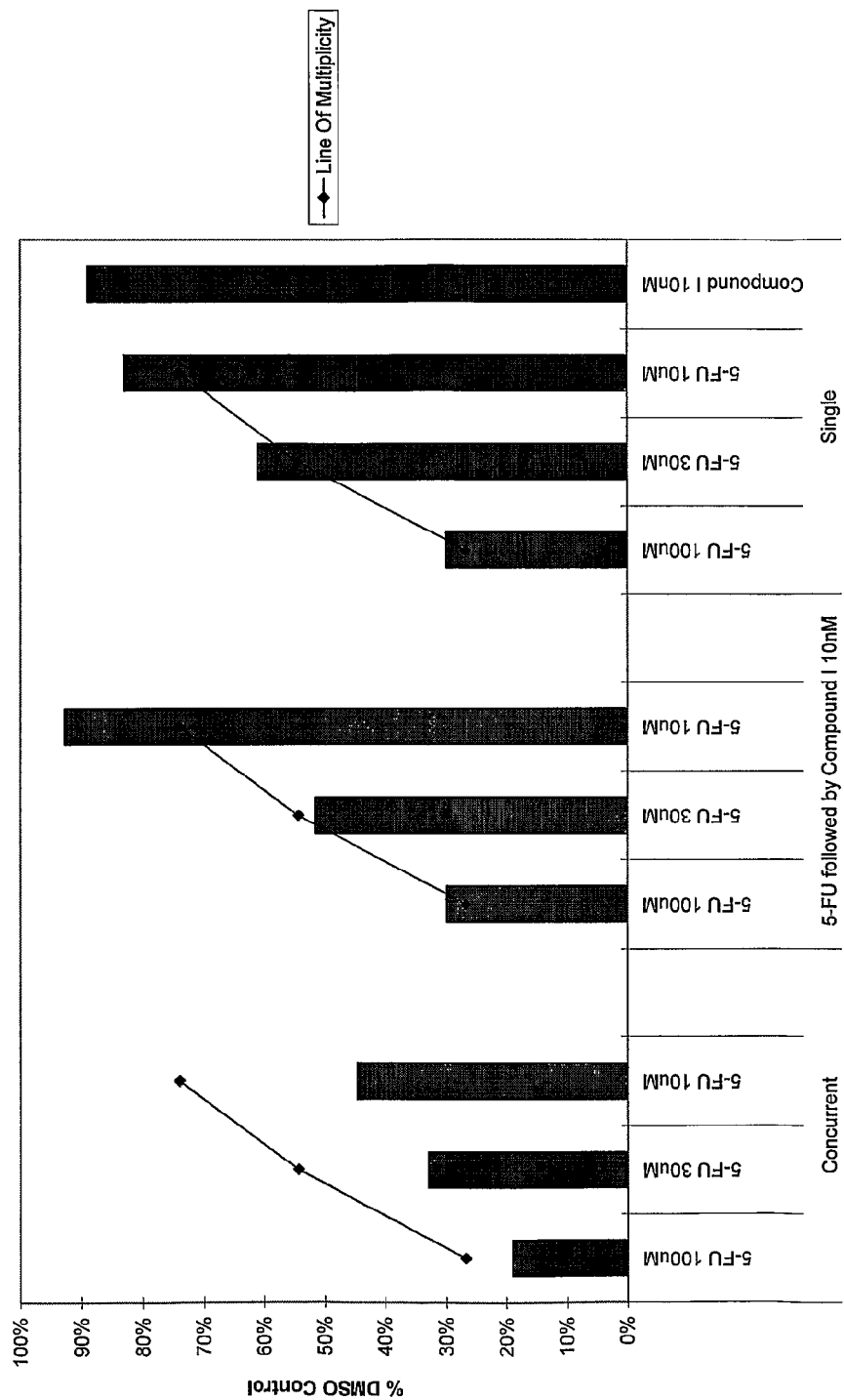
FIG. 11 shows the results of a combination Screen assay performed in HCT 116 cells for 3 concentrations of 5-FU in the presence and absence of 0.01 μM Compound I as described in the example herein. The calculated theoretical line of multiplicity is shown for comparison.

Combinations of Compound I and 5-FU were shown to be additive or potentially synergistic but not antagonistic in the Combination Screen assay performed in HCT 116 cells. An example is shown in FIG. 11 for 3 concentrations of 5-FU in the presence and absence of 0.01 µM Compound I. The calculated theoretical line of multiplicity is shown for comparison.

4. Vinblastine

Figure 12:
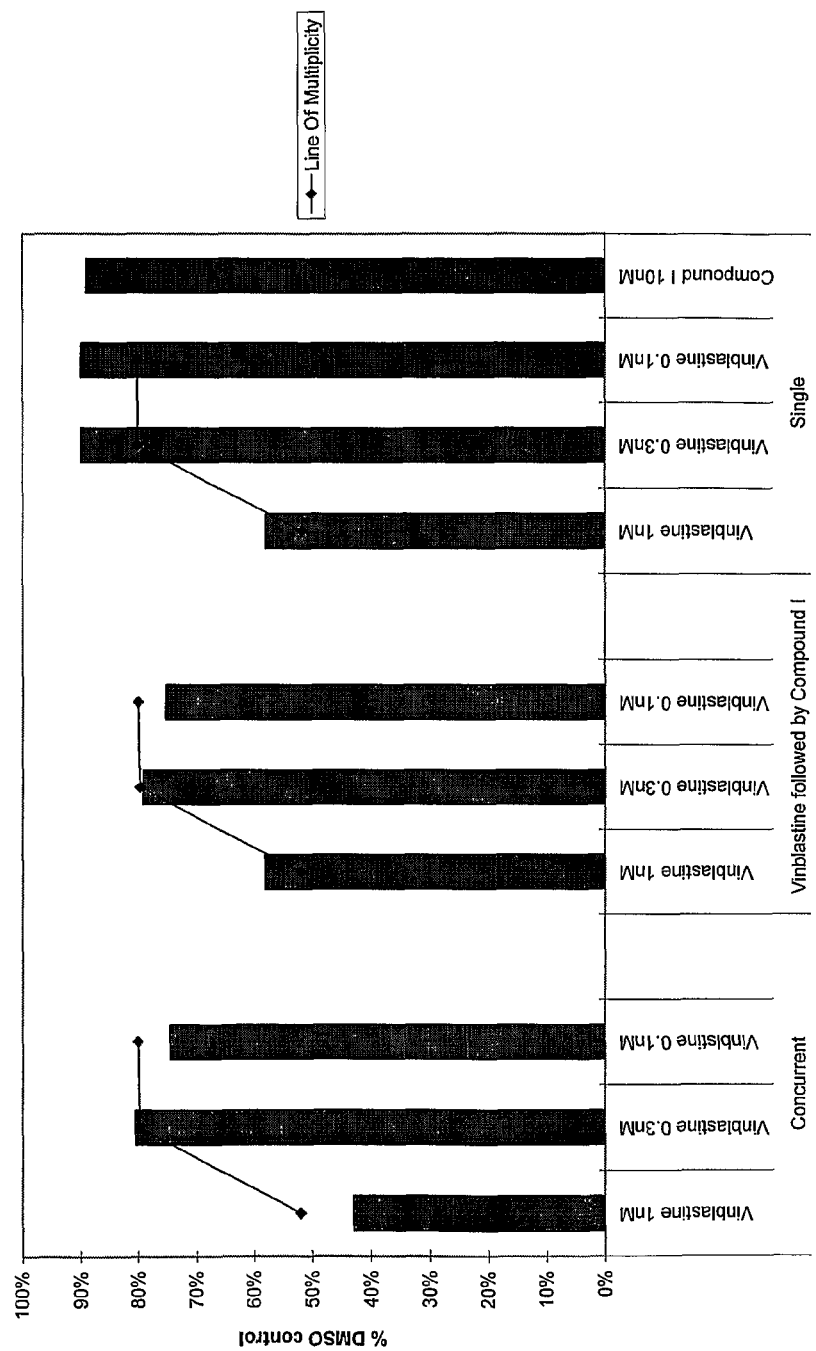
FIG. 12 shows the results of a combination Screen assay performed in HCT 116 cells for 3 concentrations of vinblastine in the presence and absence of 0.01 μM Compound I as described in the example herein. The calculated theoretical line of multiplicity is shown for comparison.

Combinations of Compound I and vinblastine were shown to be additive and not antagonistic in the Combination Screen assay performed in HCT 116 cells. An example is shown in FIG. 12 for 3 concentrations of vinblastine in the presence and absence of 0.01 µM Compound I. The calculated theoretical line of multiplicity is shown for comparison.

Xenograph Studies

The compound of formula (I) (1-cyclopropyl-3-[3-(5-morpholin-4-ylmethyl-1H-benzoimidazol-2-yl)-1H-pyrazol-4- yl]-urea) has an anti-tumour action in nude mice engrafted sub-cutaneously with human tumour derived cell lines when used as a single agent or in combination with cytotoxic agents in common use e.g taxanes. Treatment with a dosing schedule which alternates between administration of the compound of formula (I) and for example paclitaxel causes inhibition of tumour growth in such xenografts. The combination of the compound with paclitaxel at doses which individually are sub-optimal, achieved an improved inhibition of tumour growth and extended the time to tumour re-growth once treatment stopped. The tolerability of the two agents combined was not decreased compared with their individual effects. This indicates that the combination therapy with the compound has the potential to increase the anti-tumoural activity at lower doses thus improving the therapeutic index. One example of an effective combination schedule was weekly dosing of paclitaxel on day 1 each week combined with a 4× weekly dosing cycle for the compound given on days 2-5 each week.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A combination comprising an ancillary compound and the compound 1-cyclopropyl-3-[3-(5-morpholin-4-ylmethyl-1H-benzoimidazol-2-yl)-1H-pyrazol-4-yl]-urea, or a salt, tautomer or N-oxide thereof,
wherein the ancillary compound is selected from:
1. hormones, hormone agonists, hormone antagonists and hormone modulating agents, wherein said hormones, hormone agonists, hormone antagonists and hormone modulating agents are selected from corticosteroids, antiandrogens, antiestrogens and GNRAs;
2. cytokines and cytokine activating agents;
3. retinoids and rexinoids
4. monoclonal antibodies to cell surface antigen(s);
5. camptothecin compounds, wherein the camptothecin compound is selected from camptothecin and topotecan;
6. antimetabolites wherein the antimetabolite is selected from gemcitabine, capecitabine, cytarabine, ralitrexed, pemetrexed and methotrexate; or 6-mercapto purine, 6-thioguanine, cladribine, 2'-deoxycoformycin and hydroxyurea;
7. vinca alkaloids, wherein the vinca alkaloid is selected from vindesine, vinvesir, vinblastine, vincristine and vinorelbine;
8. taxanes, wherein the taxane is selected from paclitaxel and docetaxel;
9. epothilones;
10. platinum compounds, wherein the platinum compound is selected from chloro(diethylenediamino)-platinum (II) chloride; dichloro(ethylenediamino)-platinum (II); spiroplatin; iproplatin; diamino(2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato) platinum (II); (1,2-diaminocyclohexane)-cis-(pyruvato)platinum (II); onnaplatin; tetraplatin, carboplatin or oxaliplatin;
11. Topo II inhibitors, wherein said Topo II inhibitors are selected from daunorubicin, idarubicin, epirubicin; or is selected from etoposide a and teniposide; or is mitoxantrone; or is selected from losoxantrone and actinomycin D;
12. alkylating agents wherein said alkylating agents are selected from aziridine, busulfan, nitrogen mustard and nitrosourea alkylating agents;
13. signalling inhibitors, wherein said signalling inhibitor is selected from sunitinib, trastuzumab, cetuximab, gefitinib, erlotinib, bevacizumab, imatinib mesylate, sorafenib, dasatinib, lapatinib, nilotinib, vandetanib, vatalinib, CHIR-258, and axitinib;
14. CDK inhibitors, wherein said CDK inhibitors are ancillary CDK inhibitors;
15. COX-2 inhibitors;
16. HDAC inhibitors;
17. Selective immunoresponse modulators;
18. DNA methyl transferase inhibitors;
19. proteasome inhibitors;
20. Aurora inhibitors, wherein said Aurora inhibitors are ancillary Aurora inhibitors;
21. Hsp90 inhibitors;
22. Checkpoint targeting agents selected from polo-like kinase inhibitors (Plks), CHK kinase inhibitors, inhibitors of the BUB kinase family and kinesin inhibitors;
23. DNA repair inhibitors; and
24. Inhibitors of G-protein coupled receptor.

2. The combination according to claim 1 comprising the compound 1-cyclopropyl-3-[3-(5-morpholin-4-ylmethyl-1H-benzoimidazol-2-yl)-1H-pyrazol-4-yl]-urea or a salt thereof.

3. The combination according to claim 1 comprising an ancillary compound and a salt of 1-cyclopropyl-3-[3-(5-morpholin-4-ylmethyl-1H-benzoimidazol-2-yl)-1H-pyrazol-4-yl]-urea selected from the lactate and citrate salts and mixtures thereof.

4. A combination according to claim 1 wherein (A) the ancillary compound and 1-cyclopropyl-3-[3-(5-morpholin-4-ylmethyl-1H-benzoimidazol-2-yl)-1H-pyrazol-4-yl]-urea or salt, tautomer or N-oxide thereof are physically associated and are;

(a) in admixture; (b) chemically/physicochemically linked; (c) chemically/physicochemically co-packaged; or (d) unmixed but co-packaged or co-presented; or (B) the ancillary compound and 1-cyclopropyl-3-[3-(5-morpholin-4-ylmethyl-1H-benzoimidazol-2-yl)-1H-pyrazol-4-yl]-urea or salt, tautomer or N-oxide thereof are non-physically associated.

5. A combination according to claim 1 wherein the combination comprises two or more ancillary compounds.

6. A combination according to claim 1 wherein the ancillary compound is selected from:
- (a) a taxane compound selected from paclitaxel and docetaxel;
- (b) an antimetabolic compound selected from gemcitabine, capecitabine, cytarabine, ralitrexed, pemetrexed, and methotrexate;
- (c) a signalling inhibitor selected from trastuzumab, cetuximab, gefitinib, erlotinib, bevacizumab, imatinib mesylate, sorafenib, dasatinib, lapatinib, nilotinib, vandetanib, vatalinib, axitinib and CHIR-258;
- (d) a cytokine, cytokine activating agent or retinoid selected from an interferon, an interleukin, tretinoin, alitretinoin and bexarotene.
- (e) a camptothecin compound selected from camptothecin and topotecan;
- (f) a vinca alkaloid compound selected from vinorelbine, vinblastine and vincristine;
- (g) a platinum compound selected from chloro(diethylenediamino)-platinum (II) chloride; dichloro(ethylenediamino)-platinum (II); spiroplatin; iproplatin; diamino (2-ethylmalonato)platinum (II); (1,2-diaminocyclohexane)malonatoplatinum (II); (4-carboxyphthalo)-(1,2-diaminocyclohexane)platinum (II); (1,2-diaminocyclohexane)-(isocitrato)platinum (II); (1,2-diaminocyclohexane)-cis-(pyruvato) platinum (II); onnaplatin; tetraplatin, carboplatin and oxaliplatin;
- (h) a topoisomerase 2 inhibitor selected from daunorubicin, idarubicin, epirubicin; or is selected from etoposide and teniposide; or is mitoxantrone; or is selected from losoxantrone and actinomycin D;
- (i) an antiandrogen or an antiestrogen, wherein the antiandrogen is an aromatase inhibitor selected from letrozole, anastrozole, exemestane or aminoglutethimide, or is an antiandrogen selected from tamoxifen, fulvestrant, raloxifene, toremifene, droloxifene, letrazole, anastrazole, exemestane, bicalutamide, luprolide, megestrol acetate, aminoglutethimide and bexarotene;
- (j) a GnRH analog selected from goserelin and leuprolide;
- (k) a monoclonal antibody to cell surface antigens (or an anti-CD antibody) selected from CD20, CD22, CD33, CD52, rituximab, tositumomab and gemtuzumab;
- (l) an alkylating agent selected from a nitrogen mustard compound, nitrosourea compound and busulfan;
- (m) an HDAC inhibitor selected from TSA, SAHA, JNJ-16241199, LAQ-824, MGCD-0103 and PXD-101;
- (n) a COX-2 inhibitor which is celecoxib;
- (o) a DNA methylation inhibitor selected from temozolomide, decitabine and 5-azacitidine;
- (p) a proteasome inhibitor which is bortezimib; and
- (q) a CDK inhibitor selected from seliciclib, alvocidib, 7-hydroxystaurosparine, JNJ-7706621, BMS-387032, Pha533533, PD332991, ZK-304709 and AZD-5438.

7. A combination according to claim 1 comprising two or more ancillary compounds independently selected from: an antimetabolic compound, a taxane compound, an epothilone, an Hsp90 inhibitor, a signalling inhibitor, a camptothecin compound, a vinca alkaloid compound, a platinum compound, a topoisomerase 2 inhibitor, an antiandrogen, a monoclonal antibody, an alkylating agent, a histone deacetylase inhibitor (HDAC), a cyclooxygenase-2 (COX-2) inhibitor, a proteasome inhibitor, DNA methylation inhibitor, a CDK inhibitor, an Aurora inhibitor and a checkpoint targeting agent.

8. A combination according to claim 1 comprising one or more checkpoint targeting agents.

9. A combination according to claim 1 comprising one or more ancillary compounds selected from vinblastine, and paclitaxel.

10. A combination according to claim 1 wherein the ancillary compound is an agent for treating multiple myeloma selected from a vinca alkaloid compound, a selective immunoresponse modulator and a proteasome inhibitor.

11. A combination according to claim 1 wherein the ancillary compound is an agent for treating multiple myeloma selected from vincristine, lenalidomide and bortezomib.

12. A combination according to claim 1 wherein the ancillary compound is selected from a vinca alkaloid compound, a selective immunoresponse modulator and a proteasome inhibitor.

13. A combination according to claim 1 wherein the ancillary compound is selected from: paclitaxel, docetaxel, vincristine, lenalidomide and bortezomib.

14. A combination according to claim 2 wherein the ancillary compound is selected from: paclitaxel, docetaxel, vincristine, lenalidomide and bortezomib.

15. A combination according to claim 14 wherein the ancillary compound is lenalidomide.

\* \* \* \* \*

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial
<220> FEATURE:
<223> OTHER INFORMATION: synthetic Goserelin acetate
<220> FEATURE:
<222> LOCATION: (1)..(1)
<223> OTHER INFORMATION: PYRROLIDONE CARBOXYLIC ACID
<220> FEATURE:
<221> NAME/KEY: MISC_FEATURE
<222> LOCATION: (6)..(6)
<223> OTHER INFORMATION: D-Ser(Bu)
<220> FEATURE:
<221> NAME/KEY: MISC_FEATURE
<222> LOCATION: (10)..(10)
<223> OTHER INFORMATION: Azgly

<400> SEQUENCE: 1

Glu His Trp Ser Tyr Ser Leu Arg Pro Gly
1               5                   10

<210> SEQ ID NO 2
<211> LENGTH: 9
<212> TYPE: PRT
<213> ORGANISM: Artificial
<220> FEATURE:
<223> OTHER INFORMATION: synthetic Leuprolide acetate
<220> FEATURE:
<221> NAME/KEY: MISC_FEATURE
<222> LOCATION: (1)..(1)
<223> OTHER INFORMATION: 5-oxo-L-prolyl
<220> FEATURE:
<221> NAME/KEY: VARIANT
<222> LOCATION: (6)..(6)
<223> OTHER INFORMATION: D-leucyl
<220> FEATURE:
<221> NAME/KEY: MISC_FEATURE
<222> LOCATION: (9)..(9)
<223> OTHER INFORMATION: N-ethyl-L-prolinamide

<400> SEQUENCE: 2

Pro His Trp Ser Tyr Leu Leu Arg Pro
1               5

<210> SEQ ID NO 3
<211> LENGTH: 10
<212> TYPE: PRT
<213> ORGANISM: Artificial
<220> FEATURE:
```

```
<223> OTHER INFORMATION: synthetic Abarelix

<400> SEQUENCE: 3

Ala Phe Ala Ser Tyr Asn Leu Lys Pro Ala
1               5                   10

<210> SEQ ID NO 4
<211> LENGTH: 12
<212> TYPE: PRT
<213> ORGANISM: Artificial
<220> FEATURE:
<223> OTHER INFORMATION: synthetic peptide

<400> SEQUENCE: 4

Glu Ala Ile Tyr Ala Ala Pro Phe Ala Lys Lys Lys
1               5                   10

<210> SEQ ID NO 5
<211> LENGTH: 39
<212> TYPE: PRT
<213> ORGANISM: Artificial
<220> FEATURE:
<223> OTHER INFORMATION: synthetic peptide

<400> SEQUENCE: 5

Lys Thr Phe Cys Gly Thr Pro Glu Tyr Leu Ala Pro Glu Val Arg Arg
1               5                   10                  15

Glu Pro Arg Ile Leu Ser Glu Glu Gln Glu Met Phe Arg Asp Phe
                20                  25                  30

Asp Tyr Ile Ala Asp Trp Cys
        35

<210> SEQ ID NO 6
<211> LENGTH: 23
<212> TYPE: PRT
<213> ORGANISM: Artificial
<220> FEATURE:
<223> OTHER INFORMATION: synthetic peptide

<400> SEQUENCE: 6

Lys Lys Lys Val Ser Arg Ser Gly Leu Tyr Arg Ser Pro Ser Met Pro
1               5                   10                  15

Glu Asn Leu Asn Arg Pro Arg
            20

<210> SEQ ID NO 7
<211> LENGTH: 15
<212> TYPE: PRT
<213> ORGANISM: Artificial
<220> FEATURE:
<223> OTHER INFORMATION: synthetic peptide

<400> SEQUENCE: 7

Lys Val Glu Lys Ile Gly Glu Gly Thr Tyr Gly Val Val Tyr Lys
1               5                   10                  15

<210> SEQ ID NO 8
<211> LENGTH: 15
<212> TYPE: PRT
<213> ORGANISM: Artificial
<220> FEATURE:
<223> OTHER INFORMATION: synthetic peptide

<400> SEQUENCE: 8

Gly Gly Glu Glu Glu Glu Tyr Phe Glu Leu Val Lys Lys Lys Lys
1               5                   10                  15
```

```
<210> SEQ ID NO 9
<211> LENGTH: 14
<212> TYPE: PRT
<213> ORGANISM: Artificial
<220> FEATURE:
<223> OTHER INFORMATION: sythetic peptide

<400> SEQUENCE: 9

Lys Lys Lys Ser Pro Gly Glu Tyr Val Asn Ile Glu Phe Gly
1               5                   10

<210> SEQ ID NO 10
<211> LENGTH: 7
<212> TYPE: PRT
<213> ORGANISM: Artificial
<220> FEATURE:
<223> OTHER INFORMATION: synthetic peptide

<400> SEQUENCE: 10

Asp Asn Glu Tyr Phe Tyr Val
1               5
```